(12) United States Patent
Hert et al.

(10) Patent No.: US 10,640,472 B2
(45) Date of Patent: May 5, 2020

(54) PHENOXYMETHYL DERIVATIVES

(71) Applicant: Hoffmann-La Roche Inc., Little Falls, NJ (US)

(72) Inventors: Jerome Hert, Basel (CH); Daniel Hunziker, Basel (CH); Holger Kuehne, Basel (CH); Thomas Luebbers, Basel (CH); Rainer E. Martin, Basel (CH); Patrizio Mattei, Basel (CH); Werner Neidhart, Basel (CH); Hans Richter, Basel (CH); Markus Rudolph, Basel (CH); Emmanuel Pinard, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/910,307

(22) Filed: Mar. 2, 2018

(65) Prior Publication Data
US 2018/0201588 A1 Jul. 19, 2018

Related U.S. Application Data

(63) Continuation of application No. PCT/EP2016/070561, filed on Sep. 1, 2016.

(30) Foreign Application Priority Data

Sep. 4, 2015 (EP) ................... 15183953
Dec. 1, 2015 (EP) ................... 15197364

(51) Int. Cl.
| | |
|---|---|
| *A61K 31/4196* | (2006.01) |
| *A61K 31/4192* | (2006.01) |
| *A61K 31/415* | (2006.01) |
| *A61K 31/416* | (2006.01) |
| *A61K 31/4162* | (2006.01) |
| *A61K 31/50* | (2006.01) |
| *C07D 249/04* | (2006.01) |
| *C07D 249/08* | (2006.01) |
| *C07D 231/12* | (2006.01) |
| *C07D 231/20* | (2006.01) |
| *C07D 231/00* | (2006.01) |
| *C07D 231/14* | (2006.01) |
| *C07D 487/04* | (2006.01) |
| *A61P 27/02* | (2006.01) |
| *C07D 249/12* | (2006.01) |
| *C07D 409/12* | (2006.01) |

(Continued)

(52) U.S. Cl.
CPC .......... *C07D 249/08* (2013.01); *A61P 27/02* (2018.01); *C07B 41/04* (2013.01); *C07D 231/12* (2013.01); *C07D 231/20* (2013.01); *C07D 231/56* (2013.01); *C07D 237/14* (2013.01); *C07D 249/04* (2013.01); *C07D 249/12* (2013.01); *C07D 401/12* (2013.01); *C07D 403/12* (2013.01); *C07D 407/04* (2013.01); *C07D 407/12* (2013.01); *C07D 409/12* (2013.01); *C07D 413/12* (2013.01); *C07D 417/12* (2013.01); *C07D 471/04* (2013.01); *C07D 487/04* (2013.01); *C07F 7/0812* (2013.01); *C07C 205/04* (2013.01); *C07C 255/50* (2013.01); *C07C 317/14* (2013.01)

(58) Field of Classification Search
CPC ............ A61K 31/4196; A61K 31/4192; A61K 31/415; A61K 31/416; A61K 31/4162; A61K 31/50; C07D 249/04; C07D 249/08; C07D 231/12; C07D 231/20; C07D 231/00; C07D 231/14; C07D 487/04; A61P 27/02
USPC ..... 514/383, 359, 406, 247; 548/268.2, 255, 548/376.1, 360.5, 362.5; 544/239
See application file for complete search history.

(56) References Cited

U.S. PATENT DOCUMENTS

| | | |
|---|---|---|
| 3,392,149 A | 7/1968 | Emden et al. |
| 5,202,322 A | 4/1993 | Allen et al. |

(Continued)

FOREIGN PATENT DOCUMENTS

| | | |
|---|---|---|
| CA | 2768095 | 1/2011 |
| CA | 2878442 A1 | 4/2014 |

(Continued)

OTHER PUBLICATIONS

Albers, Harald, Laurens Meeteren, David Egan, Erica van Tilburg, Wouter Moolenaar and Huib Ovaa, "Discovery and Optimization of Boronic Acid Based Inhibitors of Autotaxin", Journ. Med. Chem. (2010), 53: pp. 4958-4967. (Year: 2010).*

(Continued)

*Primary Examiner* — Matthew P Coughlin
*Assistant Examiner* — Sagar Patel
(74) *Attorney, Agent, or Firm* — Katherine J. Mackenzie

(57) ABSTRACT

The invention provides novel compounds having the general formula (I)

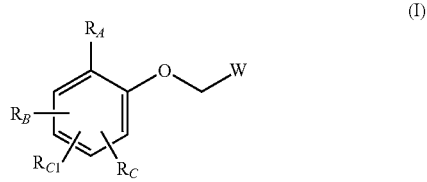

wherein $R_A$, $R_B$, $R_C$, $R_{C1}$ and W are as defined herein, compositions including the compounds and methods of using the compounds.

23 Claims, No Drawings

(51) Int. Cl.

| | | |
|---|---|---|
| *C07D 413/12* | (2006.01) | |
| *C07F 7/08* | (2006.01) | |
| *C07D 401/12* | (2006.01) | |
| *C07D 407/12* | (2006.01) | |
| *C07D 407/04* | (2006.01) | |
| *C07D 471/04* | (2006.01) | |
| *C07D 237/14* | (2006.01) | |
| *C07D 403/12* | (2006.01) | |
| *C07D 417/12* | (2006.01) | |
| *C07D 231/56* | (2006.01) | |
| *C07B 41/04* | (2006.01) | |
| C07C 205/04 | (2006.01) | |
| C07C 255/50 | (2006.01) | |
| C07C 317/14 | (2006.01) | |

(56) References Cited

U.S. PATENT DOCUMENTS

| | | | |
|---|---|---|---|
| 5,238,942 | A | 8/1993 | Chakravarty et al. |
| 5,240,928 | A | 8/1993 | Allen et al. |
| 5,290,780 | A | 3/1994 | Venkatesan et al. |
| 5,304,565 | A | 4/1994 | Morimoto et al. |
| 5,358,951 | A | 10/1994 | Levin et al. |
| 5,472,961 | A | 5/1995 | Gottschlich et al. |
| 5,470,975 | A | 11/1995 | Atwal et al. |
| 5,532,243 | A | 7/1996 | Gilligan |
| 6,821,964 | B2 | 11/2004 | Colon-Cruz et al. |
| 6,841,560 | B2 | 1/2005 | Thompson et al. |
| 8,329,907 | B2 | 11/2012 | Schultz et al. |
| 8,440,694 | B2 | 5/2013 | Turner et al. |
| 8,697,883 | B2 | 4/2014 | Abouabdellah |
| 8,841,324 | B2 | 9/2014 | Staehle et al. |
| 8,946,264 | B2 | 2/2015 | Shinozuka et al. |
| 9,029,387 | B2 | 12/2015 | Staehle et al. |
| 9,493,486 | B2 | 11/2016 | Hunziker et al. |
| 9,580,434 | B2 | 2/2017 | Mazurov et al. |
| 9,802,944 | B2 | 10/2017 | Di Giorgio et al. |
| 10,208,052 | B1 | 2/2019 | Zheng et al. |
| 2005/0203112 | A1 | 9/2005 | Castonguay et al. |
| 2008/0090802 | A1 | 4/2008 | Letourneau et al. |
| 2010/0222341 | A1 | 2/2010 | Schiemann et al. |
| 2010/0298290 | A1 | 11/2010 | Anand et al. |
| 2011/0230471 | A1 | 9/2011 | Staehle et al. |
| 2012/0015959 | A1 | 1/2012 | Staehle et al. |
| 2012/0095040 | A1 | 4/2012 | Abouabdellah et al. |
| 2012/0115852 | A1 | 5/2012 | Schultz et al. |
| 2012/0115858 | A1 | 5/2012 | Tesconi et al. |
| 2015/0353559 | A1 | 12/2015 | Hert et al. |
| 2015/0376194 | A1 | 12/2015 | Hert et al. |
| 2016/0264586 | A1 | 9/2016 | Mattei et al. |
| 2017/0008900 | A1 | 1/2017 | Di Giorgio et al. |
| 2017/0008913 | A1 | 1/2017 | Hunziker et al. |
| 2017/0029425 | A1 | 2/2017 | Hunziker et al. |
| 2017/0050960 | A1 | 2/2017 | Hert et al. |

FOREIGN PATENT DOCUMENTS

| | | |
|---|---|---|
| CN | 1751047 A1 | 3/2006 |
| CN | 102459207 A | 5/2012 |
| EP | 0417631 A2 | 3/1991 |
| EP | 2301936 A1 | 3/2011 |
| EP | 3385261 A1 | 10/2018 |
| JP | 2001-039950 | 2/2001 |
| JP | 2008-31064 | 2/2008 |
| JP | 2009-161449 | 7/2009 |
| JP | 2011-502150 | 1/2011 |
| RU | 2375352 C2 | 12/2009 |
| RU | 2 480 463 | 4/2013 |
| RU | 2 483 068 | 5/2013 |
| RU | 2 517 693 | 5/2014 |
| WO | 2015/077503 A1 | 0/5201 |
| WO | 99/40070 | 8/1999 |
| WO | 01/30780 | 5/2001 |
| WO | 02/070523 A1 | 9/2002 |
| WO | 2004/074291 A1 | 2/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | WO-2006015985 A1 * | 2/2006 ......... C07D 253/075 |
| WO | 2006/077035 A1 | 7/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008/135141 A1 | 11/2008 |
| WO | 2009/046841 A2 | 4/2009 |
| WO | 2009/054914 A1 | 4/2009 |
| WO | 2009/058347 | 5/2009 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108651 | 9/2010 |
| WO | 2010/112116 A1 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A2 | 11/2011 |
| WO | 2009/154132 | 12/2011 |
| WO | 2011/151461 A2 | 12/2011 |
| WO | 2012/020008 A1 | 2/2012 |
| WO | 2012/024620 | 2/2012 |
| WO | 2012/028243 | 3/2012 |
| WO | WO-2012080727 A2 * | 6/2012 ........... A61K 31/437 |
| WO | 2012/166415 A1 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 A1 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014/133112 A1 | 9/2014 |
| WO | 2014/139324 | 9/2014 |
| WO | 2014/139978 A1 | 9/2014 |
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/078800 A1 | 6/2015 |

(56) References Cited

FOREIGN PATENT DOCUMENTS

| WO | 2015/078803 | | 6/2015 |
|---|---|---|---|
| WO | 2015/144480 | A1 | 10/2015 |
| WO | 2015/144605 | A1 | 10/2015 |
| WO | 2015/144609 | A1 | 10/2015 |
| WO | 2015/144803 | A1 | 10/2015 |
| WO | 2015/154023 | A1 | 10/2015 |
| WO | 2016/061160 | A1 | 4/2016 |
| WO | 2016/128529 | A1 | 8/2016 |
| WO | 2016/162390 | | 10/2016 |
| WO | 2017/037146 | | 3/2017 |
| WO | 2017/037670 | A1 | 3/2017 |
| WO | 2017/050732 | A1 | 3/2017 |
| WO | 2017/050747 | A1 | 3/2017 |
| WO | 2017/050791 | A1 | 3/2017 |
| WO | 2017/050792 | A1 | 3/2017 |
| WO | 2017/053722 | A1 | 3/2017 |
| WO | 2017/091673 | A2 | 6/2017 |
| WO | 2017/139978 | A1 | 8/2017 |
| WO | 2017/005073 | A1 | 12/2017 |
| WO | 2018/167001 | A1 | 9/2018 |
| WO | 2018/167113 | A1 | 9/2018 |

OTHER PUBLICATIONS

Sheridan, "The most common chemical replacements in drug-like compounds", J. Chem. Inf. Comp. Sci. (2002), 42: pp. 103-108. (Year: 2002).*
(International Search Report—PCT/EP2016/070561 dated Oct. 23, 2016 Oct. 12, 2016).
Bora, Rajesh O., et al., "[1, 2, 4]-Oxadiazoles: Synthesis and Biological Applications" Mini-Reviews in Med. Chem 14(4):355-369 (Mar. 13, 2014).
Database Capulus (online) Chemical Abstracts Service Columbus Ohio, 1993, Database accession No. 1994:483155 RN156411-73-3, 156411-74-4 (1993).
Erdik, Ender, "Transition Metal Catalyzed Reactions of Organozinc Reagents" Tetrahedron Report No. 23 48(44):9577-9648 (Jan. 1, 1992).
Farina, V. et al. Organic Reactions "The Stille Reaction" Paquette, Leo A., New York—US:Wiley and Sons, vol. 50:1-704 (Apr. 1, 1997).
Green et al. Protective Groups in Organic Synthesis (Table of Contents only, in 4 pages), Second edition, New York:John Wiley & Sons, Inc., ( 1991).
Hall, Dennis, ed. et al. Boronic Acids: Preparation, Applications in Organic Synthesis and Medicine Hall, Dennis,Wiley,:1-571 (Jan. 1, 2006).
Hemming, K. Science of Synthesis, Product 13: 1, 2, 3-Triazoles "Product Class 6: 1,2,4-Oxadiazoles" Storr, R.C. & Gilchrist, T.L., eds., Stuttgart-DE:Thieme Verlagsgruppe, vol. 13:127-184 (Jan. 1, 2004).
Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).
Li, Jie Jack et al. Name Reactions for Homologation, Part 1 "Name Reactions for Homologation, Part 1" (Abstract of text),Wiley and Sons,:1-685 (May 1, 2009).
Mitchell, Terence N., "Palladium-Catalysed Reactions of Organotin Compounds" Synthesis 9:803-815 (Aug. 16, 1991).
Negishi, Ei-ichi, et al. Metal-Catalyzed Cross-Coupling Reactions "Chapter 1. Palladium or NickelCatalyzed CrossCoupling with Organometals Containing Zinc, Magnesium, Aluminum, and Zirconium" Diederich, Francois, Stang, Peter J., eds., Weinheim, DE: Wiley-VCH Verlag GmbH,:1-47 (Jan. 1, 2004).
Polshettiwar, Vivek, et al., "Suzuki-Miyaura Cross-Coupling Reactions in Aqueous Media: Green and Sustainable Syntheses of Biaryls" ChemSUSChem 3:502-522 (Jan. 1, 2010).
Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993 (Oct. 27, 2011).
Schlaeger, "The Protein Hydrolysate, Primatone RL, is a Cost-effective Multiple Growth Promoter of Mammalian Cell Culture in Serum-containing and Serum-free Media and Displays Anti-apoptosis Properties" J Immunol Methods 194:191-199 ( 1996).
Stille, John K., "The Palladium-Catalyzed Cross-Coupling Reactions of Organotin Reagents with Organic Electrophiles" Angew Chem. Int. Ed. Engl. 25:508-524 (Jan. 1, 1986).
Suzuki, A., et al., "Palladium-Catalyzed Cross-Coupling Reactions of Organoboron Compounds" Chem Rev. 95:2457-2483 (Jan. 31, 1995).
Suzuki, A., et al., "Recent advances in the cross-coupling reactions of organoboron derivatives with organic electrophiles, 1995-1998" J Organomet Chem 576:147-168 (Jan. 1, 1999).
Suzuki, A., et al., "Synthetic Studies via the cross-coupling reaction of organoboron derivatives with organic halides" Pure Appl Chem 63(3):419-422 (Jan. 1, 1991).
Tucker, Thomas J., et al., "Discovery of 3-{5-[(6-Amino-1H-pyrazolo[3,4-b]pyridine-3-yl)methoxy]-2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J Med Chem 51:6503-6511 (Jul. 11, 2008).
Albers et al., "Chemical Evolution of Autotaxin Inhibitors" Chem Rev 112(5):2593-2603 (May 9, 2012).
Albers et al., "Structure-Based Design of Novel Boronic Acid-Based Inhibitors of Autotaxin" Journal of Medicinal Chemistry 54(13):4619-4626 ( 2011).
Anderson, "The Process of Structure-Based Drug Design" Chemistry & Biology 10:787-797 (Sep. 2003).
Angeli et al., "Synthesis and carbonic anhydrase inhibition of polycyclic imides moieties" Bioorgan Med Chem 25(20):5373-5379 (Oct 20, 2017).
Armstrong, J., et al., "Purification and Properties of Human Erythrocyte Carbonic Anhydrases" J Biol Chem 241(21):5137-5149 (Nov. 10, 1966)
Barbayianni Efrosini, "Autotaxin inhibitorsza patent review" Expert Opin Ther Pat 23(9):1123-1132 (Sep 1, 2013)
Banesch, Matthew G.K., et al., "Autotaxin in the crosshairs: Taking aim at cancer and other inflammatory conditions" Febs Lett 588:2712-2727 (Feb. 19, 2014).
CAS Database Registry, ID#1206969-43-8 [retrieved online May 25, 2016], Feb. 22, 2010 (Feb. 22, 2010), BroadPharmz, retrieved from STN Database accession No. 1206969-43-8 the whole document.
CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.
CAS Registry Database, 1352926-14-7,Database Registry [retrieved online May 25, 2016] Chemical Abstracts Service Jan. 12, 2012 (Jan. 12, 2012), All i chem LLC: XP002707617, retrieved from STN Database accession No. 1352926-14-7 see also RN: 135295-74-6; the whole document.
CAS Registry Database, 959567-58-9, 0, pp. 1-38 Dec. 26, 2007.
Garcia-Gutierrez et al., "Novel inhibitors to Taenia solium Cu/Zn superoxide dismutase identifed by Virtual screening" J. Comp Aided Molecular Design 25: 1135-1145 (2011).
Gierse et al., "A Novel Autotaxin Inhibitor Reduces Lysophosphatidie Acid Levels in Plasma and the Site of Inflammation" Pharmacol Exp Ther 334:310-317 ( 2010).
Hoeglund et al., "Optimization of a pidemidic acid autotaxin inhibitor" Journal of Medicinal Chemistry 53:1056-1066 ( 2010).
"International Preliminary Report on Patentability—PCT/EP2018/056140":pp. 1-8 (dated Sep. 26, 2019).
"International Search Report—PCT/EP2014/054631":pp. 1-4 (dated Apr. 15, 2014).
"International Search Report—PCT/EP2014/075360":pp. 1-5 (dated Feb. 9, 2015).
"International Search Report—PCT/EP2015/056041":pp. 1-5 (dated May 6, 2015).
"International Search Report—PCT/EP2016/072277":pp. 1-5 (dated Dec. 8, 2016).

(56) References Cited

OTHER PUBLICATIONS

"International Search Report—PCT/EP2016/072349":pp. 1-5 (dated Nov. 29, 2016).
"International Search Report—PCT/EP2018/056140":pp. 1-9 (dated May 4, 2018).
"International Search Report—PCT/EP2018/056324",:pp. 1-7 (dated May 8, 2018).
"International Search Report—PCT/EP2013/061890",:pp. 1-9 (dated Sep. 17, 2013).
"International Search Report—PCT/EP2013/069679":pp. 1-3 (dated Nov. 8, 2013).
"International Search Report—PCT/EP2015/056032",:pp. 1-5 (dated Apr. 23, 2015).
"International Search Report—PCT/EP2016/057549":pp. 1-5 (dated Jun. 22, 2016).
"International Search Report—PCT/EP2016/072243":pp. 1-5 (dated Dec. 6, 2016).
"International Search Report—PCT/EP2016/072347":pp. 1-5 (dated Jan. 17, 2017).
"International Search Report—PCT/EP2016/070561":pp. 1-6 (dated Oct. 28, 2016).
Jones et al., "Novel autotaxin inhibitors for the treatment of osteoarthritis pain: Lead optimization via structure-based drug design" ACS Med Chem Lett 7(9):857-861 ( 2016).
Kung et al., "Identification of spirocyclic piperidine-azetidine inverse agonists of the ghrelin receptor" Bioorg Med Chem Lett (XP028490993), 22:4281-4287 ( 2012).
Litherland et al., "The Amino-derivatives of Pentuerythritol. Part I. Preparation." J Chem Soc:1588-1595 (Jan. 1, 1938).
Matralis et al., "Development and therapeutic potential of autotaxin small molecule inhibitors: From bench to advanced clinical trials" Med. Res. Rev.:1-38 ( 2018).
Mayo Clinic Staff, (Lupus[online], retrieved from the internet on Jan. 24, 2017; http://www.mayoclinic.org/diseases-conditions/lupus basics/definition/CON-20019676) 2017.
Orr et al., "One-pot synthesis of chiral azetidines from chloroaldehyde and chiral amines" Tetrahedron Lett 52:3618-3620 ( 2011).
Overberger et al., "Absolute Configuration of 2,7-Diazaspiro[ 4.4Inonane. A Reassignment" J. Org. Chem. 46:2757-2764 ( 1981).
Patani, G., et al., "Bioisosterism: A Rational Approach in Drug Design" Chem Rev 96(8):3147-3176 (Dec. 19, 1996).
Sheridan et al., "Cautious optimism surrounds early clinical data for PD-1 blocker" Nat Biotechnol 30(8):729-730 (Aug. 1, 2012).
Sippy et al., "Preparation and characterization of N-(3-pyridinyl) spirocyclic diamines as ligands for nicotinic acetylcholine receptors" Bioorg Med Chem Lett 19:1682-1685 (2009).
STN Columbus (STN International), pp. 1-13 ( Oct. 9, 2015).
Stocks et al., "A Practical Method for Targeted Library Design Balancing Lead-like Properties with Diversity" Chem Med Chem (XP002707616), 4:800-808 ( 2009).
Thiel "Structure-aided drug design's next generation" Nat Biotechnol 22(5):513-519 (May 1, 2004).

* cited by examiner

PHENOXYMETHYL DERIVATIVES

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

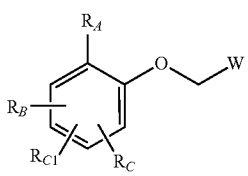

(I)

wherein
$R_A$ is selected from the group consisting of
i) $C_1$-$C_6$-alkyl,
ii) cyano-$C_1$-$C_6$-alkyl,
iii) $C_3$-$C_8$-cycloalkyl,
iv) halo-$C_1$-$C_6$-alkoxy,
v) halo-$C_1$-$C_6$-alkyl,
vi) aryl substituted with $R_G$, $R_{G1}$ and $R_{G2}$,
vii) heterocycloalkyl substituted with $R_G$, $R_{G1}$ and $R_{G2}$, and
viii) heteroaryl substituted with $R_G$, $R_{G1}$ and $R_{G2}$;
$R_B$ is selected from the group consisting of
i) $C_1$-$C_6$-alkyl,
ii) $C_3$-$C_8$-cycloalkyl,
iii) $C_1$-$C_6$-alkylsulfonyl,
iv) $C_3$-$C_8$-cycloalkylsulfonyl,
v) $C_1$-$C_6$-alkylsulfonylamino,
vi) $C_3$-$C_8$-cycloalkylsulfonylamino,
vii) aminocarbonyl,
viii) cyano,
ix) halogen,
x) halo-$C_1$-$C_6$-alkoxy,
xi) halo-$C_1$-$C_6$-alkyl,
xii) heterocycloalkyl, and
xiii) heteroaryl substituted with one H, $C_1$-$C_6$-alkyl or trialkylsilyl-$C_1$-$C_6$-alkoxy-$C_1$-$C_6$-alkyl;
$R_C$ and $R_{C1}$ are independently selected from the group consisting of
i) H,
ii)
iii) $C_3$-$C_8$-cycloalkyl,
iv) halo-$C_1$-$C_6$-alkoxy,
v) halo-$C_1$-$C_6$-alkyl, and
vi) halogen;
or $R_B$ and $R_C$ together with the carbon atoms to which they are attached form a ring system selected from the group consisting of
i) $C_3$-$C_8$-cycloalkyl substituted with one to two substituent independently selected from H, $C_1$-$C_6$-alkyl, halo-$C_1$-$C_6$-alkoxy, halo-$C_1$-$C_6$-alkyl and $C_3$-$C_8$-cycloalkyl,
ii) heterocycloalkyl substituted with one to two substituent independently selected from H, $C_1$-$C_6$-alkyl, halo-$C_1$-$C_6$-alkoxy, halo-$C_1$-$C_6$-alkyl and $C_3$-$C_8$-cycloalkyl,
iii) aryl substituted with one to two substituent independently selected from H, halogen, $C_1$-$C_6$-alkyl, halo-$C_1$-$C_6$-alkoxy, halo-$C_1$-$C_6$-alkyl and $C_3$-$C_8$-cycloalkyl, and
iv) heteroaryl substituted with one to two substituent independently selected from H, halogen, $C_1$-$C_6$-alkyl, halo-$C_1$-$C_6$-alkoxy, halo-$C_1$-$C_6$-alkyl and $C_3$-$C_8$-cycloalkyl;
W is selected from the ring systems A, B, C, D, E, F and G;

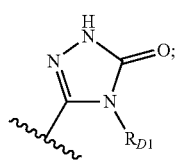

A

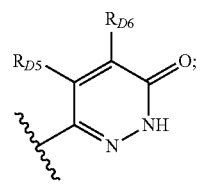

B

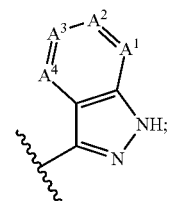

C

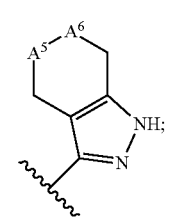

D

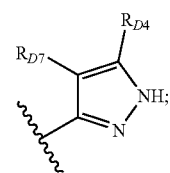

E

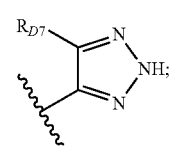

F

-continued

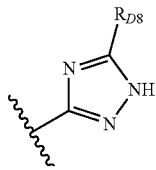
G

A¹, A³ and A⁴ are —CH— and A² is —CR$_{D2}$—,
A¹ is —N—, A² is —CR$_{D2}$—, A³ is —CH— or —N— and A⁴ is —CH—,
A¹, A³ and A⁴ are —CH— and A² is —N—,
A¹, A² and A⁴ are —CH— and A³ is —N—, or
A¹ and A³ are —CH—, A² is —CR$_{D2}$— and A⁴ is —N—;
one of A⁵ and A⁶ is —NR$_{D3}$— and the other one is —CR$_L$R$_M$—;
R$_{D1}$ is selected from the group consisting of
i) H,
ii) $C_1$-$C_6$-alkyl,
iii) halo-$C_1$-$C_6$-alkoxy,
iv) halo-$C_1$-$C_6$-alkyl, and
v) $C_3$-$C_8$-cycloalkyl;
R$_{D2}$ is selected from the group consisting of
i) H,
ii) halogen,
iii) $C_1$-$C_6$-alkoxy-$C_1$-$C_6$-alkylcarbonyl,
iv) $C_1$-$C_6$-alkoxycarbonyl,
v) $C_1$-$C_6$-alkylcarbonyl,
vi) $C_3$-$C_8$-cycloalkylcarbonyl,
vii) $C_1$-$C_6$-alkyl,
viii) $C_3$-$C_8$-cycloalkyl,
ix) hydroxy-$C_1$-$C_6$-alkoxy,
x) hydroxy-$C_1$-$C_6$-alkyl($C_1$-$C_6$-alkyl)amino,
xi) hydroxy-$C_1$-$C_6$-alkylamino,
xii) hydroxy-$C_1$-$C_6$-alkyl,
xiii) dihydroxy-$C_1$-$C_6$-alkoxy,
xiv) dihydroxy-$C_1$-$C_6$-alkyl($C_1$-$C_6$-alkyl)amino,
xv) dihydroxy-$C_1$-$C_6$-alkylamino,
xvi) dihydroxy-$C_1$-$C_6$-alkyl,
xvii) halo-$C_1$-$C_6$-alkoxy,
xviii) halo-$C_1$-$C_6$-alkyl,
xix) heterocycloalkyl,
xx) heterocycloalkylcarbonyl, and
xxi) aminocarbonyl substituted on the nitrogen atom with one to two independently selected $C_1$-$C_6$-alkyl;
R$_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl,
iv) $C_1$-$C_6$-alkylcarbonyl,
v) $C_3$-$C_8$-cycloalkylcarbonyl,
vi) $C_1$-$C_6$-alkyl,
vii) $C_3$-$C_8$-cycloalkyl,
viii) halo-$C_1$-$C_6$-alkoxy,
ix) halo-$C_1$-$C_6$-alkyl,
x) hydroxy-$C_1$-$C_6$-alkyl, and
xi) dihydroxy-$C_1$-$C_6$-alkyl,
R$_{D4}$ is selected from the group consisting of
i) H,
ii) $C_1$-$C_6$-alkoxy-$C_1$-$C_6$-alkylcarbonyl,
iii) $C_1$-$C_6$-alkoxycarbonyl,
iv) $C_1$-$C_6$-alkylcarbonyl,
v) $C_3$-$C_8$-cycloalkylcarbonyl,
vi) $C_1$-$C_6$-alkyl,
vii) $C_3$-$C_8$-cycloalkyl,
viii) halo-$C_1$-$C_6$-alkoxy,
ix) halo-$C_1$-$C_6$-alkyl,
x) heterocycloalkylcarbonyl,
xi) aminocarbonyl substituted on the nitrogen atom with one to two independently selected $C_1$-$C_6$-alkyl, and
xii) aryl substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy;
R$_{D5}$, R$_{D6}$ and R$_{D7}$ are independently selected from the group consisting of
i) H,
ii) $C_1$-$C_6$-alkyl,
iii) $C_1$-$C_6$-alkoxy
iv) halo-$C_1$-$C_6$-alkoxy,
v) halo-$C_1$-$C_6$-alkyl,
vi) $C_3$-$C_8$-cycloalkyl, and vii) $C_3$-$C_8$-cycloalkoxy;
R$_{D8}$ is selected from the group consisting of
i) H,
ii) $C_1$-$C_6$-alkyl,
iii) $C_1$-$C_6$-alkoxy
iv) halo-$C_1$-$C_6$-alkoxy,
v) halo-$C_1$-$C_6$-alkyl,
vi) $C_3$-$C_8$-cycloalkyl,
vii) $C_1$-$C_6$-alkoxy-$C_1$-$C_6$-alkylcarbonyl,
viii) $C_1$-$C_6$-alkoxycarbonyl,
ix) $C_1$-$C_6$-alkylcarbonyl,
x) $C_3$-$C_8$-cycloalkylcarbonyl,
xi) heterocycloalkylcarbonyl, and
xii) aminocarbonyl substituted on the nitrogen atom with one to two independently selected $C_1$-$C_6$-alkyl;
R$_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) $C_3$-$C_8$-cyloalkylsulfonyl,
ix) carboxy,
x) cyano,
xi) $C_3$-$C_8$-cycloalkyl,
xii) $C_3$-$C_8$-cycloalkoxy,
xiii) $C_3$-$C_8$-cycloalkylcarbonylamino-$C_1$-$C_6$-alkyl,
xiv) $C_3$-$C_8$-cycloalkylcarbonyl($C_1$-$C_6$-alkyl)amino-$C_1$-$C_6$-alkyl,
xv) $C_1$-$C_6$-alkylcarbonylamino-$C_1$-$C_6$-alkyl,
xvi) $C_1$-$C_6$-alkylcarbonyl($C_1$-$C_6$-alkyl)amino-$C_1$-$C_6$-alkyl,
xvii) halo-$C_1$-$C_6$-alkyl,
xviii) halo-$C_1$-$C_6$-alkoxy,
xix) halogen,
xx) hydroxy,
xxi) aminocarbonyl substituted on the nitrogen atom with R$_N$ and R$_O$,
xxii) aminocarbonyl-$C_1$-$C_6$-alkoxy substituted on the nitrogen atom with R$_N$ and R$_O$,
xxiii) heteroaryl substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy,
xxiv) heterocycloalkyl-$C_1$-$C_6$-alkoxy substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy, and xxv) heterocycloalkyl-$C_1$-$C_6$-alkyl substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy;

$R_{G1}$ and $R_{G2}$ are independently selected from the group consisting of
  i) H,
  ii) halogen,
  iii) $C_1$-$C_6$-alkyl,
  iv) $C_3$-$C_8$-cycloalkyl,
  v) halo-$C_1$-$C_6$-alkoxy, and
  vi) halo-$C_1$-$C_6$-alkyl;

$R_L$ and $R_M$ are independently selected from the group consisting of
  i) H, and
  ii) $C_1$-$C_6$-alkyl;

$R_N$ is selected from the group consisting of
  i) H,
  ii) $C_1$-$C_6$-alkoxy,
  iii) $C_1$-$C_6$-alkoxy-$C_1$-$C_6$-alkyl,
  iv) $C_1$-$C_6$-alkoxycarbonyl-$C_1$-$C_6$-alkyl,
  v) $C_1$-$C_6$-alkyl,
  vi) carboxy-$C_1$-$C_6$-alkyl,
  vii) $C_3$-$C_8$-cycloalkyl,
  viii) $C_3$-$C_8$-cycloalkyl-$C_1$-$C_6$-alkyl,
  ix) hydroxy-$C_1$-$C_6$-alkyl,
  x) phenyl, and
  xi) heteroaryl-$C_1$-$C_6$-alkyl;

$R_O$ is selected from the group consisting of
  i) H, and
  ii) $C_1$-$C_6$-alkyl;

or $R_N$ and $R_O$ together with the nitrogen atom to which they are attached form a heterocycloalkyl;

or pharmaceutically acceptable salts.

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPAS/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and-chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particularly, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

The term "$C_{1-6}$-alkoxy" denotes a group of the formula —O—R', wherein R' is an $C_{1-6}$-alkyl group. Examples of $C_{1-6}$-alkoxy group include methoxy, ethoxy, n-propoxy, isopropoxy, n-butoxy, isobutoxy and tert-butoxy. Particular examples are methoxy and isopropoxy.

The term "$C_{1-6}$-alkoxy-$C_{1-6}$-alkyl" denotes a $C_{1-6}$-alkyl group wherein at least one of the hydrogen atoms of the $C_{1-6}$-alkyl group is replaced by a $C_{1-6}$-alkoxy group. Particular examples are methoxymethyl, methoxyethyl, ethoxymethyl, ethoxyethyl, iso-propoxymethyl and iso-propoxyethyl. Particular example is methoxyethyl.

The term "$C_1$-$C_6$-alkoxy-$C_1$-$C_6$-alkylcarbonyl($C_1$-$C_6$-alkyl)amino-$C_1$-$C_6$-alkyl" denotes an amino-$C_1$-$C_6$-alkyl wherein the nitrogen atom is substituted by a $C_1$-$C_6$-alkyl group and by a $C_1$-$C_6$-alkoxy-$C_1$-$C_6$-alkylcarbonyl group. Particular example is an aminomethyl wherein the nitrogen atom is substituted by methyl and methoxymethylcarbonyl.

The term "$C_1$-$C_6$-alkoxy-$C_1$-$C_6$-alkylcarbonyl" denotes a group of the formula —C(O)—R', wherein R' is a $C_1$-$C_6$-alkoxy-$C_1$-$C_6$-alkyl group. Examples of $C_1$-$C_6$-alkoxy-$C_1$-$C_6$-alkylcarbonyl group include groups wherein R' is methoxymethyl, methoxyethyl, ethoxymethyl, ethoxyethyl, iso-propoxymethyl and iso-propoxyethyl. Particular example is group wherein R' is methoxymethyl.

The term "$C_1$-$C_6$-alkoxy-$C_1$-$C_6$-alkylcarbonylamino-$C_1$-$C_6$-alkyl" denotes an amino-$C_1$-$C_6$-alkyl group wherein the nitrogen atom is substituted by H and by a $C_1$-$C_6$-alkoxy-$C_1$-$C_6$-alkylcarbonyl group. Particular example is an aminomethyl wherein the nitrogen atom is substituted by H and methoxymethylcarbonyl.

The term "$C_1$-$C_6$-alkoxycarbonyl-$C_1$-$C_6$-alkyl" denotes a $C_{1-6}$-alkyl group wherein at least one of the hydrogen atoms of the $C_{1-6}$-alkyl group is replaced by a $C_1$-$C_6$-alkoxycarbonyl group. Particular examples are groups wherein the $C_1$-$C_6$-alkoxycarbonyl group is methoxycarbonyl or ethoxycarbonyl and the $C_{1-6}$-alkyl group is methyl or ethyl. More particular examples are methoxyoxopropyl and ethoxyoxoethyl.

The term "$C_1$-$C_6$-alkoxycarbonyl" denotes a group of the formula —C(O)—R', wherein R' is a $C_1$-$C_6$-alkoxy group. Examples of $C_1$-$C_6$-alkoxycarbonyl group include groups wherein R' is methoxy, ethoxy, n-propoxy, isopropoxy, n-butoxy, isobutoxy and tert-butoxy. Particular example are groups wherein R' is methoxy or tert-butoxy.

The term "$C_{1-6}$-alkyl" denotes a monovalent linear or branched saturated hydrocarbon group of 1 to 6 carbon atoms. Examples of $C_{1-6}$-alkyl include methyl, ethyl, propyl, isopropyl, n-butyl, iso-butyl, sec-butyl, tert-butyl and pentyl. Particular alkyl groups include methyl, isopropyl and tert-butyl.

The term "$C_1$-$C_6$-alkylcarbonyl($C_1$-$C_6$-alkyl)amino-$C_1$-$C_6$-alkyl" denotes an amino-$C_1$-$C_6$-alkyl wherein the nitrogen atom is substituted by a $C_1$-$C_6$-alkyl group and by a $C_1$-$C_6$-alkylcarbonyl group. Particular example is an aminomethyl wherein the nitrogen atom is substituted by methyl and methylcarbonyl or ethylcarbonyl.

The term "$C_1$-$C_6$-alkylcarbonyl" denotes a group of the formula —C(O)—R', wherein R' is a $C_1$-$C_6$-alkyl group. Examples of $C_1$-$C_6$-alkylcarbonyl group include groups wherein R' is methoxy, ethoxy, n-propoxy, isopropoxy, n-butoxy, isobutoxy and tert-butoxy. Particular example is group wherein R' is methyl.

The term "$C_1$-$C_6$-alkylcarbonylamino-$C_1$-$C_6$-alkyl" denotes an amino-$C_1$-$C_6$-alkyl wherein the nitrogen atom is substituted by a H and by a $C_1$-$C_6$-alkylcarbonyl group. Particular example is an aminomethyl wherein the nitrogen atom is substituted by H and methylcarbonyl or ethylcarbonyl.

The term "$C_1$-$C_6$-alkylsulfonyl" denotes a group of the formula —S(O)$_2$—R', wherein R' is a $C_1$-$C_6$-alkyl group. Particular example is a group wherein R' is methyl.

The term "$C_1$-$C_6$-alkylsulfonylamino" denotes a group of the formula —NH—S(O)$_2$—R', wherein R' is a $C_1$-$C_6$-alkyl group. Particular example is a group wherein R' is methyl.

The term "amino" denotes a —NH$_2$ group.

The term "aminoalkyl" denotes a $C_{1-6}$-alkyl group wherein one of the hydrogen atoms of the $C_{1-6}$-alkyl group is replaced by an amino group. Particular examples are amionmethyl, aminoethyl, aminopropyl and aminobutyl.

The term "aminocarbonyl" denotes a group of the formula —C(O)—NH$_2$.

The term "aminocarbonyl-$C_1$-$C_6$-alkoxy" denotes a $C_{1-6}$-alkoxy group wherein one of the hydrogen atoms of the $C_{1-6}$-alkoxy group is replaced by an aminocarbonyl group. Particular example is a group wherein the $C_{1-6}$-alkoxy group is methoxy.

The term "aryl" denotes a phenyl or naphtyl group. Particular example is phenyl.

The term "carboxy" denotes a —COOH group.

The term "carboxy-$C_1$-$C_6$-alkyl" denotes a $C_{1-6}$-alkyl group wherein one of the hydrogen atoms of the $C_{1-6}$-alkyl group is replaced by a carboxy group. Particular examples are carboxymethyl and carboxyethyl.

The term "cyano" denotes a —C≡N group.

The term "cyano-$C_1$-$C_6$-alkyl" denotes a $C_{1-6}$-alkyl group wherein one of the hydrogen atoms of the $C_{1-6}$-alkyl group is replaced by cyano group. Particular examples are cyanomethyl, cyanoethyl, cyanopropyl and cyanobutyl. Particular example is cyanopropyl.

The term "$C_{3-8}$-cycloalkoxy" denotes a group of the formula —O—R', wherein R' is a $C_{3-8}$-cycloalkyl. Particular example is a group wherein R' is cyclopropyl.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic $C_{3-8}$-cycloalkyl are bicyclo[2.2.1]heptanyl or bicyclo[2.2.2]octanyl. Particular $C_{3-8}$-cycloalkyl group are cyclobutyl, cyclopropyl, cyclopentyl and cyclohexyl.

Particular example of "$C_{3-8}$-cycloalkyl" formed by the substituent $R_B$ and $R_C$ together with the carbon atoms to which they are attached are cyclopentyl or cyclohexyl, more particularly cyclopentyl.

The term "$C_{3-8}$-cycloalkyl-$C_{1-6}$-alkyl" denotes a $C_{1-6}$-alkyl group wherein at least one of the hydrogen atoms of the $C_{1-6}$-alkyl group is replaced by a $C_{3-8}$-cycloalkyl group. Particular example is cyclopropylmethyl.

The term "$C_3$-$C_8$-cycloalkylcarbonyl($C_1$-$C_6$-alkyl)amino-$C_1$-$C_6$-alkyl" denotes an amino-$C_1$-$C_6$-alkyl wherein the nitrogen atom is substituted by a $C_1$-$C_6$-alkyl group and by a $C_3$-$C_8$-cycloalkylcarbonyl group. Particular example is an aminomethyl wherein the nitrogen atom is substituted by methyl and cyclopropylcarbonyl.

The term "$C_3$-$C_8$-cycloalkylcarbonyl" denotes a group of the formula —C(O)—R', wherein R' is a $C_3$-$C_8$-cycloalkyl group. Examples of $C_3$-$C_8$-cycloalkylcarbonyl are groups wherein R' is cyclopropyl.

The term "$C_3$-$C_8$-cycloalkylcarbonylamino-$C_1$-$C_6$-alkyl" denotes an amino-$C_1$-$C_6$-alkyl wherein the nitrogen atom is substituted by a H and by a $C_3$-$C_8$-cycloalkylcarbonyl group. Particular example is an aminomethyl wherein the nitrogen atom is substituted by H and cyclopropylcarbonyl.

The term "$C_3$-$C_8$-cycloalkylsulfonyl" denotes a group of the formula —S(O)$_2$—R', wherein R' is a $C_3$-$C_8$-cycloalkyl group. Examples of $C_3$-$C_8$-cycloalkylsulfonyl are groups wherein R' is cyclopropyl.

The term "$C_3$-$C_8$-cycloalkylsulfonylamino" denotes a group of the formula —NH—S(O)$_2$—R', wherein R' is a $C_3$-$C_8$-cycloalkyl group. Examples of $C_3$-$C_8$-cycloalkylsulfonyl are groups wherein R' is cyclopropyl.

The term "dihydroxy-$C_1$-$C_6$-alkoxy" denotes a $C_{1-6}$-alkoxy group wherein two of the hydrogen atoms of the dihydroxy-$C_1$-$C_6$-alkoxy group located on different carbon atoms have been each replaced by an hydroxy group. Particular example is dihydroxypropoxy. Further particular example is 2,3-dihydroxypropoxy.

The term "dihydroxy-$C_1$-$C_6$-alkyl" denotes a $C_{1-6}$-alkyl group wherein two of the hydrogen atoms of the $C_{1-6}$-alkyl group located on different carbon atoms have been each replaced by an hydroxy group. Particular example is dihydroxypropyl. Further particular example is 2,3-dihydroxypropyl.

The term "dihydroxy-$C_1$-$C_6$-alkylamino" denotes a group of the formula —NH—R', wherein R' is a dihydroxy-$C_1$-$C_6$-alkyl group. Examples of dihydroxy-$C_1$-$C_6$-alkylamino are groups wherein R' is dihydroxypropyl, more particularly 2,3-dihydroxypropyl.

The term "dihydroxy-$C_1$-$C_6$-alkyl($C_1$-$C_6$-alkyl)amino" denotes a group of the formula —NRR', wherein R is a $C_1$-$C_6$-alkyl and R' is a dihydroxy-$C_1$-$C_6$-alkyl group. Examples of dihydroxy-$C_1$-$C_6$-alkyl($C_1$-$C_6$-alkyl)amino is dihydroxypropyl(methyl)amino, further particular example is 2,3-dihydroxypropyl(methyl)amino.

The term "halo-$C_{1-6}$-alkoxy" denotes a $C_{1-6}$-alkoxy group wherein at least one of the hydrogen atoms of the $C_1$-$C_6$-alkoxy group has been replaced by the same or different halogen atoms. Particular examples are difluoromethoxy, trifluoromethoxy, difluoroethoxy and trifluoroethoxy. More particular example is trifluoromethoxy.

The term "halogen" and "halo" are used interchangeably herein and denote fluoro, chloro, bromo or iodo. Particular halogens are chloro and fluoro.

The term "halo-$C_{1-6}$-alkyl" denotes a $C_{1-6}$-alkyl group wherein at least one of the hydrogen atoms of the $C_{1-6}$-alkyl group has been replaced by the same or different halogen atoms. Particular examples are difluoromethyl, trifluoromethyl, difluoroethyl and trifluoroethyl. More particular example is trifluoromethyl.

The term "heteroaryl", alone or in combination, denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridinyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl. Particular heteroaryl groups are pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridinyl, pyridazinyl, pyrimidinyl, isoxazolyl, isothiazolyl, benzofuranyl and benzothiophenyl. More particular heteroaryl groups are benzoxazolonyl, imidazolyl, isoxazolyl, oxazolyl, thiazolyl, oxadiazolyl, pyrazinyl, pyrazolyl, pyridinyl and pyrimidinyl.

In the case of substituent $R_A$, particular heteroaryl groups are benzoxazolonyl, imidazolyl, isoxazolyl, oxazolyl, pyrazinyl, pyrazolyl, pyridinyl and pyrimidinyl. More particular examples are isoxazolyl and pyridinyl.

In the case of substituent $R_B$, particular heteroaryl groups are oxadiazolyl, imidazolyl, 1,3,4-oxazolyl and 1,2,4-oxazolyl.

Particular example of heterocycloalkyl formed by the substituent $R_B$ and $R_C$ together with the carbon atoms to which they are attached is thiazolyl.

In the case of substituent $R_G$, particular heteroaryl groups are isoxazolyl, oxazolyl and pyrazolyl. More particular examples are isoxazolyl and pyrazolyl.

The term "heteroaryl-$C_1$-$C_6$-alkyl" denotes an alkyl group wherein one of the hydrogen atoms of the $C_1$-$C_6$-alkyl group has been replaced by a heteroaryl group.

In the case of substituent $R_N$, particular heteroarylalkyl groups are pyridinylalkyl and thiophenylalkyl, more particularly pyridinylmethyl and thiophenylmethyl.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

In the case of substituent $R_{D2}$, particular example of heterocycloalkyl is hydroxyazetidinyl, more particularly 3-hydroxyazetidin-1-yl.

In the case of substituent $R_A$, particular example of heterocycloalkyl is tetrahydropyranyl.

In the case of substitutent $R_B$, particular example of heterocycloalkyl is morpholinyl.

Particular example of heterocycloalkyl formed by the substitutent $R_N$ and $R_O$ together with the nitrogen atom to which they are attached are piperidinyl, morpholinyl, pyrrolidinyl and methylpiperazinonyl.

The term "heterocycloalkyl-$C_{1-6}$-alkoxy" denotes a $C_{1-6}$-alkoxy group wherein at least one of the hydrogen atoms of the alkyl group is replaced by a heterocycloalkyl group. Particular examples are tetrahydropyranylmethoxy and tetrahydrofuranylnethoxy.

The term "heterocycloalkyl-$C_{1-6}$-alkyl" denotes a $C_{1-6}$-alkyl group wherein at least one of the hydrogen atoms of the $C_{1-6}$-alkyl group is replaced by a heterocycloalkyl group. Particular examples of heterocycloalkyl-$C_{1-6}$-alkyl are groups wherein the heterocycloalkyl group is methylpiperazinedionyl, pyrrolidinonyl and oxazolidinonyl and wherein the $C_{1-6}$-alkyl group is methyl.

The term "heterocycloalkylcarbonyl" denotes a group of the formula —C(O)—R', wherein R' is a heterocycloalkyl group. Example of heterocycloalkylcarbonyl group are groups wherein R' is 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, pyrrolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl.

In the case of substituent $R_{D3}$, particular examples of heterocycloalkylcarbonyl group is group wherein R' is pyrrolidinyl.

The term "hydroxy" denotes a —OH group.

The term "hydroxy-$C_{1-6}$-alkoxy" denotes a $C_{1-6}$-alkoxy group wherein one of the hydrogen atoms of the $C_{1-6}$-alkoxy is replaced by a hydroxy group. Particular examples are hydroxyethoxy and hydroxypropoxy. More particular examples is hydroxyethoxy.

The term "hydroxy-$C_{1-6}$-alkyl" denotes a $C_{1-6}$-alkyl group wherein one of the hydrogen atoms of the $C_{1-6}$-alkyl group is replaced by a hydroxy group. Particular examples are hydroxymethyl and hydroxyethyl. More particular example is hydroxyethyl.

The term "hydroxy-$C_1$-$C_6$-alkylamino" denotes a group of the formula —NH—R', wherein R' is an hydroxy-$C_1$-$C_6$-alkyl group. Examples of hydroxy-$C_1$-$C_6$-alkylamino include groups wherein R' is hydroxyethyl or hydroxypropyl. Particular example is a group wherein R' is hydroxyethyl.

The term "hydroxy-$C_1$-$C_6$-alkyl($C_1$-$C_6$-alkyl)amino" denotes a group of the formula —NRR', wherein R is a $C_1$-$C_6$-alkyl and R' is an hydroxy-$C_1$-$C_6$-alkyl group. Examples of hydroxy-$C_1$-$C_6$-alkyl($C_1$-$C_6$-alkyl)amino groups include groups wherein R is methyl, ethyl, propyl or isopropyl and wherein R' is hydroxyethyl or hydroxypropyl. Particular example is a group wherein R is methyl and R' is hydroxyethyl.

The term "trialkylsilyl-$C_1$-$C_6$-alkoxy-$C_1$-$C_6$-alkyl" denotes a $C_1$-$C_6$-alkyl wherein one of the hydrogen atoms of the $C_{1-6}$-alkyl group is replaced by a trialkylsilyl-$C_1$-$C_6$-alkoxy. Particular example is trimethylsilylethoxymethyl.

The term "trialkylsilyl-$C_1$-$C_6$-alkoxy" denotes a $C_1$-$C_6$-alkoxy wherein one of the hydrogen atoms of the $C_{1-6}$-alkoxy group is replaced by a trialkylsilyl. Particular example is trimethylsilylethoxyl.

The term "trialkylsilyl" denotes a group of formula —Si(R')$_3$ wherein each R' is an independently selected $C_1$-$C_6$-alkyl group. Particular example are groups wherein R' is methyl, ethyl, propyl, isopropyl, n-butyl, iso-butyl, sec-butyl, tert-butyl and pentyl. More particular examples are groups wherein all R' are identical, furthermore particularly wherein R' is methyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention provides compounds according to formula (I) as described herein, wherein The present invention provides novel compounds of formula (I)

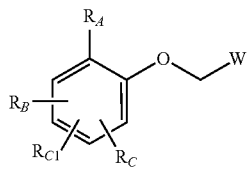
(I)

wherein
$R_A$ is selected from the group consisting of
i) $C_1$-$C_6$-alkyl,
ii) cyano-$C_1$-$C_6$-alkyl,
iii) $C_3$-$C_8$-cycloalkyl,
iv) halo-$C_1$-$C_6$-alkoxy,
v) halo-$C_1$-$C_6$-alkyl,
vi) aryl substituted with $R_G$, $R_{G1}$ and $R_{G2}$,
vii) heterocycloalkyl substituted with $R_G$, $R_{G1}$ and $R_{G2}$, and
viii) heteroaryl substituted with $R_G$, $R_{G1}$ and $R_{G2}$;
$R_B$ is selected from the group consisting of
i) $C_1$-$C_6$-alkyl,
ii) $C_3$-$C_8$-cycloalkyl,
iii) $C_1$-$C_6$-alkylsulfonyl,
iv) $C_3$-$C_8$-cycloalkylsulfonyl,
v) $C_1$-$C_6$-alkylsulfonylamino,
vi) $C_3$-$C_8$-cycloalkylsulfonylamino,
vii) aminocarbonyl,
viii) cyano,
ix) halogen,
x) halo-$C_1$-$C_6$-alkoxy,
xi) halo-$C_1$-$C_6$-alkyl,
xii) heterocycloalkyl, and
xiii) heteroaryl substituted with one H, $C_1$-$C_6$-alkyl or trialkylsilyl-$C_1$-$C_6$-alkoxy-$C_1$-$C_6$-alkyl;
$R_C$ and $R_{C1}$ are independently selected from the group consisting of
i) H,
ii) $C_1$-$C_6$-alkyl,
iii) $C_3$-$C_8$-cycloalkyl,
iv) halo-$C_1$-$C_6$-alkoxy,
v) halo-$C_1$-$C_6$-alkyl, and
vi) halogen;
or $R_B$ and $R_C$ together with the carbon atoms to which they are attached form a ring system selected from the group consisting of
i) $C_3$-$C_8$-cycloalkyl substituted with one to two substituent independently selected from H, $C_1$-$C_6$-alkyl, halo-$C_1$-$C_6$-alkoxy, halo-$C_1$-$C_6$-alkyl and $C_3$-$C_8$-cycloalkyl,
ii) heterocycloalkyl substituted with one to two substituent independently selected from H, $C_1$-$C_6$-alkyl, halo-$C_1$-$C_6$-alkoxy, halo-$C_1$-$C_6$-alkyl and $C_3$-$C_8$-cycloalkyl,
iii) aryl substituted with one to two substituent independently selected from H, halogen, $C_1$-$C_6$-alkyl, halo-$C_1$-$C_6$-alkoxy, halo-$C_1$-$C_6$-alkyl and $C_3$-$C_8$-cycloalkyl, and
iv) heteroaryl substituted with one to two substituent independently selected from H, halogen, $C_1$-$C_6$-alkyl, halo-$C_1$-$C_6$-alkoxy, halo-$C_1$-$C_6$-alkyl and $C_3$-$C_8$-cycloalkyl;
W is selected from the ring systems A, B, C, D, E, F and G;

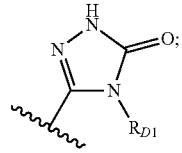
A

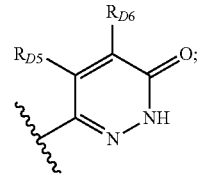
B

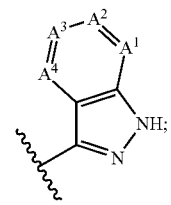
C

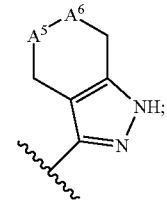
D

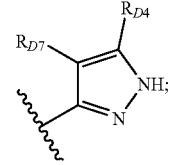
E

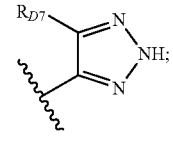
F

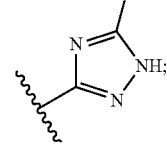
G $A^1$, $A^3$ and $A^4$ are —CH— and $A^2$ is —$CR_{D2}$—,
$A^1$ is —N—, $A^2$ is —$CR_{D2}$—, $A^3$ is —CH— or —N— and $A^4$ is —CH—,
$A^1$, $A^3$ and $A^4$ are —CH— and $A^2$ is —N—,
$A^1$, $A^2$ and $A^4$ are —CH— and $A^3$ is —N—, or
$A^1$ and $A^3$ are —CH—, $A^2$ is —$CR_{D2}$— and $A^4$ is —N—;
one of $A^5$ and $A^6$ is —$NR_{D3}$— and the other one is —$CR_L R_M$—;
$R_{D1}$ is selected from the group consisting of
i) H,
ii) $C_1$-$C_6$-alkyl,
iii) halo-$C_1$-$C_6$-alkoxy,
iv) halo-$C_1$-$C_6$-alkyl, and
v) $C_3$-$C_8$-cycloalkyl;

$R_{D2}$ is selected from the group consisting of
i) H,
ii) halogen,
iii) $C_1$-$C_6$-alkoxy-$C_1$-$C_6$-alkylcarbonyl,
iv) $C_1$-$C_6$-alkoxycarbonyl,
v) $C_1$-$C_6$-alkylcarbonyl,
vi) $C_3$-$C_8$-cycloalkylcarbonyl,
vii) $C_1$-$C_6$-alkyl,
viii) $C_3$-$C_8$-cycloalkyl,
ix) hydroxy-$C_1$-$C_6$-alkoxy,
x) hydroxy-$C_1$-$C_6$-alkyl($C_1$-$C_6$-alkyl)amino,
xi) hydroxy-$C_1$-$C_6$-alkylamino,
xii) hydroxy-$C_1$-$C_6$-alkyl,
xiii) dihydroxy-$C_1$-$C_6$-alkoxy,
xiv) dihydroxy-$C_1$-$C_6$-alkyl($C_1$-$C_6$-alkyl)amino,
xv) dihydroxy-$C_1$-$C_6$-alkylamino,
xvi) dihydroxy-$C_1$-$C_6$-alkyl,
xvii) halo-$C_1$-$C_6$-alkoxy,
xviii) halo-$C_1$-$C_6$-alkyl,
xix) heterocycloalkyl,
xx) heterocycloalkylcarbonyl, and
xxi) aminocarbonyl substituted on the nitrogen atom with one to two independently selected $C_1$-$C_6$-alkyl;
$R_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl,
iv) $C_1$-$C_6$-alkylcarbonyl,
v) $C_3$-$C_8$-cycloalkylcarbonyl,
vi) $C_1$-$C_6$-alkyl,
vii) $C_3$-$C_8$-cycloalkyl,
viii) halo-$C_1$-$C_6$-alkoxy,
ix) halo-$C_1$-$C_6$-alkyl,
x) hydroxy-$C_1$-$C_6$-alkyl, and
xi) dihydroxy-$C_1$-$C_6$-alkyl,
$R_{D4}$ is selected from the group consisting of
i) H,
ii) $C_1$-$C_6$-alkoxy-$C_1$-$C_6$-alkylcarbonyl,
iii) $C_1$-$C_6$-alkoxycarbonyl,
iv) $C_1$-$C_6$-alkylcarbonyl,
v) $C_3$-$C_8$-cycloalkylcarbonyl,
vi) $C_1$-$C_6$-alkyl,
vii) $C_3$-$C_8$-cycloalkyl,
viii) halo-$C_1$-$C_6$-alkoxy,
ix) halo-$C_1$-$C_6$-alkyl,
x) heterocycloalkylcarbonyl, and
xi) aminocarbonyl substituted on the nitrogen atom with one to two independently selected $C_1$-$C_6$-alkyl;
$R_{D5}$, $R_{D6}$ and $R_{D7}$ are independently selected from the group consisting of
i) H,
ii) $C_1$-$C_6$-alkyl,
iii) $C_1$-$C_6$-alkoxy
iv) halo-$C_1$-$C_6$-alkoxy,
v) halo-$C_1$-$C_6$-alkyl,
vi) $C_3$-$C_8$-cycloalkyl, and
vii) $C_3$-$C_8$-cycloalkoxy;
$R_{D8}$ is selected from the group consisting of
i) H,
ii) $C_1$-$C_6$-alkyl,
iii) $C_1$-$C_6$-alkoxy
iv) halo-$C_1$-$C_6$-alkoxy,
v) halo-$C_1$-$C_6$-alkyl,
vi) $C_3$-$C_8$-cycloalkyl,
vii) $C_1$-$C_6$-alkoxy-$C_1$-$C_6$-alkylcarbonyl,
viii) $C_1$-$C_6$-alkoxycarbonyl,
ix) $C_1$-$C_6$-alkylcarbonyl,
x) $C_3$-$C_8$-cycloalkylcarbonyl,
xi) heterocycloalkylcarbonyl, and
xii) aminocarbonyl substituted on the nitrogen atom with one to two independently selected $C_1$-$C_6$-alkyl;
$R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) $C_3$-$C_8$-cyloalkylsulfonyl,
ix) carboxy,
x) cyano,
xi) $C_3$-$C_8$-cycloalkyl,
xii) $C_3$-$C_8$-cycloalkoxy,
xiii) $C_3$-$C_8$-cycloalkylcarbonylamino-$C_1$-$C_6$-alkyl,
xiv) $C_3$-$C_8$-cycloalkylcarbonyl($C_1$-$C_6$-alkyl)amino-$C_1$-$C_6$-alkyl,
xv) $C_1$-$C_6$-alkylcarbonylamino-$C_1$-$C_6$-alkyl,
xvi) $C_1$-$C_6$-alkylcarbonyl($C_1$-$C_6$-alkyl)amino-$C_1$-$C_6$-alkyl,
xvii) halo-$C_1$-$C_6$-alkyl,
xviii) halo-$C_1$-$C_6$-alkoxy,
xix) halogen,
xx) hydroxy,
xxi) aminocarbonyl substituted on the nitrogen atom with $R_N$ and $R_O$,
xxii) aminocarbonyl-$C_1$-$C_6$-alkoxy substituted on the nitrogen atom with $R_N$ and $R_O$,
xxiii) heteroaryl substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy,
xxiv) heterocycloalkyl-$C_1$-$C_6$-alkoxy substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy, and
xxv) heterocycloalkyl-$C_1$-$C_6$-alkyl substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy;
$R_{G1}$ and $R_{G2}$ are independently selected from the group consisting of
i) H,
ii) halogen,
iii) $C_1$-$C_6$-alkyl,
iv) $C_3$-$C_8$-cycloalkyl,
v) halo-$C_1$-$C_6$-alkoxy, and
vi) halo-$C_1$-$C_6$-alkyl;
$R_L$ and $R_M$ are independently selected from the group consisting of
i) H, and
ii) $C_1$-$C_6$-alkyl;

$R_N$ is selected from the group consisting of
xii) H,
xiii) $C_1$-$C_6$-alkoxy,
xiv) $C_1$-$C_6$-alkoxy-$C_1$-$C_6$-alkyl,
xv) $C_1$-$C_6$-alkoxycarbonyl-$C_1$-$C_6$-alkyl,
xvi) $C_1$-$C_6$-alkyl,
xvii) carboxy-$C_1$-$C_6$-alkyl,
xviii) $C_3$-$C_8$-cycloalkyl,
xix) $C_3$-$C_8$-cycloalkyl-$C_1$-$C_6$-alkyl,
xx) hydroxy-$C_1$-$C_6$-alkyl,
xxi) phenyl, and
xxii) heteroaryl-$C_1$-$C_6$-alkyl;
$R_O$ is selected from the group consisting of
i) H, and
ii) $C_1$-$C_6$-alkyl;
or $R_N$ and $R_O$ together with the nitrogen atom to which they are attached form a heterocycloalkyl;
or pharmaceutically acceptable salts.

In another embodiment, the present invention provides novel compounds of formula (I)

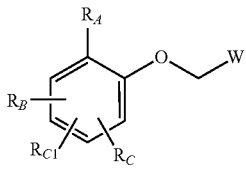

(I)

wherein
$R_A$ is selected from the group consisting of
i) $C_1$-$C_6$-alkyl,
ii) cyano-$C_1$-$C_6$-alkyl,
iii) $C_3$-$C_8$-cycloalkyl,
iv) halo-$C_1$-$C_6$-alkoxy,
v) halo-$C_1$-$C_6$-alkyl,
vi) aryl substituted with $R_G$, $R_{G1}$ and $R_{G2}$,
vii) heterocycloalkyl substituted with $R_G$, $R_{G1}$ and $R_{G2}$, and
viii) heteroaryl substituted with $R_G$, $R_{G1}$ and $R_{G2}$;
$R_B$ is selected from the group consisting of
i) $C_1$-$C_6$-alkyl,
ii) $C_3$-$C_8$-cycloalkyl,
iii) $C_1$-$C_6$-alkylsulfonyl,
iv) $C_3$-$C_8$-cycloalkylsulfonyl,
v) $C_1$-$C_6$-alkylsulfonylamino,
vi) $C_3$-$C_8$-cycloalkylsulfonylamino,
vii) aminocarbonyl,
viii) cyano,
ix) halogen,
x) halo-$C_1$-$C_6$-alkoxy,
xi) halo-$C_1$-$C_6$-alkyl,
xii) heterocycloalkyl, and
xiii) heteroaryl substituted with one H, $C_1$-$C_6$-alkyl or trialkylsilyl-$C_1$-$C_6$-alkoxy-$C_1$-$C_6$-alkyl;
$R_C$ and $R_{C1}$ are independently selected from the group consisting of
i) H,
ii) $C_1$-$C_6$-alkyl,
iii) $C_3$-$C_8$-cycloalkyl,
iv) halo-$C_1$-$C_6$-alkoxy,
v) halo-$C_1$-$C_6$-alkyl, and
vi) halogen;
or $R_B$ and $R_C$ together with the carbon atoms to which they are attached form a ring system selected from the group consisting of i) $C_3$-$C_8$-cycloalkyl substituted with one to two substituent independently selected from H, $C_1$-$C_6$-alkyl, halo-$C_1$-$C_6$-alkoxy, halo-$C_1$-$C_6$-alkyl and $C_3$-$C_8$-cycloalkyl,
ii) heterocycloalkyl substituted with one to two substituent independently selected from H, $C_1$-$C_6$-alkyl, halo-$C_1$-$C_6$-alkoxy, halo-$C_1$-$C_6$-alkyl and $C_3$-$C_8$-cycloalkyl,
iii) aryl substituted with one to two substituent independently selected from H, halogen, $C_1$-$C_6$-alkyl, halo-$C_1$-$C_6$-alkoxy, halo-$C_1$-$C_6$-alkyl and $C_3$-$C_8$-cycloalkyl, and
iv) heteroaryl substituted with one to two substituent independently selected from H, halogen, $C_1$-$C_6$-alkyl, halo-$C_1$-$C_6$-alkoxy, halo-$C_1$-$C_6$-alkyl and $C_3$-$C_8$-cycloalkyl;
W is selected from the ring systems A, B, C, D and E;

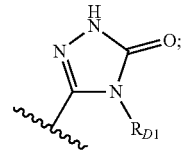

A

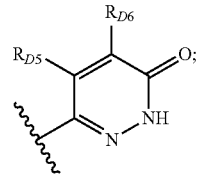

B

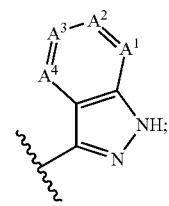

C

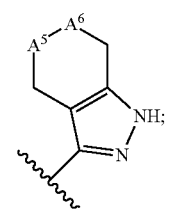

D

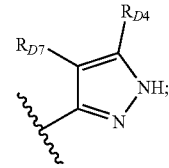

E $A^1$, $A^3$ and $A^4$ are —CH— and $A^2$ is —$CR_{D2}$—,
$A^1$ is —N—, $A^2$ is —$CR_{D2}$—, $A^3$ is —CH— or —N— and $A^4$ is —CH—,
$A^1$, $A^3$ and $A^4$ are —CH— and $A^2$ is —N—,
$A^1$, $A^2$ and $A^4$ are —CH— and $A^3$ is —N—, or
$A^1$ and $A^3$ are —CH—, $A^2$ is —$CR_{D2}$— and $A^4$ is —N—;
one of $A^5$ and $A^6$ is —$NR_{D3}$— and the other one is —$CR_L R_M$—;

$R_{D1}$ is selected from the group consisting of
i) H,
ii) $C_1$-$C_6$-alkyl,
iii) halo-$C_1$-$C_6$-alkoxy,
iv) halo-$C_1$-$C_6$-alkyl, and
v) $C_3$-$C_8$-cycloalkyl;

$R_{D2}$ is selected from the group consisting of
i) H,
ii) halogen,
iii) $C_1$-$C_6$-alkoxy-$C_1$-$C_6$-alkylcarbonyl,
iv) $C_1$-$C_6$-alkoxycarbonyl,
v) $C_1$-$C_6$-alkylcarbonyl,
vi) $C_3$-$C_8$-cycloalkylcarbonyl,
vii) $C_1$-$C_6$-alkyl,
viii) $C_3$-$C_8$-cycloalkyl,
ix) hydroxy-$C_1$-$C_6$-alkoxy,
x) hydroxy-$C_1$-$C_6$-alkyl($C_1$-$C_6$-alkyl)amino,
xi) hydroxy-$C_1$-$C_6$-alkylamino,
xii) hydroxy-$C_1$-$C_6$-alkyl,
xiii) dihydroxy-$C_1$-$C_6$-alkoxy,
xiv) dihydroxy-$C_1$-$C_6$-alkyl($C_1$-$C_6$-alkyl)amino,
xv) dihydroxy-$C_1$-$C_6$-alkylamino,
xvi) dihydroxy-$C_1$-$C_6$-alkyl,
xvii) halo-$C_1$-$C_6$-alkoxy,
xviii) halo-$C_1$-$C_6$-alkyl,
xix) heterocycloalkyl,
xx) heterocycloalkylcarbonyl, and
xxi) aminocarbonyl substituted on the nitrogen atom with one to two independently selected $C_1$-$C_6$-alkyl;

$R_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl,
iv) $C_1$-$C_6$-alkylcarbonyl,
v) $C_3$-$C_8$-cycloalkylcarbonyl,
vi) $C_1$-$C_6$-alkyl,
vii) $C_3$-$C_8$-cycloalkyl,
viii) halo-$C_1$-$C_6$-alkoxy,
ix) halo-$C_1$-$C_6$-alkyl,
x) hydroxy-$C_1$-$C_6$-alkyl, and
xi) dihydroxy-$C_1$-$C_6$-alkyl, $R_{D4}$ is selected from the group consisting of
i) H,
ii) $C_1$-$C_6$-alkoxy-$C_1$-$C_6$-alkylcarbonyl,
iii) $C_1$-$C_6$-alkoxycarbonyl,
iv) $C_1$-$C_6$-alkylcarbonyl,
v) $C_3$-$C_8$-cycloalkylcarbonyl,
vi) $C_1$-$C_6$-alkyl,
vii) $C_3$-$C_8$-cycloalkyl,
viii) halo-$C_1$-$C_6$-alkoxy,
ix) halo-$C_1$-$C_6$-alkyl,
x) heterocycloalkylcarbonyl, and
xi) aminocarbonyl substituted on the nitrogen atom with one to two independently selected $C_1$-$C_6$-alkyl;

$R_{D5}$, $R_{D6}$ and $R_{D7}$ are independently selected from the group consisting of
i) H,
ii) $C_1$-$C_6$-alkyl,
iii) $C_1$-$C_6$-alkoxy
iv) halo-$C_1$-$C_6$-alkoxy,
v) halo-$C_1$-$C_6$-alkyl,
vi) $C_3$-$C_8$-cycloalkyl, and
vii) $C_3$-$C_8$-cycloalkoxy, $R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) $C_3$-$C_8$-cyloalkylsulfonyl,
ix) carboxy,
x) cyano,
xi) $C_3$-$C_8$-cycloalkyl,
xii) $C_3$-$C_8$-cycloalkoxy,
xiii) $C_3$-$C_8$-cycloalkylcarbonylamino-$C_1$-$C_6$-alkyl,
xiv) $C_3$-$C_8$-cycloalkylcarbonyl($C_1$-$C_6$-alkyl)amino-$C_1$-$C_6$-alkyl,
xv) $C_1$-$C_6$-alkylcarbonylamino-$C_1$-$C_6$-alkyl,
xvi) $C_1$-$C_6$-alkylcarbonyl($C_1$-$C_6$-alkyl)amino-$C_1$-$C_6$-alkyl,
xvii) halo-$C_1$-$C_6$-alkyl,
xviii) halo-$C_1$-$C_6$-alkoxy,
xix) halogen,
xx) aminocarbonyl substituted on the nitrogen atom with $R_N$ and $R_O$,
xxi) aminocarbonyl-$C_1$-$C_6$-alkoxy substituted on the nitrogen atom with $R_N$ and $R_O$,
xxii) heteroaryl substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy,
xxiii) heterocycloalkyl-$C_1$-$C_6$-alkoxy substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy, and
xxiv) heterocycloalkyl-$C_1$-$C_6$-alkyl substituted with one H, $C_1$-$C_6$-alkyl, $C_3$-$C_8$-cycloalkyl, halo-$C_1$-$C_6$-alkyl, halo-$C_1$-$C_6$-alkoxy, benzyl or aryl, wherein benzyl and aryl are substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy;

$R_{G1}$ and $R_{G2}$ are independently selected from the group consisting of
i) H,
ii) halogen,
iii) $C_1$-$C_6$-alkyl,
iv) $C_3$-$C_8$-cycloalkyl,
v) halo-$C_1$-$C_6$-alkoxy, and
vi) halo-$C_1$-$C_6$-alkyl;

$R_L$ and $R_M$ are independently selected from the group consisting of
i) H, and
ii) $C_1$-$C_6$-alkyl;

$R_N$ is selected from the group consisting of
i) H,
ii) $C_1$-$C_6$-alkoxy,
iii) $C_1$-$C_6$-alkoxy-$C_1$-$C_6$-alkyl,
iv) $C_1$-$C_6$-alkoxycarbonyl-$C_1$-$C_6$-alkyl,
v) $C_1$-$C_6$-alkyl,
vi) carboxy-$C_1$-$C_6$-alkyl,
vii) $C_3$-$C_8$-cycloalkyl,
viii) $C_3$-$C_8$-cycloalkyl-$C_1$-$C_6$-alkyl,
ix) hydroxy-$C_1$-$C_6$-alkyl,
x) phenyl, and
xi) heteroaryl-$C_1$-$C_6$-alkyl;

$R_O$ is selected from the group consisting of
i) H, and
ii) $C_1$-$C_6$-alkyl;
or $R_N$ and $R_O$ together with the nitrogen atom to which they are attached form a heterocycloalkyl;
or pharmaceutically acceptable salts.

A particular embodiment of the present invention provides compounds according to formula (I) as described herein, wherein
$R_A$ is selected from the group consisting of
i) $C_1$-$C_6$-alkyl,
ii) cyano-$C_1$-$C_6$-alkyl,
iii) $C_3$-$C_8$-cycloalkyl,
iv) aryl substituted with $R_G$ and $R_{G1}$,
v) heterocycloalkyl substituted with $R_G$ and $R_{G1}$, and
vi) heteroaryl substituted with $R_G$ and $R_{G1}$;
$R_B$ is selected from the group consisting of
i) $C_1$-$C_6$-alkyl,
ii) $C_1$-$C_6$-alkylsulfonyl,
iii) $C_1$-$C_6$-alkylsulfonylamino,
iv) aminocarbonyl,
v) cyano,
vi) halogen,
vii) heterocycloalkyl, and
viii) heteroaryl substituted with one H, $C_1$-$C_6$-alkyl or trialkylsilyl-$C_1$-$C_6$-alkoxy-$C_1$-$C_6$-alkyl;
$R_{C1}$ is H and $R_C$ is selected from the group consisting of
i) H,
ii) $C_1$-$C_6$-alkyl, and
iii) halogen;
or $R_B$ and $R_C$ together with the carbon atoms to which they are attached form a ring system selected from the group consisting of
i) heterocycloalkyl substituted with one to two substituent independently selected from H and $C_1$-$C_6$-alkyl, and
ii) heteroaryl substituted with one to two substituent independently selected from
H and $C_1$-$C_6$-alkyl;
W is selected from the ring systems A, B, C, D and E;

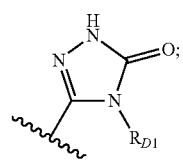
A

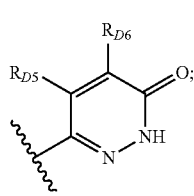
B

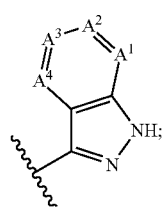
C

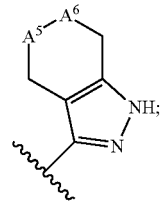
D

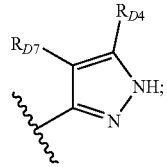
E

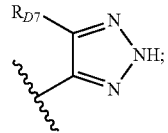
F $A^1$, $A^3$ and $A^4$ are —CH— and $A^2$ is —$CR_{D2}$—,
$A^1$ is —N—, $A^2$ is —$CR_{D2}$—, $A^3$ is —CH— or —N— and $A^4$ is —CH—,
$A^1$, $A^3$ and $A^4$ are —CH— and $A^2$ is —N—, or
$A^1$ and $A^3$ are —CH—, $A^2$ is —$CR_{D2}$— and $A^4$ is —N—;
one of $A^5$ and $A^6$ is —$NR_{D3}$— and the other one is —$CR_L R_M$—;
$R_{D1}$ is $C_1$-$C_6$-alkyl;
$R_{D2}$ is selected from the group consisting of
i) H,
ii) halogen,
iii) hydroxy-$C_1$-$C_6$-alkoxy,
iv) hydroxy-$C_1$-$C_6$-alkyl($C_1$-$C_6$-alkyl)amino,
v) hydroxy-$C_1$-$C_6$-alkylamino,
vi) dihydroxy-$C_1$-$C_6$-alkoxy,
vii) dihydroxy-$C_1$-$C_6$-alkyl($C_1$-$C_6$-alkyl)amino, and
viii) heterocycloalkyl;
$R_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl, and
iv) $C_1$-$C_6$-alkylcarbonyl;
$R_{D4}$ is selected from the group consisting of
i) H,
ii) $C_1$-$C_6$-alkoxycarbonyl,
iii) heterocycloalkylcarbonyl,
iv) aminocarbonyl substituted on the nitrogen atom with one to two independently selected $C_1$-$C_6$-alkyl, and
v) aryl substituted with one to three substituents independently selected from H, $C_1$-$C_6$-alkyl, $C_3$-$C_8$-cycloalkyl, halo-$C_1$-$C_6$-alkyl and halo-$C_1$-$C_6$-alkoxy;
$R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) carboxy, ix) cyano,
x) $C_3$-$C_8$-cycloalkoxy,
xi) $C_3$-$C_8$-cycloalkylcarbonylamino-$C_1$-$C_6$-alkyl,
xii) $C_3$-$C_8$-cycloalkylcarbonyl($C_1$-$C_6$-alkyl)amino-$C_1$-$C_6$-alkyl,
xiii) halo-$C_1$-$C_6$-alkyl,
xiv) halogen,
xv) hydroxy,
xvi) aminocarbonyl substituted on the nitrogen atom with $R_N$ and $R_O$,
xvii) aminocarbonyl-$C_1$-$C_6$-alkoxy substituted on the nitrogen atom with $R_N$ and $R_O$,
xviii) heteroaryl substituted with one H or $C_1$-$C_6$-alkyl,
xix) heterocycloalkyl-$C_1$-$C_6$-alkoxy substituted with one H or $C_1$-$C_6$-alkyl, and
xx) heterocycloalkyl-$C_1$-$C_6$-alkyl substituted with one H or $C_1$-$C_6$-alkyl;

$R_{G1}$ and $R_{G2}$ are independently selected from the group consisting of
i) H,
ii) halogen,
iii) $C_1$-$C_6$-alkyl, and
iv) halo-$C_1$-$C_6$-alkoxy;

$R_L$ and $R_M$ are H;

$R_N$ is selected from the group consisting of
i) H,
ii) $C_1$-$C_6$-alkoxy,
iii) $C_1$-$C_6$-alkoxy-$C_1$-$C_6$-alkyl,
iv) $C_1$-$C_6$-alkoxycarbonyl-$C_1$-$C_6$-alkyl,
v) $C_1$-$C_6$-alkyl,
vi) carboxy-$C_1$-$C_6$-alkyl,
vii) $C_3$-$C_8$-cycloalkyl,
viii) $C_3$-$C_8$-cycloalkyl-$C_1$-$C_6$-alkyl,
ix) hydroxy-$C_1$-$C_6$-alkyl,
x) phenyl, and
xi) heteroaryl-$C_1$-$C_6$-alkyl;

$R_O$ is selected from the group consisting of
i) H, and
ii) $C_1$-$C_6$-alkyl;

or $R_N$ and $R_O$ together with the nitrogen atom to which they are attached form a heterocycloalkyl;
or pharmaceutically acceptable salts.

A particular embodiment of the present invention provides compounds according to formula (I) as described herein, wherein
$R_A$ is selected from the group consisting of
i) $C_1$-$C_6$-alkyl,
ii) cyano-$C_1$-$C_6$-alkyl,
iii) $C_3$-$C_8$-cycloalkyl,
iv) aryl substituted with $R_G$ and $R_{G1}$,
v) heterocycloalkyl substituted with $R_G$ and $R_{G1}$, and
vi) heteroaryl substituted with $R_G$ and $R_{G1}$;

$R_B$ is selected from the group consisting of
i) $C_1$-$C_6$-alkyl,
ii) $C_1$-$C_6$-alkylsulfonyl,
iii) $C_1$-$C_6$-alkylsulfonylamino,
iv) aminocarbonyl,
v) cyano,
vi) halogen,
vii) heterocycloalkyl, and
viii) heteroaryl substituted with one H, $C_1$-$C_6$-alkyl or trialkylsilyl-$C_1$-$C_6$-alkoxy-$C_1$-$C_6$-alkyl;

$R_{C1}$ is H and $R_C$ is selected from the group consisting of
i) H,
ii) $C_1$-$C_6$-alkyl, and
iii) halogen;

or $R_B$ and $R_C$ together with the carbon atoms to which they are attached form a ring system selected from the group consisting of
i) heterocycloalkyl substituted with one to two substituent independently selected from H and $C_1$-$C_6$-alkyl, and
ii) heteroaryl substituted with one to two substituent independently selected from H and $C_1$-$C_6$-alkyl;

W is selected from the ring systems A, B, C, D and E;

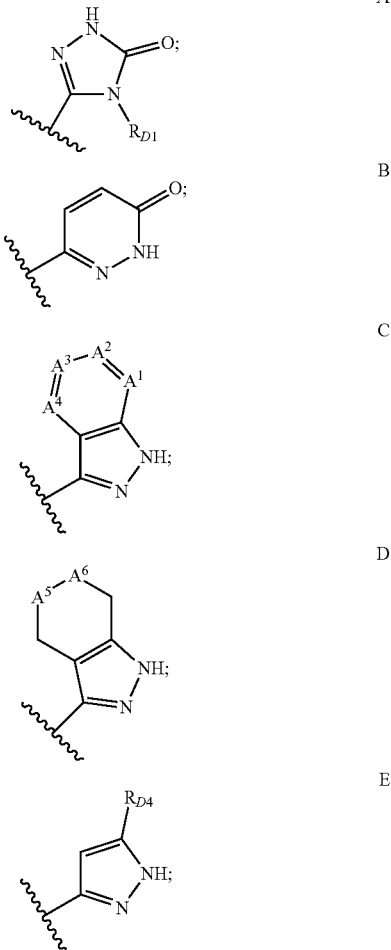

$A^1$, $A^3$ and $A^4$ are —CH— and $A^2$ is —$CR_{D2}$—,
$A^1$ is —N—, $A^2$ is —$CR_{D2}$—, $A^3$ is —CH— or —N— and $A^4$ is —CH—,
$A^1$, $A^3$ and $A^4$ are —CH— and $A^2$ is —N—, or
$A^1$ and $A^3$ are —CH—, $A^2$ is —$CR_{D2}$— and $A^4$ is —N—;
one of $A^5$ and $A^6$ is —$NR_{D3}$— and the other one is —$CR_L R_M$—;

$R_D$, is $C_1$-$C_6$-alkyl;

$R_{D2}$ is selected from the group consisting of
i) H,
ii) halogen,
iii) hydroxy-$C_1$-$C_6$-alkoxy,
iv) hydroxy-$C_1$-$C_6$-alkyl($C_1$-$C_6$-alkyl)amino,
v) hydroxy-$C_1$-$C_6$-alkylamino,
vi) dihydroxy-$C_1$-$C_6$-alkoxy,
vii) dihydroxy-$C_1$-$C_6$-alkyl($C_1$-$C_6$-alkyl)amino, and
viii) heterocycloalkyl;

$R_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl, and
iv) $C_1$-$C_6$-alkylcarbonyl;
$R_{D4}$ is selected from the group consisting of
i) H,
ii) $C_1$-$C_6$-alkoxycarbonyl,
iii) heterocycloalkylcarbonyl, and
iv) aminocarbonyl substituted on the nitrogen atom with one to two independently selected $C_1$-$C_6$-alkyl;
$R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) carboxy,
ix) cyano,
x) $C_3$-$C_8$-cycloalkoxy,
xi) $C_3$-$C_8$-cycloalkylcarbonylamino-$C_1$-$C_6$-alkyl,
xii) $C_3$-$C_8$-cycloalkylcarbonyl($C_1$-$C_6$-alkyl)amino-$C_1$-$C_6$-alkyl,
xiii) halo-$C_1$-$C_6$-alkyl,
xiv) halogen,
xv) hydroxy,
xvi) aminocarbonyl substituted on the nitrogen atom with $R_N$ and $R_O$,
xvii) aminocarbonyl-$C_1$-$C_6$-alkoxy substituted on the nitrogen atom with $R_N$ and $R_O$,
xviii) heteroaryl substituted with one H or $C_1$-$C_6$-alkyl,
xix) heterocycloalkyl-$C_1$-$C_6$-alkoxy substituted with one H or $C_1$-$C_6$-alkyl, and
xx) heterocycloalkyl-$C_1$-$C_6$-alkyl substituted with one H or $C_1$-$C_6$-alkyl;
$R_{G1}$ and $R_{G2}$ are independently selected from the group consisting of
i) H,
ii) halogen,
iii) $C_1$-$C_6$-alkyl, and
iv) halo-$C_1$-$C_6$-alkoxy;
$R_L$ and $R_M$ are H;
$R_N$ is selected from the group consisting of
xii) H,
xiii) $C_1$-$C_6$-alkoxy,
xiv) $C_1$-$C_6$-alkoxy-$C_1$-$C_6$-alkyl,
xv) $C_1$-$C_6$-alkoxycarbonyl-$C_1$-$C_6$-alkyl,
xvi) $C_1$-$C_6$-alkyl,
xvii) carboxy-$C_1$-$C_6$-alkyl,
xviii) $C_3$-$C_8$-cycloalkyl,
xix) $C_3$-$C_8$-cycloalkyl-$C_1$-$C_6$-alkyl,
xx) hydroxy-$C_1$-$C_6$-alkyl,
xxi) phenyl, and
xxii) heteroaryl-$C_1$-$C_6$-alkyl;
$R_O$ is selected from the group consisting of
i) H, and
ii)
or $R_N$ and $R_O$ together with the nitrogen atom to which they are attached form a heterocycloalkyl;
or pharmaceutically acceptable salts.

A particular embodiment of the present invention provides compounds according to formula (I) as described herein, wherein $R_A$ is selected from the group consisting of
i)
ii) cyano-$C_1$-$C_6$-alkyl,
iii) $C_3$-$C_8$-cycloalkyl,
iv) aryl substituted with $R_G$ and $R_{G1}$,
v) heterocycloalkyl substituted with $R_G$ and $R_{G1}$, and
vi) heteroaryl substituted with $R_G$ and $R_{G1}$;
$R_B$ is selected from the group consisting of
i)
ii) $C_1$-$C_6$-alkylsulfonyl,
iii) $C_1$-$C_6$-alkylsulfonylamino,
iv) aminocarbonyl,
v) cyano,
vi) halogen,
vii) heterocycloalkyl, and
viii) heteroaryl substituted with one H, $C_1$-$C_6$-alkyl or trialkylsilyl-$C_1$-$C_6$-alkoxy-$C_1$-$C_6$-alkyl;
$R_{C1}$ is H and $R_C$ is selected from the group consisting of
i) H,
ii) $C_1$-$C_6$-alkyl, and
iii) halogen; or $R_B$ and $R_C$ together with the carbon atoms to which they are attached form a ring system selected from the group consisting of
i) heterocycloalkyl substituted with one to two substituent independently selected from H and $C_1$-$C_6$-alkyl, and
ii) heteroaryl substituted with one to two substituent independently selected from H and $C_1$-$C_6$-alkyl;
W is selected from the ring systems A, B, C, D and E;

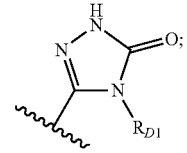

A

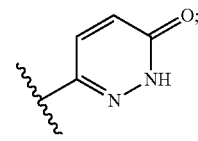

B

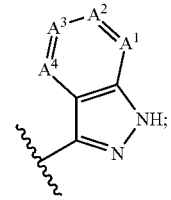

C

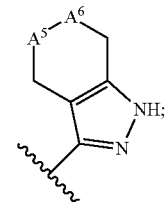

D

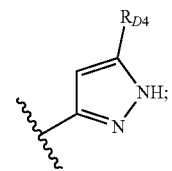

E $A^1$, $A^3$ and $A^4$ are —CH— and $A^2$ is —$CR_{D2}$—,
$A^1$ is —N—, $A^2$ is —$CR_{D2}$—, $A^3$ is —CH— or —N— and $A^4$ is —CH—,
$A^1$, $A^3$ and $A^4$ are —CH— and $A^2$ is —N—, or
$A^1$ and $A^3$ are —CH—, $A^2$ is —$CR_{D2}$— and $A^4$ is —N—;
one of $A^5$ and $A^6$ is —$NR_{D3}$— and the other one is —$CR_L R_M$—;

$R_{D'}$ is $C_1$-$C_6$-alkyl;

$R_{D2}$ is selected from the group consisting of
i) H,
ii) halogen,
iii) hydroxy-$C_1$-$C_6$-alkoxy,
iv) hydroxy-$C_1$-$C_6$-alkyl($C_1$-$C_6$-alkyl)amino,
v) hydroxy-$C_1$-$C_6$-alkylamino,
vi) dihydroxy-$C_1$-$C_6$-alkoxy,
vii) dihydroxy-$C_1$-$C_6$-alkyl($C_1$-$C_6$-alkyl)amino, and
viii) heterocycloalkyl;

$R_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl, and
iv) $C_1$-$C_6$-alkylcarbonyl;

$R_{D4}$ is selected from the group consisting of
i) H,
ii) $C_1$-$C_6$-alkoxycarbonyl,
iii) heterocycloalkylcarbonyl, and
iv) aminocarbonyl substituted on the nitrogen atom with one to two independently selected $C_1$-$C_6$-alkyl;

$R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) carboxy,
ix) cyano,
x) $C_3$-$C_8$-cycloalkoxy,
xi) $C_3$-$C_8$-cycloalkylcarbonylamino-$C_1$-$C_6$-alkyl,
xii) $C_3$-$C_8$-cycloalkylcarbonyl($C_1$-$C_6$-alkyl)amino-$C_1$-$C_6$-alkyl,
xiii) halo-$C_1$-$C_6$-alkyl,
xiv) halogen,
xv) aminocarbonyl substituted on the nitrogen atom with $R_N$ and $R_O$,
xvi) aminocarbonyl-$C_1$-$C_6$-alkoxy substituted on the nitrogen atom with $R_N$ and $R_O$,
xvii) heteroaryl substituted with one H or $C_1$-$C_6$-alkyl,
xviii) heterocycloalkyl-$C_1$-$C_6$-alkoxy substituted with one H or $C_1$-$C_6$-alkyl, and
xix) heterocycloalkyl-$C_1$-$C_6$-alkyl substituted with one H or $C_1$-$C_6$-alkyl;

$R_{G1}$ and $R_{G2}$ are independently selected from the group consisting of
i) H,
ii) halogen,
iii) $C_1$-$C_6$-alkyl, and
iv) halo-$C_1$-$C_6$-alkoxy;

$R_L$ and $R_M$ are H;

$R_N$ is selected from the group consisting of
i) H,
ii) $C_1$-$C_6$-alkoxy,
iii) $C_1$-$C_6$-alkoxy-$C_1$-$C_6$-alkyl,
iv) $C_1$-$C_6$-alkoxycarbonyl-$C_1$-$C_6$-alkyl,
v) $C_1$-$C_6$-alkyl,
vi) carboxy-$C_1$-$C_6$-alkyl,
vii) $C_3$-$C_8$-cycloalkyl,
viii) $C_3$-$C_8$-cycloalkyl-$C_1$-$C_6$-alkyl,
ix) hydroxy-$C_1$-$C_6$-alkyl,
x) phenyl, and
xi) heteroaryl-$C_1$-$C_6$-alkyl;

$R_O$ is selected from the group consisting of
i) H, and
ii) $C_1$-$C_6$-alkyl;
or $R_N$ and $R_O$ together with the nitrogen atom to which they are attached form a heterocycloalkyl;
or pharmaceutically acceptable salts.

Another embodiment of the present invention provides compounds according to formula (I) as described herein, wherein $R_A$ is selected from the group consisting of
i) $C_1$-$C_6$-alkyl,
ii) cyano-$C_1$-$C_6$-alkyl,
iii) $C_3$-$C_8$-cycloalkyl,
iv) aryl substituted with $R_G$ and $R_{G1}$,
v) heterocycloalkyl substituted with $R_G$ and $R_{G1}$, and
vi) heteroaryl substituted with $R_G$ and $R_{G1}$.

A particular embodiment of the present invention provides compounds according to formula (I) as described herein, wherein $R_A$ is selected from the group consisting of
i) $C_1$-$C_6$-alkyl,
ii) cyano-$C_1$-$C_6$-alkyl,
iii) $C_3$-$C_8$-cycloalkyl,
iv) phenyl substituted with $R_G$ and $R_{G1}$,
v) tetrahydropyranyl substituted with $R_G$ and $R_{G1}$, and
vi) heteroaryl substituted with $R_G$ and $R_{G1}$, wherein heteroaryl is selected from benzoxazolonyl, imidazolyl, isoxazolyl, oxazolyl, pyrazinyl, pyrazolyl, pyridinyl and pyrimidinyl.

A more particular embodiment of the present invention provides compounds according to formula (I) as described herein, wherein $R_A$ is selected from the group consisting of
i) $C_1$-$C_6$-alkyl,
ii) $C_3$-$C_8$-cycloalkyl,
iii) phenyl substituted with $R_G$ and $R_{G1}$, and
iv) heteroaryl substituted with $R_G$ and $R_{G1}$, wherein heteroaryl is selected from isoxazolyl and pyridinyl.

A furthermore particular embodiment of the present invention provides compounds according to formula (I) as described herein, wherein $R_A$ is selected from the group consisting of
i) $C_1$-$C_6$-alkyl, and
ii) phenyl substituted with $R_G$ and $R_{G1}$.

Another furthermore particular embodiment of the present invention provides compounds according to formula (I) as described herein, wherein $R_A$ is $C_1$-$C_6$-alkyl.

Another furthermore particular embodiment of the present invention provides compounds according to formula (I) as described herein, wherein $R_A$ is phenyl substituted with $R_G$ and $R_{G1}$.

Another embodiment of the present invention provides compounds according to formula
(I) as described herein, wherein $R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl, vii) $C_1$-$C_6$-alkylsulfonyl,
viii) carboxy,
ix) cyano,
x) $C_3$-$C_8$-cycloalkoxy,
xi) $C_3$-$C_8$-cycloalkylcarbonylamino-$C_1$-$C_6$-alkyl,
xii) $C_3$-$C_8$-cycloalkylcarbonyl($C_1$-$C_6$-alkyl)amino-$C_1$-$C_6$-alkyl,
xiii) halo-$C_1$-$C_6$-alkyl,
xiv) halogen,
xv) hydroxy,
xvi) aminocarbonyl substituted on the nitrogen atom with $R_N$ and $R_O$,
xvii) aminocarbonyl-$C_1$-$C_6$-alkoxy substituted on the nitrogen atom with $R_N$ and $R_O$,
xviii) heteroaryl substituted with one H or $C_1$-$C_6$-alkyl,
xix) heterocycloalkyl-$C_1$-$C_6$-alkoxy substituted with one H or $C_1$-$C_6$-alkyl, and
xx) heterocycloalkyl-$C_1$-$C_6$-alkyl substituted with one H or $C_1$-$C_6$-alkyl.

Another embodiment of the present invention provides compounds according to formula (I) as described herein, wherein $R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) carboxy,
ix) cyano,
x) $C_3$-$C_8$-cycloalkoxy,
xi) $C_3$-$C_8$-cycloalkylcarbonylamino-$C_1$-$C_6$-alkyl,
xii) $C_3$-$C_8$-cycloalkylcarbonyl($C_1$-$C_6$-alkyl)amino-$C_1$-$C_6$-alkyl,
xiii) halo-$C_1$-$C_6$-alkyl,
xiv) halogen,
xv) aminocarbonyl substituted on the nitrogen atom with $R_N$ and $R_O$,
xvi) aminocarbonyl-$C_1$-$C_6$-alkoxy substituted on the nitrogen atom with $R_N$ and $R_O$,
xvii) heteroaryl substituted with one H or $C_1$-$C_6$-alkyl,
xviii) heterocycloalkyl-$C_1$-$C_6$-alkoxy substituted with one H or $C_1$-$C_6$-alkyl, and
xix) heterocycloalkyl-$C_1$-$C_6$-alkyl substituted with one H or $C_1$-$C_6$-alkyl.

A particular embodiment of the present invention provides compounds according to formula (I) as described herein, wherein $R_G$ is selected from the group consisting of
i) H,
ii) $C_1$-$C_6$-alkoxy,
iii) $C_1$-$C_6$-alkoxy-$C_1$-$C_6$-alkylcarbonyl($C_1$-$C_6$-alkyl)amino-$C_1$-$C_6$-alkyl,
iv) $C_3$-$C_8$-cycloalkoxy,
v) halogen,
vi) hydroxy,
vii) aminocarbonyl substituted on the nitrogen atom with $R_N$ and $R_O$,
viii) aminocarbonyl-$C_1$-$C_6$-alkoxy substituted on the nitrogen atom with $R_N$ and $R_O$,
ix) heteroaryl substituted with one H or $C_1$-$C_6$-alkyl, and
x) heterocycloalkyl-$C_1$-$C_6$-alkyl substituted with one H or $C_1$-$C_6$-alkyl.

Another particular embodiment of the present invention provides compounds according to formula (I) as described herein, wherein $R_G$ is selected from the group consisting of
i) H,
ii) $C_1$-$C_6$-alkoxy,
iii) $C_1$-$C_6$-alkoxy-$C_1$-$C_6$-alkylcarbonyl($C_1$-$C_6$-alkyl)amino-$C_1$-$C_6$-alkyl,
iv) $C_3$-$C_8$-cycloalkoxy,
v) halogen,
vi) aminocarbonyl substituted on the nitrogen atom with $R_N$ and $R_O$,
vii) aminocarbonyl-$C_1$-$C_6$-alkoxy substituted on the nitrogen atom with $R_N$ and $R_O$,
viii) heteroaryl substituted with one H or $C_1$-$C_6$-alkyl, and
ix) heterocycloalkyl-$C_1$-$C_6$-alkyl substituted with one H or $C_1$-$C_6$-alkyl.

Another embodiment of the present invention provides compounds according to formula (I) as described herein, wherein $R_{G1}$ is selected from the group consisting of
i) H,
ii) halogen,
iii) $C_1$-$C_6$-alkyl, and
iv) halo-$C_1$-$C_6$-alkoxy.

A particular embodiment of the present invention provides compounds according to formula (I) as described herein, wherein $R_{G1}$ is selected from the group consisting of
i) H, and
ii) halogen.

Another embodiment of the present invention provides compounds according to formula (I) as described herein, wherein $R_{G2}$ is H.

Another embodiment of the present invention provides compounds according to formula (I) as described herein, wherein $R_L$ and $R_M$ are H.

Another embodiment of the present invention provides compounds according to formula (I) as described herein, wherein $R_N$ is selected from the group consisting of
i) $C_1$-$C_6$-alkoxy-$C_1$-$C_6$-alkyl, and
ii) $C_1$-$C_6$-alkyl.

Another particular embodiment of the present invention provides compounds according to formula (I) as described herein, wherein $R_O$ is $C_1$-$C_6$-alkyl.

Another particular embodiment of the present invention provides compounds according to formula (I) as described herein, wherein $R_N$ and $R_O$ together with the nitrogen atom to which they are attached form morpholinyl, pyrrolidinyl or methylpiperazinonyl.

Another particular embodiment of the present invention provides compounds according to formula (I) as described herein, wherein $R_B$ is selected from the group consisting of
i) $C_1$-$C_6$-alkyl,
ii) $C_1$-$C_6$-alkylsulfonyl,
iii) $C_1$-$C_6$-alkylsulfonylamino,
iv) aminocarbonyl,
v) cyano,
vi) halogen,
vii) heterocycloalkyl, wherein heteroaryl is selected from oxadiazolyl, imidazolyl, 1,3,4-oxazolyl and 1,2,4-oxazolyl, and
viii) morpholinyl substituted with one H, $C_1$-$C_6$-alkyl or trialkylsilyl-$C_1$-$C_6$-alkoxy-$C_1$-$C_6$-alkyl.

A more particular embodiment of the present invention provides compounds according to formula (I) as described herein, wherein $R_B$ is selected from the group consisting of
i) cyano, and
ii) halogen.

A furthermore particular embodiment of the present invention provides compounds according to formula (I) as described herein, wherein $R_B$ is halogen.

Another particular embodiment of the present invention provides compounds according to formula (I) as described herein, wherein $R_C$ is selected from the group consisting of
i) H,
ii) $C_1$-$C_6$-alkyl, and
iii) halogen.

A more particular embodiment of the present invention provides compounds according to formula (I) as described herein, wherein $R_C$ is $C_1$-$C_6$-alkyl.

Another particular embodiment of the present invention provides compounds according to formula (I) as described herein, wherein $R_{C1}$ is H.

Another particular embodiment of the present invention provides compounds according to formula (I) as described herein, wherein W is selected from the ring systems A, B and C.

Another particular embodiment of the present invention provides compounds according to formula (I) as described herein, wherein W is selected from the ring systems A and C.

A more particular embodiment of the present invention provides compounds according to formula (I) as described herein, wherein W is the ring system A.

Another particular embodiment of the present invention provides compounds according to formula (I) as described herein, wherein $R_{D1}$ is $C_1$-$C_6$-alkyl.

Another particular embodiment of the present invention provides compounds according to formula (I) as described herein, wherein $R_{D2}$ is selected from the group consisting of
i) H,
ii) halogen,
iii) hydroxy-$C_1$-$C_6$-alkoxy,
iv) hydroxy-$C_1$-$C_6$-alkyl($C_1$-$C_6$-alkyl)amino,
v) hydroxy-$C_1$-$C_6$-alkylamino,
vi) dihydroxy-$C_1$-$C_6$-alkoxy,
vii) dihydroxy-$C_1$-$C_6$-alkyl($C_1$-$C_6$-alkyl)amino, and
viii) heterocycloalkyl.

A more particular embodiment of the present invention provides compounds according to formula (I) as described herein, wherein $R_{D2}$ is selected from the group consisting of
i) H,
ii) hydroxy-$C_1$-$C_6$-alkoxy, and
iii) hydroxy-$C_1$-$C_6$-alkyl($C_1$-$C_6$-alkyl)amino.

Another particular embodiment of the present invention provides compounds according to formula (I) as described herein, wherein $R_{D3}$ is selected from the group consisting of
i) H,
ii) $C_1$-$C_6$-alkoxy-$C_1$-$C_6$-alkylcarbonyl,
iii) $C_1$-$C_6$-alkoxycarbonyl, and
iv) $C_1$-$C_6$-alkylcarbonyl.

Another particular embodiment of the present invention provides compounds according to formula (I) as described herein, wherein $R_{D4}$ is selected from the group consisting of
i) H,
ii) $C_1$-$C_6$-alkoxycarbonyl,
iii) heterocycloalkylcarbonyl, and
iv) aminocarbonyl substituted on the nitrogen atom with one to two independently selected $C_1$-$C_6$-alkyl.

A particular embodiment of the present invention provides compounds according to formula I(a) as described herein,

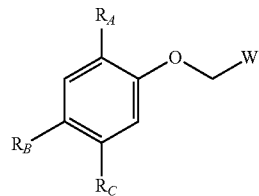

or pharmaceutically acceptable salts.

A further particular embodiment of the present invention provides compounds according to formula I(b) as described herein,

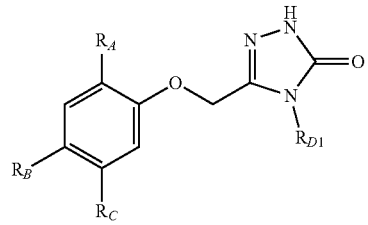

wherein
$R_A$ is selected from the group consisting of
i) $C_1$-$C_6$-alkyl, and
ii) phenyl substituted with $R_G$ and $R_{G1}$;
$R_B$ is selected from the group consisting of
i) cyano, and
ii) halogen;
$R_C$ is selected from the group consisting of
i) H,
ii) $C_1$-$C_6$-alkyl, and
iii) halogen;
$R_{D1}$ is $C_1$-$C_6$-alkyl;
$R_G$ is selected from the group consisting of
i) H,
ii) $C_1$-$C_6$-alkoxy,
iii) $C_1$-$C_6$-alkoxy-$C_1$-$C_6$-alkylcarbonyl($C_1$-$C_6$-alkyl)amino-$C_1$-$C_6$-alkyl,
iv) halogen,
v) aminocarbonyl substituted on the nitrogen atom with $R_N$ and $R_O$,
vi) aminocarbonyl-$C_1$-$C_6$-alkoxy substituted on the nitrogen atom with $R_N$ and $R_O$,
vii) heteroaryl substituted with one H or $C_1$-$C_6$-alkyl, wherein heteroaryl is isoxazolyl, oxazolyl or pyrazolyl, and
viii) heterocycloalkyl-$C_1$-$C_6$-alkoxy substituted with one H or $C_1$-$C_6$-alkyl, wherein heterocycloalkyl-$C_1$-$C_6$-alkoxy is tetrahydropyranylmethoxy or tetrahydrofuranylmethoxy;
$R_{G2}$ is H and $R_{G1}$ is selected from the group consisting of
i) H, and
ii) halogen;
$R_N$ is selected from the group consisting of
i) $C_1$-$C_6$-alkoxy-$C_1$-$C_6$-alkyl, and
ii) $C_1$-$C_6$-alkyl;
$R_O$ is $C_1$-$C_6$-alkyl;
or $R_N$ and $R_O$ together with the nitrogen atom to which they are attached form morpholinyl, pyrrolidinyl or methylpiperazinonyl;
or pharmaceutically acceptable salts.

A further particular embodiment of the present invention provides compounds according to formula I(b) as described herein,

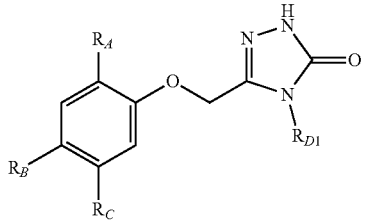

wherein
$R_A$ is selected from the group consisting of
i) $C_1$-$C_6$-alkyl, and
ii) phenyl substituted with $R_G$ and $R_{G1}$;
$R_B$ is selected from the group consisting of
i) cyano, and
ii) halogen;
$R_{D1}$ is $C_1$-$C_6$-alkyl;
$R_G$ is selected from the group consisting of
i) H,
ii) $C_1$-$C_6$-alkoxy,
iii) $C_1$-$C_6$-alkoxy-$C_1$-$C_6$-alkylcarbonylamino-$C_1$-$C_6$-alkyl,
iv) $C_1$-$C_6$-alkoxy-$C_1$-$C_6$-alkylcarbonyl($C_1$-$C_6$-alkyl)amino-$C_1$-$C_6$-alkyl,
v) $C_1$-$C_6$-alkoxycarbonyl,
vi) $C_1$-$C_6$-alkyl,
vii) $C_1$-$C_6$-alkylsulfonyl,
viii) carboxy,
ix) cyano,
x) $C_3$-$C_8$-cycloalkoxy,
xi) $C_3$-$C_8$-cycloalkylcarbonylamino-$C_1$-$C_6$-alkyl,
xii) $C_3$-$C_8$-cycloalkylcarbonyl($C_1$-$C_6$-alkyl)amino-$C_1$-$C_6$-alkyl,
xiii) halo-$C_1$-$C_6$-alkyl,
xiv) halogen,
xv) aminocarbonyl substituted on the nitrogen atom with $R_N$ and $R_O$,
xvi) aminocarbonyl-$C_1$-$C_6$-alkoxy substituted on the nitrogen atom with $R_N$ and $R_O$,
xvii) heteroaryl substituted with one H, $C_1$-$C_6$-alkyl, wherein heteroaryl is isoxazolyl, oxazolyl or pyrazolyl,
xviii) heterocycloalkyl-$C_1$-$C_6$-alkoxy substituted with one H, $C_1$-$C_6$-alkyl, wherein heterocycloalkyl-$C_1$-$C_6$-alkoxy is tetrahydropyranylmethoxy or tetrahydrofuranylmethoxy, and
xix) heterocycloalkyl-$C_1$-$C_6$-alkyl substituted with one H, $C_1$-$C_6$-alkyl, wherein heterocycloalkyl-$C_1$-$C_6$-alkyl is methyldioxopiperazinylmethyl, oxopyrrolidinylmethyl or oxooxazolidinylmethyl;
$R_{G2}$ is H and $R_{G1}$ is selected from the group consisting of
i) H,
ii) halogen,
iii) $C_1$-$C_6$-alkyl,
iv) halo-$C_1$-$C_6$-alkoxy, and
$R_N$ is selected from the group consisting of
i) H,
ii) $C_1$-$C_6$-alkoxy,
iii) $C_1$-$C_6$-alkoxy-$C_1$-$C_6$-alkyl,
iv) $C_1$-$C_6$-alkoxycarbonyl-$C_1$-$C_6$-alkyl,
v) $C_1$-$C_6$-alkyl,
vi) carboxy-$C_1$-$C_6$-alkyl,
vii) $C_3$-$C_8$-cycloalkyl,
viii) $C_3$-$C_8$-cycloalkyl-$C_1$-$C_6$-alkyl,
ix) hydroxy-$C_1$-$C_6$-alkyl,
x) phenyl, and
xi) heteroaryl-$C_1$-$C_6$-alkyl, wherein heteroaryl-$C_1$-$C_6$-alkyl is are pyridinylalkyl or thiophenylalkyl;
$R_O$ is selected from the group consisting of
i) H, and
ii) $C_1$-$C_6$-alkyl;
or $R_N$ and $R_O$ together with the nitrogen atom to which they are attached form piperidinyl, morpholinyl, pyrrolidinyl or methylpiperazinonyl;
or pharmaceutically acceptable salts.

A furthermore particular embodiment of the present invention provides compounds according to formula I(b) as described herein,

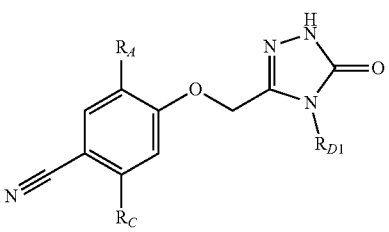

wherein
$R_A$ is $C_1$-$C_6$-alkyl;
$R_C$ is selected from the group consisting of
i) $C_1$-$C_6$-alkyl, and
ii) halogen;
$R_{D1}$ is $C_1$-$C_6$-alkyl;
or pharmaceutically acceptable salts.

Particular examples of compounds of formula (I) as described herein are selected from
3-[(2-tert-butyl-4-chloro-5-methylphenoxy)methyl]-4-methyl-1H-1,2,4-triazol-5-one;
3-[(2-tert-butyl-4-chloro-5-fluorophenoxy)methyl]-4-methyl-1H-1,2,4-triazol-5-one;
3-[(3,3-dimethyl-6-propan-2-yl-1,2-dihydroinden-5-yl)oxymethyl]-4-methyl-1H-1,2,4-triazol-5-one;
3-[[2-tert-butyl-4-(3-methyl-1,2,4-oxadiazol-5-yl)phenoxy]methyl]-4-methyl-1H-1,2,4-triazol-5-one;
3-[[2-tert-butyl-4-[1-(2-trimethylsilylethoxymethyl)imidazol-2-yl]phenoxy]methyl]-4-methyl-1H-1,2,4-triazol-5-one;
3-[[2-tert-butyl-4-(1-methylimidazol-2-yl)phenoxy]methyl]-4-methyl-1H-1,2,4-triazol-5-one;
3-[[2-tert-butyl-oxazol-2-yl)phenoxy]methyl]-4-methyl-1H-1,2,4-triazol-5-one;
3-[(2-tert-butyl-4-morpholin-4-ylphenoxy)methyl]-4-methyl-1H-1,2,4-triazol-5-one;
3-[[2-tert-butyl-4-(3-methylimidazol-4-yl)phenoxy]methyl]-4-methyl-1H-1,2,4-triazol-5-one;
3-[[2-tert-butyl-4-(5-methyl-1,3,4-oxadiazol-2-yl)phenoxy]methyl]-4-methyl-1H-1,2,4-triazol-5-one;
4-[(4-methyl-5-oxo-1H-1,2,4-triazol-3-yl)methoxy]-3-propan-2-ylbenzonitrile;
2-methyl-4-[(4-methyl-5-oxo-1H-1,2,4-triazol-3-yl)methoxy]-5-propan-2-ylbenzonitrile;
3-tert-butyl-4-[(4-methyl-5-oxo-1H-1,2,4-triazol-3-yl)methoxy]benzonitrile;

3-[(4-chloro-2-cyclopropyl-5-methyl sulfonylphenoxy) methyl]-4-methyl-1H-1,2,4-triazol-5-one;
3-[(2-tert-butyl-4-methylsulfonylphenoxy)methyl]-4-methyl-1H-1,2,4-triazol-5-one;
5-tert-butyl-2-methyl-4-[(4-methyl-5-oxo-1H-1,2,4-triazol-3-yl)methoxy]benzonitrile;
4-tert-butyl-2-methyl-5-[(4-methyl-5-oxo-1H-1,2,4-triazol-3-yl)methoxy]benzonitrile;
3-[[2-tert-butyl-4-[3-(2-trimethylsilyl-ethoxymethyl)imidazol-4-yl]phenoxy]-methyl]-4-methyl-1H-1,2,4-triazol-5-one;
3-[(4-chloro-2-cyclopropyl-5-methylphenoxy)methyl]-4-methyl-1H-1,2,4-triazol-5-one;
3-[(4-chloro-2-cyclohexyl-5-methylphenoxy)methyl]-4-methyl-1H-1,2,4-triazol-5-one;
3-[[4-chloro-5-methyl-2-(oxan-4-yl)phenoxy]methyl]-4-methyl-1H-1,2,4-triazol-5-one;
2-chloro-4-cyclopropyl-5-[(4-methyl-5-oxo-1H-1,2,4-triazol-3-yl)methoxy]benzonitrile;
N-[2-chloro-4-cyclopropyl-5-[(4-methyl-5-oxo-1H-1,2,4-triazol-3-yl)methoxy]phenyl]methanesulfonamide;
4-tert-butyl-3-[(4-methyl-5-oxo-1H-1,2,4-triazol-3-yl)methoxy]benzonitrile;
4-tert-butyl-3-[(4-methyl-5-oxo-1H-1,2,4-triazol-3-yl)methoxy]benzamide;
5-tert-butyl-2-methyl-4-[(5-oxo-4-propan-2-yl-1H-1,2,4-triazol-3-yl)methoxy]benzonitrile;
4-methyl-3-[(5-methyl-2-propan-2-ylphenoxy)methyl]-1H-1,2,4-triazol-5-one;
3-[(4-chloro-5-methyl-2-propan-2-ylphenoxy)methyl]-4-methyl-1H-1,2,4-triazol-5-one;
3-[(4-chloro-2-propan-2-ylphenoxy)methyl]-4-methyl-1H-1,2,4-triazol-5-one;
3-[(6-cyclopropyl-2-methyl-1,3-benzothiazol-5-yl)oxymethyl]-4-methyl-1H-1,2,4-triazol-5-one;
3-[(4-chloro-2-cyclobutyl-5-methylphenoxy)methyl]-4-methyl-1H-1,2,4-triazol-5-one;
3-[[2-tert-butyl-4-(1H-imidazol-2-yl)phenoxy]methyl]-4-methyl-1H-1,2,4-triazol-5-one;
3-[[2-tert-butyl-4-(1H-imidazol-5-yl)phenoxy]methyl]-4-methyl-1H-1,2,4-triazol-5-one;
3-[(4-chloro-5-methyl-2-phenylphenoxy)methyl]-4-methyl-1H-1,2,4-triazol-5-one;
3-[[4-chloro-2-(2-chlorophenyl)-5-methylphenoxy]methyl]-4-methyl-1H-1,2,4-triazol-5-one;
3-[[4-chloro-2-(3-chlorophenyl)-5-methylphenoxy]methyl]-4-methyl-1H-1,2,4-triazol-5-one;
3-[[4-chloro-2-(4-chlorophenyl)-5-methylphenoxy]methyl]-4-methyl-1H-1,2,4-triazol-5-one;
3-[5-chloro-4-methyl-2-[(4-methyl-5-oxo-1H-1,2,4-triazol-3-yl)methoxy]phenyl]benzonitrile;
3-[[4-chloro-5-methyl-2-(3-methylsulfonylphenyl)phenoxy]methyl]-4-methyl-1H-1,2,4-triazol-5-one;
3-[[4-chloro-5-methyl-2-(2-methyl sulfonylphenyl)phenoxy]methyl]-4-methyl-1H-1,2,4-triazol-5-one;
3-[[4-chloro-5-methyl-2-[3-(piperidine-1-carbonyl)phenyl]phenoxy]methyl]-4-methyl-1H-1,2,4-triazol-5-one;
3-[5-chloro-4-methyl-2-[(4-methyl-5-oxo-1H-1,2,4-triazol-3-yl)methoxy]phenyl]-N-cyclohexylbenzamide;
3-[[4-chloro-5-methyl-2-[3-(morpholine-4-carbonyl)phenyl]phenoxy]methyl]-4-methyl-1H-1,2,4-triazol-5-one;
3-[5-chloro-4-methyl-2-[(4-methyl-5-oxo-1H-1,2,4-triazol-3-yl)methoxy]phenyl]benzamide;
3-[5-chloro-4-methyl-2-[(4-methyl-5-oxo-1H-1,2,4-triazol-3-yl)methoxy]phenyl]-N,N-dimethylbenzamide;
3-[5-chloro-4-methyl-2-[(4-methyl-5-oxo-1H-1,2,4-triazol-3-yl)methoxy]phenyl]-N-phenylbenzamide;
3-chloro-5-[5-chloro-4-methyl-2-[(4-methyl-5-oxo-1H-1,2,4-triazol-3-yl)methoxy]phenyl]benzamide;
3-[5-chloro-4-methyl-2-[(4-methyl-5-oxo-1H-1,2,4-triazol-3-yl)methoxy]phenyl]-N-cyclopropyl-4-fluorobenzamide;
4-[(4-methyl-5-oxo-1H-1,2,4-triazol-3-yl)methoxy]-3-phenylbenzonitrile;
3-[5-chloro-4-methyl-2-[(4-methyl-5-oxo-1H-1,2,4-triazol-3-yl)methoxy]phenyl]-N-(2-methoxyethyl)benzamide;
3-[[4-chloro-2-(2-chloropyridin-3-yl)-5-methylphenoxy]methyl]-4-methyl-1H-1,2,4-triazol-5-one;
3-[[4-chloro-2-(6-chloropyridin-2-yl)-5-methylphenoxy]methyl]-4-methyl-1H-1,2,4-triazol-5-one;
5-[5-chloro-4-methyl-2-[(4-methyl-5-oxo-1H-1,2,4-triazol-3-yl)methoxy]phenyl]pyridine-3-carboxamide;
3-[[4-chloro-2-(6-methoxypyridin-2-yl)-5-methylphenoxy]methyl]-4-methyl-1H-1,2,4-triazol-5-one;
3-[(4-chloro-5-methyl-2-pyrazin-2-ylphenoxy)methyl]-4-methyl-1H-1,2,4-triazol-5-one;
3-[(4-chloro-5-methyl-2-pyrimidin-2-ylphenoxy)methyl]-4-methyl-1H-1,2,4-triazol-5-one;
3-[[4-chloro-5-methyl-2-[2-methyl-5-(trifluoromethyl)pyrazol-3-yl]phenoxy]methyl]-4-methyl-1H-1,2,4-triazol-5-one;
3-[[4-chloro-5-methyl-2-(1,2-oxazol-5-yl)phenoxy]methyl]-4-methyl-1H-1,2,4-triazol-5-one;
3-[[4-chloro-5-methyl-2-(1,3-oxazol-5-yl)phenoxy]methyl]-4-methyl-1H-1,2,4-triazol-5-one;
3-[[4-chloro-5-methyl-2-(3-methyl imidazol-4-yl)phenoxy]methyl]-4-methyl-1H-1,2,4-triazol-5-one;
3-[[4-chloro-2-(1H-imidazol-5-yl)-5-methylphenoxy]methyl]-4-methyl-1H-1,2,4-triazol-5-one;
3-[[4-chloro-5-methyl-2-(1,3-oxazol-2-yl)phenoxy]methyl]-4-methyl-1H-1,2,4-triazol-5-one;
3-[[4-chloro-5-methyl-2-(2-methylpyrazol-3-yl)phenoxy]methyl]-4-methyl-1H-1,2,4-triazol-5-one;
2-chloro-4-[(4-methyl-5-oxo-1H-1,2,4-triazol-3-yl)methoxy]-5-phenylbenzonitrile;
2-chloro-5-(4-fluorophenyl)-4-[(4-methyl-5-oxo-1H-1,2,4-triazol-3-yl)methoxy]benzonitrile;
3-[4-chloro-5-cyano-2-[(4-methyl-5-oxo-1H-1,2,4-triazol-3-yl)methoxy]phenyl]-N-methylbenzamide,
2-chloro-4-[(4-methyl-5-oxo-1H-1,2,4-triazol-3-yl)methoxy]-5-[3-(1H-pyrazol-3-yl)phenyl]benzonitrile;
2-chloro-5-[3-(5-methyl-1,2,4-oxadiazol-3-yl)phenyl]-4-[(4-methyl-5-oxo-1H-1,2,4-triazol-3-yl)methoxy]benzonitrile;
3-[5-chloro-4-methyl-2-[(4-methyl-5-oxo-1H-1,2,4-triazol-3-yl)methoxy]phenyl]-N-(2-hydroxyethyl)benzamide;
2-chloro-5-[3-(5-methyl-1,3,4-oxadiazol-2-yl)phenyl]-4-[(4-methyl-5-oxo-1H-1,2,4-triazol-3-yl)methoxy]benzonitrile;
3-[5-chloro-4-methyl-2-[(4-methyl-5-oxo-1H-1,2,4-triazol-3-yl)methoxy]phenyl]-4-fluoro-N,N-dimethylbenzamide;
3-[4-chloro-5-cyano-2-[(4-methyl-5-oxo-1H-1,2,4-triazol-3-yl)methoxy]phenyl]-N,N-dimethylbenzamide;
3-[[4-chloro-2-[2-fluoro-5-(morpholine-4-carbonyl)phenyl]-5-methylphenoxy]methyl]-4-methyl-1H-1,2,4-triazol-5-one;
2-chloro-4-[(4-methyl-5-oxo-1H-1,2,4-triazol-3-yl)methoxy]-5-[3-(morpholine-4-carbonyl)phenyl]benzonitrile;
methyl 3-[5-chloro-4-methyl-2-[(4-methyl-5-oxo-1H-1,2,4-triazol-3-yl)methoxy]phenyl]benzoate;
3-[5-chloro-4-methyl-2-[(4-methyl-5-oxo-1H-1,2,4-triazol-3-yl)methoxy]phenyl]benzoic acid;

methyl 3-[[3-[5-chloro-4-methyl-2-[(4-methyl-5-oxo-1H-1,2,4-triazol-3-yl)methoxy]phenyl]benzoyl]amino]propanoate;

3-[5-chloro-4-methyl-2-[(4-methyl-5-oxo-1H-1,2,4-triazol-3-yl)methoxy]phenyl]-N-(2-hydroxyethyl)-N-methylbenzamide;

ethyl 2-[[3-[5-chloro-4-methyl-2-[(4-methyl-5-oxo-1H-1,2,4-triazol-3-yl)methoxy]phenyl]benzoyl]amino]acetate;

3-[[3-[5-chloro-4-methyl-2-[(4-methyl-5-oxo-1H-1,2,4-triazol-3-yl)methoxy]phenyl]benzoyl]amino]propanoic acid;

2-[[3-[5-chloro-4-methyl-2-[(4-methyl-5-oxo-1H-1,2,4-triazol-3-yl)methoxy]phenyl]benzoyl]amino]acetic acid;

methyl 3-[5-chloro-4-methyl-2-[(4-methyl-5-oxo-1H-1,2,4-triazol-3-yl)methoxy]phenyl]-4-methylbenzoate;

3-[5-chloro-4-methyl-2-[(4-methyl-5-oxo-1H-1,2,4-triazol-3-yl)methoxy]phenyl]-4-methylbenzoic acid;

3-[5-chloro-4-methyl-2-[(4-methyl-5-oxo-1H-1,2,4-triazol-3-yl)methoxy]phenyl]-N,N,4-trimethylbenzamide;

3-[5-chloro-4-methyl-2-[(4-methyl-5-oxo-1H-1,2,4-triazol-3-yl)methoxy]phenyl]-4-(trifluoromethoxy)benzamide;

3-[[4-chloro-2-(2-methoxypyridin-3-yl)-5-methylphenoxy]methyl]-4-methyl-1H-1,2,4-triazol-5-one;

2-chloro-5-(2-methoxypyridin-3-yl)-4-[(4-methyl-5-oxo-1H-1,2,4-triazol-3-yl)methoxy]benzonitrile;

3-[[4-chloro-2-(5-ethoxy-2-fluorophenyl)-5-methyl phenoxy]methyl]-4-methyl-1H-1,2,4-triazol-5-one;

3-[[4-chloro-2-(2-methoxyphenyl)-5-methylphenoxy]methyl]-4-methyl-1H-1,2,4-triazol-5-one;

3-[[4-chloro-2-(2-fluoro-5-propan-2-yloxyphenyl)-5-methylphenoxy]methyl]-4-methyl-1H-1,2,4-triazol-5-one;

3-[[4-chloro-2-[2-fluoro-5-(2-methylpropoxy)phenyl]-5-methylphenoxy]methyl]-4-methyl-1H-1,2,4-triazol-5-one;

3-[[4-chloro-2-[2-methoxy-5-(trifluoromethyl)phenyl-5-methylphenoxy]methyl]-4-methyl-1H-1,2,4-triazol-5-one;

3-[[4-chloro-2-(2-methoxy-5-propan-2-ylphenyl)-5-methylphenoxy]methyl]-4-methyl-1H-1,2,4-triazol-5-one;

2-chloro-5-[2-fluoro-5-(morpholine-4-carbonyl)phenyl]-4-[(4-methyl-5-oxo-1H-1,2,4-triazol-3-yl)methoxy]benzonitrile;

3-[[4-chloro-2-[2-fluoro-5-(pyrrolidine-1-carbonyl)phenyl]-5-methylphenoxy]methyl]-4-methyl-1H-1,2,4-triazol-5-one;

3-[5-chloro-4-methyl-2-[(4-methyl-5-oxo-1H-1,2,4-triazol-3-yl)methoxy]phenyl]-N-cyclopropyl-4-fluoro-N-methylbenzamide;

3-[5-chloro-4-methyl-2-[(4-methyl-5-oxo-1H-1,2,4-triazol-3-yl)methoxy]phenyl]-4-fluoro-N-(2-hydroxyethyl)-N-methylbenzamide;

4-[3-[5-chloro-4-methyl-2-[(4-methyl-5-oxo-1H-1,2,4-triazol-3-yl)methoxy]phenyl]-4-fluorobenzoyl]-1-methylpiperazin-2-one;

3-[5-chloro-4-methyl-2-[(4-methyl-5-oxo-1H-1,2,4-triazol-3-yl)methoxy]phenyl]-N-cyclopentyl-4-fluoro-N-methylbenzamide;

3-[[4-chloro-2-[2-fluoro-5-(oxolan-3-ylmethoxy)phenyl]-5-methylphenoxy]methyl]-4-methyl-1H-1,2,4-triazol-5-one;

3-[5-chloro-4-methyl-2-[(4-methyl-5-oxo-1H-1,2,4-triazol-3-yl)methoxy]phenyl]-4-fluoro-N-methyl-N-(thiophen-2-ylmethyl)benzamide;

3-[[4-chloro-2-[2-fluoro-5-(piperidine-1-carbonyl)phenyl]-5-methylphenoxy]methyl]-4-methyl-1H-1,2,4-triazol-5-one;

3-[5-chloro-4-methyl-2-[(4-methyl-5-oxo-1H-1,2,4-triazol-3-yl)methoxy]phenyl]-N-(cyclopropylmethyl)-4-fluoro-N-methylbenzamide;

3-[5-chloro-4-methyl-2-[(4-methyl-5-oxo-1H-1,2,4-triazol-3-yl)methoxy]phenyl]-4-fluoro-N-methyl-N-(pyridin-2-ylmethyl)benzamide;

3-[[4-chloro-2-[2-fluoro-5-(oxan-4-ylmethoxy)phenyl]-5-methylphenoxy]methyl]-4-methyl-1H-1,2,4-triazol-5-one;

3-[5-chloro-4-methyl-2-[(4-methyl-5-oxo-1H-1,2,4-triazol-3-yl)methoxy]phenyl]-4-fluoro-N-(2-methoxyethyl)-N-methylbenzamide;

3-[[4-chloro-2-[2-fluoro-5-(oxolan-2-ylmethoxy)phenyl]-5-methylphenoxy]methyl]-4-methyl-1H-1,2,4-triazol-5-one;

2-[3-[5-chloro-4-methyl-2-[(4-methyl-5-oxo-1H-1,2,4-triazol-3-yl)methoxy]phenyl]-4-fluorophenoxy]-N,N-dimethylacetamide;

1-[[3-[5-chloro-4-methyl-2-[(4-methyl-5-oxo-1H-1,2,4-triazol-3-yl)methoxy]phenyl]-4-fluorophenyl]methyl]-4-methylpiperazine-2,5-dione;

7-[5-chloro-4-methyl-2-[(4-methyl-5-oxo-1H-1,2,4-triazol-3-yl)methoxy]phenyl]-6-fluoro-3-methyl-1,3-benzoxazol-2-one;

N-[[3-[5-chloro-4-methyl-2-[(4-methyl-5-oxo-1H-1,2,4-triazol-3-yl)methoxy]phenyl]-4-fluorophenyl]methyl]-2-methoxy-N-methyl acetamide;

N-[[3-[5-chloro-4-methyl-2-[(4-methyl-5-oxo-1H-1,2,4-triazol-3-yl)methoxy]phenyl]-4-fluorophenyl]methyl]cyclopropanecarboxamide;

N-[[3-[5-chloro-4-methyl-2-[(4-methyl-5-oxo-1H-1,2,4-triazol-3-yl)methoxy]phenyl]-4-fluorophenyl]methyl]-N-methylcyclopropanecarboxamide;

3-[[4-chloro-2-[2-fluoro-5-[(2-oxopyrrolidin-1-yl)methyl]phenyl]-5-methylphenoxy]methyl]-4-methyl-1H-1,2,4-triazol-5-one;

3-[[3-[5-chloro-4-methyl-2-[(4-methyl-5-oxo-1H-1,2,4-triazol-3-yl)methoxy]phenyl]-4-fluorophenyl]methyl]-1,3-oxazolidin-2-one;

N-[[3-[5-chloro-4-methyl-2-[(4-methyl-5-oxo-1H-1,2,4-triazol-3-yl)methoxy]phenyl]-4-fluorophenyl]methyl]-2-methoxyacetamide;

2-chloro-5-(2-fluorophenyl)-4-[(4-methyl-5-oxo-1H-1,2,4-triazol-3-yl)methoxy]benzonitrile;

2-chloro-5-(3-fluorophenyl)-4-[(4-methyl-5-oxo-1H-1,2,4-triazol-3-yl)methoxy]benzonitrile;

3-[5-chloro-4-methyl-2-[(4-methyl-5-oxo-1H-1,2,4-triazol-3-yl)methoxy]phenyl]-4-(trifluoromethoxy)benzonitrile;

2-chloro-5-[2-fluoro-5-(oxolan-2-ylmethoxy)phenyl]-4-[(4-methyl-5-oxo-1H-1,2,4-triazol-3-yl)methoxy]benzonitrile;

2-chloro-5-(2-fluoro-3-methoxyphenyl)-4-[(4-methyl-5-oxo-1H-1,2,4-triazol-3-yl)methoxy]benzonitrile;

2-chloro-5-(2-fluoro-5-propan-2-yloxyphenyl)-4-[(4-methyl-5-oxo-1H-1,2,4-triazol-3-yl)methoxy]benzonitrile;

3-[[4-chloro-2-(2-fluoro-3-methoxyphenyl)-5-methylphenoxy]methyl]-4-methyl-1H-1,2,4-triazol-5-one;

2-chloro-5-(2,3-difluorophenyl)-4-[(4-methyl-5-oxo-1H-1,2,4-triazol-3-yl)methoxy]benzonitrile;

3-[[4-chloro-2-(5-cyclopropyl oxy-2-fluorophenyl)-5-methylphenoxy]methyl]-4-methyl-1H-1,2,4-triazol-5-one;

2-chloro-5-(5-chloro-2-fluorophenyl)-4-[(4-methyl-5-oxo-1H-1,2,4-triazol-3-yl)methoxy]benzonitrile;

2-chloro-5-(2,5-difluorophenyl)-4-[(4-methyl-5-oxo-1H-1,2,4-triazol-3-yl)methoxy]benzonitrile;

2-chloro-5-(5-cyclopropyloxy-2-fluorophenyl)-4-[(4-methyl-5-oxo-1H-1,2,4-triazol-3-yl)methoxy]benzonitrile;

2-chloro-5-[2-fluoro-5-(trifluoromethyl)phenyl]-4-[(4-methyl-5-oxo-1H-1,2,4-triazol-3-yl)methoxy]benzonitrile;

3-[(4-chloro-5-methyl-2-propan-2-ylphenoxy)methyl]-1H-pyridazin-6-one;

3-[(4-chloro-2-cyclopropyl-5-methylphenoxy)methyl]-1H-pyridazin-6-one;

3-[(4-chloro-5-fluoro-2-propan-2-ylphenoxy)methyl]-1H-pyridazin-6-one;

3-[(5-chloro-4-methyl-2-propan-2-ylphenoxy)methyl]-1H-pyridazin-6-one;

3-[(4-chloro-2-cyclobutyl-5-methylphenoxy)methyl]-1H-pyridazin-6-one;

3-[(4-chloro-2-cyclohexyl-5-methylphenoxy)methyl]-1H-pyridazin-6-one;

3-[[(4-chloro-5-methyl-2-(oxan-4-yl)phenoxy]methyl]-1H-pyridazin-6-one;

3-[(2-tert-butyl-4-chloro-5-methylphenoxy)methyl]-1H-pyridazin-6-one;

2-[5-chloro-4-methyl-2-[(6-oxo-1H-pyridazin-3-yl)methoxy]phenyl]-2-methylpropanenitrile;

3-[(2-tert-butyl-4-methyl sulfonylphenoxy)methyl]-1H-indazole;

3-[(4-chloro-5-methyl-2-propan-2-ylphenoxy)methyl]-1H-indazole;

3-[(2-tert-butyl-4-chloro-5-methylphenoxy)methyl]-1H-pyrazolo[3,4-b]pyridine;

5-tert-butyl-2-methyl-4-(1H-pyrazolo[3,4-b]pyridin-3-ylmethoxy)benzonitrile;

5-[5-chloro-4-methyl-2-(1H-pyrazolo[3,4-b]pyridin-3-ylmethoxy)phenyl]-1,2-oxazole 3-[(2-tert-butyl-4-chloro-5-methylphenoxy)methyl]-6-fluoro-1H-pyrazolo[3,4-b]pyridine;

2-[[3-[(2-tert-butyl-4-chloro-5-methylphenoxy)methyl]-1H-pyrazolo[3,4-b]pyridin-6-yl]amino]ethanol;

2-[[3-[(2-tert-butyl-4-chloro-5-methylphenoxy)methyl]-1H-pyrazolo[3,4-b]pyridin-6-yl]-methylamino]ethanol;

3-[(2-tert-butyl-5-methyl-4-methylsulfonylphenoxy)methyl]-1H-pyrazolo[3,4-b]pyridine;

3-[(2-tert-butyl-5-methyl-4-methylsulfonylphenoxy)methyl]-1H-indazole;

2-[[3-[(2-tert-butyl-4-chloro-5-fluorophenoxy)methyl]-1H-pyrazolo[3,4-b]pyridin-6-yl]amino]ethanol;

3-[(2-tert-butyl-4-chloro-5-fluorophenoxy)methyl]-6-fluoro-1H-pyrazolo[3,4-b]pyridine;

2-[[3-[(2-tert-butyl-4-chloro-5-methylphenoxy)methyl]-1H-pyrazolo[3,4-b]pyridin-6-yl]oxy]ethanol;

2-[[3-[(2-tert-butyl-4-chloro-5-fluorophenoxy)methyl]-1H-pyrazolo[3,4-b]pyridin-6-yl]-methylamino]ethanol;

3-[[3-[(2-tert-butyl-4-chloro-5-methylphenoxy)methyl]-1H-pyrazolo[3,4-b]pyridin-6-yl]oxy]propane-1,2-diol;

3-[5-chloro-4-methyl-2-(1H-pyrazolo[3,4-b]pyridin-3-ylmethoxy)phenyl]-N-(2-methoxyethyl)benzamide;

[3-[5-chloro-4-methyl-2-(1H-pyrazolo[3,4-b]pyridin-3-ylmethoxy)phenyl]phenyl]-morpholin-4-ylmethanone;

3-[5-chloro-4-methyl-2-(1H-pyrazolo[3,4-b]pyridin-3-ylmethoxy)phenyl]-N,N-dimethylbenzamide;

3-[5-chloro-4-methyl-2-(1H-pyrazolo[3,4-b]pyridin-3-ylmethoxy)phenyl]-N-(2-hydroxyethyl)benzamide;

3-[[4-chloro-2-(2-methoxypyridin-3-yl)-5-methylphenoxy]methyl]-1H-pyrazolo[3,4-b]pyridine;

3-[5-chloro-4-methyl-2-(1H-pyrazolo[3,4-b]pyridin-3-ylmethoxy)phenyl]-4-fluoro-N,N-dimethylbenzamide;

[3-[5-chloro-4-methyl-2-(1H-pyrazolo[3,4-b]pyridin-3-ylmethoxy)phenyl]-4-fluorophenyl]-morpholin-4-ylmethanone;

3-[(2-tert-butyl-4-chloro-5-methylphenoxy)methyl]-1H-pyrazolo[4,3-b]pyridine;

3-[5-chloro-4-methyl-2-(1H-pyrazolo[4,3-b]pyridin-3-ylmethoxy)phenyl]-N,N-dimethylbenzamide;

3-[(2-tert-butyl-4-chloro-5-fluorophenoxy)methyl]-1H-pyrazolo[4,3-b]pyridine;

2-[[3-[(2-tert-butyl-4-chloro-5-methylphenoxy)methyl]-1H-pyrazolo[3,4-d]pyrimidin-6-yl]-methylamino]ethanol;

3-[[3-[(2-tert-butyl-4-chloro-5-methylphenoxy)methyl]-1H-pyrazolo[3,4-d]pyrimidin-6-yl]-methylamino]propane-1,2-diol;

3-[5-chloro-4-methyl-2-(1H-pyrazolo[4,3-b]pyridin-3-ylmethoxy)phenyl]-4-fluoro-N,N-dimethylbenzamide;

1-[3-[(2-tert-butyl-4-chloro-5-methylphenoxy)methyl]-1H-pyrazolo[3,4-d]pyrimidin-6-yl]azetidin-3-ol;

2-[[3-[(2-tert-butyl-4-chloro-5-methylphenoxy)methyl]-1H-pyrazolo[3,4-d]pyrimidin-6-yl]amino]ethanol;

2-[[3-[(2-tert-butyl-4-chloro-5-methylphenoxy)methyl]-1H-pyrazolo[3,4-d]pyrimidin-6-yl]oxy]ethanol;

5-tert-butyl-4-[[6-(3-hydroxyazetidin-1-yl)-1H-pyrazolo[3,4-d]pyrimidin-3-yl]methoxy]-2-methylbenzonitrile;

5-tert-butyl-4-[[6-[2-hydroxyethyl(methyl)amino]-1H-pyrazolo[3,4-d]pyrimidin-3-yl]methoxy]-2-methylbenzonitrile;

3-[[3-[(2-tert-butyl-4-chloro-5-methylphenoxy)methyl]-1H-pyrazolo[3,4-d]pyrimidin-6-yl]oxy]propane-1,2-diol;

5-tert-butyl-4-[[6-(2-hydroxyethylamino)-1H-pyrazolo[3,4-d]pyrimidin-3-yl]methoxy]-2-methylbenzonitrile;

5-tert-butyl-4-[[6-[2,3-dihydroxypropyl(methyl)amino]-1H-pyrazolo[3,4-d]pyrimidin-3-yl]methoxy]-2-methylbenzonitrile;

5-tert-butyl-4-[[6-(2,3-dihydroxypropoxy)-1H-pyrazolo[3,4-d]pyrimidin-3-yl]methoxy]-2-methylbenzonitrile;

5-tert-butyl-4-[[6-(2-hydroxyethoxy)-1H-pyrazolo[3,4-d]pyrimidin-3-yl]methoxy]-2-methylbenzonitrile;

4-[3-[5-chloro-4-methyl-2-(1H-pyrazolo[3,4-b]pyridin-3-ylmethoxy)phenyl]-4-fluorobenzoyl]-1-methylpiperazin-2-one;

3-[5-chloro-4-methyl-2-(1H-pyrazolo[3,4-b]pyridin-3-ylmethoxy)phenyl]-4-fluoro-N-(2-methoxyethyl)-N-methylbenzamide;

4-[3-[5-chloro-2-(1H-indazol-3-ylmethoxy)-4-methylphenyl]-4-fluorobenzoyl]-1-methylpiperazin-2-one;

[3-[5-chloro-4-methyl-2-(1H-pyrazolo[3,4-b]pyridin-3-ylmethoxy)phenyl]-4-fluorophenyl]-pyrrolidin-1-ylmethanone;

2-chloro-5-[2-fluoro-5-(pyrrolidine-1-carbonyl)phenyl]-4-(1H-pyrazolo[3,4-b]pyridin-3-ylmethoxy)benzonitrile;

4-[3-[5-chloro-4-methyl-2-(1H-pyrazolo[3,4-c]pyridin-3-ylmethoxy)phenyl]-4-fluorobenzoyl]-1-methylpiperazin-2-one;

3-[(2-tert-butyl-4-methylsulfonylphenoxy)methyl]-1H-pyrazolo[3,4-b]pyridine;

3-[5-chloro-4-methyl-2-(1H-pyrazolo[3,4-c]pyridin-3-ylmethoxy)phenyl]-4-fluoro-N-(2-methoxyethyl)-N-methylbenzamide;

3-[[4-chloro-2-(2-methoxypyridin-3-yl)-5-methylphenoxy]methyl]-1H-pyrazolo[3,4-c]pyridine;

4-tert-butyl-2-methyl-5-(1H-pyrazolo[3,4-b]pyridin-3-ylmethoxy)benzonitrile;

4-tert-butyl-2-methyl-5-(1H-pyrazolo[3,4-c]pyridin-3-ylmethoxy)benzonitrile;

tert-butyl 3-((2-tert-butyl-4-chloro-5-methylphenoxy)methyl)-6,7-dihydro-1H-pyrazolo[4,3-c]pyridine-5(4H)-carboxylate;
1-(3-((2-tert-butyl-4-chloro-5-methylphenoxy)methyl)-6,7-dihydro-1H-pyrazolo[4,3-c]pyridin-5(4H)-yl)ethanone;
1-(3-((2-tert-butyl-4-chloro-5-methylphenoxy)methyl)-6,7-dihydro-1H-pyrazolo[4,3-c]pyridin-5(4H)-yl)-2-methoxyethanone;
3-((2-tert-butyl-4-chloro-5-methylphenoxy)methyl)-4,5,6,7-tetrahydro-1H-pyrazolo[3,4-c]pyridine;
1-(3-((2-tert-butyl-4-chloro-5-methylphenoxy)methyl)-4,5-dihydro-1H-pyrazolo[3,4-c]pyridin-6(7H)-yl)ethanone;
1-(3-((2-tert-butyl-4-chloro-5-methylphenoxy)methyl)-4,5-dihydro-1H-pyrazolo[3,4-c]pyridin-6(7H)-yl)-2-methoxyethanone;
3-((4-chloro-2-(2-methoxypyridin-3-yl)-5-methylphenoxy)methyl)-4,5,6,7-tetrahydro-1H-pyrazolo[3,4-c]pyridine;
1-(3-((4-chloro-2-(2-methoxypyridin-3-yl)-5-methylphenoxy)methyl)-4,5-dihydro-1H-pyrazolo[3,4-c]pyridin-6(7H)-yl)ethanone;
3-((2-tert-butyl-4-chloro-5-methylphenoxy)methyl)-1H-pyrazole;
4-((1H-pyrazol-3-yl)methoxy)-5-tert-butyl-2-methylbenzonitrile;
methyl 3-((2-(tert-butyl)-4-chloro-5-methylphenoxy)methyl)-1H-pyrazole-5-carboxylate;
(3-((2-(tert-butyl)-4-chloro-5-methylphenoxy)methyl)-1H-pyrazol-5-yl)(pyrrolidin-1-yl)methanone;
3-((2-(tert-butyl)-4-chloro-5-methylphenoxy)methyl)-N,N-dimethyl-1H-pyrazole-5-carboxamide;
and pharmaceutically acceptable salts thereof.
Also particular examples of compounds of formula (I) as described herein are selected from
4-tert-butyl-2-chloro-5-[(4-methyl-5-oxo-1H-1,2,4-triazol-3-yl)methoxy]benzonitrile;
2-chloro-5-[2-fluoro-5-(trifluoromethoxy)phenyl]-4-[(4-methyl-5-oxo-1H-1,2,4-triazol-3-yl)methoxy]benzonitrile;
2-chloro-5-[2-fluoro-5-(2,2,2-trifluoroethoxy)phenyl]-4-[(4-methyl-5-oxo-1H-1,2,4-triazol-3-yl)methoxy]benzonitrile;
3-[[4-chloro-2-(2-methoxypyridin-3-yl)-5-methylphenoxy]methyl]-1H-pyridazin-6-one;
3-[[4-chloro-2-(2-hydroxypyridin-3-yl)-5-methyl phenoxy]methyl]-1H-pyridazin-6-one;
2-chloro-4-[(6-oxo-1H-pyridazin-3-yl)methoxy]-5-phenyl-benzonitrile;
4-tert-butyl-2-methyl-5-[(6-oxo-1H-pyridazin-3-yl)methoxy]benzonitrile;
2-chloro-5-(5-cyclopropyloxy-2-fluorophenyl)-4-[(6-oxo-1H-pyridazin-3-yl)methoxy]benzonitrile;
4-tert-butyl-2-chloro-5-(1H-pyrazolo[3,4-c]pyridin-3-ylmethoxy)benzonitrile;
2-chloro-5-(5-cyclopropyloxy-2-fluorophenyl)-4-(1H-pyrazolo[3,4-c]pyridin-3-ylmethoxy)benzonitrile;
4-tert-butyl-2-chloro-5-(1H-pyrazolo[3,4-b]pyridin-3-ylmethoxy)benzonitrile
2-chloro-5-(5-cyclopropyloxy-2-fluorophenyl)-4-(1H-pyrazolo[3,4-b]pyridin-3-ylmethoxy)benzonitrile;
2-chloro-5-[2-fluoro-5-(trifluoromethoxy)phenyl]-4-(1H-pyrazolo[4,3-c]pyridin-3-ylmethoxy)benzonitrile;
2-chloro-5-[2-fluoro-5-(trifluoromethoxy)phenyl]-4-(1H-pyrazolo[3,4-b]pyridin-3-ylmethoxy)benzonitrile;
and pharmaceutically acceptable salts thereof.
Further particular examples of compounds of formula (I) as described herein are selected from
3-[(2-tert-butyl-4-chloro-5-methylphenoxy)methyl]-4-methyl-1H-1,2,4-triazol-5-one;
3-[(2-tert-butyl-4-chloro-5-fluorophenoxy)methyl]-4-methyl-1H-1,2,4-triazol-5-one;
3-tert-butyl-4-[(4-methyl-5-oxo-1H-1,2,4-triazol-3-yl)methoxy]benzonitrile;
5-tert-butyl-2-methyl-4-[(4-methyl-5-oxo-1H-1,2,4-triazol-3-yl)methoxy]benzonitrile;
4-tert-butyl-2-methyl-5-[(4-methyl-5-oxo-1H-1,2,4-triazol-3-yl)methoxy]benzonitrile;
3-[(4-chloro-2-cyclohexyl-5-methylphenoxy)methyl]-4-methyl-1H-1,2,4-triazol-5-one;
5-tert-butyl-2-methyl-4-[(5-oxo-4-propan-2-yl-1H-1,2,4-triazol-3-yl)methoxy]benzonitrile;
3-[(4-chloro-5-methyl-2-propan-2-ylphenoxy)methyl]-4-methyl-1H-1,2,4-triazol-5-one;
3-[(4-chloro-2-cyclobutyl-5-methylphenoxy)methyl]-4-methyl-1H-1,2,4-triazol-5-one;
3-[[4-chloro-5-methyl-2-[3-(morpholine-4-carbonyl)phenyl]phenoxy]methyl]-4-methyl-1H-1,2,4-triazol-5-one;
3-[[4-chloro-5-methyl-2-(1,2-oxazol-5-yl)phenoxy]methyl]-4-methyl-1H-1,2,4-triazol-5-one;
2-chloro-4-[(4-methyl-5-oxo-1H-1,2,4-triazol-3-yl)methoxy]-5-phenylbenzonitrile;
2-chloro-4-[(4-methyl-5-oxo-1H-1,2,4-triazol-3-yl)methoxy]-5[3-(1H-pyrazol-3-yl)phenyl]benzonitrile;
2-chloro-5-[3-(5-methyl-1,2,4-oxadiazol-3-yl)phenyl]-4-[(4-methyl-5-oxo-1H-1,2,4-triazol-3-yl)methoxy]benzonitrile;
3-[5-chloro-4-methyl-2-[(4-methyl-5-oxo-1H-1,2,4-triazol-3-yl)methoxy]phenyl]-4-fluoro-N,N-dimethylbenzamide;
3-[[4-chloro-2-(2-methoxypyridin-3-yl)-5-methylphenoxy]methyl]-4-methyl-1H-1,2,4-triazol-5-one;
3-[[4-chloro-2-(2-fluoro-5-propan-2-yloxyphenyl)-5-methylphenoxy]methyl]-4-methyl-1H-1,2,4-triazol-5-one;
3-[[4-chloro-2-[2-fluoro-5-(pyrrolidine-1-carbonyl)phenyl]-5-methylphenoxy]methyl]-4-methyl-1H-1,2,4-triazol-5-one;
4-[3-[5-chloro-4-methyl-2-[(4-methyl-5-oxo-1H-1,2,4-triazol-3-yl)methoxy]phenyl]-4-fluorobenzoyl]-1-methyl-piperazin-2-one;
3-[5-chloro-4-methyl-2-[(4-methyl-5-oxo-1H-1,2,4-triazol-3-yl)methoxy]phenyl]-4-fluoro-N-(2-methoxyethyl)-N-methylbenzamide;
3-[[4-chloro-2-[2-fluoro-5-(oxolan-2-ylmethoxy)phenyl]-5-methylphenoxy]methyl]-4-methyl-1H-1,2,4-triazol-5-one;
2-[3-[5-chloro-4-methyl-2-[(4-methyl-5-oxo-1H-1,2,4-triazol-3-yl)methoxy]phenyl]-4-fluorophenoxy]-N,N-dimethylacetamide;
N-[[3-[5-chloro-4-methyl-2-[(4-methyl-5-oxo-1H-1,2,4-triazol-3-yl)methoxy]phenyl]-4-fluorophenyl]methyl]-2-methoxy-N-methylacetamide;
2-chloro-5-(2-fluorophenyl)-4-[(4-methyl-5-oxo-1H-1,2,4-triazol-3-yl)methoxy]benzonitrile;
2-chloro-5-(2-fluoro-3-methoxyphenyl)-4-[(4-methyl-5-oxo-1H-1,2,4-triazol-3-yl)methoxy]benzonitrile;
2-chloro-5-(2-fluoro-5-propan-2-yloxyphenyl)-4-[(4-methyl-5-oxo-1H-1,2,4-triazol-3-yl)methoxy]benzonitrile;
3-[[4-chloro-2-(5-cyclopropyloxy-2-fluorophenyl)-5-methylphenoxy]methyl]-4-methyl-1H-1,2,4-triazol-5-one;
2-chloro-5-(5-cyclopropyloxy-2-fluorophenyl)-4-[(4-methyl-5-oxo-1H-1,2,4-triazol-3-yl)methoxy]benzonitrile;
5-tert-butyl-2-methyl-4-(1H-pyrazolo[3,4-b]pyridin-3-ylmethoxy)benzonitrile;

2-[[3-[(2-tert-butyl-4-chloro-5-methylphenoxy)methyl]-1H-pyrazolo[3,4-d]pyrimidin-6-yl]-methylamino]ethanol;
2-[[3-[(2-tert-butyl-4-chloro-5-methylphenoxy)methyl]-1H-pyrazolo[3,4-d]pyrimidin-6-yl]oxy]ethanol;
2-chloro-5-[2-fluoro-5-(pyrrolidine-1-carbonyl)phenyl]-4-(1H-pyrazolo[3,4-b]pyridin-3-ylmethoxy)benzonitrile;
3-[5-chloro-4-methyl-2-(1H-pyrazolo[3,4-c]pyridin-3-ylmethoxy)phenyl]-4-fluoro-N-(2-methoxyethyl)-N-methylbenzamide;
and pharmaceutically acceptable salts thereof.

Also further particular examples of compounds of formula (I) as described herein are selected from
2-chloro-5-(5-cyclopropyloxy-2-fluorophenyl)-4-[(6-oxo-1H-pyridazin-3-yl)methoxy]benzonitrile;
4-tert-butyl-2-chloro-5-(1H-pyrazolo[3,4-b]pyridin-3-ylmethoxy)benzonitrile;
and pharmaceutically acceptable salts thereof.

Also particular examples of compounds of formula (I) as described herein are selected from
4-[(2-tert-Butyl-4-chloro-5-methylphenoxy)methyl]-2H-triazole;
3-[(2-tert-Butyl-4-chloro-5-methylphenoxy)methyl]-5-phenyl-1H-pyrazole; and
5-tert-Butyl-2-methyl-4-[(5-phenyl-1H-pyrazol-3-yl)methoxy]benzonitrile.

Further particular examples of compounds of formula (I) as described herein are selected from
5-tert-butyl-2-methyl-4-[(4-methyl-5-oxo-1H-1,2,4-triazol-3-yl)methoxy]benzonitrile;
5-tert-butyl-2-chloro-4-[(4-methyl-5-oxo-1H-1,2,4-triazol-3-yl)methoxy]benzonitrile; and
5-tert-butyl-2-fluoro-4-[(4-methyl-5-oxo-1H-1,2,4-triazol-3-yl)methoxy]benzonitrile;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

A general description of the invention is given in the following sections. To obtain compounds of formula (I), either in an unprotected or protected fashion (PG=protecting group), the key step is usually a coupling reaction between a suitable phenol building block A1, where $R_A$ is the mandatory ortho substituent to the aryl-hydroxy group, $R_B$ is a substituent in another position of the phenyl ring that usually needs to be introduced or modified (involving suitable protection if there are any potentially interfering functional groups within $R_A$ and $R_B$), and $R_C$ is any other functional group that is usually present in the starting materials and remains unchanged, with the desired building block A2 to provide a substituted phenylether of formula A3 (Scheme 1). Within the context of this invention, A2 usually consists of a 5 or 6-membered heterocycle containing two adjacent nitrogen atoms, one of which is bearing a hydrogen (or a suitable protecting group PG if the nitrogen is kept protected), and a methyl group that is substituted by a suitable leaving group X. X can be halogen such as for example chloro, bromo or iodo or any other suitable leaving group such as tosylate or mesylate. A2 can also be bicyclic, where a 6 membered ring that is either aromatic or saturated and that may contain more nitrogen atoms and additional substituents is fused to the primary 5-membered heterocycle. The coupling reaction between A1 and A2, which can both carry orthogonal protecting groups PG, PG', or PG" if needed, is usually carried out in the presence of a base such as potassium carbonate, cesium carbonate or sodium hydride an appropriate solvent such as THF, DMF, $CH_3CN$ or similar at temperatures ranging from minus 20° C. to the boiling point of the solvent or at even higher temperatures in sealed vessels to provide coupling product A3a. In many cases, if protection was not required, A3a is equal to A3 and is already an example of a structure of formula (I), however, if A3a contains any protecting groups PG or PG' or PG" such as for example BOC or trityl, tert-butyl, pMB, MOM, SEM, benzyl or or similar, they can be removed under known conditions which are depending on the nature of the protecting group PG. BOC, tert-butyl, pMB and trityl, MOM, SEM for example, can be removed in the presence of an acid such as TFA, HCl, HBr, $H_2SO_4$ or similar in a suitable solvent such as $CH_2Cl_2$, THF, water, dioxane or similar, whereas benzyl or similar can be removed by catalytic hydrogenation (e.g. $H_2$, Pd on carbon or similar, in ethanol, methanol water, EtOAc or HOAc or the like, at various temperatures). SEM can also be removed by fluoride treatment (e.g. tetrabutylammonium fluoride in, HMPT or DMPU or similar). Protecting group strategies for many functional groups (including conditions for protection and deprotection) are well described for example in "Protective Groups in Organic Chemistry" by T. W. Greene and P. G. M. Wutts, 5th Ed., 2014, John Wiley & Sons, N.Y. Deprotection of A3a, if required, which can comprise several steps if PG, PG' or PG" are orthogonal, will provide the de-protected compound of formula A3 which corresponds to the compounds of formula (I) as outlined in the claims.

Scheme 1:

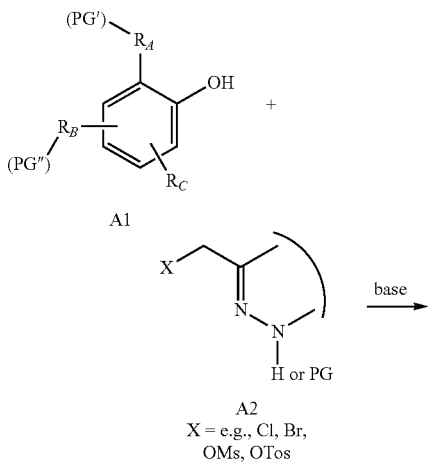

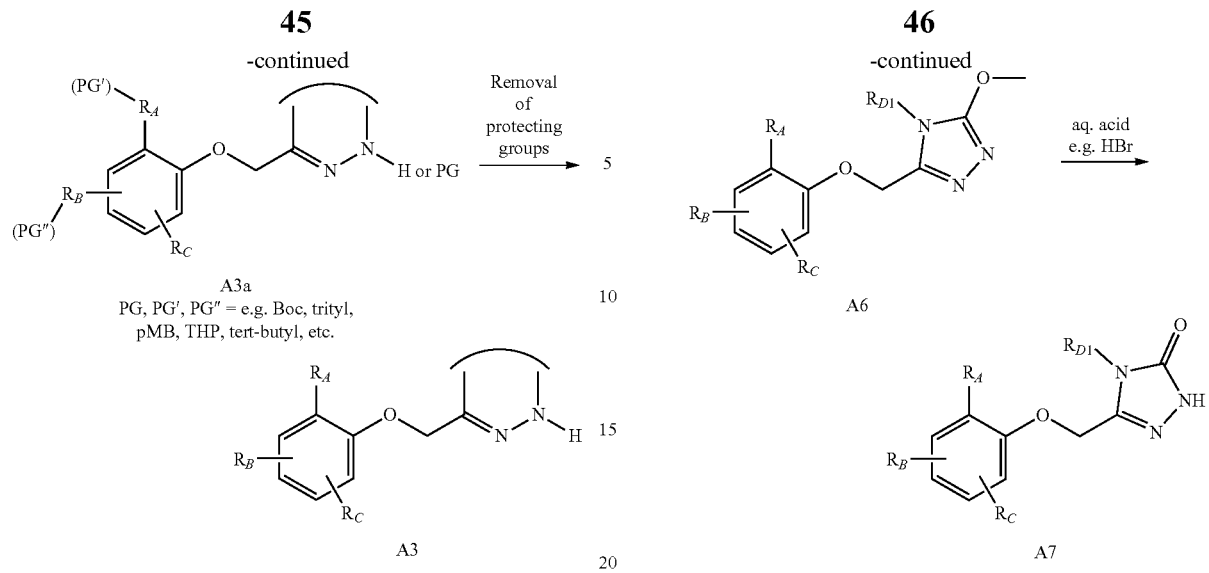

Subsequent Modifications of Coupling Products

In some cases, depending on the nature of the building block A2 used for the coupling reaction, the coupling product is not yet the desired material and further modifications which are distinct from simple protecting group manipulations are required to produce a compound of formula A3 (Scheme 2).

For Triazolones: If, for example, a commercial triazole building block such as A4 with $R_{D1}$=methyl is used as A2 in the coupling reaction with phenol A1, which is done under conditions which are described above, then suitable downstream transformations of the intermediate coupling product A5 include: 1) the treatment of A5 with sodium methoxide in a solvent such as methanol at temperatures ranging from 0° C. to the reflux temperature of the solvent to provide heteroaryl-methyl ether A6, and 2) the hydrolysis of A6 in the presence of a strong acid such as HCl, HBr, $H_2SO_4$ or p-toluenesulfonic acid or similar in solvents such as acetic acid containing some water at temperatures ranging from 0° C. to 130° C. to provide triazolones of formula A7, which are a subset of the compounds of formula A3 shown in Scheme 1.

For Pyridazinones: If, for example, a commercial pyridazinon building block such as A8 is used in the coupling reaction with phenol A1, then the subsequent transformations that are needed to produce pyridazinones of formula A10, which are a subset of the examples of formula A3, are outlined in Scheme 3. In this case, a phenol building block of formula A1 is treated with a suitable 3-chloro-6-chloromethyl-pyridazine A8 to provide an chloropyridazine intermediate of formula A9. Chloromethyl-pyridazines of formula A9 are commercially available or can be made according to known procedures from the literature. The coupling reaction is performed in the presence of a base and under conditions which are described above. Intermediate A10 can be converted to the desired pyridazinones of formula A3 using different methods. Method a, for example, is based on the treatment of A9 with a suitable base such as NaOH, KOH or similar in the presences of water or solvent containing some water at temperatures ranging from −20° C. to the boiling point of the solvents used to afford the desired pyridaziones of formula A10. Alternatively, according to method b, conversion of A9 to A10 is also possible for example by treatment of A9 with a carboxylic acid such as acetic acid, formic acid or similar, at temperatures ranging from 0° C. to 150° C., followed by aqueous workup.

Scheme 2:

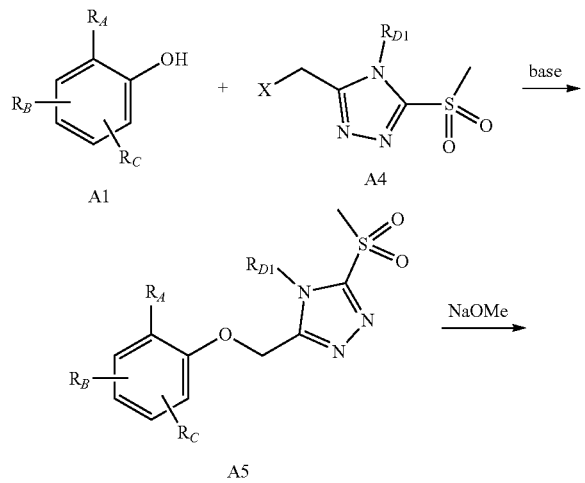

Scheme 3:

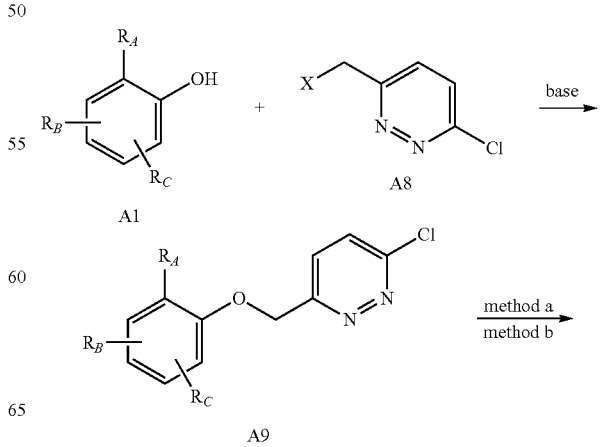

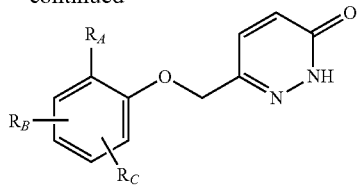

method a: NaOH in EtOH, reflux
method b: AcOH, reflux

Further Elaboration of Suitable Compounds of Formula A3

In some cases, the coupling reaction between phenol A1 and building block A2 produces a bicyclic intermediate such as for example thioether A11 (Scheme 4). A11 can be used to introduce for example suitable solubilizing groups that further alter the overall properties of the compounds. To achieve this, the protecting group PG of A11 is removed by the appropriate treatment depending on the nature of PG: for example, Boc, trityl of THP groups can be all removed by treatment with strong acids such as HBr, HCl, TFA or the like in an appropriate solvent such as dioxane, water, ethanol, methanol or DCM or the like at temperatures ranging from −20° C. to the boiling point of the solvent. Subsequently after removal of PG, the intermediate is oxidized to provide methylsulfone A12. Suitable oxidizing agents are for example m-CPBA in DCM, ozone in MeOH/$H_2$O, $H_2O_2$, $KMnO_4$ in water/AcOH or many others. Treatment of A12 with a suitable amine $NR_FR_{F'}$ as defined in Scheme 4, which can be in excess, in a solvent such as THF or N-methylpyrrolidone or DMSO or the like at temperatures ranging from 0° C. to the boiling point of the solvent or up to 200° C. in a sealed tube or microwave will provide aminopyrimidines of formula A13.

Alternatively, A12 can be treated with an appropriate alcohol HO—$R_H$ (suitably protected as THP presence of a base such as NaH, KH, $Cs_2CO_3$, $Na_2CO_3$ or the like in a suitable solvent such as DMF, THF, DMA or dioxane or the like at temperatures ranging from 0° C. to the boiling point of the solvent, to provide a compound of formula A14. Any side chain protecting groups can easily be removed by treatment with an acid such as TFA in DCM for a THP group or for example aqueous HCl for an acetonide to provide the desired unprotected compounds of formula A15.

Scheme 4:

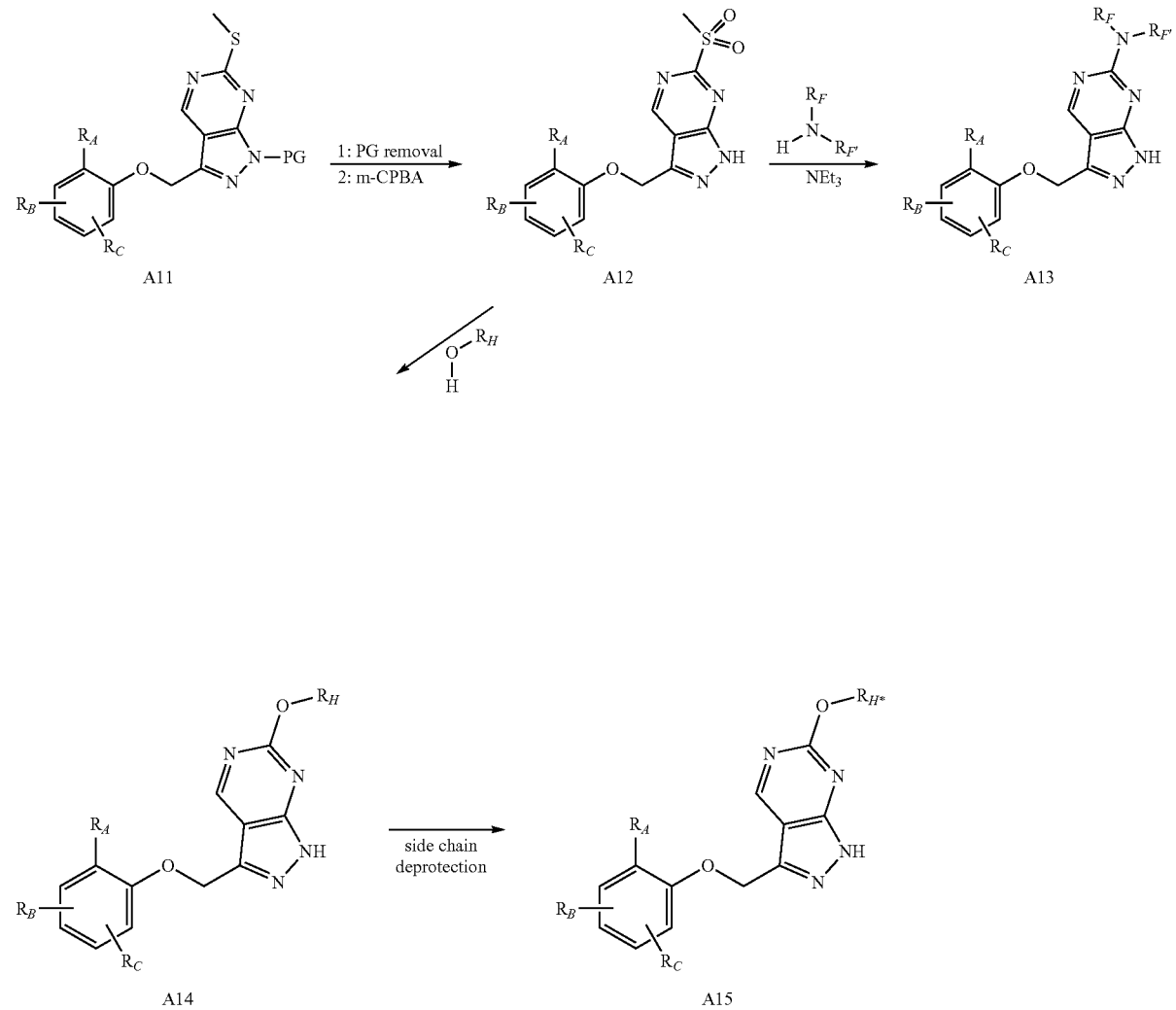

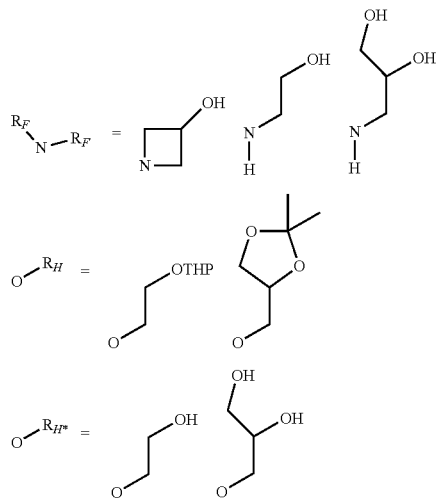

Similar to what was described above for pyrimidines, a protected fluoropyridine of formula A16 (PG=trityl or Boc) (Scheme 5) can be treated with an appropriate alcohol HO—$R_H$ (suitably protected as THP ethers or acetonides if it contains multiple OH groups, as defined in Scheme 5) in the presence of a base such as NaH, KH, $Cs_2CO_3$, $Na_2CO_3$ or the like in a suitable solvent such as DMF, DMA, THF or the like at temperatures ranging from 0° C. to the boiling point of the solvent, to provide a substituted hydroxypyridine of formula A17. Any protecting groups on the pyrazole (PG=e.g. trityl, Boc, PMB) and any side chain protecting groups (THP, acetonide or similar) can easily be removed by treatment with an acid such as TFA in DCM or for example with aqueous HCl, HBr or the like to provide the desired unprotected compounds of formula A18.

Scheme 5:

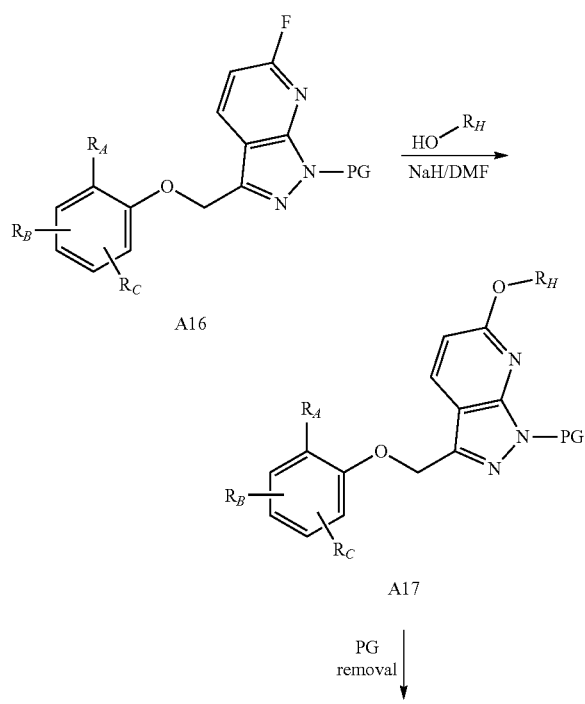

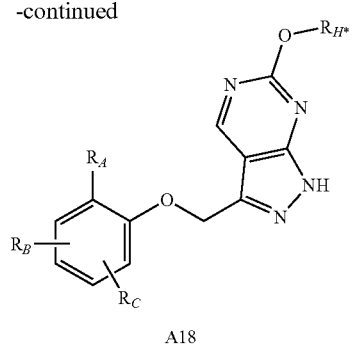

In some cases, the coupling reaction between phenol A1 and building block A2 produces a suitably protected bicyclic intermediate such as for example pyrazolopiperidines A19 (Scheme 6). These compounds carry for example a Boc group at the piperidine nitrogen $Y^1$ or $Y^2$ and optionally a protecting group PG on the pyrazole, which, as described above can be for example Boc, trityl, THP or similar. For further elaboration, all protecting groups are removed under the appropriate conditions such as TFA in DCM or HCl in dioxane or similar to provide the unprotected piperidine derivative A20. In order to obtain suitable compounds for this invention, A19 is treated with an acid chloride in the presence of a base such as $NEt_3$, Huenigs base, pyridine or the like in a solvent such as DCM, DMF, dioxane or similar to provide the desired substituted piperidines of formula A21 which are defined as shown in Scheme6. The latter transformation is also possible with carboxylic acids that are activated in many other different ways; suitable conditions are well known to those skilled in the art.

Scheme 6:

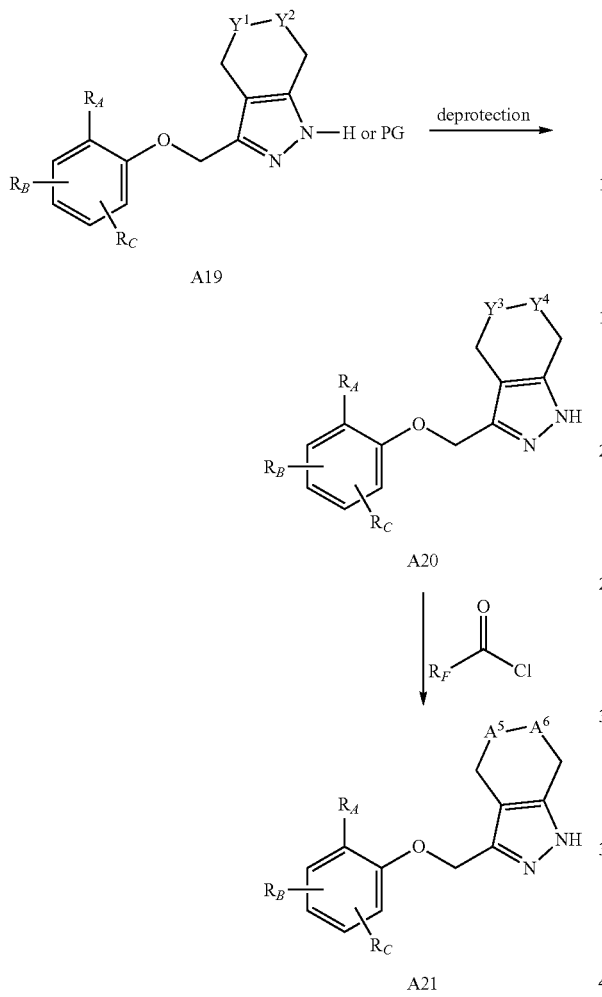

Y¹, Y²: one of Y¹ and Y² is e.g. CH₂, the other N-Boc
Y³, Y⁴: one of Y³ and Y⁴ is e.g. CH₂, the other NH
A⁵, A⁶ see claims
with R_{D3} = for example Scheme 7:

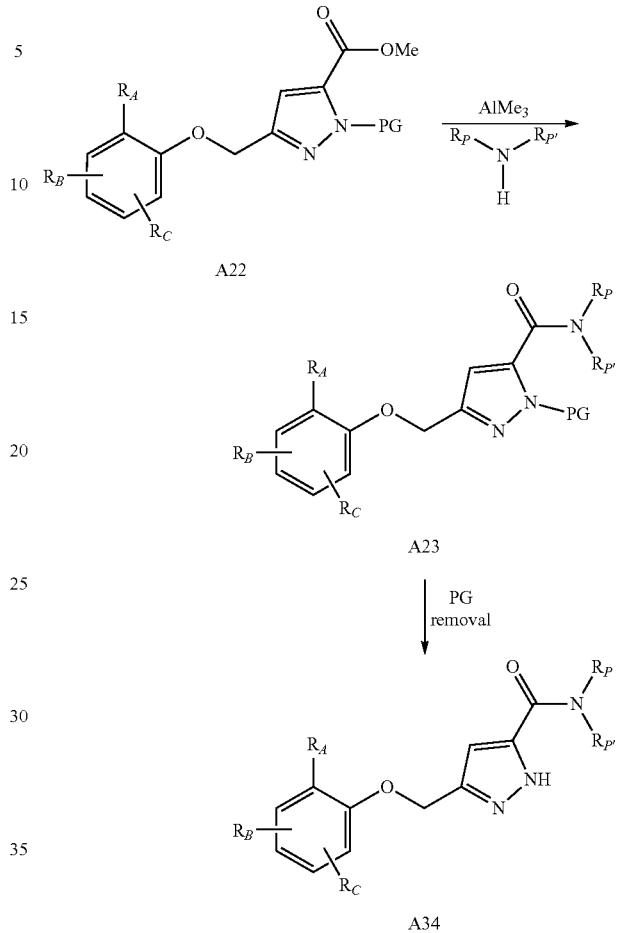

General Synthesis of Specific Subsets of Intermediates of Formula A2 Used in this Invention

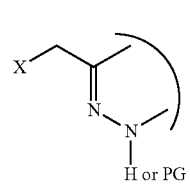

X = e.g. Cl, Br, OMs, OTos

In some cases, the coupling reaction between phenol A1 and building block A2 produces a suitably protected pyrazole-carboxylic acid ester A22 (Scheme 7). While such a compound is itself an example of a compound of formula (I) after the usual removal of the pyrazole protecting group PG, the ester group is also useful for further elaboration. A22 can for example be treated with a suitable amine $NR_P R_{P'}$ in the presence of AlMe₃ in a proper solvent such as DCM, CH₃Cl, THF or dioxane or similar at temperatures ranging from −20° C. to the boiling point of the solvent to provide a carboxylic acid amide of formula A23. Removal of the pyrazole protecting group under the appropriated conditions mentioned above will then provide the desired pyrazole-carboxylic acid amide A34, which is an example of a compound of formula (I) and in which the substituents $R_P$ and $R_{P'}$ are defined by $R_{D4}$ in the claim.

A) Substituted Triazolones

Triazolone intermediates of formula B5 in which $R_{D1}$ can be more complex than methyl are a subset of compounds of formula A2 and can be made according to the sequence that is shown in Scheme 8. A suitably N-substituted hydrazinecarboxamide of formula B1 which is commercially available or can be made according to methods known in the literature is treated with benzyloxyacetylchloride B2 and an aqueous base such as NaOH, KOH, K₂CO₃ or similar in a suitable solvent such as THF or the like to provide a protected triazolone intermediate of formula B3. This intermediate can be easily de-benzylated using conditions known in the art that include for example hydrogenation with suitable catalysts such as Pd/C, PtO$_2$, Pd(OH)$_2$/C or similar in solvents such as methanol, acetic acid, ethyl acetate or even water to provide the hydroxymethyl intermediate B4. Introduction of the leaving group X to provide the desired building block B5 is affected using suitable conditions which are dependent on the leaving group to be introduced. If, for example, X=Cl, intermediate B4 can be treated with COCl$_2$ to provide B5 with X=Cl. If, for example, X=Br, treatment with CBr$_4$ and PPh$_3$ could be used. If X=mesylate or tosylate, then B4 could be treated with the appropriate sulfonyl chloride (methanesulfonyl chloride or p-toluenesulfonylchloride) in the presence of a base such as trietylamine, pyridine, DMAP, Huenig's base or similar in a suitable solvent such as CH$_2$Cl$_2$ or THF or similar at temperatures ranging from –78° C. to the boiling point of the solvent to provide B5 in which R$_{D1}$ is defined according to the claims.

Scheme 8:

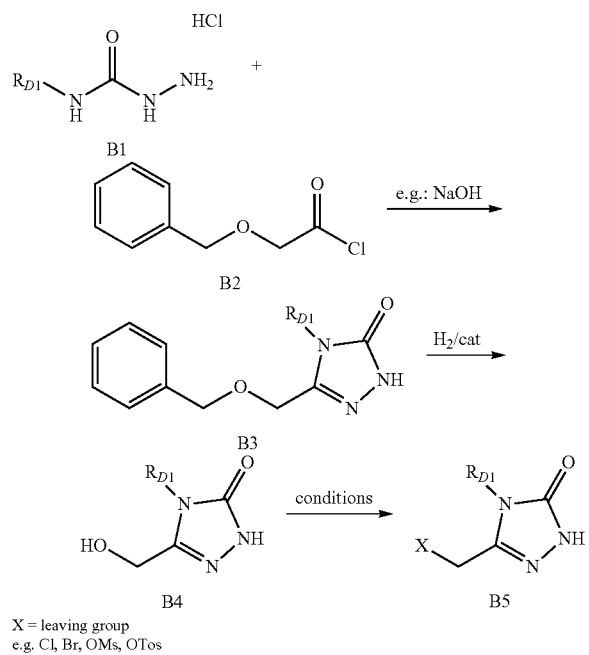

X = leaving group
e.g. Cl, Br, OMs, OTos

B) 1H-Pyrazolo Pyridines, Pyrazolo Pyrimidines, Indazoles and Similar

Appropriately functionalized Pyrazolo pyridines, pyrazolo pyrimidines and indazoles B13 are again a subset of the building blocks of formula A2 that are used in this invention to make compounds of formula (I) (Scheme 9A). Suitable precursors for the synthesis of these bicyclic compounds of formula B13 are commercially available or can be made according to procedures that are described in the literature. For example, it is possible to use indazolones or azaindazolones B6 as starting materials. Such compounds are commercially available or can be made new. An example for making a new compound of formula B6 will be given further below.

To elaborate B6, the material can be treated with POBr$_3$ to obtain the brominated intermediate B7. The chloro derivative may also be envisioned although it might be less reactive in the subsequent transformations; in this case the appropriate reagent has to be applied (e.g. POCl$_3$ for the chloro derivative). Intermediate B7 is then protected at the nitrogen with an appropriate protecting group PG to provide B8. PG can for example be a PMB group or a trityl group or similar. Suitable conditions which are dependent on the nature of the protecting group to be introduced have to be applied; e.g. for PG=PMB chloromethyl-4-methoxybenzene in the presence of a base such as Cs$_2$CO$_3$, Na$_2$CO$_3$ or similar in a solvent such as DMF, THF or CH$_3$CN or similar at temperatures ranging from 0° C. to the boiling point of the solvent, or for PG=trityl chlorodiphenylmethyl-benzene in the presence of a base such as triethylamine, Huenig's base, Na$_2$CO$_3$ or Cs$_2$CO$_3$ or similar in a solvent like THF, DMF or similar at temperatures ranging from 0° C. to the boiling point of the solvent. To obtain ester B10 from bromide B8, the material is treated with carbon monoxide in the presence of methanol, a suitable Pd catalyst such as for example Pd(OAc)$_2$ and an appropriate ligand such as for example 1,3-bis(diphenylphosphino)-propan (dppp) in a suitable solvent such as DMF and the appropriate temperature. Depending on the position of the nitrogen(s) and the substituent R$_E$, suitable esters B9 might be commercially available and can be converted to the desired intermediate B10 using conditions as described above for the conversion of B7 to B8. To be able to introduce a leaving group at the exocyclic carbon, the ester group of B10 can be reduced to the alcohol B11 using conditions well known in the art such as LiBH4 or NaBH$_4$ in MeOH, EtOH or THF or similar or DIBAL in toluene or DCM or similar at temperatures ranging from –20° to the boiling point of the solvent. Note that in some cases and depending on the conditions and nature of the heterocycle of B10 some overreduction may be observed, providing compound B12. If this happens, re-oxidation with an appropriate oxidation oxidation agent [Ox] such as for example chloranil and an anhydrous solvent such as toluene, benzene or DCM can re-create B11. To obtain the desired intermediate B13 which is exemplified here with a bromide as a leaving group, B11 can be treated for example with PBr$_3$ or alternatively with CBr$_4$ in the presence of PPh$_3$ in a suitable solvent such as CH$_3$CN or DCM or similar. Other leaving groups such as a chloride or mesylate or tosylate may also be possible; conditions to make those are known to those skilled in the art.

Starting materials of formula B6 are either commercially available or can be made according to Scheme 9B if a specific substitution pattern is needed. In the particular example shown below, the suitably substituted precursor B14 is treated with hydrazine in ethanol to provide hydrazide B15. Treatment of B15 with a base such as aqueous NaOH or KOH solution with heating will provide the corresponding indazolone derivative B16, which can be subjected to the synthetic steps indicated above.

Scheme 9:

9A)

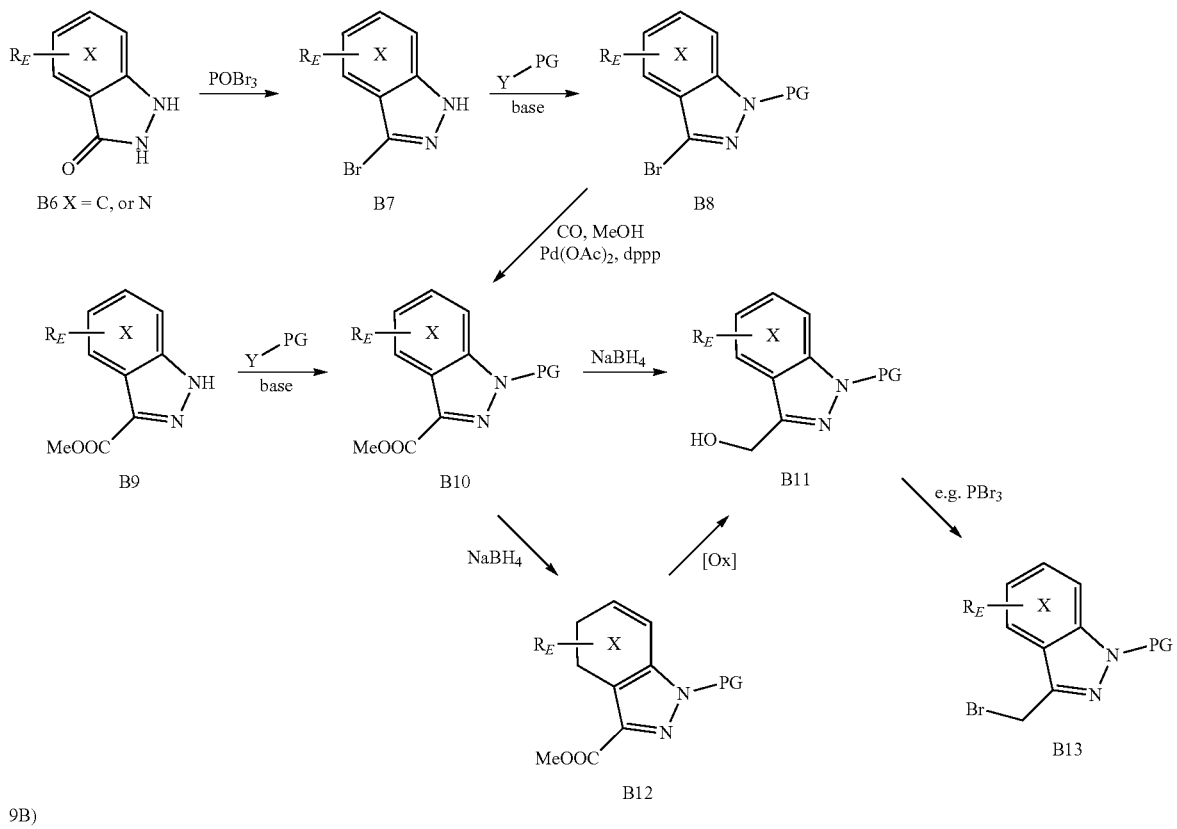

9B)

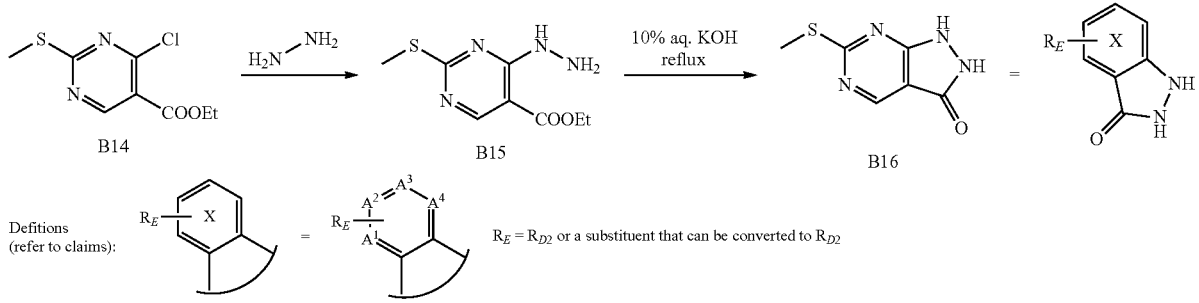

Defitions
(refer to claims):  $R_E \text{---} X \bigcirc = R_E \text{---} A^1 \overset{A^2 = A^3}{\underset{}{\bigcirc}} A^4$  $R_E = R_{D2}$ or a substituent that can be converted to $R_{D2}$ C) Pyrazolopiperidines Appropriately functionalized pyrazolo piperidines (one Y=N-Boc) or tetrahydroindazoles (both Y=CH$_2$) B19 are another subset of the building blocks of formula A2 that are used in this invention to make compounds of formula (I) (Scheme 10A). Suitable precursors for the synthesis of these bicyclic compounds of formula B19 are commercially available or can be made according to procedures that are described in the literature. A suitable precursor or intermediate is for example a an ester of formula B17, which are may be protected with a suitable protecting group PG such as for example Boc or trityl. Such esters can be reduced to the hydroxymethyl derivative B18 using appropriate reducing agents such as NaBH$_4$, LiBH$_4$ or DIBAL or similar in solvents such as MeOH, EtOH, THF or similar. As described above, introduction of the leaving group X to provide the desired building block B19 is affected using suitable conditions which are dependent on the leaving group to be introduced. If, for example, X=Cl, intermediate B18 can be treated with COCl$_2$ to provide B19 with X=Cl. If, for example, X=Br, treatment with CBr$_4$ and PPh$_3$ could be used. If X=mesylate or tosylate, then B18 could be treated with the appropriate sulfonyl chloride (methanesulfonyl chloride or p-toluenesulfonylchloride) in the presence of a base such as trietylamine, pyridine, DMAP, Huenig's base or similar in a suitable solvent such as CH$_2$Cl$_2$ or THF or similar at temperatures ranging from −78° C. to the boiling point of the solvent to provide building block B19.

If a suitable starting material B17 is not commercially available, which can be the case for some of the pyrazolo-piperidines with one Y=N-Boc, then one possible synthetic approach is outlined in Scheme 10B. Commercially available Boc-piperidin-4-one B20 is subjected to an aldol type reaction with ethyl diazoacetate and a suitable base such as LDA, LiHMDS or the like in a solvent such as THF or ether or similar at temperatures ranging from −78° C. to the boiling point of the solvent to provide intermediate B21. B21 can be dehydrated to provide B22, a step that is performed by treatment with a common dehydrating agent such as POCl₃ or similar. Cyclization of B22 to provide the desired pyrazolopiperidine B23 is achieved for example by heating of B22 in a solvent like toluene or xylene or similar up to the boiling point of the solvent. Alternatively, if a solvent with a lower boiling point such as THF or benzene or similar is used, the transformation may be done in a sealed tube or for example in a microwave.

Scheme 10:

10A)

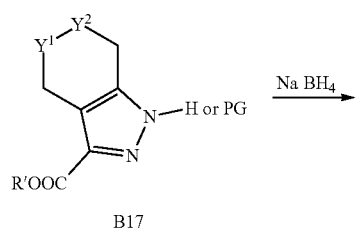

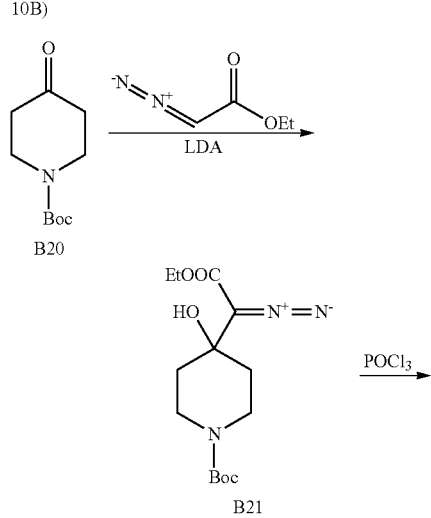

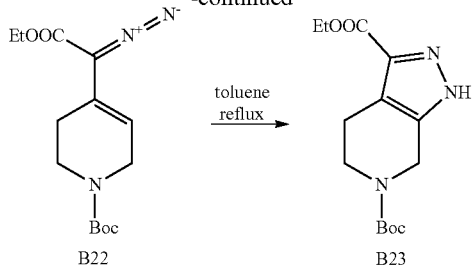

$Y^1$, $Y^2$: one of $Y^1$ and $Y^2$ is e.g. $CH_2$, the other N-Boc
X is e.g.: Cl, Br or $OSO_2Me$ D) Pyrazoles and Pyrazole-Carboxylic Acid Derivatives Appropriately functionalized pyrazols B26 or B29 are another subset of suitable building blocks of formula A2 that are used in this invention to make compounds of formula (I) (Scheme 11). Suitable precursors for the synthesis of compounds of formula B26 and B29, respectively, are commercially available or can be made according to procedures that are described in the literature. As outlined in Scheme 11A, a suitable precursor is methylpyrazole B24, which can be protected for example with di-tert-butyldicarbonate under conditions that are well known to those skilled in the art to provide the Boc-protected intermediate B25. Other protecting groups instead of Boc may be used in this transformation, as exemplified below in the synthesis for B29. To obtain the desired building block B26 with a leaving group, intermediate B25 is treated with NBS and dibenzoylperoxide in $CCl_4$ to provide the bromomethyl building block B26.

Scheme 11:

11A)

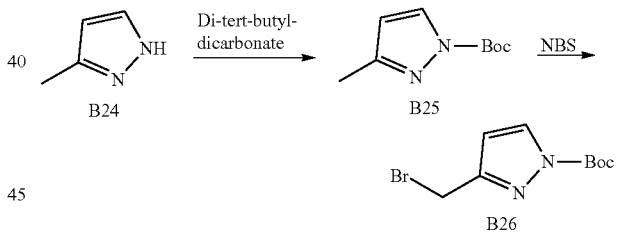

11B)

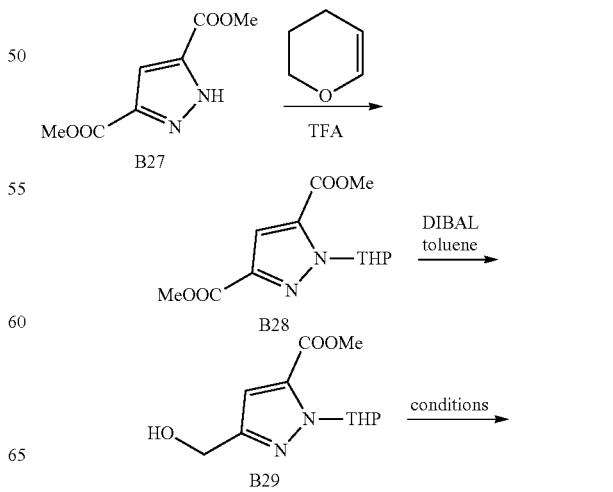

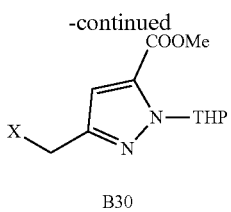

B30

X = leaving group e.g. Cl, Br, OMs OTos

If pyrazoles with some additional substitution are desired, they can be made for example from the commercially available diester B27 (Scheme 11B). B27 can be protected for example as a hemi-aminal with THP: in this case B27 is treated with dihydropyran and TFA or another suitable acid such as p-tolenesulfoninic acid or similar in a solvent such as DCM or THF or the like to provide the protected diester intermediate B28. A single ester group can then be reduced with DIBAL in solvent such as toluene, benzene or DCM at temperatures ranging from −78° C. to the boiling point of the solvent to give hydroxymethyl derivative B29. In analogy to what was described for other building blocks, introduction of the leaving group X to provide the desired building block B30 is affected using suitable conditions which are dependent on the leaving group to be introduced. If, for example, X=Cl, intermediate B29 can be treated with COCl₂ to provide B30 with X=Cl. If, for example, X=Br, treatment with CBr₄ and PPh₃ could be used. If X=mesylate or tosylate, then B29 could be treated with the appropriate sulfonyl chloride (methanesulfonyl chloride or p-toluenesulfonyl-chloride) in the presence of a base such as trietylamine, pyridine, DMAP, Huenig's base or similar in a suitable solvent such as CH₂Cl₂ or THF or similar at temperatures ranging from −78° C. to the boiling point of the solvent to provide building block B30.

General Synthesis of Phenol Building Blocks of Formula A1 Used in this Invention

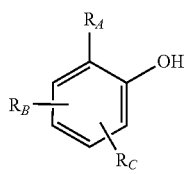

A1

Introduction and Elaboration of Ortho Substituent $R_A$ with $R_A \neq$ aryl

In this section, the synthesis of various phenol building blocks of the general formula A1 is described. While $R_A$ designates the substituent in ortho position to the OH group, $R_B$ is a substituent hat needs to be introduced that may need further elaboration during the synthesis and $R_C$ are one or several substituents that are present from the beginning and are carried through the synthesis. For some of the preferred phenol intermediates with the ortho-substituent $R_A$=tert-butyl, access is possible based on the corresponding phenol lacking the $R_A$ substituent. In these cases as outlined in Scheme 12, a suitable phenol precursor C1 without the ortho-substituent $R_A$ is then treated for example with tert-butanol (C2, X=OH) as a precursor of the tert-butyl substituent in the presence of a strong acid such as sulfuric acid or p-toluenesulfonic acid, phosphoric acid or the like in a suitable solvent such as acetic acid or similar at temperatures ranging from room temperature to the boiling point of the solvent or at even higher temperatures up to 250° C. for example in a sealed tube or in a microwave to provide a o-tert-butylphenol of formula C3. Other sources for the tert-butyl substituent such as isobutylene, 2-chloro-2-methylbutane (C2; X=Cl), 2-bromo-2-methylbutane (C2; X=Br), tert-butylmethylether (C2; X=OMe), or similar can also be used in such a transformation and suitable additives such as AlCl₃ or ZnCl₂ can be used to promote the reaction. Depending on the substitution pattern of the starting material, regioisomers may be obtained that need to be identified and separated.

Scheme 12:

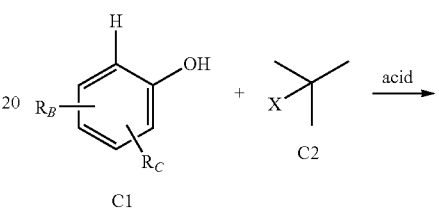

A possible synthesis of phenol intermediates with $R_A$ substituents that are different from tert-butyl or iso-butyl can be accomplished as outlined in Scheme 13. A key intermediate is for example an iodide of structure C6 which is suitably protected with a PG (for example, PG can be a methyl group, a benzyl group or a MOM group or similar, depending on the compatibility of the protecting group with the conditions to be used in the synthesis) (Scheme 13A). In the context of this invention, C6 can be made from a commercially available, suitably protected nitrophenol C4, which can be reduced to the corresponding aniline C5 by methods and reagents (indicated by [red]) well known in the literature such as reduction by catalytic hydrogenation using hydrogen gas and a suitable catalyst such as Pd on carbon or similar or other reductive conditions such as zinc dust or iron in the presence of a weak acid such as ammonium chloride solution or acetic acid in suitable solvents such as water, ethanol, methanol or mixtures thereof. Introduction of the iodine is accomplished using well known conditions such as for example treatment of C5 with sodium nitrite and potassium iodide in water under heating to provide intermediate C6.

As outlined in Scheme 13B, aliphatic or alicyclic $R_A$ residues can then be introduced by treating precursor C6 with a suitable aliphatic or alicyclic boronate or borolane C7 (M=B(OH)₂ or B(OR)₂) and an appropriate catalyst such as Pd(OAc)₂ or PdCl₂ or similar in the presence of an suitable ligand such as triphenylphosphine, tricyclohexylphosphine or the like in a solvent such as DMF, water or toluene or mixtures thereof at temperatures ranging from temperature to 150° C. to provide coupling products C8. In some cases such as for example if $R_A$=cyclopropyl, then the protecting group can be removed to provide the desired phenol building block C9 directly. Conditions for the removal of PG will depend on the nature of PG: If PG is PG from C8A to obtain building blocks of formula C9 will be done as described above for intermediate C8.

Scheme 13:

13A)

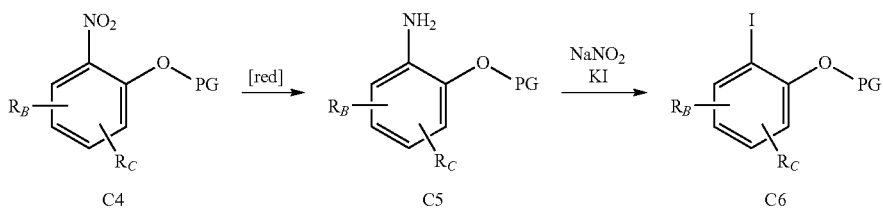

13B)

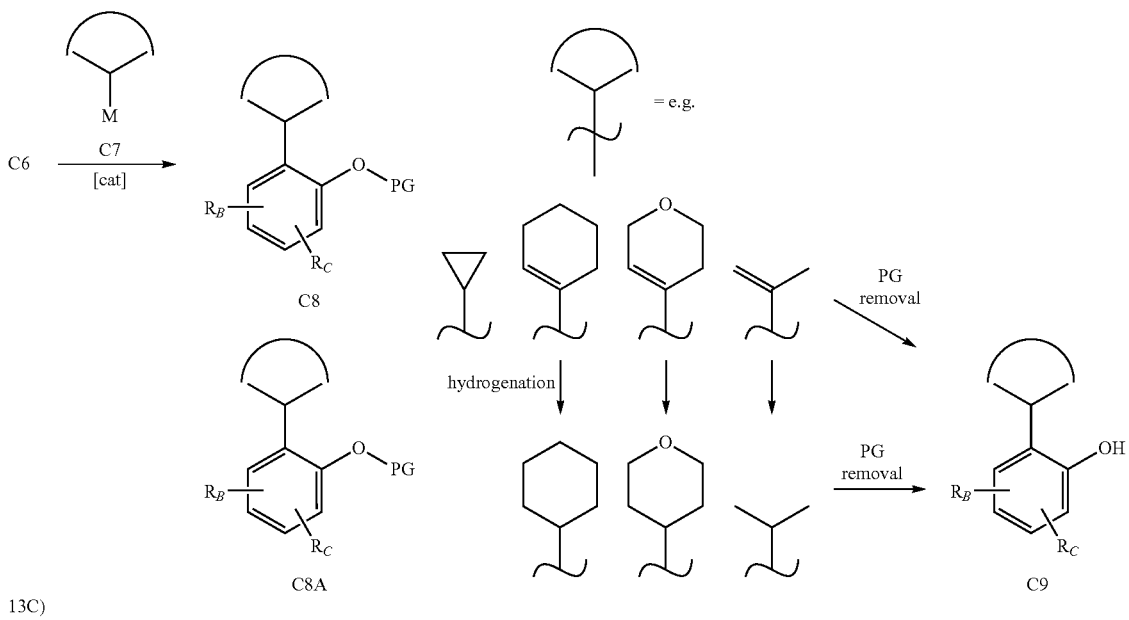

13C)

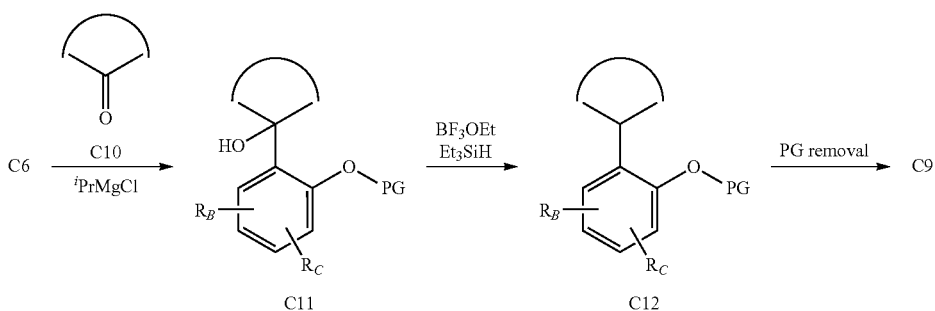

PG = Me (or e.g. Bz, MOM)

methyl, then the removal can be accomplished for example by treatment of C8 for example with BBr$_3$ in a solvent such as DCM or the like to provide C9. If, for example PG is a benzyl group, then removal will be accomplished for example with catalytic hydrogenation (e.g. Pd/C, H$_2$ gas). If PG=MOM, then removal will be accomplished for example by acid treatment (e.g. aq HCl in THF or similar).

In other cases, if C8 contains a double bond (e.g. cyclohexenyl, dihydopyranyl or propenyl), reduction of the double bond can be easily accomplished with catalytic hydrogenation under conditions described before (e.g. H$_2$, Pd/C) to obtain intermediates C8A. Then again, removal of An alternative approach to introduce certain R$_A$-substituents is outlined in Scheme 13C). In this approach, iodide C6 is treated first with isopropylmagnesiumchloride, resulting in iodine-magnesium exchange, followed by addition of a suitable ketone C10 in inert solvents such as THF or ether or similar at temperatures ranging from −78° C. to the boiling point of the solvent, to provide tertiary alcohol C11. Reduction of the tertiary alcohol C11 to provide aliphatic or alicyclic intermediate C12 can be done using conditions known in the literature; e.g. by treatment by BF$_3$OEt$_2$ and triethylsilane in solvents such as DCM or CHCl$_3$ or the like at temperatures ranging from −78° C. to the boiling point of the solvent. Again, PG removal from C12 to provide building blocks of formula C9 can be done as described above for C8 and C8A, respectively.

Introduction and Elaboration of $R_B$—Synthesis of Various Intermediates

In many cases in the context of this invention, suitable starting materials are commercially available or easily accessible that already bear the desired ortho-substituent $R_A$. In these cases, introduction and elaboration of the desired substituent $R_B$ in the proper position is required, while other substituents $R_C$ might be present and are usually carried through the synthesis unchanged. Depending on the nature of $R_B$ to be introduced, different precursors are required and the phenolic hydroxy group needs to be suitably protected in order to be compatible with the anticipated reaction conditions (Scheme 14). For example, suitable starting points are commercially available phenylbromides C13 with $R_A$ being in the scope of the claims as defined within formula (I). C13 can be 0-protected to provide C14: suitable protecting groups PG are for example methyl, benzyl or MOM. Conditions for introduction vary depending on the nature of PG, but usually a base such as $Cs_2CO_3$, NaH, $Na_2CO_3$ or the like in a suitable solvent such as DMF, DMSO, THF or $CH_3CN$ or the like as well as a reagent for the protecting group such as MeI, benzylchloride or -bromide or MOM-Cl at temperature ranging from −20° to the boiling point of the solvent are used for this transformation. A cyano group can then be introduced to provide arylnitrile C15, using conditions well known in the art. $Zn(CN)_2$, in the presence of zinc, 1,1'-bis(diphenylphosphino)ferrocen (dppf) and $Pd_2(dba)_3$ in solvents like DMF at temperatures ranging from room temperature up to the boiling point of the solvent or alternatively conditions such as CuCN in anhydrous DMF at elevated temperatures up to the boiling point of DMF are examples for suitable conditions for this transformation.

The cyano group can be hydrolyzed to provide free carboxylic acid C16; suitable conditions comprise the presence of aqueous NaOH or KOH solution in solvents such as EtOH or MeOH or the like at temperatures ranging from 0° C. to the boiling point of the solvent. While the carboxylic acid C16 itself can be a useful intermediate for further elaboration towards $R_B$, an ester group might be preferable. To obtain for example a methyl ester C17, C16 can be treated with a base such as $Cs_2CO_3$, NaH or $K_2CO_3$ or the like followed with MeI in a solvent such as DMF, DMSO, THF or $CH_2CN$ or the like temperatures ranging from 0° C. to the boiling point of the solvent. Alternatively, treatment with a strong acid (catalytic up to stoichiometric amounts) such as $H_2SO_4$ or p-toluenesulfonic acid in boiling methanol with or without a water trap can achieve the same transformation to ester C17.

Scheme 14:

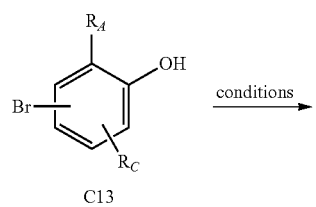

C13

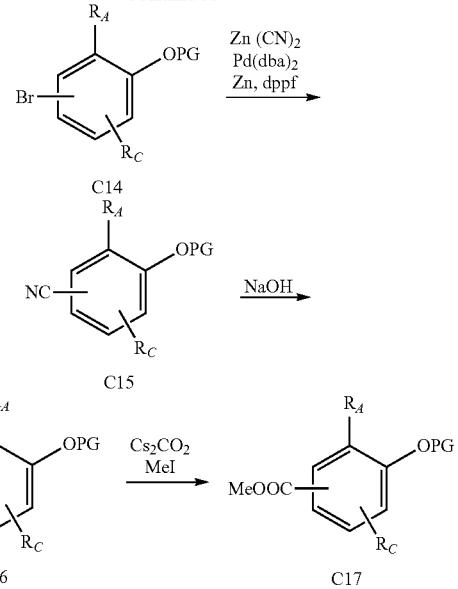

Introduction and Elaboration of $R_B$ Based on bromides of Formula C14

One way to elaborate $R_B$ based on arylbromides C14 is the use of Pd catalyzed coupling reactions such as Suzuki, Stille or Buchwald reactions or similar. Suitable conditions to achieve these transformations have been extensively reviewed in the literature. Three options to obtain intermediates C18 are shown in Scheme 15, where bromide C14 is either treated with M-HET, which can for example be a heterocyclic stannane such as 2-tributylstannyl oxazole (Stille conditions) or a heterocyclic boronate or borolane such as 1-methyl-5-(4,4,5,5-tetramethyl-[1,3,2]dioxaborolane-2-yl-1H-imidazole (Suzuki conditions), or alternatively for Buchwald conditions with a nitrogen containing heterocycle such as morpholine. In terms of conditions, Stille reactions can be done using for example catalysts like $PdCl_2(dppf)_2$ DCM complex or the like in solvents such as dioxane or the like, whereas Suzuki type reactions can be with $PdCl_2(dppf)_2$ DCM complex in the presence of a base such as $Na_2CO_3$ or $K_2CO_3$ or the like in solvents such as DMF. Buchwald reactions can be done with catalysts such as $Pd_2(dba)_3$ and a suitable ligand such xantphos in the presence of a base such as potassium tert-butylate in solvents such as anhydrous toluene. In all cases the reactions are done at temperatures ranging from room temperature to 150° C. (or higher, if sealed tubes are used). Removal of the protecting groups PG of C18 to obtain phenols C19 can be done as described above for compounds of formula C8 or C8A.

Scheme 15:

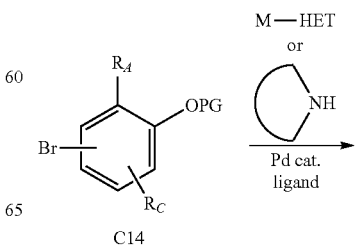

C14

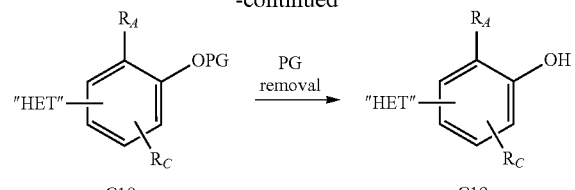

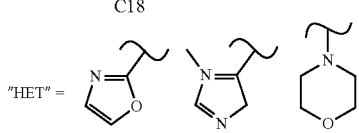

In some special cases where the desired heterocyclic stannane or boronate building blocks are not accessible, stepwise elaboration may be necessary to introduce the desired heterocyles starting from bromide C14. An example for such a stepwise approach is given in Scheme 16. Treatment of bromide C14 in a Heck type reaction with n-butyl vinylether in the presence of a Pd catalyst such as Pd(OAc)$_2$ or PdCl$_2$ or similar and a bidentate ligand such as bis(diphenylphosphino)propane and a base such as K$_2$CO$_3$ or the like in a solvent like water or DMF or mixtures thereof at temperatures ranging from room temperature up to 200° C. followed by acidic workup using aqueous mineral acids such as HCl or HBr or similar will provide acetyl derivative C20. Subsequently, treatment of C20 with bromine itself or alternatively with a bromine source such as Bu$_4$NBr$_3$ in a solvent such as THF, ether, dioxane or the like will provide bromoacetyl intermediate C21. This intermediate can be converted to the desired imidazole derivative C22 by treatment with excess formamide at temperatures ranging from 100-200° C. IN this case, in order to be able to perform the coupling step shown in Scheme 1, a suitable protection of the imidazole heterocycle is required. While a number of different suitable protecting groups can be envisioned (see: Green and Wuts., Protecting Groups in Organic Synthesis, J. Wiley & Sons), Scheme 16 shows the use of the SEM group, which can be introduced to C22 by treatment with SEMCl and a suitable base such as NaH, KO$^t$Bu, LDA or Cs$_2$CO$_3$ or similar in THF, ether or DMF or similar at temperatures ranging from −20° C. to the boiling point of the solvent to provide protected imidazole C23. Removal of the protecting groups PG of C23 to obtain phenols C24 to be used in the coupling reaction with the building blocks of formula A2 can be done as described above in for compounds of formula C8 or C8A.

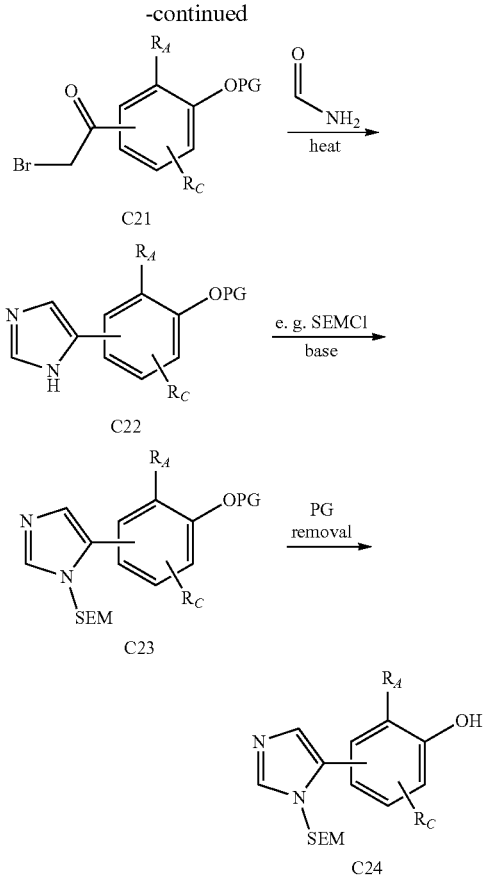

An option for the introduction of a sulfone residue R$_B$ to bromides C14 is shown in Scheme 16. To achieve this transformation, C14 is treated for example with sodium sulfonate and in the presence of a copper complex which is preformed from copper iodide and L-proline in the presence of a base sodium hydroxide or the like. The coupling reaction to provide sulfones of formula C25 is done in solvents such as DMSO or similar at temperatures ranging from room temperature to 130° C. Removal of the protecting group PG of C25 to obtain phenols C26 can be done as described above for compounds of formula C8 or C8A.

Scheme 16:

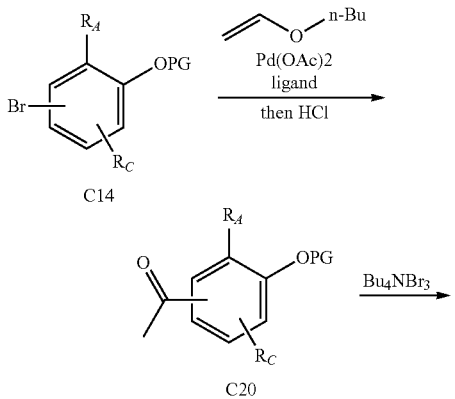

Scheme 17:

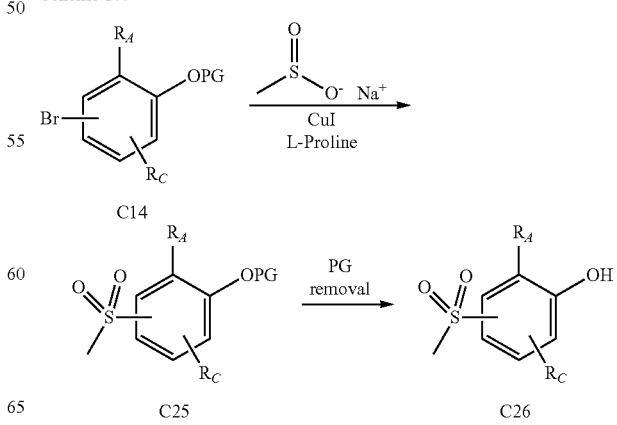

Introduction and Elaboration of $R_B$ Based on Carboxylic Acid Esters of Formula C17

Carboxylic acid esters of formula C17 are other possible precursors for the introduction and/or elaboration of $R_B$, if $R_B$ is for example a certain type of heterocycle. An example of such an approach is shown in Scheme 18A. According to this strategy, C17 is treated with a base such as NaH, $Cs_2CO_3$, $Na_2CO_3$ or similar followed by N-hydroxyacetamidine in a solvent such as DMF, THF or similar at temperatures ranging from −20° C. to the boiling point of the solvent. This treatment will provide the corresponding 1,2, 4-oxadiazole C27, which can be de-protected to provide phenol C28 under suitable conditions which are depending on the nature of PG as described above for C8 and C8A.

Scheme 18:

A)

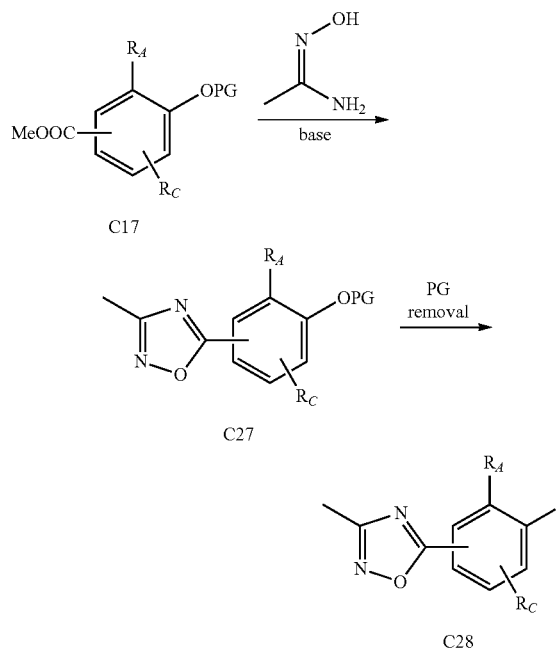

B)

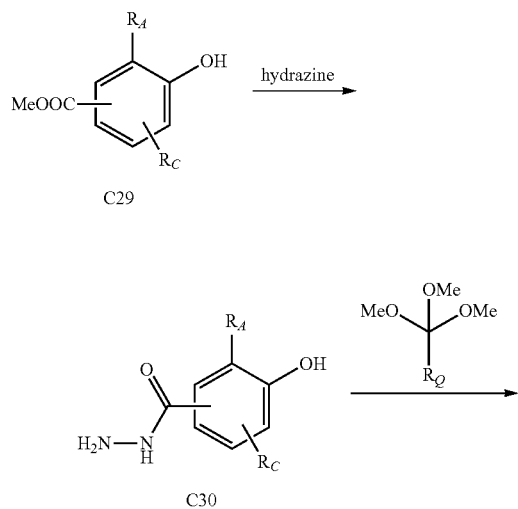

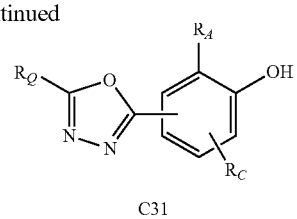

$R_Q$: e.g. H, small alkyl

An alternative route to introduce heterocyclic substituents to arylester starting materials C17 is outlined in Scheme 18B. In this particular case, the protecting group PG on the phenol has already been removed earlier, for example at the stage of C17, providing the de-protected ester C29. This material can be treated with hydrazine in a solvent like methanol, ethanol, DMSO or water or similar at temperatures up to 100° C. to provide acylhydrazide C30. To obtain the desired 1,3,4-oxadiazoles C31, C30 can be treated with an excess of carboxylic acid ortho ester (e.g. trimethylorthoacetate for $R_Q$=Me) at temperatures up to 200° C. It is conceivable to use other carboxylic acid ortho esters, which may result in compounds of formula C31 with heterocyclic substituents that carry an $R_Q$ other than methyl.

Introduction and Elaboration of $R_B$ Based on Nitriles of Formula C15

Aryl nitriles of formula C32 are other possible precursors for the introduction and/or elaboration of $R_B$, if $R_B$ is for example another type of heterocycle, i.e. certain imidazole derivatives. An example of such an approach is shown in Scheme 19. According to this strategy, arylnitrile C15 is treated initially with excess ethylenediamine and $P_2S_5$ in a sealed tube at temperatures from room temperature to 150° C. to provide dihydroimidazole C32. C32 can be oxidized with an appropriate oxidation agent [Ox] to provide imidazole derivative C33. Appropriate oxidation agents and conditions are for example diazetoxy-iodobenzene/$K_2CO_3$/DMSO, $KMnO_4$/$Al_2O_3$/$CH_3CN$, isocyanuric chloride/DBU/$CH_3CN$. The imidazol nitrogen of C32 can then be alkylated with an alkylating agent $R_R$—X, where $R_R$ is for example an alkyl group and X is a leaving group such as iodine or bromine or tosylate in the presence of a base such as NaH, $Cs_2CO_3$ or $Na_2CO_3$ or similar in a solvent such as DMF, THF, $CH_3CN$ or similar at temperatures from −20° C. to the boiling point of the solvent to provide the N-alkylated intermediate C34. Alternatively, $R_R$ can also be a protecting group such as SEM or MOM or the like (orthogonal to phenol protecting group PG) that can be removed again later to recreate the free imidazole at an appropriate stage. Removal of the protecting group PG of C34 to obtain phenols C35 to be used in the coupling reaction with head groups of formula A2 can be done as described above for compounds of formula C8 or C8A.

Scheme 19:

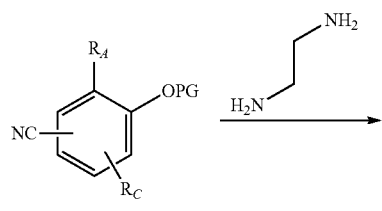

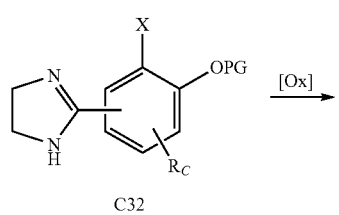

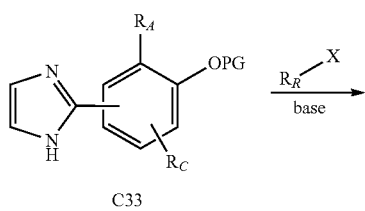

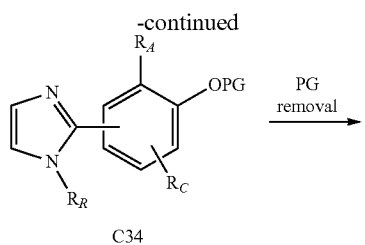

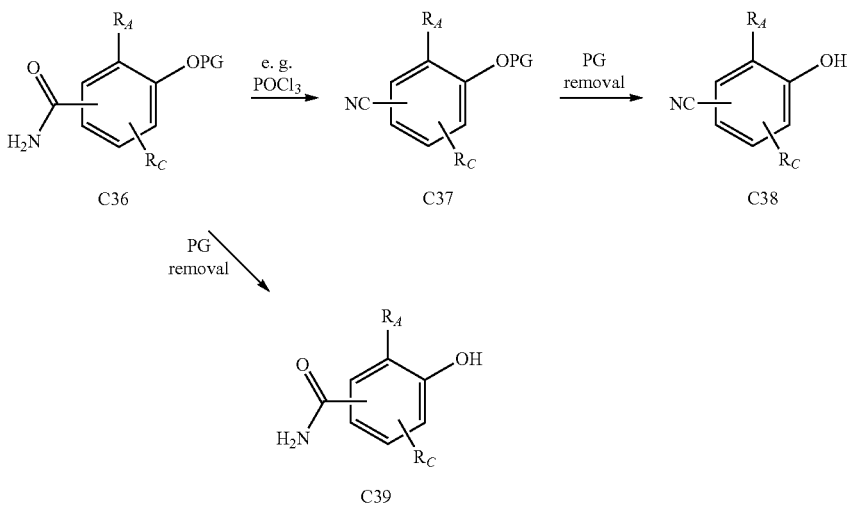

$R_R$: e.g. H, $C_1$-$C_6$ alkyl or SEM

While the approaches outlined above show the preferred routes to many of the intermediates and examples shown in this invention, some specific compounds with special substitution patterns can be made via alternative routes, again depending on the precursors that are conveniently available or accessible. For example, introduction of nitrile groups can not only be done as shown earlier in Scheme 14, but nitriles can also be formed by dehydration for carboxylic acid amides (Scheme 20). If the protecting group is removed at the stage of primary amide, then the resulting phenols can also be used as intermediates of formula A1.

Scheme 20:

Introduction and Elaboration of Both $R_A$ and $R_B$

In some specific cases and particularly if there is a need to introduce and elaborate both $R_A$ and $R_B$, more complex routes that include protecting group strategies have to be worked out in addition to the ones described above to be able to produce suitable phenol intermediates of formula A1. Such a route to an intermediate is outlined in Scheme 21A below.

A suitable starting material is for example C40 that contains an aryl-amine and substituent X (X=e.g. Br, I) besides $R_C$ and the OH group. C40 is protected for example with di-tert-butyldicarbonate in the presence of a base such as $NEt_3$, Huenig's base, DMAP or pyridine or similar in a solvent such as DCM, THF or ether or the like at temperatures from $-20°$ C. to the boiling point of the solvent provide the tris-Boc intermediate C41. $R_A$ can now be introduced for example by using an appropriate boronic acid or borolane C42 in the presence of an appropriate catalyst such as $Pd(OAc)_2$ or $PdCl_2$ or similar in the presence of an suitable ligand such as triphenylphosphine, tricyclohexylphosphine or the like in a solvent such as DMF, water or toluene or mixtures thereof at temperatures ranging from room temperature to $150°$ C. to provide coupling products C43 carrying the appropriate RA substituent. Removal of the Boc protecting groups is then easily possible using standard acid treatment such as for example TFA in DCM, HCl in dioxane or similar or aq. HCl, at appropriate temperatures, to provide amino-hydroxy intermediate C44. One example of further elaboration of the amino group consists of treatment with sodium nitrite in water in the presence of an acid such as $H_2SO_4$ or HCl or similar, followed by potassium iodide, to provide iodide C45. It is then possible to introduce for example a cyano group by treatment of C45 with CuCN in a solvent such as DMF or DMSO or the like at temperatures from room temperature to $150°$ C. to provide nitrile C46 with $R_B$=CN. Alternatively, the amino group of intermediate C44 can be modified differently, for example by acylation as shown in Scheme 21 by sulfonylation. For sulfonylation, C44 is treated with the appropriate sulfonyl chloride C47 ($R_F$ is for example small alkyl) in the presence of a base such as pyridine, DMAP, $NEt_3$ or Hunig's base in a solvent such as DMF, DCM, or THF at temperatures ranging from $-20°$ C. to the boiling point of the solvent, followed by treatment with NAOH, KOH or LiOH in water, to provide sulfonamide C48 with $R_B$=$NHSO_2R_F$.

Scheme 21:

A)

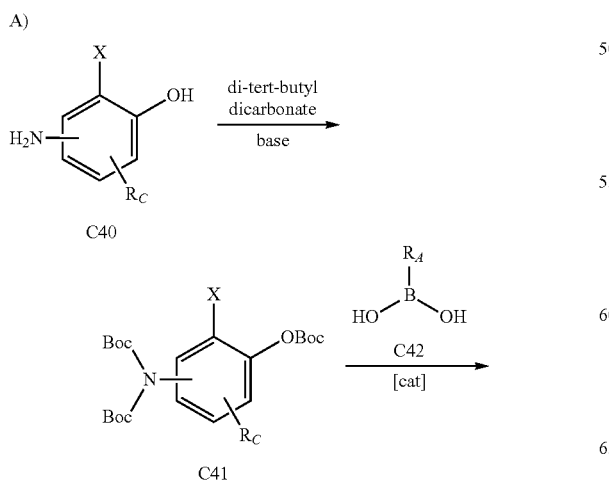

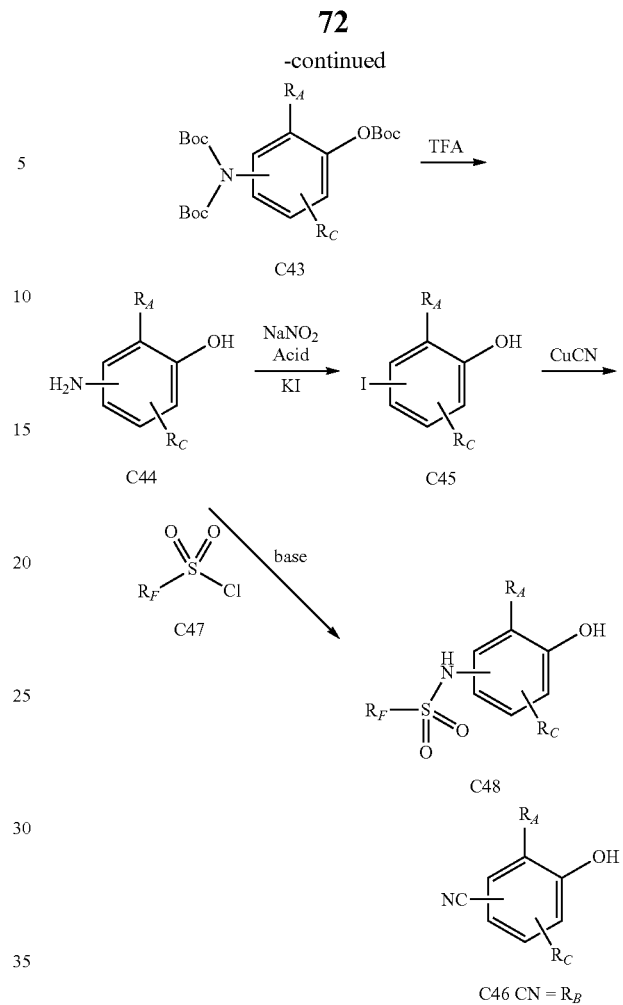

B)

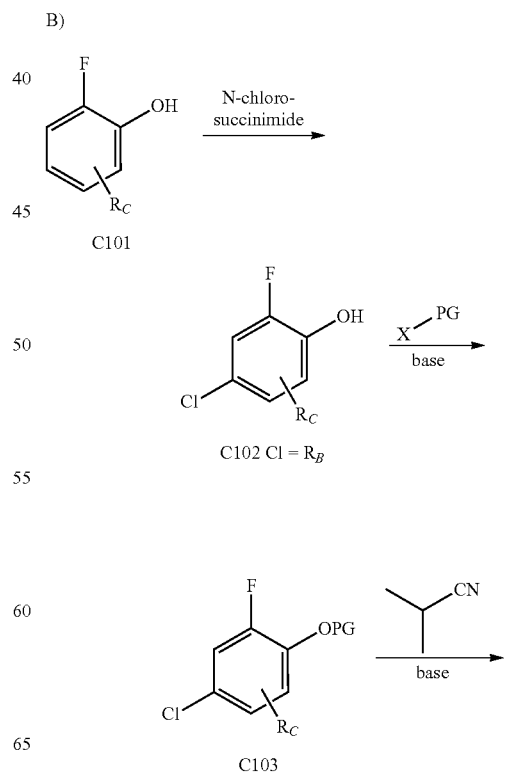

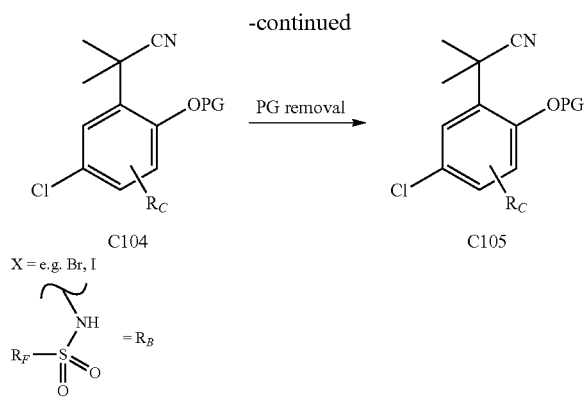

X = e.g. Br, I $R_F—S(=O)(=O)—NH—$ = $R_B$

Another option of introducing both $R_A$ and $R_B$ is shown in Scheme 21B. In this particular case, phenol C101 can be chlorinated for example in para-position to the hydroxyl group with a chlorinating agent such as N-chloro-succinimide in the presence of a strong acid such as triflic acid or the like in an acidic solvent such as acetic acid or formic acid or similar at temperatures ranging from room temperature to the boiling point of the solvent. A person skilled in the art will acknowledge that the site of chlorination may be dependent on the other substituents present on the aryl ring of C101. Usually, it will be required to protect the free hydroxyl group of the product C102 for further elaboration, providing intermediate C103. Suitable protecting groups PG such benzyl or MOM or SEM or similar as well as conditions for introduction have been discussed above. Introduction of $R_A$ which corresponds to a 2-methyl-propionitril-2-yl group in this case can be achieved for example by treatment of C103 with isobutyronitrile in the presence of a non-nucleophilic strong base such as KHMDS or NaHMDS in a solvent such as toluene or benzene or the like in a sealed tube at temperatures ranging from room temperature to 160° C. to provide intermediate C104 with the desired substitution pattern. Conditions for removal of the protecting group PG of C104 to obtain phenol C105 to be used in the coupling reaction with head groups of formula A2 will be dependent on the nature of PG and can be done as described above for compounds of formula C8 or C8A.

Introduction and Elaboration of Ortho Substituent $R_A$ for Phenols C49 with $R_A$=Substituted Aryl

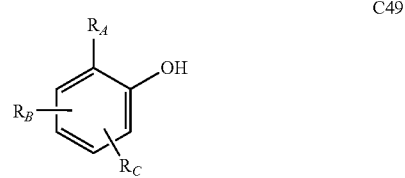

$R_A$ = substituted aryl or heteroaryl

The general sequences depicted in Schemes 22-29 may be of considerable length and a person skilled in the art will acknowledge that the sequence of reactions steps as depicted in Schemes 22 to 29 may be varied depending on reactivity and nature of the intermediates. Similar to what was described earlier, if one of the starting materials or intermediates contain one or more functional groups which are not stable or are reactive under the reaction conditions of one or more reaction steps, appropriate protecting groups (as described, e.g. in "Protective Groups in Organic Chemistry" by T. W. Greene and P. G. M. Wutts, 5th Ed., 2014, John Wiley & Sons, N.Y.) can be introduced before the critical step applying methods well known in the art. Such protecting groups can be removed at a later stage of the synthesis using standard methods described in the literature.

Synthesis of phenol intermediates C49 in which $R_A$ signifies an optionally substituted aryl or heteroaryl substituent can be accomplished, for example, as outlined in Scheme 22 from intermediates C6 which are commercially available or can be prepared as described under Scheme13. Reaction of C6 with (substituted) boronic acids $R_A$—B(OH)$_2$ or boronic esters $R_A$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1st Ed., 2005, John Wiley & Sons, New York) using a suitable catalyst (e.g. dichloro[1,1'-bis(diphenylphosphino)-ferrocene]palladium (II) dichloromethane adduct, tetrakis(triphenylphosphine) palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates C50 (step a). Suzuki reactions of this type are broadly described in literature (e.g. A. Suzuki, *Pure Appl. Chem.* 1991, 63, 419-422; A. Suzuki, N. Miyaura, *Chem. Rev.* 1995, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R_A BF_3 K$ can be used in the cross-coupling reaction applying a palladium catalyst such as, e.g. tetrakis(triphenylphosphine) palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates C50 can be also synthesized from C6 with (substituted) aryl- or heteroaryl tin reagents $R_A$—SnR$_3$ (R=e.g. Me or n-Bu; either commercially available or prepared according to literature procedures) in the presence of a suitable catalyst (e.g. tetrakis-(triphenylphosphine)palladium(0), benzylbis(triphenylphosphine)-palladium(II) chloride, bis(triphenylphosphine)palladium(II) dichloride or dichloro[1,1'-bis(diphenylphosphino)-ferrocene]palladium (II) dichloromethane adduct) in an appropriate solvent such as THF, dioxane, DMF (N,N-dimethylformamide) or HMPA (hexamethylphosphoramide) or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina et al., *J. Org. React.* 1998, 50, 1-652; T. N. Mitchell, *Synthesis* 1992, 9, 803-815) and well known to those skilled in the art (step a).

Alternatively, intermediates C50 can be synthesized from reaction of intermediates C6 with (substituted) aryl- or heteroaryl zinc halides $R_A$—ZnX (X=Cl, Br or I) (either commercially available or synthesized by methods described in literature) using a nickel (e.g. tetrakis(triphenylphosphine)nickel(0)) or palladium catalyst (e.g. tetrakis (triphenylphosphine) palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 4343-4354) and well known to those skilled in the art (step a). Removal of the protecting group PG in intermediates C50 by methods known to those skilled in the art and as described for example in "Protective Groups in Organic Chemistry" by T. W. Greene and P. G. M. Wutts, 5th Ed., 2014, John Wiley & Sons, N.Y. (e.g. a benzyl group by hydrogenation using a suitable catalyst such as palladium on carbon in an appropriate solvent such as MeOH, EtOH, EtOAc or mixtures thereof; a methyl group by reaction with boron tribromide in an appropriate solvent such as dichloromethane) furnishes intermediates C49 (step b), which are a subset of the desired phenol building blocks of formula A1.

Intermediates C51 may also be prepared from intermediates C6 by first removing the protective group PG from intermediates C6 using the conditions described before (step c) and converting the resulting intermediates C51 into intermediates C49 by applying for example Suzuki, Stille or Negishi cross-coupling reactions as described above (step d).

Cross-coupling reactions between phenyl boronic acids or aryl boronic esters C52 substituted with a carboxyl or ester group and with $R_{G1}$ that corresponds to a substituent according to the claims, either commercially available or which can be synthesized by methods known to persons skilled in the art, with intermediate C6 under the reaction conditions described under Scheme 22, step a, yields biaryl intermediates C53 (step a). Cleavage of the carboxylic acid ester functionality in intermediates C53 under basic (e.g. methyl or ethyl esters with lithium or sodium hydroxide in polar solvents such as methanol, $H_2O$ or THF or mixtures of said solvents) or neutral conditions (e.g. a benzyl group Bn by hydrogenation using a suitable catalyst such as palladium on carbon in an appropriate solvent such as MeOH, EtOH, EtOAc or mixtures thereof) furnishes intermediates C54 (step b). Further esters include, but are not limited to, e.g. allyl esters that can be cleaved by methods known to those skilled in the art and as described for example in "Protective Groups in Organic Chemistry" by T. W. Greene and P. G. M. Wutts, 5th Ed., 2014, John Wiley & Sons, N.Y., applying an orthogonal protecting group strategy that will allow removal of the ester protective group without affecting other protecting groups such as the phenol protective group PG. Reaction of intermediates C54 with amines of the type $R^c$—$NH_2$ furnishes intermediates C55 (step c). Amide couplings of this type are widely described in the literature and can be accomplished by the usage of coupling reagents such as, e.g., CDI, DCC, HATU, HBTU, HOBT, TBTU or Mukaiyama reagent in a suitable solvent, e.g., DMF, DMA, DCM or dioxane, optionally in the presence of a base (e.g., $NEt_3$, Scheme 22:

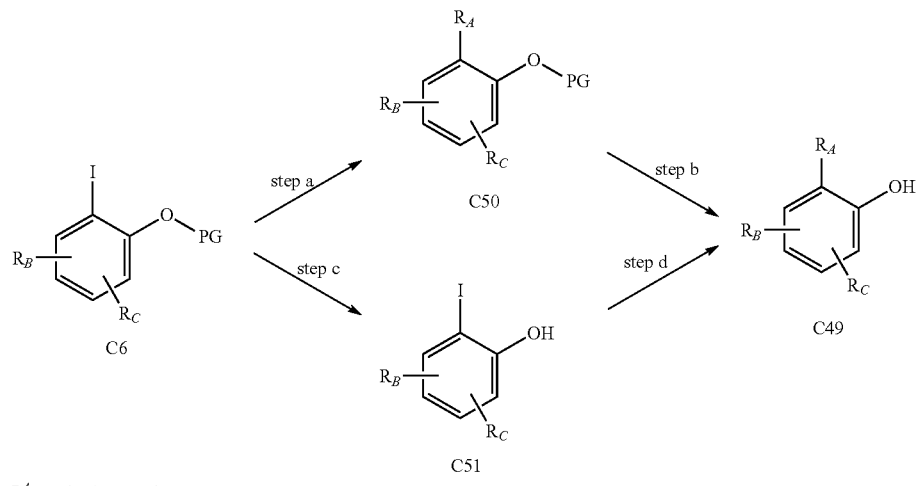

$R^A$ = aryl or heteroaryl
PG = protective group

If the building blocks (i.e. the substituted aryl or heteroaryl boronic acids $R_A$—$B(OH)_2$ or boronic esters, aryl- or heteroaryl tin reagents $R_A$—$SnR_3$, or (substituted) aryl- or heteroaryl zinc halides $R_A$—ZnX) for the preparation of intermediates C49 from intermediates C6 are not commercially available or unstable under the reaction conditions applied, intermediates C49 can be alternatively prepared according to the procedures described below.

For example, intermediates C56 and C58 in which $R_A$ signifies a phenyl ring appropriately substituted with $R_{G1}$ (see claims) and substituted by a secondary or tertiary amide functionality can be synthesized according to Scheme 23.

DIPEA (Huenig's base) or DMAP). Alternatively, in a two-step procedure, the carboxylic acid functionality in intermediates C54 can be converted into its acid chloride by treatment with, e.g. thionyl chloride, neat or optionally in a solvent such as DCM. Reaction of the acid chloride with $R^c$—$NH_2$ in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields intermediates C55 (step c). Removal of the protective group PG of C55 applying the methods described before furnishes intermediates C56 (step d).

Intermediates C58 can be prepared as well from intermediates C54 by coupling with secondary amines of the type $R^cR^dNH$ by applying the reaction conditions described above to give the tertiary amide C57 (step e). Subsequent removal of the protective group PG by applying the reaction conditions outlined before furnishes intermediates C58 (step f).

Intermediates C57 can alternatively be prepared by alkylation of intermediates C55 with compounds $R^d$-LG in which LG signifies a suitable leaving group such as bromo (or another leaving group such as chloro, iodo or $OSO_2$alkyl, $OSO_2$fluoroalkyl, $OSO_2$aryl) using an appropriate base and solvent such as sodium hydride in tetrahydrofuran to furnish intermediates C57 (step g). Amide substituents $R^c$, $R^d$ used in Scheme 23 are defined by the appropriate subset of substituents of $R_G$ as defined in the claims.

(II) complex with dichloromethane in 1,4-dioxane at temperatures ranging from room temperature to the boiling point of the solvent or solvent mixture (step b). Suitable conditions for cross-coupling reaction of intermediates C61 with intermediate C6 (step c) were described above. Removal of the protective group PG in intermediates C62 by applying literature procedures or the reaction conditions outlined before furnishes intermediates C63 (step d).

Intermediates C62 can alternatively be prepared from intermediates C67 by applying an orthogonal protecting group strategy (removal of one protecting group, in any order, using reagents and conditions that do not affect other protecting groups in the target compound). The hydroxy group in optionally substituted bromo-phenols C59 can be protected by methods known to those skilled in the art and as described for example in "Protective Groups in Organic Scheme 23:

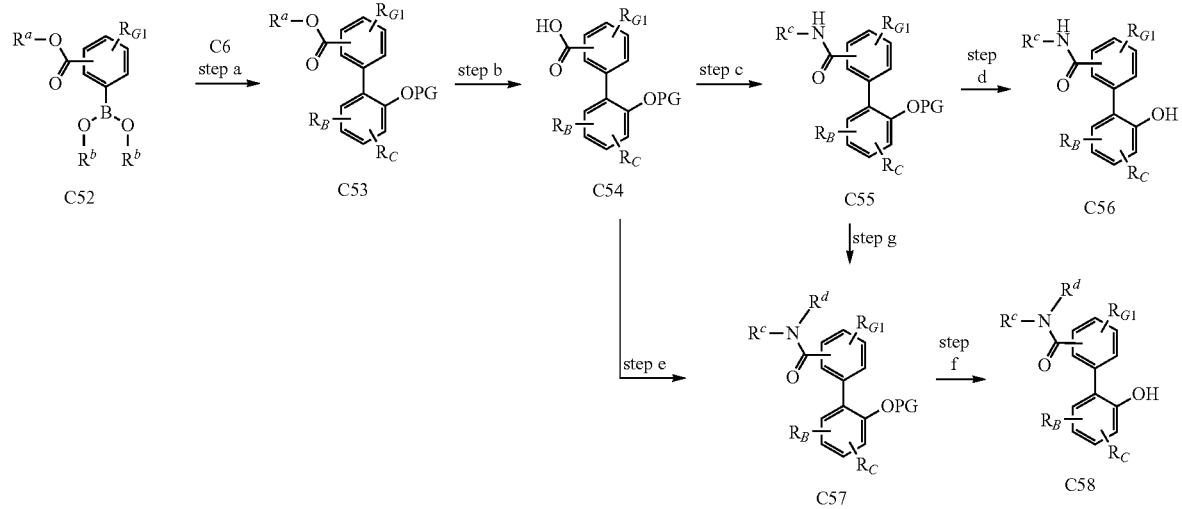

$R^a$ = e.g. Me, Et, Bn
$R^b$ = e.g. H, Me, "pinacol"
PG = protective group

Intermediates C63 in which $R_A$ signifies a phenyl ring appropriately substituted with $R_{G1}$ and substituted by an alkoxy, haloalkoxy, arylalkoxy or heteroarylalkyoxy substituent can be synthesized for example according to Scheme 24. Alkylation of bromo-phenols C59, optionally substituted with $R_{G1}$ as defined by the scope of the claims, which are either commercially available or can be prepared by methods known to those skilled in the art, with compounds of the type $R_SLG$ in which $R_S$ is defined by a subset of the scope of $R_G$ in the claims and LG signifies a suitable leaving group such as bromo (or another leaving group such as chloro, iodo or $OSO_2$alkyl, $OSO_2$fluoroalkyl, $OSO_2$aryl) using an appropriate base and solvent such as potassium carbonate in acetone or sodium hydride in tetrahydrofuran yields intermediates C60 (step a). Intermediates C60 can be converted to the corresponding boronic acids or boronic acid esters C61 using literature procedures as described for example in "Boronic Acids—Preparation and Applications in Organic Synthesis and Medicine" by Dennis G. Hall (ed.) 1st Ed., 2005, John Wiley & Sons, New York, for example using 4,4,4',4',5,5,5',5'-octamethyl-2,2'-bi(1,3,2-dioxaborolane (CAS RN 73183-34-3) in the presence of a suitable base, catalyst and solvent system such as potassium acetate, [1,1'-bis(diphenylphosphino)ferrocene]dichloropalladium Chemistry" by T. W. Greene and P. G. M. Wutts, 5th Ed., 2014, John Wiley & Sons, N.Y. (e.g. a methoxymethyl (MOM) group by reacting the optionally substituted bromophenols with methoxymethyl chloride in the presence of a base in a suitable solvent such as NaH in THF at temperatures ranging from 0° C. to the boiling point of the solvent) to give intermediates C64 (step e). Intermediates C64 in turn can be converted into intermediates C116 (step f) as outlined above under step b. Subsequent cross-coupling of intermediates C65 with intermediates C6 (step g) by applying the reaction conditions described above for step c furnishes intermediates C66. Selective removal of the protective group PG' in intermediates C66 on the optionally substituted phenyl substituent $R_A$ yields intermediates C67 (step h). Intermediates C67 in turn can be transformed into intermediates C62 through alkylation with compounds of the type $R_S$-LG in which $R_S$ is defined by a subset of the scope of $R_G$ in the claims and LG signifies a suitable leaving group such as bromo (or another leaving group such as chloro, iodo or $OSO_2$alkyl, $OSO_2$fluoroalkyl, $OSO_2$aryl) and using the reaction conditions described before yields intermediates C113 (step i).

Scheme 24:

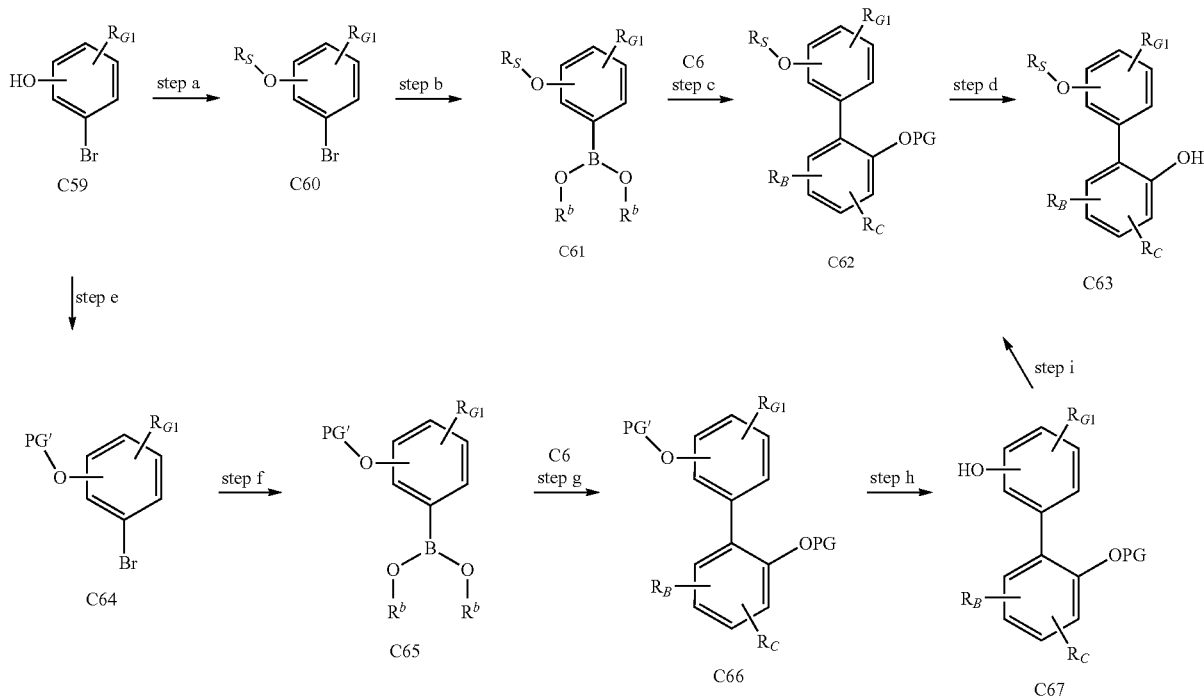

$R^b$ = e.g. H, Me, "pinacol"
PG = Protective group
PG' = Protective group, "orthogonal" to PG Intermediates C74 in which $R_A$ signifies a phenyl ring appropriately substituted with $R_{G1}$ and connected via a methylene ($CH_2$) linker to an N-linked lactam or cyclic urethane can be synthesized for example according to Scheme 25. The benzylic alcohol function in starting material C68 which are either commercially available or can be prepared readily according to literature procedures can be converted to a suitable leaving group LG such as bromo (e.g. by reacting intermediates C119 with tetrabromomethane in the presence of triphenylphosphine in THF as solvent) or another leaving group such as chloro, iodo or $OSO_2$alkyl, $OSO_2$fluoroalkyl, $OSO_2$aryl, to give intermediates C69 (step a). Reaction of intermediates C69 with lactams or cyclic urethanes C68 in the presence of a suitable base and solvent system such as sodium hydride in DMF yields intermediates C71 (step b). Intermediates C71 can be converted to their corresponding boronic acids or boronic esters C72 using common literature procedures as described for example in "Boronic Acids—Preparation and Applications in Organic Synthesis and Medicine" by Dennis G. Hall (ed.) 1st Ed., 2005, John Wiley & Sons, New York, for example using 4,4,4',4',5,5,5',5'-octamethyl-2,2'-bi(1,3,2-dioxaborolane (CAS RN 73183-34-3) in the presence of a suitable base, catalyst and solvent system such as potassium acetate, [1,1'-bis(diphenylphosphino)ferrocene]dichloropalladium (II) complex with dichloromethane in 1,4-dioxane, at temperatures ranging from room temperature to the boiling point of the solvent or solvent mixture (step c). Cross-coupling reaction of intermediates C72 with intermediate C6 under the reaction conditions described before yields intermediates C73 (step d). Removal of the protective group PG in intermediates C73 by applying literature procedures or the reaction conditions outlined before furnishes intermediates C74 (step e). Intermediates C74 can be also prepared from cross-coupling reactions of intermediates C72 with building block C51 by applying the methods described before (step f).

Scheme 25:

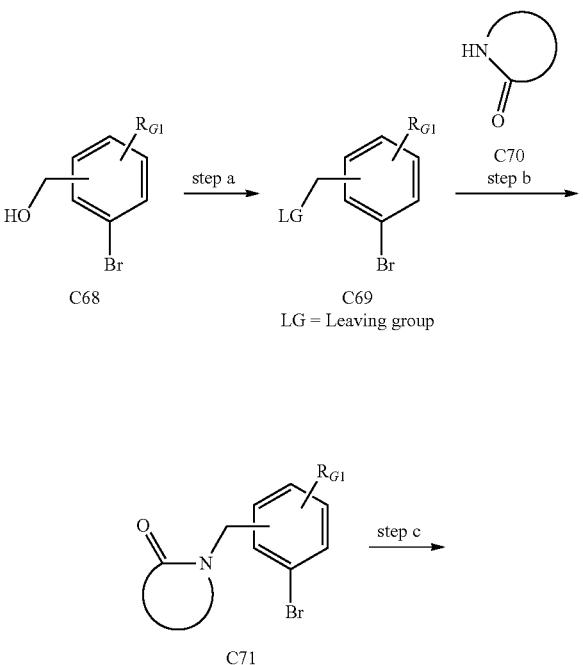

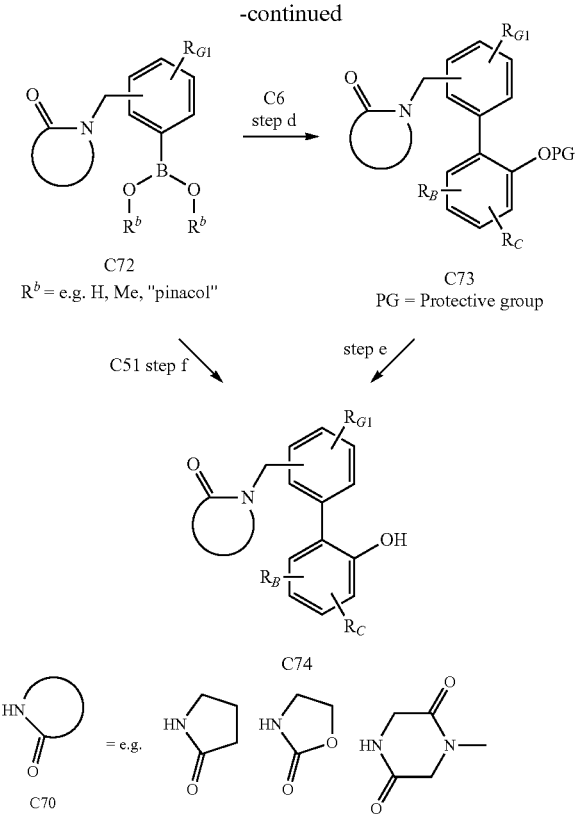

Intermediates C79 and C83 in which $R_A$ signifies a phenyl ring appropriately substituted with $R_{G1}$ and which is connected via a methylene (CH$_2$) linker to an N-linked secondary or tertiary carboxylic acid amide group can be synthesized for example according to Scheme 26. Acylation of the amine group in benzylic amines C75 which are either commercially available or can be readily prepared according to literature procedures, with carboxylic acids of the type $R_T$—COOH furnishes intermediates C76 (step a). Amide couplings of this type are widely described in the literature and can be accomplished by the usage of many different coupling reagents such as, e.g., CDI, DCC, HATU, HBTU, HOBT, TBTU or Mukaiyama reagent in a suitable solvent, e.g., DMF, DMA, DCM or dioxane, optionally in the presence of a base (e.g., NEt$_3$, DIPEA (Huenig's base) or DMAP). Alternatively, the carboxylic acids $R_T$—COOH can be converted into their acid chlorides before the coupling reaction by treatment with, e.g. thionyl chloride, neat or optionally in a solvent such as DCM. Reaction of the acid chloride with intermediates C75 in an appropriate solvent such as DCM or DMF and a base, e.g. NEt$_3$, Huenig's base, pyridine, DMAP or lithium bis(trimethylsilyl)amide at temperatures ranging from 0° C. to the reflux temperature of the solvent or solvent mixture yields compounds C76 (step a). Intermediates C76 can be converted into their boronic acids or boronic ester intermediates C77 using literature procedures as described for example in "Boronic Acids—Preparation and Applications in Organic Synthesis and Medicine" by Dennis G. Hall (ed.) 1st Ed., 2005, John Wiley & Sons, New York and applying methods described before (step b). Cross-coupling of intermediates C77 with intermediates C6 using the reaction conditions described before yields intermediates C78 (step c). Removal of the protective group PG in intermediates C78 is done by applying literature procedures or the reaction conditions described before to give intermediates C79 (step d).

Intermediates C83 in which $R_A$ signifies a phenyl ring which is connected via a methylene (CH$_2$) linker to an N-linked tertiary amide group can be prepared from intermediates C76 for example by N-alkylation of intermediates C76 with compounds of the type $R_U$-LG in which LG signifies a suitable leaving group such as bromo (or another leaving group such as chloro, iodo or OSO$_2$alkyl, OSO$_2$fluoroalkyl, OSO$_2$aryl) using an appropriate base and solvent such as sodium hydride in tetrahydrofuran to furnish intermediates C80 (step e). In analogy to the description above for C76, C77, C78 and C79, intermediates C80 can be converted into intermediates C81 (step f), C82 (step g) and finally C83 (step h) applying the methods described before. Intermediates C81 can alternatively also be prepared by alkylation of intermediates C77 with compounds of the type type $R_U$-LG and applying the conditions described under step e above (step i). Intermediates C82 can be also prepared by alkylation of intermediates C78 with compounds of the type $R_U$-LG and applying the conditions described under step e above (step j). Both $R_T$ and $R_U$ used in Scheme 26 are defined by the appropriate subset of substituents of the scope of $R_G$ as outlined in the claims.

Scheme 26:

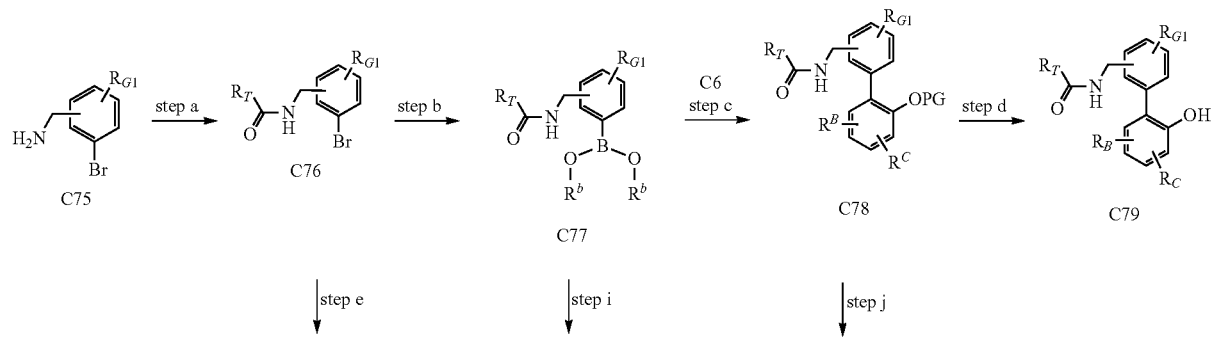

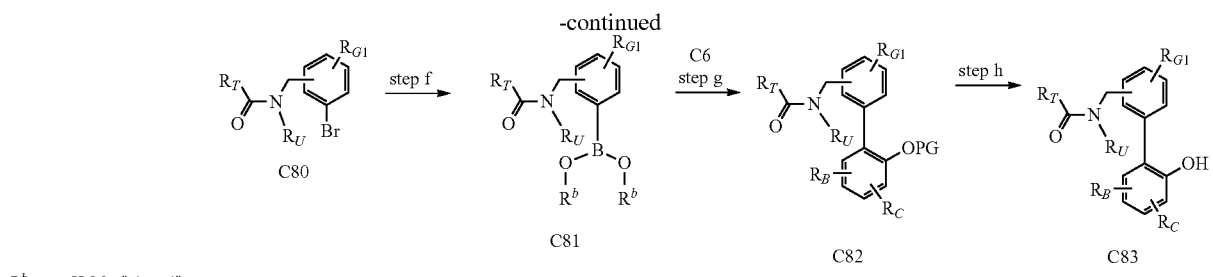

$R^b$ = e.g. H, Me, "pinacol"
PG = Protective group

Intermediates C49 in which $R_A$ signifies an aryl ring which is further substituted by a heteroaryl ring and for which the suitable boronic acids $R_A$—B(OH)$_2$ or boronic esters $R_A$—B(OR')$_2$, tin reagents $R_A$—SnR$_3$ or zinc halides R—ZnX for the introduction of substituents $R_A$ into intermediates CC6 or C51 are not available or unstable under the reaction conditions to be applied, intermediates C49 can be synthesized for example according to Schemes 27 to 29 and by methods described in literature. Persons skilled in the art will acknowledge that this methodology is also applicable to a variety of other heteroaryl systems.

For example, intermediates C87 in which $R_A$ signifies a phenyl ring appropriately substituted with $R_{G1}$ and substituted by a [1.3.4]oxadiazol-2-yl ring in which $R_V$ is for example alkyl, cycloalkyl, trifluoromethyl, benzyl or phenyl or similar, can be prepared from intermediates C53 (see Scheme 23 for preparation) according to Scheme 27. Selective cleavage of the carboxylic acid ester functionality in intermediates C53 (e.g. methyl or ethyl esters with lithium or sodium hydroxide in polar solvents such as methanol, H$_2$O or THF or mixtures of said solvents; further esters include, but are not limited to, e.g. benzyl or allyl esters that can be cleaved by methods known to those skilled in the art and as described for example in "Protective Groups in Organic Chemistry" by T. W. Greene and P. G. M. Wutts, 5th Ed., 2014, John Wiley & Sons, N.Y.) and in which $R^a$ is chosen in such a way that the hydroxyl protective group PG is not affected under the reaction conditions applied for the cleavage of $R^a$ ("orthogonal protecting group strategy") furnishes intermediates C84 (step a). Reaction of intermediates C84 with acyl hydrazines of the type $R_V$—C(O)NHNH$_2$ yields intermediates C85 (step b). Amide couplings of this type are widely described in the literature and can be accomplished by the usage of coupling reagents such as, e.g., CDI, DCC, HATU, HBTU, HOBT, TBTU or Mukaiyama reagent in a suitable solvent, e.g., DMF, DMA, DCM or dioxane, optionally in the presence of a base (e.g., NEt$_3$, DIPEA (Huenig's base) or DMAP). Alternatively, the carboxylic acid functionality in intermediates C84 can be converted into its acid chloride by treatment with, e.g. thionyl chloride, neat or optionally in a solvent such as DCM. Reaction of the acid chloride with acyl hydrazines of the type $R_V$—C(O)NHNH$_2$ in an appropriate solvent such as DCM or DMF and a base, e.g. NEt$_3$, Huenig's base, pyridine, DMAP or lithium bis(trimethylsilyl)amide at temperatures ranging from 0° C. to the reflux temperature of the solvent or solvent mixture yields the 1,2-diacyl hydrazide intermediates C85 (step b). Cyclization of the diacyl hydrazide group in intermediates C135 using a suitable cyclodehydration agent such as POCl$_3$, SOCl$_2$, Burgess reagent or diethylaminodifluorosulfinium tetrafluoroborate)(Xtal-Fluor-E®) either neat or using an appropriate solvent such as dichloromethane, optionally in the presence of an acid such as acetic acid at temperatures ranging from room temperature to the boiling pint of the solvent or solvent mixture, furnishes the 1,3,4-oxadiazole intermediates C86 (step c). Synthesis of this type of 1,3,4-oxadiazoles is well known in the art and has been also described in literature, e.g. M.-F. Pouliot et al., Org. Mom. Chem. 2012, 10(5), 988. Removal of the protective group PG of C86 to provide C87 is done by methods known to those skilled in the art and as described for example in "Protective Groups in Organic Chemistry" by T. W. Greene and P. G. M. Wutts, 5th Ed., 2014, John Wiley & Sons, N.Y. (e.g. a benzyl group by hydrogenation using a suitable catalyst such as palladium on carbon in an appropriate solvent such as MeOH, EtOH, EtOAc or mixtures thereof; a methyl group by reaction with boron tribromide in an appropriate solvent such as dichloromethane) (step d).

Scheme 27:

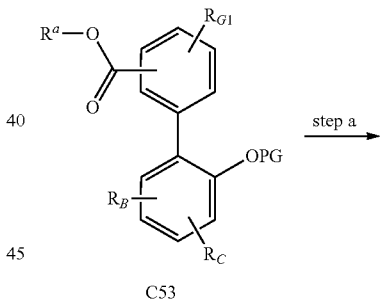

C53

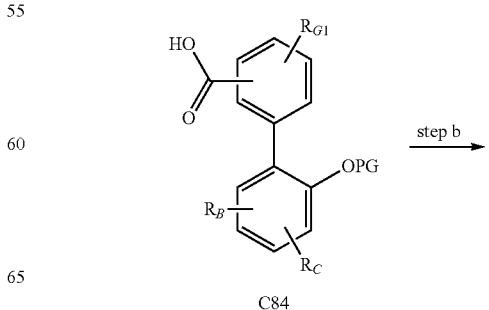

C84

-continued

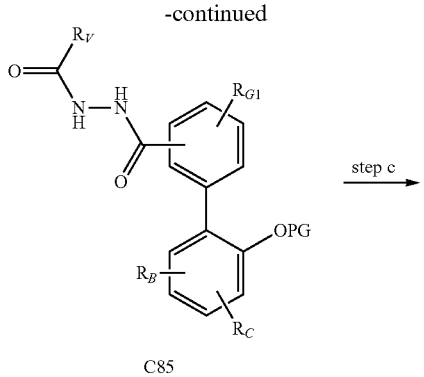

C85

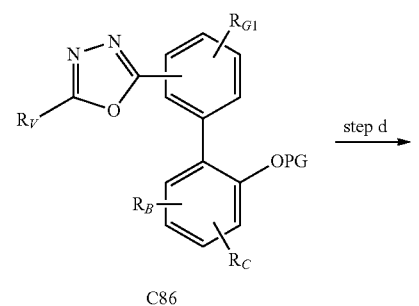

C86

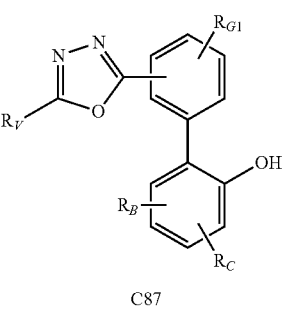

C87

$R^a$ = e.g. Me, Et, Bn
PG = Protective group "orthogonal" to $R^a$

Intermediates C93 in which $R_A$ signifies a phenyl ring appropriately substituted with $R_{G1}$ and substituted by a [1.2.4]oxadiazol-5-yl ring in which $R_W$ is for example alkyl, cycloalkyl, trifluoromethyl, benzyl or phenyl or similar can be prepared according to Scheme 28 for example from intermediates C88. Syntheses of [1.2.4]oxadiazoles are broadly described in literature, for example in R. O. Bora et al., Mini-Reviews Med. Chem. 2013, 13 or K. Hemming, Sci. Synthesis 2004, 13, 127. Nitrile intermediates C88 which are either commercially available or can be prepared by methods well known in the art, can be converted into their boronic esters such as pinacol esters C89 by literature procedures, for example by reaction of intermediates C88 with pinacol in a suitable solvent such as THF (step a). The cyano functionality in intermediates C89 can be transformed into an amidoxime group by methods known in the art, for example by reaction with hydroxylamine (optionally as its hydrochloride salt) in a suitable solvent such as EtOH in the presence of a base like, e.g. Huenig's base to give intermediates C90 (step b). Cyclization of the amidoxime functionality in intermediates C90 with an activated carboxylic acid derivative carrying the substituent $R_W$ such as the corresponding acid anhydride, acid chloride, acid ester or ortho ester at temperatures ranging from room temperature to the boiling point of the solvent yields intermediates C91 which are often obtained without isolation of the intermittently formed 0-acylated amidoxime intermediate (step c). Intermediates C91 can be reacted with intermediates C6 in cross-coupling reactions using the conditions described under Scheme 22, step a, to furnish intermediates C92 (step d). Removal of the protective group in intermediates C92 by methods known to those skilled in the art, as described for example in "Protective Groups in Organic Chemistry" by T. W. Greene and P. G. M. Wutts, 5th Ed., 2014, John Wiley & Sons, N.Y. and as described before furnishes the desired phenol intermediates C93 (step e).

Intermediates C92 can alternatively be prepared from intermediates C88 by performing cross-coupling reactions with intermediate C6 as the first step of the sequence as described under Scheme 22, step a, to give intermediates C94 (step f), then conversion of the cyano group into an amidoxime functionality using the methods described above to provide C95 (step g) and then cyclization of C95 with an activated carboxylic acid carrying substituent $R_W$ under the conditions outlined before to give intermediates C92 (step h). Intermediates C94 can also be prepared from intermediates C89 by cross-coupling reaction with intermediates C6 by application of the reaction conditions described before (step i).

Scheme 28:

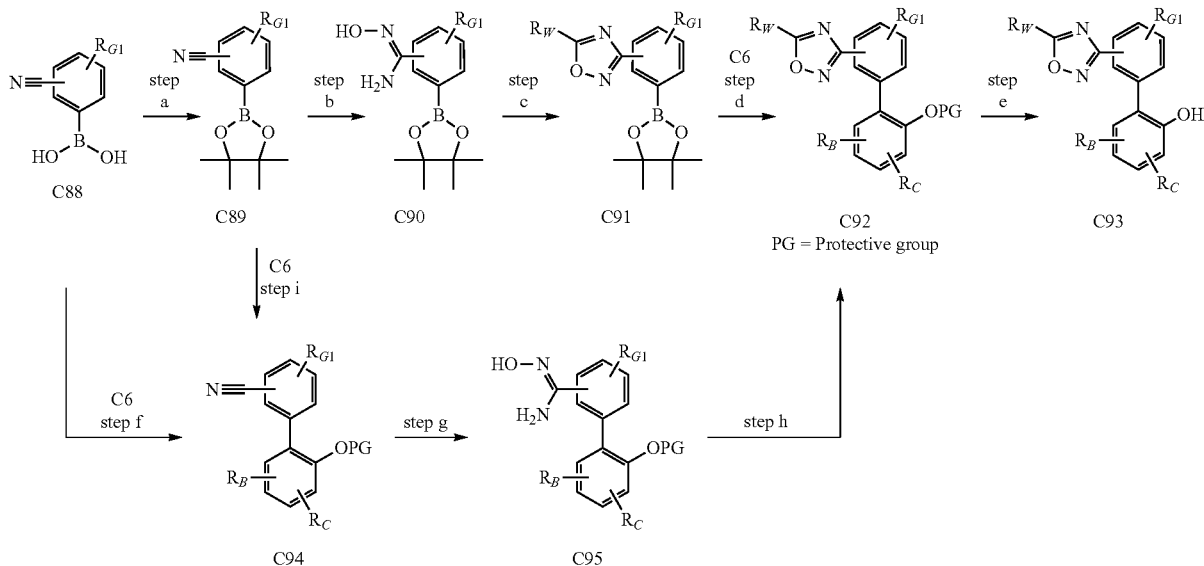

PG = Protective group

Intermediates C100 in which $R_A$ signifies a phenyl ring appropriately substituted with $R_{G1}$ and substituted by a tert-butyl protected 1H-pyrazol-3-yl group can be prepared for example as depicted in Scheme 29. Cross-coupling of intermediates C96, either commercially available or prepared according to literature procedures, with intermediates C6, applying the methods described under Scheme 22 (step a), yields intermediates C97 (step a). The acetyl group in intermediates C97 can be transformed into a 3-dimethyl-amino-acryloyl group applying published procedures, for example by reaction with N,N-dimethylformamide dimethyl acetal, preferentially at elevated temperatures, to give intermediates C98 (step b). Reaction of C98 with tert-butyl hydrazine in a suitable solvent such as ethanol or methanol or similar, preferably at elevated temperatures furnishes pyrazole intermediates C99 (step c). Chemoselective removal of the phenol protective group PG in intermediates C99 by applying an orthogonal protective group strategy as outlined before provides intermediates C100 (step d).

Alkylation of the phenol group of C100 with the desired head group A2 as described under Scheme 1 and subsequent removal of the tert-butyl protecting group of the pyrazole by methods known in the art and as described for example in "Protective Groups in Organic Chemistry" by T. W. Greene and P. G. M. Wutts, 5th Ed., 2014, John Wiley & Sons, N.Y. (e.g. a tert-butyl group under acidic conditions such as HCl in dioxane in a suitable solvent such as dichloromethane) furnishes the final products of formula A3.

Scheme 29:

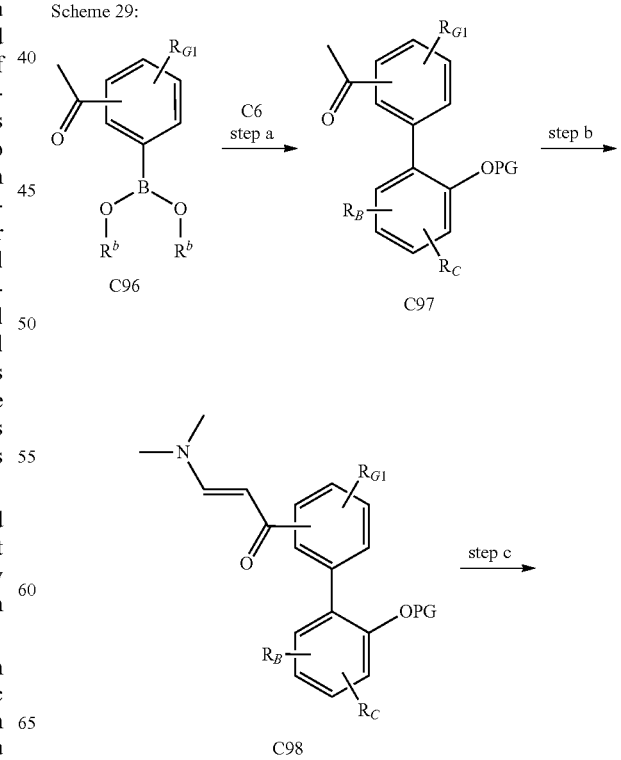

89

-continued

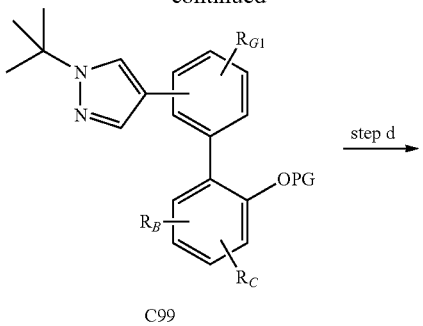

C99

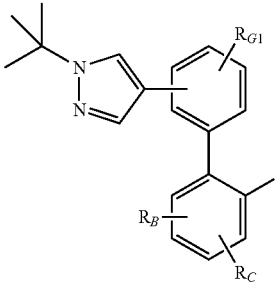

C100

$R^b$ = e.g. H, Me, "pinacol"
PG = Protective group

Also an embodiment of the present invention is a process to prepare a compound of formula (I) as defined above comprising the reaction of a compound of formula (II) in the presence of a compound of formula (III);

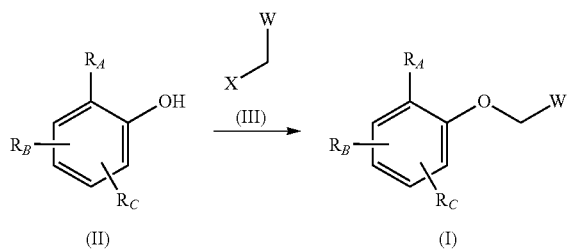

wherein $R_A$, $R_B$, $R_C$ and W are as defined herein and X is halogen, mesylate or tosylate.

In particular, in the presence of a base, particularly in the presence of potassium carbonate, optionally in the presence of potassium iodide, in a solvent such as acetone and at a temperature comprised between −78° C. and reflux, particularly between room temperature and reflux.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis of ocular conditions, particularly glaucoma.

The present invention also relates to the use of a compound according to formula (I) as described herein for the preparation of a medicament for the treatment or prophylaxis of ocular conditions, particularly glaucoma.

90

Also an object of the invention is a method for the treatment or prophylaxis of ocular conditions, particularly glaucoma, which method comprises administering an effective amount of a compound according to formula (I) as described herein.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

Also an embodiment of the present invention provides compounds of formula (I) as described herein, when manufactured according to any one of the described processes.

Assay Procedures

Production of Human Full Length ATX, with and Without His Tag

Autotaxin (ATX—ENPP2) cloning: cDNA was prepared from commercial human hematopoietic cells total RNA and used as template in overlapping PCR to generate a full length human ENPP2 ORF with or without a 3'-6xHis tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6xHis tag.

ATX Fermentation: Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification: 20 liter of culture supernatant were conditioned for ultrafiltration by adding Brij 35 to a final concentration of 0.02% and by adjusting the pH to 7.0 using 1 M HCl. Then the supernatant was first microfiltered through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylmino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row O. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo 630/690 nm) and $IC_{50}$ values were calculated from these readouts.

| Example | ATX Ic50 [µM] |
| --- | --- |
| A 1 | 0.002 |
| A 2 | 0.01 |
| A 3 | 0.025 |
| A 4 | 0.059 |
| A 6 | 0.523 |
| A 7 | 0.013 |
| A 8 | 1.6 |
| A 9 | 2.613 |
| A 10 | 0.104 |
| A 11 | 0.015 |
| A 12 | 0.001 |
| A 13 | 0.002 |

| Example | ATX Ic50 [μM] |
|---|---|
| A 14 | 1.891 |
| A 15 | 0.23 |
| A 16 | 0.005 |
| A 17 | 0.035 |
| A 19 | 0.015 |
| A 20 | 0.008 |
| A 21 | 0.062 |
| A 22 | 0.173 |
| A 23 | >27 |
| A 24 | 0.091 |
| A 25 | 0.958 |
| A 26 | 0.012 |
| A 27 | 0.019 |
| A 28 | 0.005 |
| A 29 | 0.05 |
| A 30 | 0.009 |
| A 31 | 0.019 |
| A 32 | 3.768 |
| A 34 | 0.028 |
| B 1 | 0.003 |
| B 2 | 0.001 |
| B 3 | 0.001 |
| B 4 | 0.006 |
| B 5 | 0.003 |
| B 6 | 0.008 |
| B 7 | 4.195 |
| B 8 | 0.01 |
| B 9 | 0.012 |
| B 10 | 0.023 |
| B 11 | 0.166 |
| B 12 | 0.022 |
| B 13 | 0.006 |
| B 14 | 0.079 |
| B 15 | 0.011 |
| B 16 | 0.025 |
| B 17 | 0.016 |
| B 18 | 0.052 |
| B 19 | 0.065 |
| B 20 | 0.913 |
| B 21 | 0.104 |
| B 22 | 0.227 |
| B 23 | 0.212 |
| B 24 | 0.126 |
| B 25 | 0.02 |
| B 26 | 0.495 |
| B 27 | 3.717 |
| B 28 | 5.941 |
| B 29 | 0.078 |
| B 30 | 0.467 |
| B 31 | 0.043 |
| B 32 | 0.031 |
| B 33 | 0.115 |
| B 34 | 0.051 |
| B 35 | 0.081 |
| B 36 | 0.082 |
| B 37 | 0.079 |
| B 38 | 0.008 |
| B 39 | 0.093 |
| B 40 | 0.015 |
| B 41 | 0.040 |
| B 42 | 0.021 |
| B 43 | 1.102 |
| B 44 | 0.013 |
| B 45 | 0.029 |
| B 46 | 0.007 |
| B 47 | 0.082 |
| B 48 | 0.192 |
| B 49 | 0.008 |
| B 50 | 0.173 |
| B 51 | 0.017 |
| B 52 | 0.012 |
| B 53 | 0.042 |
| B 54 | 0.029 |
| B 55 | 0.009 |
| B 56 | 0.015 |
| B 57 | 0.011 |
| B 58 | 0.016 |
| B 59 | 0.025 |
| B 60 | 0.011 |
| B 61 | 0.01 |
| B 62 | 0.009 |
| B 63 | 0.01 |
| B 64 | 0.021 |
| B 65 | 0.013 |
| B 66 | 0.007 |
| B 67 | 0.006 |
| B 68 | 0.007 |
| B 69 | 0.009 |
| B 70 | 0.004 |
| B 71 | 0.009 |
| B 72 | 0.010 |
| B 73 | 0.009 |
| B 74 | 0.006 |
| B 75 | 0.01 |
| B 76 | 0.011 |
| B 77 | 0.015 |
| B 78 | 0.007 |
| B 79 | 0.010 |
| B 80 | 0.005 |
| B 81 | 0.003 |
| B 82 | 0.008 |
| B 83 | 0.008 |
| B 84 | 0.019 |
| B 85 | 0.021 |
| B 86 | 0.049 |
| B 87 | 0.005 |
| B 88 | 0.001 |
| B 89 | 0.004 |
| B 90 | 0.007 |
| B 91 | 0.004 |
| B 92 | 0.001 |
| B 93 | 0.005 |
| B 94 | 0.005 |
| B 95 | 0.006 |
| B 96 | 0.037 |
| B 97 | 0.008 |
| B 98 | 0.009 |
| C 1 | 0.019 |
| C 2 | 0.022 |
| C 3 | 0.004 |
| C 4 | 0.003 |
| C 5 | 0.001 |
| C 6 | 0.007 |
| C 7 | 0.022 |
| C 8 | 0.005 |
| C 9 | 0.046 |
| C 10 | 0.032 |
| C 11 | 5.978 |
| C 12 | 0.003 |
| C 13 | 0.04 |
| C 14 | 0.005 |
| D 1 | 244.592 |
| D 2 | 0.014 |
| D 3 | 0.004 |
| D 4 | 0.009 |
| D 5 | 0.001 |
| D 6 | 0.019 |
| D 7 | 0.012 |
| D 8 | 0.006 |
| D 9 | 0.215 |
| D 10 | >82 |
| D 11 | 0.0045 |
| D 12 | 0.001 |
| D 13 | 13.186 |
| D 14 | 0.013 |
| D 15 | 0.006 |
| D 16 | 0.018 |
| D 17 | 0.002 |
| D 18 | 0.017 |
| D 19 | 0.035 |
| D 20 | 0.022 |
| D 21 | 0.009 |

-continued

| Example | ATX IC50 [µM] |
|---|---|
| D 22 | 0.01 |
| D 23 | 0.021 |
| D 24 | 0.099 |
| D 25 | 0.018 |
| D 26 | 0.014 |
| D 27 | 0.008 |
| D 28 | 0.098 |
| D 29 | 0.01 |
| D 30 | 0.009 |
| D 31 | 0.007 |
| D 32 | 0.008 |
| D 33 | 0.006 |
| D 34 | 0.002 |
| D 35 | 0.009 |
| D 36 | 0.008 |
| D 37 | 0.006 |
| D 38 | 0.009 |
| D 39 | 0.008 |
| D 40 | 0.006 |
| D 41 | 0.007 |
| D 42 | 0.006 |
| D 43 | 0.007 |
| D 44 | 0.009 |
| D 45 | 0.023 |
| D 46 | 0.004 |
| D 47 | 0.011 |
| D 48 | 0.032 |
| D 49 | 0.002 |
| D 50 | 0.001 |
| D 51 | 0.069 |
| D 52 | 0.002 |
| D 53 | 0.008 |
| D 54 | 0.028 |
| D 55 | 0.003 |
| E 1 | 0.746 |
| E 2 | 41.319 |
| E 3 | 80.381 |
| E 4 | 0.019 |
| E 5 | 0.017 |
| E 6 | 0.015 |
| E 7 | 0.202 |
| E 8 | 0.069 |
| F 1 | 0.027 |
| F 2 | 0.018 |
| F 3 | 0.01 |
| F 4 | 0.008 |
| F 5 | 0.015 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragees, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS:=Chemical Abstracts Service Registry Number; HPLC=high performance liquid chromatography; MS=mass spectrum; sat.=saturated; rt=room temperature; TLC=thin layer chromatography; NMR: nuclear magnetic resonance spectrum;

Intermediates A

Intermediate A2:

2-tert-Butyl-4-chloro-5-fluorophenol

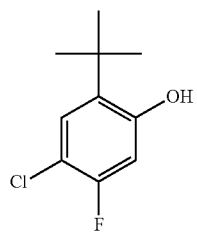

To a solution of 4-chloro-3-fluorophenol (CAS: 2713-33-9; 1.14 g) in acetic acid (6.0 mL) were added tert-butanol (1.73 g), followed by sulfuric acid (1.53 g) at rt under an argon atmosphere. The mixture was then heated to 80° C. for 17 hours. TLC showed that the reaction was not complete and thus the reaction was refluxed (88° C.) for another 30 hours. While there was still some starting material visible on TLC, the reaction mixture was cooled down to rt and poured into ice/water. The aqueous phase was then extracted two times with ethyl acetate and the combined organic layers were washed with brine, dried over $Na_2SO_4$, filtered and evaporated. The crude material was purified by flash chromatography on silica gel with a gradient of 0% to 25% EtOAc in heptane as an eluent, to provide the title compound as a brown liquid (320 mg). MS (m/z): 201.1 [M−H]⁻.

Intermediate A4:

2-tert-Butyl-4-(3-methyl-1,2,4-oxadiazol-5-yl)phenol

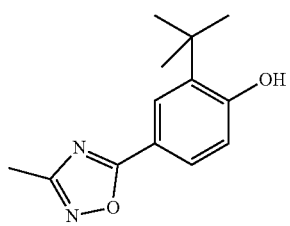 [SMILES: Cc1noc(-c2ccc(O)c(C(C)(C)C)c2)n1]

Step 1: 1-Benzyloxy-4-bromo-2-tert-butyl-benzene

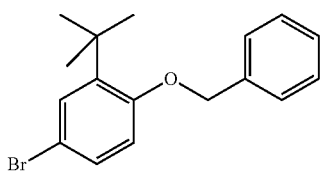 [SMILES: CC(C)(C)c1cc(Br)ccc1OCc1ccccc1]

This material which is known in the literature (CAS: 33839-2-2) was made as follows:

To a solution of 4-bromo-2-tert-butyl-phenol (CAS: 10323-39-4; 8 g) in anhydrous acetonitrile (150 mL) was added $Cs_2CO_3$ (22.7 g) followed by benzyl bromide (6.26 mL) at 25° C. and the mixture was stirred at 85° C. for 3 h. The reaction mixture was cooled to 25° C., filtered and the filtrate was evaporated under reduced pressure. The resulting residue was purified by column chromatography over silica gel (gradient of 3-5% ethyl acetate in hexanes) to provide 1-benzyloxy-4-bromo-2-tert-butyl-benzene (11.0 g) as an off white solid. ¹H-NMR (400 MHz, δ, DMSO-D₆): 1.32 (s, 9H), 5.14 (s, 2H), 7.04 (d, 1H), 7.28-7.50 (m, ~7H).

Step 2: 4-Benzyloxy-3-tert-butyl-benzonitrile

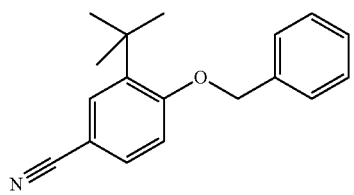 [SMILES: CC(C)(C)c1cc(C#N)ccc1OCc1ccccc1]

This material which is known in the literature (CAS: 847943-59-3) was made as follows:

To a solution of 1-benzyloxy-4-bromo-2-tert-butyl-benzene (4.5 g) in anhydrous DMF (100 mL) were added $Zn(CN)_2$ (3.30 g), dppf (782 mg) and Zn (229 mg) under argon atmosphere and the reaction mixture was purged with argon for 10 minutes. Then, $Pd_2(dba)_3$ (645 mg) was added at 25° C. and the reaction mixture was purged again with argon for 10 min. The mixture was then stirred at 110° C. for 16 h. The mixture was cooled, filtered and the filtrate was evaporated under reduced pressure. The residue was purified by column chromatography over silica gel (5-7% ethyl acetate in hexanes) to afford the title compound (3.2 g) as an off white solid. MS (m/z): 265.0 [M]⁺.

Step 3: 4-Benzyloxy-3-tert-butyl-benzoic acid

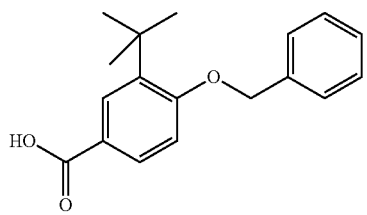 [SMILES: CC(C)(C)c1cc(C(=O)O)ccc1OCc1ccccc1]

This material which is known in the literature (CAS: 146852-63-3) was made as follows:

To a solution of 4-benzyloxy-3-tert-butyl-benzonitrile (800 mg) in MeOH (30 mL) was added 6N aq. NaOH solution (40 mL) at 25° C. and the reaction mixture was refluxed for 16 h. The mixture was cooled to 25° C. and the solvent was evaporated under reduced pressure. The resulting residue was diluted with water, acidified with conc. HCl and extracted with EtOAc (2×50 ml). The combined organic layers were washed with brine, dried over $Na_2SO_4$ and evaporated under reduced pressure to afford the title compound (830 mg) as a brown solid. MS (m/z): 285.2 [M+H]⁻.

Step 4: 4-Benzyloxy-3-tert-butyl-benzoic acid methyl ester

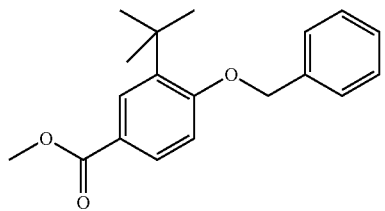 [SMILES: COC(=O)c1ccc(OCc2ccccc2)c(C(C)(C)C)c1]

This material which is known in the literature (CAS: 146852-62-2) was made as follows:

To a solution of 4-benzyloxy-3-tert-butyl-benzoic acid (830 mg) in anhydrous DMF (30 mL) at 25° C. were added $Cs_2CO_3$ (1.9 g) followed iodomethane (0.273 mL) and the reaction mixture was stirred at 25° C. for 3 h. The reaction mixture was then filtered and the filtrate was evaporated under reduced pressure. The residue was purified by column chromatography over silica gel (gradient of 3-5% ethyl acetate in hexanes) to afford the title compound (740 mg) as an off white solid. MS (m/z): 299.3 $[M+H]^+$.

Step 5: 5-(4-Benzyloxy-3-tert-butyl-phenyl)-3-methyl-[1,2,4]oxadiazole

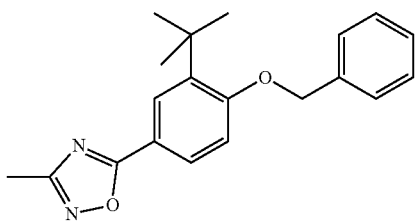 [SMILES: Cc1noc(-c2ccc(OCc3ccccc3)c(C(C)(C)C)c2)n1]

To a solution of 4-benzyloxy-3-tert-butyl-benzoic acid methyl ester (740 mg) and N-hydroxy-acetamidine (229.7 mg) in anhydrous DMF (30 mL) was added NaH (218 mg) in portions at 25° C. and the reaction mixture was stirred at 25° C. for 3 h. The mixture was then quenched with water and extracted with EtOAc (2×50 mL). The combined organic layers were washed with brine, dried over $Na_2SO_4$, filtered and evaporated under reduced pressure. The residue was purified by column chromatography over silica gel (gradient of 7-10% EtOAc in hexane) to afford the title compound (650 mg) as an off white solid. MS (m/z): 323.0 $[M+H]^-$.

Step 6: 2-tert-Butyl-4-(3-methyl-[1,2,4]oxadiazol-5-yl)-phenol

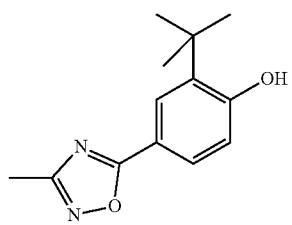 [SMILES: Cc1noc(-c2ccc(O)c(C(C)(C)C)c2)n1]

To a solution of 5-(4-benzyloxy-3-tert-butyl-phenyl)-3-methyl-[1,2,4]oxadiazole (300 mg) in anhydrous DCM (30 mL) kept at −78° C. was added $BBr_3$ (1M solution in DCM, 2.79 mL) and the reaction mixture was stirred at −78° C. for 2 h. The mixture was quenched with saturated aqueous $NaHCO_3$ solution (20 mL) and was extracted with DCM (2×30 mL). The combined organic layers were washed with brine, dried over $Na_2SO_4$ and evaporated under reduced pressure. The residue was purified by column chromatography over silica gel (gradient of 5-20% EtOAc in hexanes) to afford the title compound (150 mg) as an off white solid. MS (m/z): 233.2 $[M+H]^+$.

Intermediate A5:

2-tert-Butyl-4-[1-(2-trimethylsilylethoxymethyl)imidazol-2-yl]phenol

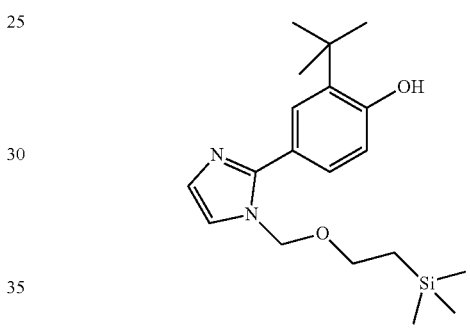

Step 1: 2-(4-Benzyloxy-3-tert-butyl-phenyl)-4,5-dihydro-1H-imidazole

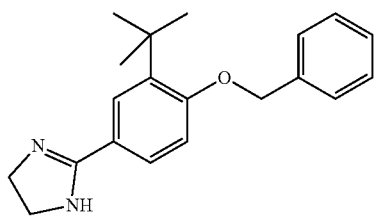 [SMILES: CC(C)(C)c1cc(C2=NCCN2)ccc1OCc1ccccc1]

To a solution of 4-benzyloxy-3-tert-butyl-benzonitrile (1.4 g), obtained in intermediate A1, Step 2, in ethylenediamine (20 mL) in a sealed tube was added $P_2S_5$ (0.985 mg) at 25° C. and the reaction mixture was kept under pressure with stirring at 120° C. for 2 h. The reaction mixture was cooled to 25° C. and was then poured into water (100 mL). The mixture was stirred for 30 minutes and the resulting precipitate was collected by filtration and dried in vacuo to afford the title compound (1.45 g) as an off white solid. MS (m/z): 308.9 $[M+H]^+$.

Step 2: 2-(4-Benzyloxy-3-tert-butyl-phenyl)-1H-imidazole

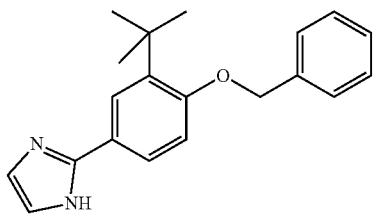 [SMILES: CC(C)(C)c1cc(-c2ncc[nH]2)ccc1OCc1ccccc1]

To a solution of 2-(4-benzyloxy-3-tert-butyl-phenyl)-4,5-dihydro-1H-imidazole (1.4 g) in DMSO (50 mL) were added potassium carbonate (690 mg) and diacetoxy-iodobenzene (1.61 g) and the reaction mixture was stirred at 25° C. for 16 h in the dark. The mixture was then diluted with water and was extracted with dichloromethane (2×40 mL). The combined organic layers were dried over $Na_2SO_4$, filtered and concentrated in vacuo. The residue was purified by column chromatography over amino silica gel (gradient of 33-40% EtOAc in hexanes) to afford the title compound (805 mg) as an off white solid. MS (m/z): 306.8 $[M+H]^+$.

Step 3: 2-(4-Benzyloxy-3-tert-butyl-phenyl)-1-(2-trimethylsilanyl-ethoxymethyl)-1H-imidazole

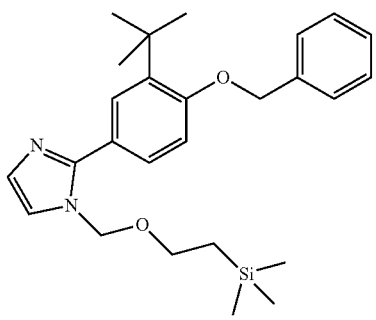 [SMILES: CC(C)(C)c1cc(-c2nccn2COCC[Si](C)(C)C)ccc1OCc1ccccc1]

To a suspension of NaH (16 mg) in anhydrous DMF (10 mL) at 0° C. was added a solution of 2-(4-benzyloxy-3-tert-butyl-phenyl)-1H-imidazole (500 mg) in anhydrous DMF (5 mL) and the reaction mixture was stirred at 25° C. for 30 minutes. Then, SEM-chloride (0.087 ml) was added dropwise at 25° C. and the reaction mixture was stirred at 25° C. for 2 h. The mixture was then quenched with water and was extracted with EtOAc (2×50 mL). The combined organic layers were washed with brine, dried over $Na_2SO_4$ and evaporated in vacuo. The residue was purified by column chromatography over silica gel (gradient of 30-40% ethyl acetate in hexanes) to afford the title compound (310 mg) as a sticky, colorless liquid. MS (m/z): 436.9 $[M]^+$.

Step 4: 2-tert-Butyl-4-[1-(2-trimethylsilanyl-ethoxymethyl)-1H-imidazol-2-yl]-phenol

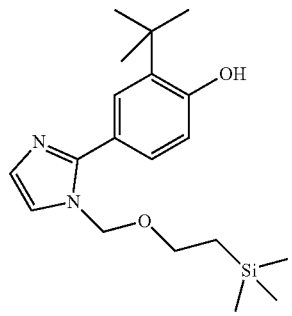 [SMILES: CC(C)(C)c1cc(-c2nccn2COCC[Si](C)(C)C)ccc1O]

A solution of 2-(4-benzyl oxy-3-tert-butyl-phenyl)-1-(2-trimethylsilanyl-ethoxymethyl)-1H-imidazole (300 mg) in MeOH (20 mL) was purged with argon for 10 min and then $Pd(OH)_2$ (100 mg) was added. An atmosphere of hydrogen was introduced and the reaction mixture was stirred under $H_2$ at 25° C. for 6 h. The mixture was filtered and the filtrate was evaporated in vacuo to afford the title compound (200 mg) as an off white solid. MS (m/z): 347.0 $[M+H]^-$.

Intermediate A6

2-tert-Butyl-4-(1-methylimidazol-2-yl)phenol

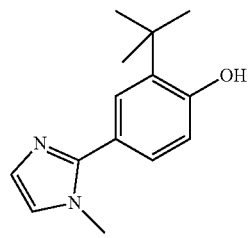 [SMILES: Cn1ccnc1-c1ccc(O)c(C(C)(C)C)c1]

Step 1: 2-(4-Benzyloxy-3-tert-butyl-phenyl)-1-methyl-1H-imidazole

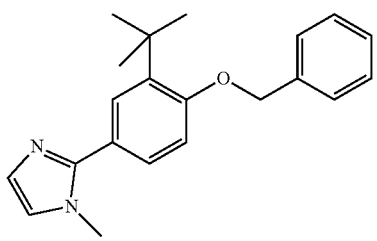 [SMILES: Cn1ccnc1-c1ccc(OCc2ccccc2)c(C(C)(C)C)c1]

A suspension of NaH (60% in mineral oil, 31 mg) in anhydrous THF (15 mL) was cooled to 0° C. and a solution of 2-(4-benzyloxy-3-tert-butyl-phenyl)-1H-imidazole (200 mg), obtained in Intermediate A5, Step 2, in THF (20 mL) was then added at 0° C. The reaction mixture was stirred at 0° C. for 30 min and then iodomethane (0.049 mL) was added at 0° C. Stirring was continued at 0° C. for 3 h. The mixture was quenched with water and was extracted with EtOAc (2×50 mL). The combined organic layers were washed with brine, dried over Na$_2$SO$_4$, filtered and evaporated under reduced pressure. The residue was purified by column chromatography over silica gel (gradient of 60-70% EA in hexanes) to afford the title compound (175 mg) as a sticky solid. MS (m/z): 320.8 [M+H]$^+$.

Step 2:
2-tert-Butyl-4-(1-methylimidazol-2-yl)phenol

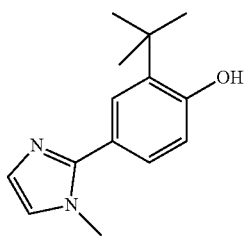 [SMILES: Cn1ccnc1-c1ccc(O)c(C(C)(C)C)c1]

The title compound was obtained from 2-(4-benzyloxy-3-tert-butyl-phenyl)-1-methyl-1H-imidazole in analogy to Intermediate 5, Step 4 as an off white solid. MS (m/z): 230.7 [M+H]$^+$.

Intermediate A7

2-tert-Butyl-4-(1,3-oxazol-2-yl)phenol

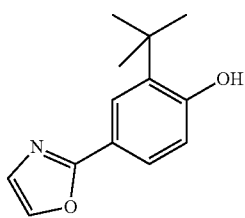 [SMILES: CC(C)(C)c1cc(-c2ncco2)ccc1O]

Step 1:
2-(3-tert-Butyl-4-methoxymethoxy-phenyl)-oxazole

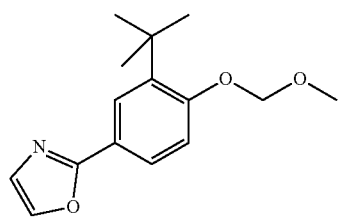 [SMILES: COCOc1ccc(-c2ncco2)cc1C(C)(C)C]

A solution of 4-bromo-2-tert-butyl-1-methoxymethoxy-benzene (500 mg, made from 4-bromo-2-tert-butyl-phenol according to WO2013079223) and 2-tributylstannanyl-oxazole (0.92 mL) in anhydrous dioxane (10 mL) in a sealed tube was purged with argon for 10 min. Then, PdCl$_2$(dppf)$_2$CH$_2$Cl$_2$ complex (149.5 mg) was added and the reaction mixture was purged again with argon for 10 min. The mixture was then stirred at 100° C. for 4 h and was then cooled to 25° C., filtered and the filtrate was evaporated under reduced pressure. The residue was purified by column chromatography over silica gel (gradient of 5-10% ethyl acetate in hexanes) to afford the title compound (350 mg) as a light brown liquid. MS (m/z): 262.8 [M+H]$^+$.

Step 2: 2-tert-Butyl-4-oxazol-2-yl-phenol

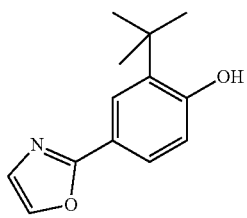 [SMILES: CC(C)(C)c1cc(-c2ncco2)ccc1O]

To a solution of 2-(3-tert-butyl-4-methoxymethoxy-phenyl)-oxazole (200 mg) in anhydrous DCM (10 mL) at 0-5° C. was added 4N HCl in dioxane (2.5 mL) and the reaction mixture was stirred at 25° C. for 28 h. The solvent was evaporated under reduced pressure and the residue was purified by column chromatography over silica gel (gradient of 8-15% ethyl acetate in hexanes) to afford the title compound (120 mg) as an off white solid. MS (m/z): 217.9 [M+H]$^+$.

Intermediate A8

2-tert-Butyl-4-morpholin-4-ylphenol

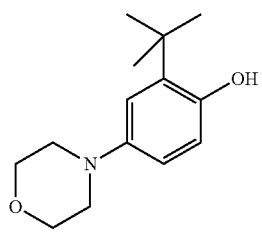 [SMILES: CC(C)(C)c1cc(N2CCOCC2)ccc1O]

Step 1: 4-(3-tert-Butyl-4-methoxymethoxy-phenyl)-morpholine

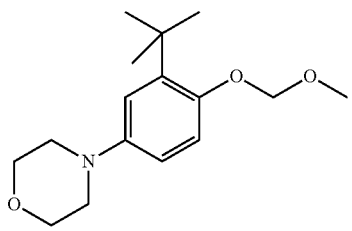 [SMILES: COCOc1ccc(N2CCOCC2)cc1C(C)(C)C]

To a solution of 4-bromo-2-tert-butyl-1-methoxymethoxy-benzene (900 mg, made from 4-bromo-2-tert-butyl-phenol according to WO2013079223) and morpholine (0.44 mL) in anhydrous toluene (10 mL) in a sealed tube were added NaOtBu (475 mg) and xantphos (76.2 mg) at 25° C. The tube was purged with argon for 10 min and then Pd$_2$(dba)$_3$ (60.3 mg) was added and the tube was again purged with argon for 10 min. Then, the mixture was stirred under pressure for 16 at 110° C. and was then cooled to 25° C. and filtered. The filtrate was evaporated under reduced pressure and the resulting crude material was purified by column chromatography (gradient of 7-10% ethyl acetate in hexanes) to afford the title compound (560 mg) as a sticky liquid. ¹H-NMR (400 MHz, δ, CDCl₃): 1.38 (s, 9H), 3.04-3.10 (m, 4H), 3.48 (s, 3H), 3.80-3.90 (m, 4H), 5.17 (s, 2H), 6.69 (dd, 1H), 6.93 (d, 1H), 7.04 (d, 1H).

Step 2: 2-tert-Butyl-4-morpholin-4-yl-phenol

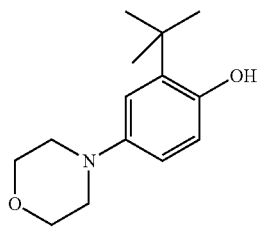

The title compound was obtained from 4-(3-tert-butyl-4-methoxymethoxy-phenyl)-morpholine using the conditions described in Intermediate A7, Step 2, as an off white solid. MS (m/z): 235.9 [M+H]⁺.

Intermediate A9

2-tert-Butyl-4-(1-methyl-1H-imidazol-2-yl)-phenol

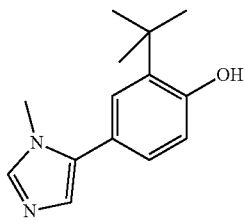 [SMILES: Cn1cncc1-c1ccc(O)c(C(C)(C)C)c1]

To a solution of 4-bromo-2-tert-butyl-phenol (CAS: 10323-39-4, 200 mg) and 1-methyl-5-(4,4,5,5-tetramethyl-[1,3,2]dioxaborolan-2-yl)-1H-imidazole (272 mg) in anhydrous DMF (10 mL) was added K₂CO₃ (362 mg) at 25° C. under a nitrogen atmosphere. The reaction mixture was purged with argon for 10 min, and then PdCl₂(dppf)₂ DCM complex (14.2 mg) was added. The vessel was again purged with argon for 10 min and the reaction mixture was stirred at 120° C. for 28 h. The mixture was cooled to 25° C., filtered and the filtrate was evaporated under reduced pressure. The residue was purified by column chromatography over silica gel (gradient of 2-5% MeOH in DCM) to afford the title compound (124 mg) as a brown solid. MS (m/z): 230.9 [M+H]⁺.

Intermediate A10

2-tert-butyl-4-(5-methyl-1,3,4-oxadiazol-2-yl)phenol

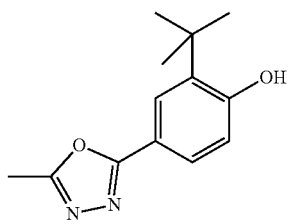 [SMILES: Cc1nnc(-c2ccc(O)c(C(C)(C)C)c2)o1]

Step 1: 3-tert-Butyl-4-hydroxy-benzoic acid methyl ester

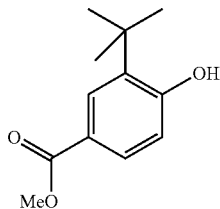

To a solution of 3-tert-butyl-4-hydroxy-benzoic acid (CAS: 66737-88-0, 3 g) in anhydrous MeOH (40 mL) was added dropwise conc. H₂SO₄ (0.4 mL) at 25° C. and the reaction mixture was stirred at reflux for 16 h. Then, the solvent was evaporated under reduced pressure. The residue was diluted with DCM (50 mL) and the solution was washed with water and brine, dried over Na₂SO₄ and filtered. The filtrate was evaporated under reduced pressure and the residue was purified by column chromatography over silica gel (gradient of 0.5-1% MeOH in DCM) to afford the title compound (2.8 g) as an off white solid. MS (m/z): 209.4 [M+H]⁺.

Step 2: 3-tert-Butyl-4-hydroxy-benzoic acid hydrazide

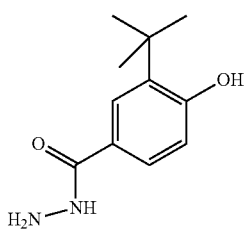

To a solution of 3-tert-butyl-4-hydroxy-benzoic acid methyl ester (3.7 g) in anhydrous MeOH (40 mL) in a sealed tube was added hydrazine hydrate (4.36 mL) at 25° C. and the reaction mixture was heated under pressure at to 65° C. for 16 h. The mixture was then cooled to 25° C. and the solvent was evaporated under reduced pressure. The residue was purified by column chromatography over silica gel (gradient of 2-4% MeOH in DCM) to afford the title compound (2.8 g, 75%) as off white solid. MS (m/z): 209.1 [M+H]⁺.

Step 3: 2-tert-butyl-4-(5-methyl-1,3,4-oxadiazol-2-yl)phenol

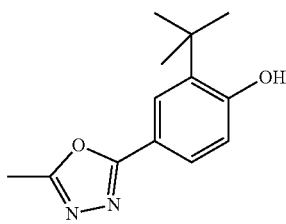 [SMILES: Cc1nnc(-c2ccc(O)c(C(C)(C)C)c2)o1]

To a suspension of 3-tert-butyl-4-hydroxy-benzoic acid hydrazide (1.5 g) in triethyl orthoacetate (25 mL) was heated to reflux at 150° C. for 7 h. The reaction mixture was then cooled to 25° C. and the solvent was evaporated under reduced pressure. The residue was diluted with DCM (50 mL) and was washed with water and brine. The organic layer was dried over Na$_2$SO$_4$, filtered, and evaporated under reduced pressure. The crude material was purified by column chromatography over silica gel (gradient of 2-3% MeOH in DCM) to afford the title compound (1.15 g) as an off white solid. MS: 233.1 [M+H]$^+$.

Intermediate A14:

4-Chloro-2-cyclopropyl-5-methylsulfonylphenol

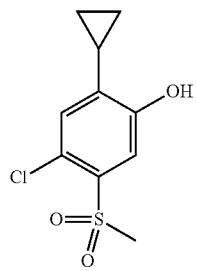

Step 1: 1-Bromo-2-chloro-5-fluoro-4-nitrobenzene

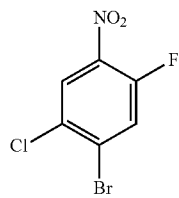 [SMILES: O=[N+]([O-])c1cc(Cl)c(Br)cc1F]

To a stirred solution of 2-bromo-1-chloro-4-fluorobenzene (CAS: 201849-15-2; 10 g) in sulfuric acid (95-97%; 100 mL) was gradually added potassium nitrate (5.82 g) at −5° C. The reaction mixture was stirred at −5° C. for 1.5 hours and was then poured on 400 mL ice-water. The precipitate was filtered and dried in vacuo to provide the title compound as a colorless solid (11.54 g). MS (m/z): 253 [M]$^+$.

Step 2:
1-Bromo-2-chloro-5-methoxy-4-nitrobenzene

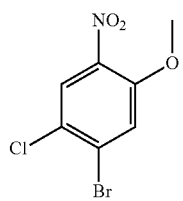

To a solution of 1-bromo-2-chloro-5-fluoro-4-nitrobenzene (11.0 g) in methanol (110 mL) was slowly added sodium methoxide (2.45 g) at 0° C. and the reaction mixture was stirred at 0° C. for 1.5 hours. The suspension was poured on water and was extracted with EtOAc. The combined organic extracts were dried with MgSO$_4$, filtered and concentrated in vacuo to provide the title compound as a yellow solid (11.2 g). MS (m/z): 265 [M]$^+$.

Step 3:
1-Chloro-4-methoxy-2-methylsulfonyl-5-nitrobenzene

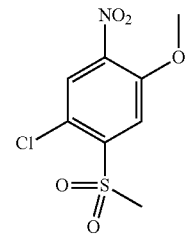 [SMILES: COc1cc(S(C)(=O)=O)c(Cl)cc1[N+](=O)[O-]]

To a solution of L-proline (61.3 mg) in DMSO (2 mL) was added sodium hydroxide (24.0 mg) and the mixture was stirred at rt for 30 minutes. Copper(I)iodide (114 mg), 1-bromo-2-chloro-5-methoxy-4-nitrobenzene (0.20 g) and sodium methanesulfinate (173 mg) were added. The reaction mixture was heated to 60° C. to give a turbid blue solution. After 5 hours, the reaction was allowed to cool down to room temperature. The mixture was poured on 50 mL 10% aqueous NaHCO$_3$ solution and 50 mL EtOAc and the layers were filtered to remove any precipitates. The filtrated layers were then separated. The aqueous layer was extracted a second time with 50 mL EtOAc and the organic layers were washed with 50 mL brine, dried over MgSO$_4$, filtered and concentrated in vacuo to give the title compound as a yellow solid (122 mg). MS (m/z): 265 [M]$^+$.

Step 4:
5-Chloro-2-methoxy-4-methylsulfonylaniline

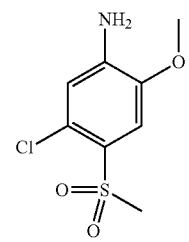

To a mixture of ethanol (2.00 mL) and water (2.00 mL) was added acetic acid (140 µL) and this mixture was stirred under reflux for 10 minutes. To the solution thus obtained was added iron (163 mg) and 1-chloro-4-methoxy-2-methylsulfonyl-5-nitrobenzene (200 mg) and the mixture was stirred for additional 20 minutes. After cooling, 20 mL of acetone was added and the iron was filtered off through a pad of dicalite and washed with 20 mL of acetone. The filtrate was concentrated in vacuo and the residue was purified by silica gel chromatography, eluting with a gradient of n-heptane in ethyl acetate (100/0 to 50/50). This provided the title compound as white crystals (177 mg). MS (m/z): 235 [M]$^-$.

Step 5:
1-Chloro-5-iodo-4-methoxy-2-methylsulfonylbenzene

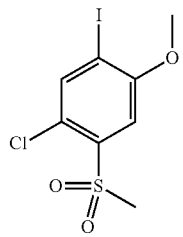

To a suspension of 5-chloro-2-methoxy-4-methylsulfonylaniline (1.50 g) in semi-concentrated HCl (18.5%, 15.1 g) was added dropwise at 0-5° C. a solution of sodium nitrite (461 mg) in water (3.66 mL). The initial suspension gradually cleared and turned nearly into a solution. This mixture was stirred for 1 hour at 0° C. and was then added dropwise to a stirred suspension of potassium iodide (3.17 g) in aq. HBr (48%, 21.0 mL) at rt. Stirring was continued for 30 minutes at rt. The reaction mixture was poured on 100 mL 2M aqueous $Na_2CO_3$ solution and 50 mL EtOAc and the layers were separated. The aqueous layer was extracted and a second time with 100 mL EtOAc. The organic layers were washed with $Na_2S_2O_3$ and brine (50 mL), dried over $MgSO_4$, filtered and concentrated in vacuo. The residue was purified by silica gel chromatography, eluting with a gradient of n-heptane in ethyl acetate (100/0 to 50/50) to provide the title compound as a light yellow solid (950 mg). MS (m/z): 346 $[M]^+$.

Step 6: 4-Chloro-2-iodo-5-methylsulfonylphenol

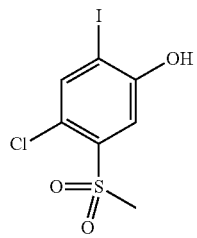

To a solution of 1-chloro-5-iodo-4-methoxy-2-methylsulfonylbenzene (750 mg) in AcOH (15.6 g) was added aqueous HBr (48%, 4.7 ml) and the clear, colorless solution was stirred at reflux for 4 days in a sealed tube. The reaction mixture was cooled, poured on 100 mL water and 100 mL EtOAc and the layers were separated. The aqueous layer was extracted a second time with 100 mL EtOAc. The organic layers were washed with 100 mL brine, dried over $MgSO_4$, filtered and concentrated in vacuo. The compound was purified by silica gel chromatography, eluting with a gradient of n-heptane in ethyl acetate (100/0 to 60/40) to give the title compound as a light yellow solid (625 mg). MS (m/z): 330.87 $[M-H]^-$.

Step 7:
4-Chloro-2-cyclopropyl-5-methylsulfonylphenol

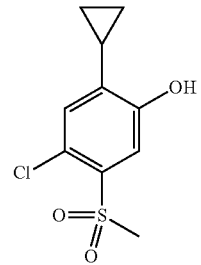

To a suspension of 4-chloro-2-iodo-5-methylsulfonylphenol (200 mg) in toluene (3 mL) were added under argon potassium cyclopropyltrifluoroborate (178 mg), water (0.21 mL), cesium carbonate (490 mg), palladium (II) acetate (6.75 mg) and butyldi-1-adamantylphosphine (21.6 mg) and the mixture was stirred in a sealed tube at 125° C. for 66 hours. The reaction mixture was cooled and poured on sat. aqueous $NH_4Cl$ solution and ethyl acetate and the layers were separated. The aqueous layer was extracted twice with additional ethyl acetate. The organic layers were dried over $MgSO_4$, filtered, treated with silica gel and evaporated. The compound was purified by silica gel chromatography, eluting with a gradient of n-heptane in ethyl acetate (100/0 to 50/50) to provide the title compound as a colorless solid (72 mg). MS (m/z): 245 $[M]^+$.

Intermediate A15:

2-tert-Butyl-4-methylsulfonylphenol

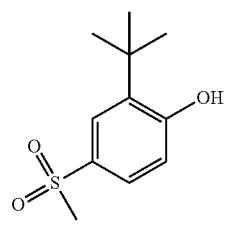

Step 1:
4-Bromo-2-tert-butyl-1-phenylmethoxybenzene

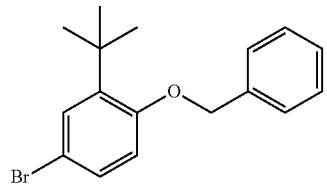 [SMILES: CC(C)(C)c1cc(Br)ccc1OCc1ccccc1]

To a solution of 4-bromo-2-tert-butylphenol (CAS: 10323-39-4; 500 mg) in DMF (5 mL) was added NaH (114 mg) and the reaction mixture was stirred for 10 minutes at rt. Then, benzylchloride (290 mg) was added and the reaction mixture was stirred for 2 hours at rt. The mixture was poured on 30 mL 10% aqueous $NH_4Cl$ solution and 30 mL EtOAc and the layers were separated. The aqueous layer was extracted a second time with 30 mL EtOAc. The organic layers were washed with 30 mL brine, dried over MgSO₄, filtered and concentrated in vacuo. The residue was purified by silica gel chromatography eluting with a gradient of n-heptane in ethyl acetate (100/0 to 80/20) to give the title compound as a colorless solid (583 mg. MS (m/z): 318 [M]⁺.

Step 2: 2-tert-Butyl-4-methylsulfonyl-1-phenyl-methoxybenzene

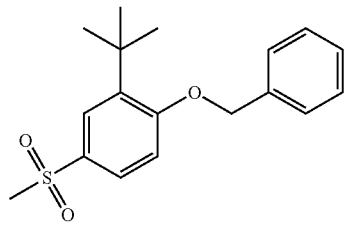 [SMILES: CC(C)(C)c1cc(S(C)(=O)=O)ccc1OCc1ccccc1]

To a solution of L-proline (88.3 mg) in DMSO (10 mL) was added sodium hydroxide (34.6 mg) and the mixture was stirred at room temperature for 30 minutes. Copper(I)iodide (165 mg), 4-bromo-2-tert-butyl-1-phenylmethoxybenzene (345 mg) and sodium methanesulfinate (249 mg) were added. The reaction mixture was heated to 60° C. to give a turbid blue solution and then the reaction was stirred for 2 hours at 60° C. TLC and LC-MS showed no conversion. Again, sodium methanesulfinate (249 mg) was added and the reaction mixture was stirred for 2 hours at 60° C. TLC and LS-MS showed again no conversion. The reaction mixture was transferred into a sealed tube and stirred at 135° C. over night. TLC and LC-MS showed complete conversion and LC-MS showed the presence of the desired mass. The reaction mixture was poured on 50 mL 10% aqueous NH₄Cl solution and 50 mL EtOAc and the layers were separated. The aqueous layer was extracted a second time with 50 mL EtOAc. The organic layers were washed with brine (50 mL), dried over MgSO₄, filtered and concentrated in vacuo. The compound was purified by silica gel chromatography, eluting with a gradient of n-heptane in ethyl acetate (100/0 to 60/40) to provide the title compound as a colorless solid (278 mg). MS (m/z): 317.12 [M−H]⁻.

Step 3: 2-tert-Butyl-4-methylsulfonylphenol

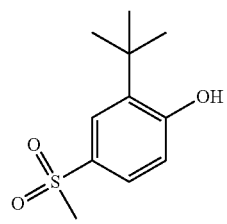

To a solution of 2-tert-butyl-4-methylsulfonyl-1-phenyl-methoxybenzene (250 mg) in MeOH (3 mL) and ethyl acetate (3 mL) was added Pd on charcoal (10% Pd, 25 mg) under an argon atmosphere. The reaction was evacuated and purged with hydrogen. The reaction was stirred for 18 hours at 1.7 bar under H₂-atmosphere. The reaction mixture was then filtered through a filter aid (dicalite) and the filtrate was concentrated in vacuo. The residue was purified by silica gel chromatography, eluting with a gradient of n-heptane in ethyl acetate (100/0 to 50/50) to provide the title compound as colorless solid (140 mg). MS (m/z): 227.08 [M−H]⁻.

Intermediate A16:

5-tert-Butyl-4-hydroxy-2-methylbenzonitrile

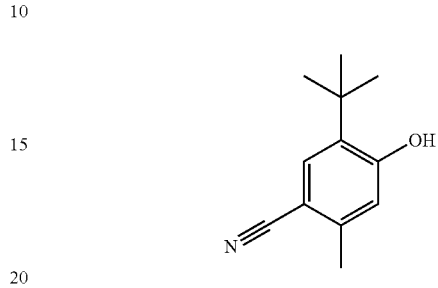

To a solution of 4-bromo-2-tert-butyl-5-methylphenol (CAS: 51345-97-2, 0.45 g), made from 4-bromo-3-methyl-phenol according to WO2005058798 or WO2008059026, in DMF (4 mL) under argon were added water (40 µL), 1,1'-bis(diphenylphosphino)ferrocene (30.8 mg), zinc cyanide (120 mg), zinc (4.84 mg), zinc acetate (13.6 mg) and tris(dibenzylideneacetone)-dipalladium (0) (16.9 mg). The reaction mixture was capped and heated in a microwave oven for 30 minutes at 180° C. The reaction mixture was then poured into saturated aqueous NH₄Cl solution containing a small volume of water, and ethyl acetate, and the layers were separated. The aqueous layer was extracted twice with ethyl acetate. The organic layers were dried over MgSO₄, filtered, treated with silica gel and evaporated. The compound was purified by silica gel chromatography eluting with a gradient of n-heptane in ethyl acetate (100/0 to 75/25) to give the title compound (160 mg) as a light brown solid. MS (m/z): 188.11 [M−H]⁻.

Intermediate A17:

4-tert-butyl-5-hydroxy-2-methylbenzonitrile

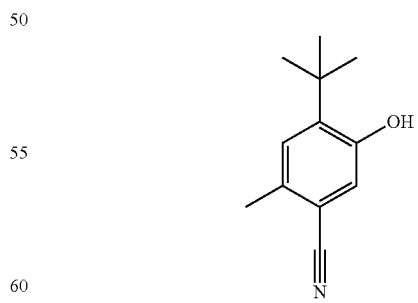

This material was made in analogy to Intermediate A16 from 5-bromo-2-tert-butyl-4-methylphenol (CAS 1237614-78-6), made from 3-bromo-4-methylphenol according to WO2005058798 or WO2008059026), as a light yellow solid. MS (m/z): 188.11 [M−H]⁻.

Intermediate A18:

2-tert-Butyl-4-[3-(2-trimethylsilanyhethoxymethyl)-3H-imidazol-4-yl]-phenol

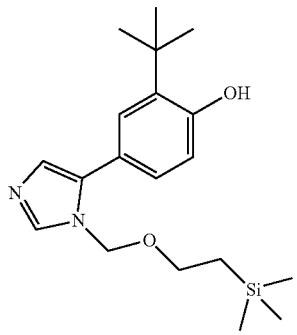 [SMILES: CC(C)(C)c1cc(-c2cncn2COCC[Si](C)(C)C)ccc1O]

Step 1:
1-(4-Benzyloxy-3-tert-butyl-phenyl)-ethanone

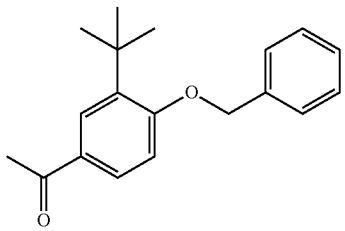 [SMILES: CC(=O)c1ccc(OCc2ccccc2)c(C(C)(C)C)c1]

To a solution of 1-benzyloxy-4-bromo-2-tert-butyl-benzene (Intermediate A15, Step 1, 5.0 g) in DMF (40 mL) and water (4 mL) were added n-butylvinylether (8.1 mL), 1.3-bis(diphenylphosphino)propane (1.61 g), $K_2CO_3$ (2.60 g) and $Pd(OAc)_2$ (351 mg) at 25° C. Then, the mixture was purged with argon and was stirred at 150° C. for 5 h. The mixture was cooled to 25° C., diluted with aq 2N HCl (25 mL) and stirred at 25° C. for 2 h. The mixture was extracted with EtOAc (2×100 mL) and the combined organic layers were washed with sat aq. $NaHCO_3$ solution. The organic layer was dried over $Na_2SO_4$, filtered and evaporated under reduced pressure. The residue was purified by column chromatography over silica gel (5% ethyl acetate in hexanes) to afford the title compound (1.6 g) as a brown liquid. MS (m/z): 283.2 $[M+H]^-$.

Step 2: 1-(4-Benzyloxy-3-tert-butyl-phenyl)-2-bromo-ethanone

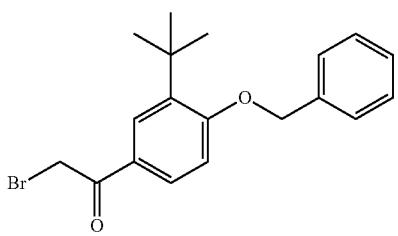 [SMILES: CC(C)(C)c1cc(C(=O)CBr)ccc1OCc1ccccc1]

To a solution of 1-(4-benzyloxy-3-tert-butyl-phenyl)-ethanone (1.0 g) in anhydrous THF (20 mL) and MeOH (10 mL) was added a solution of $Bu_4NBr_3$ (1.71 g) in THF (10 mL) at 25° C. and the reaction mixture was stirred at 50° C. for 5 h. The mixture was cooled to 25° C. and the solvent was evaporated under reduced pressure. The residue was purified by column chromatography over silica gel (5% ethyl acetate in hexane) to afford the title compound (800 mg) as colorless liquid that was used without further characterization.

Step 3:
5-(4-Benzyloxy-3-tert-butyl-phenyl)-1H-imidazole

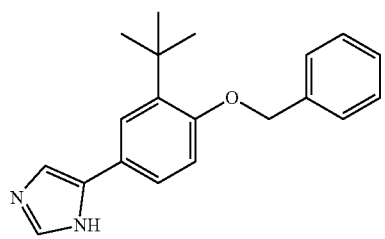 [SMILES: CC(C)(C)c1cc(-c2cnc[nH]2)ccc1OCc1ccccc1]

A solution of 1-(4-benzyloxy-3-tert-butyl-phenyl)-2-bromo-ethanone (800 mg) in formamide (30 mL) was stirred at 160-170° C. for 4 h. The reaction mixture was then cooled to 25° C. and was diluted with EtOAc (30 mL) and water (30 mL). The organic layer was separated and the aqueous layer was extracted with more EtOAc (2×30 mL). The combined organic layers were dried over $Na_2SO_4$, filtered and evaporated under reduced pressure. The residue was purified by column chromatography over amine silica gel (gradient of 5-10% MeOH in DCM) to afford the title compound (330 mg) as light yellow solid. MS (m/z): 306.9 $[M+H]^+$.

Step 4: 5-(4-Benzyloxy-3-tert-butyl-phenyl)-1-(2-trimethylsilanyl-ethoxymethyl)-1H-imidazole

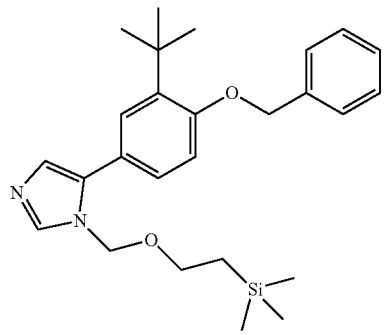 [SMILES: CC(C)(C)c1cc(-c2cncn2COCC[Si](C)(C)C)ccc1OCc1ccccc1]

To a suspension of NaH (51 mg) in anhydrous THF (20 mL) was added dropwise a solution of 5-(4-benzyloxy-3-tert-butyl-phenyl)-1H-imidazole (330 mg) in anhydrous THF (10 mL) at 25° C. The reaction mixture was stirred at 25° C. for 30 min and then (2-chloromethoxy-ethyl)-trimethyl-silane (0.287 ml) was added dropwise at 25° C. The reaction mixture was stirred at 25° C. for 3 h, was then quenched with water and was extracted with EtOAc (2×50 mL). The combined organic layers were washed with brine, dried over $Na_2SO_4$, filtered and evaporated under reduced pressure. The residue was purified by column chromatography over silica gel (40% ethyl acetate in hexanes) to get the title compound (310 mg) as an off white solid. MS (m/z): 436.9 [M+H]+.

Step 5: 2-tert-Butyl-4-[3-(2-trimethylsilanyl-ethoxymethyl)-3H-imidazol-4-yl]-phenol

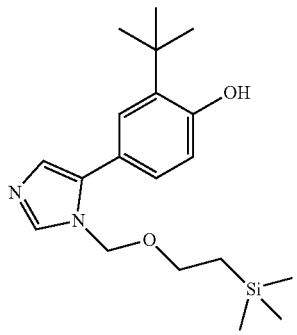

To a solution of 5-(4-benzyloxy-3-tert-butyl-phenyl)-1-(2-trimethylsilanyl-ethoxymethyl)-1H-imidazole (170 mg) in MeOH (20 mL) was purged with argon for 10 min and then Pd(OH)$_2$ (100 mg) was added at 25° C. The reaction mixture was stirred at 25° C. for 4 h under a H$_2$ atmosphere. The mixture was then filtered and the filtrate was evaporated under reduced pressure to afford the title compound (170 mg) as an off white solid. MS (m/z): 347.0 [M+H]+.

Intermediate A19

4-chloro-2-cyclopropyl-5-methylphenol

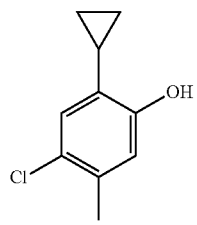

Step 1: 5-Chloro-2-methoxy-4-methyl-phenylamine

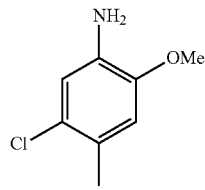

To a solution of 1-chloro-4-methoxy-2-methyl-5-nitro-benzene (CAS: 101080-03-9, 10.64 g) in MeOH (250 mL) and water (125 mL) were added Zn dust (24.15 g) and NH$_4$Cl (31.05 g) at 25° C. and the reaction mixture was stirred for 2 h at 25° C. The mixture was filtered through a celite pad and the filtrate was evaporated, diluted with DCM (300 mL) and washed with water (2×200 mL). The organic layer was dried over Na$_2$SO$_4$, filtered and evaporated to provide the title compound (8.99 g) as a light brown solid. $^1$H NMR (400 MHz, CDCl$_3$): 2.25 (3H, s), 3.80 (3H, s), 6.60 (1H, s), 6.68 (1H, s).

Step 2: 1-Chloro-5-iodo-4-methoxy-2-methyl-benzene

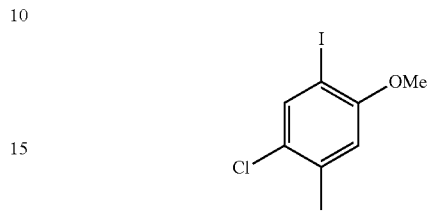

To a suspension of 5-chloro-2-methoxy-4-methyl-phenylamine (8.98 g) in conc. HCl (37%, 84 mL) was added a solution of NaNO$_2$ (7.22 g) in water (70 mL) at 0° C. After stirring the reaction mixture for 30 min at 0° C., a solution of KI (34.74 g) in water (176 mL) was added and the reaction mixture was then stirred at 25° C. for 16 h. The reaction mixture was diluted with ethyl acetate (250 mL) and the organic layer was separated, washed with water (100 mL), saturated sodium thiosulfate solution (100 mL) and brine (50 mL). The organic layer was dried over Na$_2$SO$_4$, filtered and evaporated to get a crude material which was purified by flash chromatography over silica gel (hexanes) to afford the title compound (11.9 g) as a yellow solid. $^1$H NMR (400 MHz, CDCl$_3$) δ: 2.32 (3H, s), 3.84 (3H, s), 6.65 (1H, s), 7.68 (1H, s).

Step 3: 4-Chloro-2-iodo-5-methyl-phenol

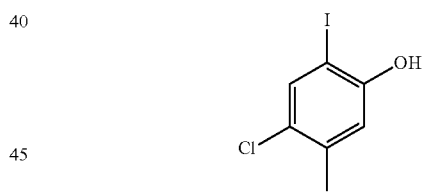

To a stirred solution of 1-chloro-5-iodo-4-methoxy-2-methyl-benzene (3.13 g) in anhydrous DCM (20 mL) at 0° C. was added a solution of 1M boron tribromide in DCM (44.4 ml) and the resulting solution was stirred for 2 h at 25° C. The reaction mixture was quenched with saturated aqueous sodium bicarbonate solution and was diluted with DCM (20 mL). The organic layer was separated and washed with water (25 mL) and brine (25 mL). The organic layer was dried over Na$_2$SO$_4$, filtered and evaporated under reduced pressure. The residue was purified by flash silica gel chromatography (gradient of 5-10% ethyl acetate in hexanes) to afford the title compound as a brown solid (2.89 g). $^1$H NMR (400 MHz, CDCl$_3$) δ: 2.30 (3H, s), 5.12 (1H, s), 6.86 (1H, s), 7.57 (1H, s).

Step 4: 4-Chloro-2-cyclopropyl-5-methyl-phenol

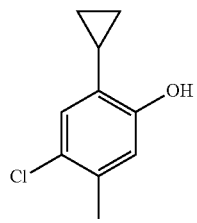

To a solution of 4-chloro-2-iodo-5-methyl-phenol (500 mg) in toluene (8.5 mL) and water (0.5 mL) were added cyclopropylboronic acid (416 mg), $K_3PO_4$ (1.31 g), $Pd(OAc)_2$ (33 mg) and tricyclohexylphosphine (94 mg) and the reaction mixture was heated at 100° C. for 16 h. The mixture was filtered through celite and the filtrate was washed with brine. The organic layer was dried over $Na_2SO_4$ and was vaporated in vacuo. The residue was purified by flash chromatography over silica gel (gradient of 2-5% ethyl acetate in hexanes) to afford the title compound (210 mg) as a brown liquid. $^1$H NMR (400 MHz, $CDCl_3$): 0.59-0.62 (2H, m), 0.92-0.96 (2H, m), 1.69-1.76 (1H, m), 5.29 (1H, s), 6.86 (1H, s), 7.57 (1H, s).

Intermediates A19A and A19B

The following Intermediates were synthesized from 4-chloro-2-iodo-5-methyl-phenol and the suitable boronate building block in analogy to Intermediate A19, Step 4:

Intermediate A20:

4-Chloro-2-cyclohexyl-5-methyl-phenol

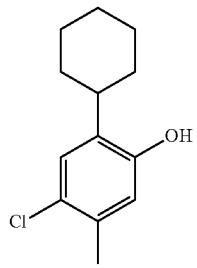

To a solution of 4-chloro-2-cyclohex-1-enyl-5-methyl-phenol (Intermediate A19A, 202 mg) in methanol (10 mL) was added Pd on carbon (10% Pd, 25 mg) and the reaction mixture was stirred at 25° C. under hydrogen atmosphere for 45 min. The mixture was then filtered through celite and the filtrate was evaporated under reduced pressure to afford the title compound (190 mg) as a colorless liquid. $R_f$=0.3 (10% ethyl acetate in hexane)

The following Intermediate was synthesized from the corresponding precursor in analogy to Intermediate A20:

| Intermediate | Systematic Name | Building block | Analytics |
|---|---|---|---|
| A19A | 4-chloro-2-(cyclohexen-1-yl)-5-methylphenol | cyclohexene-1-boronic acid pinacol ester | Rf: 0.4 (10% ethyl acetate in hexanes) |
| A19B | 4-Chloro-2-(3,6-dihydro-2H-pyran-4-yl)-5-methyl-phenol | 3,6-dihydro-2H-pyran-4-boronic acid pinacol ester | $^1$H NMR (400 MHz, $CDCl_3$): 2.29 (3H, s), 2.38-2.40 (2H, m), 3.92 (2H, t, J = 4), 4.28-4.29 (2H, m), 5.33 (1H, s), 5.92 (1H, s) 6.77 (1H, s), 7.05 (1H, s). |

| Intermediate | Systematic Name | Building block | Analytics |
|---|---|---|---|
| A21 | 4-chloro-5-methyl-2-(oxan-4-yl)phenol 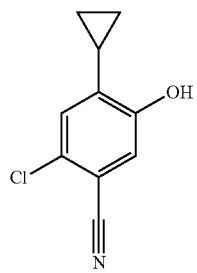 [SMILES: N#Cc1cc(O)c(C2CC2)cc1Cl] | 4-Chloro-2-(3,6-dihydro-2H-pyran-4-yl)-5-methyl-phenol Intermediate A19B | $^1$H NMR (400 MHz, CDCl$_3$): 1.72-1.78 (4H, m), 2.27 (3H, s), 3.01-3.05 (1H, m), 3.51-3.57 (2H, m), 4.05-4.07 (2H, m), 5.33 (1H, s), 4.73 (1H, s) 6.60 (1H, s), 7.09 (1H, s). |

Intermediate A22

2-Chloro-4-cyclopropyl-5-hydroxy-benzonitrile

Step 1: 5-Amino-2-bromo-4-chloro-phenol

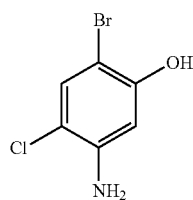

To a solution of 4-bromo-2-chloro-5-methoxy-phenylamine (CAS: 98446-54-9, 2.05 g) in anhydrous DCM (40 mL) at 0° C. was added a solution of BBr$_3$ in DCM (1M, 86.7 mL) and the reaction mixture was stirred at 25° C. for 12 h. The mixture was quenched with saturated aqueous NaHCO$_3$ solution (40 mL) and was extracted with DCM (2×60 mL). The combined organic layers were dried over Na$_2$SO$_4$ and were evaporated under reduced pressure to afford the title compound (1.9 g) as a brown solid. $^1$H NMR (400 MHz, DMSO-D$_6$): 5.36 (2H, s), 6.41 (1H, s), 7.21 (1H, s), 9.94 (1H, s).

Step 2: Carbonic acid 2-bromo-5-(di tert-butoxycarbonyl)amino-4-chloro-phenyl ester tert-butyl ester

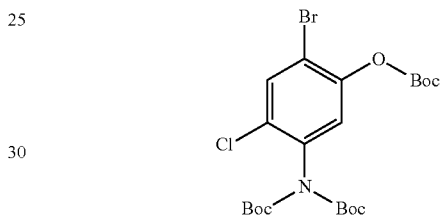

To a stirred solution of 5-amino-2-bromo-4-chloro-phenol (1.9 g) in anhydrous THF (40 mL) at 25° C. were added di-tert-butyldicarbonate ("Boc anhydride", 10.96 mL), Et$_3$N (7.12 mL) and DMAP (10 mg) and the reaction mixture was refluxed for 12 h. The solvent was evaporated under reduced pressure and the residue was purified by flash chromatography over silica gel (gradient of 2-5% ethyl acetate/in hexanes) to afford the desired compound (3.82 g) as a white solid. MS (m/z): 522.1 [M]$^+$.

Step 3: Carbonic acid 5-(di tert-butoxycarbonyl)amino-4-chloro-2-cyclopropyl-phenyl ester tert-butyl ester

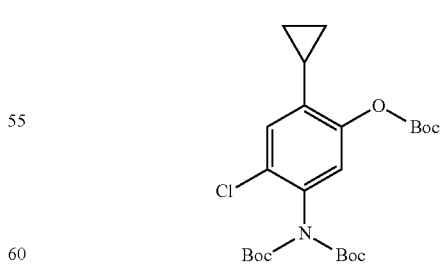

The title compound was obtained in analogy to intermediate A19, Step 4, from carbonic acid 2-bromo-5-(di tert-butoxycarbonyl)amino-4-chloro-phenyl ester tert-butyl ester and cyclopropylboronic acid as a colorless, sticky liquid. MS (m/z): 484.0 [M]$^+$.

Step 4: 5-Amino-4-chloro-2-cyclopropyl-phenol

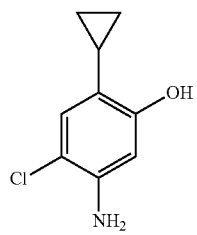 [SMILES: Nc1cc(O)c(C2CC2)cc1Cl]

To a solution of carbonic acid 5-(di tert-butoxycarbonyl)amino-4-chloro-2-cyclopropyl-phenyl ester tert-butyl ester (1.05 g) in DCM (20 mL) was added TFA (6.45 mL) and the reaction mixture was stirred at 25° C. for 2 h. The solvent was evaporated under reduced pressure and the residue was diluted with DCM (50 mL). The solution was washed with saturated aqueous NaHCO$_3$ solution (30 mL) and water (20 mL). The organic layer was dried over anhydrous Na$_2$SO$_4$, filtered and evaporated to afford the title compound (397 mg) as a brown solid. $^1$H NMR (400 MHz, DMSO-D$_6$) δ: 0.42-0.46 (2H, m), 0.70-0.74 (2H, m), 1.80-1.87 (1H, m), 4.94 (2H, s), 6.26 (1H, s), 6.51 (1H, s), 9.11 (1H, s).

Step 5: 4-Chloro-2-cyclopropyl-5-iodo-phenol

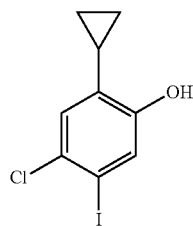 [SMILES: Oc1cc(I)c(Cl)cc1C1CC1]

To a suspension of 5-amino-4-chloro-2-cyclopropyl-phenol (395 mg) in water (1 mL) at 0° C. was added slowly conc. H$_2$SO$_4$ (1.29 mL), followed by a solution of NaNO$_2$ (148 mg) in water (5.5 mL) at 0° C. After stirring the reaction mixture for 10 more minutes, a solution of KI (714 mg) in water (1 mL) was added and reaction mixture was heated at 60° C. for 2 h. The mixture was cooled to 25° C. and extracted with DCM (2×30 mL). The combined organic extracts were dried over Na$_2$SO$_4$, filtered and evaporated. The residue was purified by flash chromatography over silica gel (gradient of 2-5% ethyl acetate in hexanes) to afford the title compound (241 mg) as a yellow liquid. MS (m/z): 292.8 [M−H]$^-$.

Step 6: 2-Chloro-4-cyclopropyl-5-hydroxy-benzonitrile

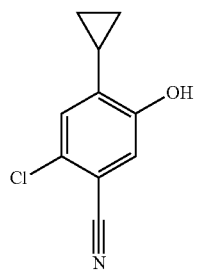 [SMILES: N#Cc1cc(O)c(C2CC2)cc1Cl]

To a solution of 4-chloro-2-cyclopropyl-5-iodo-phenol (238 mg) in anhydrous DMF (5 mL) was added CuCN (145 mg) and the reaction mixture was heated at 100° C. for 24 h. The solvent was evaporated in vacuo and the residue was purified by flash chromatography over silica gel (gradient of 5-10% ethyl acetate in hexanes) to afford the title compound (120 mg) as a yellow solid. $^1$H NMR (400 MHz, CDCl$_3$): 0.68-0.72 (2H, m), 1.06-1.10 (2H, m), 1.86-1.89 (1H, m), 5.64 (1H, s), 7.09 (1H, s), 7.10 (1H, s).

Intermediate A23

N-(2-Chloro-4-cyclopropyl-5-hydroxy-phenyl)-methanesulfonamide

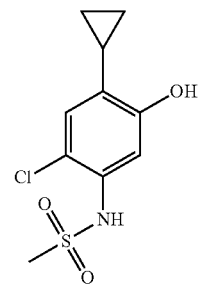 [SMILES: CS(=O)(=O)Nc1cc(O)c(C2CC2)cc1Cl]

To a solution of 5-amino-4-chloro-2-cyclopropyl-phenol (78 mg), obtained in Intermediate A22, Step 4, in DCM (5 mL) were added pyridine (0.04 mL) and methanesulfonyl chloride (0.03 mL) at 0° C. and the reaction mixture was then stirred at 25° C. for 12 h. The mixture was quenched with 6N aqueous NaOH solution (5 mL) and water (10 mL). The organic layer was separated and the aqueous phase was extracted with additional DCM (20 mL). The aqueous layer was cooled to 0° C., acidified with conc. HCl and extracted with ethyl acetate (2×20 mL). The combined organic ethyl acetate extracts were washed with brine, dried over Na$_2$SO$_4$ and concentrated under reduced pressure. The residue was purified by flash chromatography over silica gel (gradient of 5-20% ethyl acetate in hexanes) to provide the title compound (58 mg) as a brown solid. $^1$H NMR (400 MHz, DMSO-D$_6$): 0.62-0.65 (2H, m), 0.84-0.89 (2H, m), 1.97-2.05 (1H, m), 2.95 (3H, s), 6.80 (1H, s), 6.91 (1H, s), 9.19 (1H, s), 9.80 (1H, s).

Intermediate A24:

4-tert-Butyl-3-hydroxy-benzonitrile

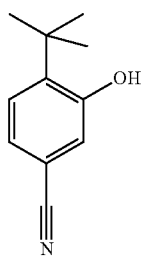

Step 1: 4-tert-Butyl-3-methoxy-benzamide

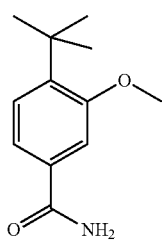

A solution of 4-tert-butyl-3-methoxy-benzoic acid (CAS: 79822-46-1; 2 g) in SOCl$_2$ (5 mL) was refluxed for 2 h. Excess SOCl$_2$ was evaporated in vacuo and the residue was dissolved in THF (5 mL) and conc. aqueous NH$_3$ solution (2 mL) was added dropwise at 0° C. The reaction mixture was stirred at rt for 1 h and was then extracted with ethyl acetate (2×20 mL). The combined organic extracts were dried over Na$_2$SO$_4$ and were evaporated under reduced pressure to afford the title compound (1.95 g) as a white solid. $^1$H NMR (400 MHz, CDCl$_3$): 1.36 (9H, s), 3.88 (3H, s), 6.0 (2H, bs), 7.20 (1H, dd, J=4 Hz, 12 Hz), 7.30 (1H, d, J=12 Hz), 7.42 (1H, d, J=4 Hz).

Step 2: 4-tert-Butyl-3-methoxy-benzonitrile

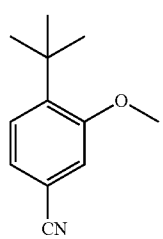

A solution of 4-tert-butyl-3-methoxy-benzamide (500 mg, 2.41 mmol) in POCl$_3$ (5 mL) was refluxed for 6 h. Excess POCl$_3$ was evaporated in vacuo and the residue was dissolved in ethyl acetate (30 mL) and washed with saturated aqueous NaHCO$_3$ solution (25 mL). The organic layer was dried over Na$_2$SO$_4$, filtered, and was then evaporated under reduced pressure. The crude material was purified by flash chromatography over silica gel (5% ethyl acetate in hexane) to provide the title compound (360 mg) as a colorless liquid. MS (M/z): 189.0 [M]$^+$.

Step 3: 4-tert-Butyl-3-hydroxy-benzonitrile

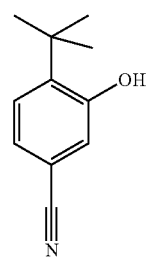

The title compound was obtained in analogy to intermediate A22, Step 1, from 4-tert-butyl-3-methoxy-benzonitrile by treatment with BBr$_3$ as a yellow oil. $^1$H NMR (400 MHz, CDCl$_3$): 1.39 (9H, s), 5.41 (1H, s), 6.93 (1H, d, J=4 Hz), 7.17 (1H, dd, J=4 Hz, 12 Hz), 7.33 (1H, d, J=8 Hz).

The following Intermediate was synthesized from the corresponding precursor in analogy to Intermediate A24, Step 3:

| Intermediate | Systematic Name | Building block | Analytics |
|---|---|---|---|
| A25 | 4-tert-Butyl-3-hydroxy-benzamide | 4-tert-butyl-3-methoxybenzamide Intermediate A24, Step 1 | $^1$H NMR (400 MHz, CDCl$_3$): 1.55 (9H, s), 5.73 (1H, s), 7.16 (1H, dd, J = 4 Hz, 12 Hz), 7.30 (1H, d, J = 12 Hz), 7.34 (1H, d, J = 4 Hz). |

Intermediate A30:

6-Cyclopropyl-2-methylbenzo[d]thiazol-5-ol

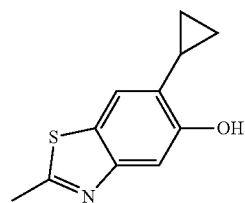

Step 1: 6-Iodo-5-methoxy-2-methylbenzo[d]thiazole

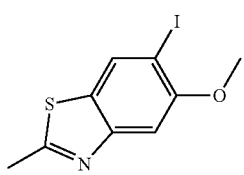

A solution of 5-methoxy-2-methylbenzo[d]thiazol-6-amine (CAS: 89976-71-6; 1.0 g) in water (2.6 mL) and conc. hydrochloric acid (2.54 mL) was cooled down to 0° C. Then, a solution of sodium nitrite (373 mg) in water (2.6 mL) was added dropwise over 3 minutes. The brown solution was stirred at 0° C. for 5 minutes and was then added dropwise to a vigourously stirred suspension of potassium iodide (2.56 g) in HBr solution (48% in water, 12.2 mL) over 5 minutes at rt. Stirring at rt was continued for 20 minutes. The reaction mixture was poured into 2M aqueous $Na_2CO_3$ solution (60 mL) and ethyl acetate (50 mL) and the layers were separated. The aqueous layer was extracted twice with ethyl acetate (30 mL, each). The organic layers were washed once with aqueous $Na_2S_2O_3$ solution (50 mL) and once with brine (20 mL), dried over $MgSO_4$, filtered, treated with silica gel and evaporated. The compound was purified twice by silica gel chromatography on a 50 g column using an MPLC system eluting with a gradient of n-heptane/ethyl acetate (100/0 to 50/50) to provide the title compound as a slightly impure, light brown solid (0.66 g). MS (m/z): 306.4 $[M+H]^+$.

Step 2: 6-Iodo-2-methylbenzo[d]thiazol-5-ol

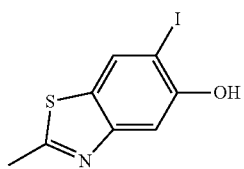

To a solution of 6-iodo-5-methoxy-2-methylbenzo[d]thiazole (0.625 g) in dichloromethane (4 mL) in a sealed tube under argon at room temperature was added dropwise tribromoborane (1M in DCM; 2.25 mL) and the light brown suspension was stirred at reflux (oil bath at 60° C.) for 1.5 hours. No product was detected at this point. More DCM (4.00 mL) and tribromoborane (1M in dichloromethane; 2.25 mL) were added after 3 hours and stirring was continued at 60° C. over the weekend. The reaction mixture was poured into water and DCM (containing a small volume of methanol) and the layers were separated. The aqueous layer was extracted twice with DCM. The organic layers were washed once with brine, dried over $MgSO_4$, filtered and evaporated. The residue was taken up in ethyl acetate and dichloromethane and was partially evaporated until a suspension formed. This suspension was filtered, washed with a small amount of ethyl acetate and dried in vacuo to provide the title compound as a light brown solid (455 mg). MS (m/z): 292.3 $[M+H]^+$.

Step 3: 6-cyclopropyl-2-methyl-1,3-benzothiazol-5-ol

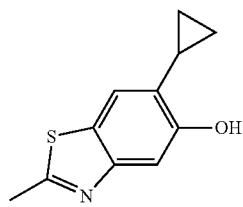

To a suspension of 6-iodo-2-methylbenzo[d]thiazol-5-ol (0.15 g) in toluene (3 mL) were added under argon potassium cyclopropyltrifluoroborate (152 mg), water (0.21 mL), cesium carbonate (420 mg), palladium (II) acetate (5.78 mg) and butyldi-1-adamantylphosphine (18.5 mg) and the mixture was stirred in a sealed tube at 125° C. for 66 hours. The reaction mixture was poured into saturated aqueous $NH_4Cl$ solution and ethyl acetate and the layers were separated. The aqueous layer was extracted twice with ethyl acetate. The organic layers were combined, dried over $MgSO_4$, filtered, treated with silica gel and evaporated. The compound was purified by silica gel chromatography on a 10 g column using an MPLC system eluting with a gradient of n-heptane in ethyl acetate (100/0 to 0/100) to provide the title compound as a light brown solid. MS (m/z): 206.06 $[M+H]^+$.

According to LC-MS, the material contains some 2-methylbenzo[d]thiazol-5-ol as an impurity.

Intermediate A31

4-Chloro-2-cyclobutyl-5-methyl-phenol

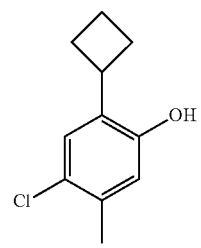

Step 1: 1-(5-Chloro-2-methoxy-4-methyl-phenyl)-cyclobutanol

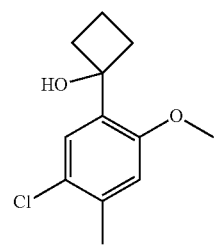

To a solution of 1-chloro-5-iodo-4-methoxy-2-methylbenzene (1 g), Intermediate A19, Step 2, in anhydrous THF (20 mL) was added dropwise isopropyl magnesium chloride (2M in THF, 2.12 mL) at −40° C. under a nitrogen atmosphere and the reaction mixture was stirred at −40° C. for 1 h. Then, a solution of cyclobutanone (298 mg) in anhydrous THF (3 mL) was added dropwise to the reaction mixture at −40° C. and stirring was continued at 25° C. for 11 h. The reaction mixture was quenched with saturated aqueous NH₄Cl solution and was extracted with ethyl acetate (2×30 mL). The combined organic layers were dried over Na₂SO₄, filtered, and evaporated under reduced pressure. The residue was purified by flash chromatography over silica gel (gradient of 5-15% ethyl acetate in hexanes) to afford the title compound (431 mg) as a colorless liquid. $^1$H NMR (400 MHz, CDCl₃): 1.55-1.66 (1H, m), 1.96-2.06 (1H, m), 2.31-2.41 (5H, m), 2.43-2.48 (2H, m) 3.48 (1H, s), 3.85 (3H, s), 6.75 (1H, s), 7.23 (1H, s).

Step 2:
1-Chloro-5-cyclobutyl-4-methoxy-2-methyl-benzene

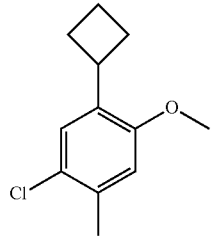

To a mixture of 1-(5-chloro-2-methoxy-4-methyl-phenyl)-cyclobutanol (428 mg) and triethyl silane (0.362 mL) in anhydrous DCM (20 mL) at −78° C. under argon atmosphere was added dropwise boron trifluoride etherate (0.237 mL) and the reaction mixture was allowed to warm to −40° C. within a period of 3 h. Stirring was then continued at −40° C. for another 2 h. The reaction mixture was then poured into 10% aqueous KHCO₃ solution (30 mL) and was extracted with DCM (3×30 mL). The combined organic layers were dried (Na₂SO₄), filtered, and evaporated. The residue was purified by column chromatography over silica gel (gradient of 0-5% ethyl acetate in hexanes) to provide the title compound (370 mg) as a colorless liquid. $^1$H NMR (400 MHz, CDCl₃): 1.78-1.81 (1H, m), 1.91-2.06 (3H, m), 2.24-2.32 (5H, m), 3.62-3.75 (1H, m), 3.38 (3H, s), 6.63 (1H, s), 7.12 (1H, s).

Step 3: 4-Chloro-2-cyclobutyl-5-methyl-phenol

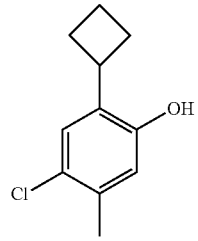

The title compound was obtained in analogy to Intermediate A19, Step 3, from 4-chloro-2-cyclobutyl-5-methyl-phenol by treatment with BBr₃ in DCM as a brown solid (327 mg). $^1$H NMR (400 MHz, CDCl3): 1.82-1.89 (1H, m), 1.98-2.16 (3H, m), 2.27 (3H, s), 2.31-2.42 (2H, m) 3.53-3.59 (1H, m), 4.50 (1H, s), 6.61 (1H, s), 7.09 (1H, s).

Intermediate A34

4-(tert-Butyl)-2-chloro-5-hydroxybenzonitrile

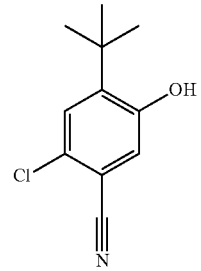

Step 1: 5-Bromo-2-(tert-butyl)-4-chlorophenol

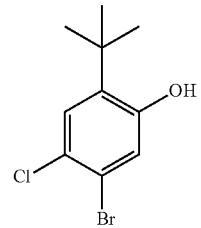

To a solution of 3-bromo-4-chlorophenol (2.0 g, CAS: 13659-24-0) in acetic acid (6.0 mL) were added tert-butanol (1.07 g, 1.36 mL) followed by sulfuric acid (946 mg, 517 μL) at room temperature under an argon atmosphere. The mixture was heated to 70° C. for 80 hours. More tert-butanol (715 mg, 905 μL) and sulfuric acid (756 mg, 413 μL) were added and the mixture was heated to 90° C. for another 24 hours. The reaction mixture was cooled to room temperature and was then poured into ice/water. The aqueous layer was extracted twice with ethyl acetate. The organic layers were washed once with brine, dried over Na₂SO₄, filtered and evaporated. Residual tert-butanol was removed by evaporation from toluene (200 mL) to dryness. The crude material was purified by flash chromatography (0% to 20% ethyl acetate in heptane) to give the title compound as a light brown liquid (506 mg, 19%). MS (ESI): m/z=263.1 [M−H]⁻.

Step 2:
4-(tert-Butyl)-2-chloro-5-hydroxybenzonitrile

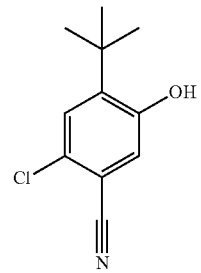

5-Bromo-2-(tert-butyl)-4-chlorophenol (501 mg), 1,1'-bis(diphenylphosphino)-ferrocene (31.6 mg), zinc granules (4.97 mg), zinc cyanide (123 mg), zinc acetate (14 mg), tris(dibenzylidene-acetone)dipalladium(0) (17.4 mg) were dissolved in dimethylformamide (5.0 mL) and water (50 µL) at room temperature. The mixture was then subjected to microwave irradiation for 30 minutes at 180° C. The reaction mixture was cooled to room temperature and was then poured then into ice/water. The aqueous layer was acidified with sat. NH$_4$Cl solution and was extracted twice with ethyl acetate. The organic layers were washed once with brine, dried over Na$_2$SO$_4$, filtered and evaporated. Residual DMF was removed by evaporation from toluene (150 mL) to dryness. The crude material was purified by flash chromatography (0% to 20% ethyl acetate in heptane) to give the title compound as a light yellow solid (71 mg, 18%). MS (ESI): m/z=208.1 [M−H]$^+$.

Intermediate A35

5-tert-butyl-2-chloro-4-hydroxy-benzonitrile

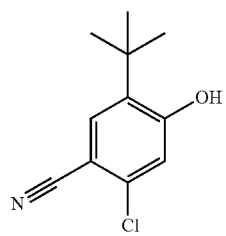

Step 1: 4-bromo-2-tert-butyl-5-chloro-phenol

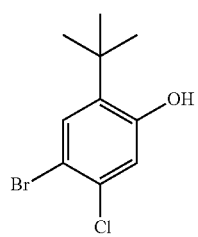

To a sealable vessel containing 4-bromo-3-chlorophenol (23 g, 111 mmol) was added acetic acid (115 mL), tBuOH (48 mL, 499 mmol), and sulfuric acid (30 mL, 333 mmol). The vessel was sealed and heated to 90° C. with vigorous stirring. After 18 h, an additional charge of tBuOH (48 mL, 499 mmol), and sulfuric acid (30 mL, 333 mmol) was added, and heating was continued at 90° C. After 5 h, the reaction was cooled to room temperature then partitioned between ethylacetate and water. The layers were separated, and the aqueous phase washed again with ethylacetate. The combined organic phases were washed twice with water, once with brine, dried over MgSO$_4$, filtered and concentrated. The resulting crude mixture was purified on SiO$_2$, eluting first with 100% hexanes, then ramping to 25% ethylacetate in hexanes to yield 9.76 g of the title compound which was used in the next step without further purification (60% pure, measured by NMR).

Step 2: 5-tert-butyl-2-chloro-4-hydroxy-benzonitrile

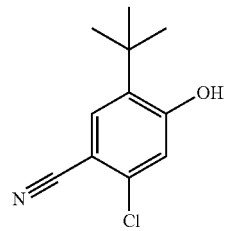

To 4-bromo-2-tert-butyl-5-chloro-phenol (9.76 g, 60% pure, 22.2 mmol) was added DMF (80 mL) then CuCN (4 g, 44.7 mmol). The resulting mixture was heated to 170° C. for 8 h Upon reaction completion, the mixture was cooled then partitioned between ethylacetate and water. The resulting suspension was filtered over celite and rinsed with ethylacetate. The layers were separated, and the aqueous phase washed again with ethylacetate. The combined organic phases were washed with water, brine, dried over MgSO4, filtered and concentrated. The resulting crude mixture was purified on SiO2, eluting with 0-60% ethylacetate in hexanes to yield 2.59 g of the title compound (56% yield).

Intermediate A36

5-tert-butyl-2-fluoro-4-hydroxy-benzonitrile

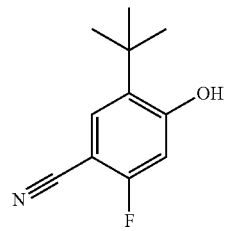

Step 1: 2-tert-butyl-4-chloro-5-fluoro-phenol

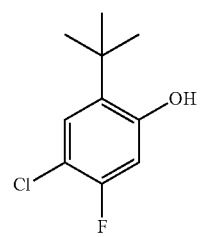

The title compound was prepared in analogy to intermediate A35, step 1, from 4-chloro-3-fluorophenol (5 g) and was obtained (4.4 g, 64%).

Step 2: 5-tert-butyl-2-fluoro-4-hydroxy-benzonitrile

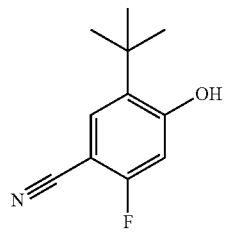

To 2-tert-butyl-4-chloro-5-fluoro-phenol (108 mg, 0.53 mmol) was added dioxane/water (1:1, 2 mL), potassium acetate (10 mg, 0.11 mmol), and K$_4$[Fe(CN)$_6$].3H$_2$O (113 mg, 0.27 mmol). Nitrogen gas was bubbled through for 20 minutes. 2-Di-tert-butylphosphino-2',4',6'-triisopropylbiphenyl (11 mg, 0.027 mmol) and [(2-Di-tert-butylphosphino-2,4,6-triisopropyl-1,1-biphenyl)-2-(2-amino-1,1-biphenyl)]palladium(II) methanesulfonate (21 mg, 0.027 mmol) were added and the mixture was heated to 100° C. for 3 h. Upon reaction completion, the mixture was cooled then partitioned between ethylacetate and brine. The resulting suspension was filtered over celite and rinsed with ethylacetate. The layers were separated, the organic phases were washed twice with brine, dried over magnesiumsulfate, filtered and concentrated. The resulting crude mixture was purified on SiO2 eluting with 0-100% ethylacetate in hexanes) to yield 61.3 mg of the title compound (60% yield).

Intermediates B

Intermediate B1:

4-Chloro-5-methyl-2-phenylphenol

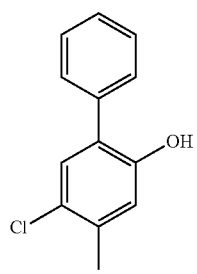

Step 1: 5-Chloro-2-methoxy-4-methylaniline

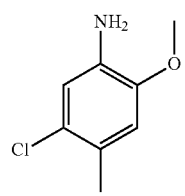

To a solution of 1-chloro-4-methoxy-2-methyl-5-nitrobenzene (0.15 g, prepared as described in WO2011/141716) in THF (0.22 mL) were added Fe(acac)$_3$ (52.6 mg, CAS: 14024-18-1) and 1,1,3,3-tetramethyldisiloxane (300 mg, CAS: 3277-26-7) and the reaction mixture was stirred at reflux in a sealed tube for 15 hours. The reaction mixture was allowed to cool to rt, treated with EtOAc (5 mL) and extracted with aqueous 25% HCl solution (2 mL). The aqueous layer was extracted once more with EtOAc (5 mL). The aqueous layer was then adjusted to approx. pH 8 to 9 using solid NaHCO$_3$ and was then extracted three times with EtOAc. The combined organic layers were dried over MgSO$_4$, filtered and evaporated to give the title compound as a brown solid (0.1 g; 78%). MS (ESI): m/z=172.4 [M+H]$^+$.

Step 2: 1-Chloro-5-iodo-4-methoxy-2-methylbenzene

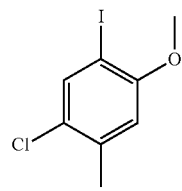

To conc. aqueous HCl (127 μL) at 0° C. was added NaNO$_2$ (57.5 mg, CAS: 7632-00-0). To this mixture was added dropwise over 7 minutes a solution of 5-chloro-2-methoxy-4-methylaniline (0.13 g) in AcOH (1.5 mL) and the resulting mixture was stirred at rt for 30 minutes. This mixture was added dropwise via syringe to a stirred solution of KI (377 mg, CAS: 7681-11-0) in 48% aqueous HBr (2 mL) at room temperature. The brown mixture was stirred at rt for another 2 hours. The reaction mixture was poured on 2M aqueous Na$_2$CO$_3$ solution and EtOAc and the layers were separated. The aqueous layer was extracted twice with EtOAc. The organic layers were washed once with brine, dried over MgSO$_4$, filtered and evaporated. The residue was purified by silica gel chromatography on a 10 g column using an MPLC (ISCO) system eluting with a gradient of n-heptane in EtOAc (100/0 to 50/50) to give the title compound as a light brown solid (0.134 g; 63%). MS (EI): m/z=282 [M].

Step 3: 4-Chloro-2-iodo-5-methylphenol

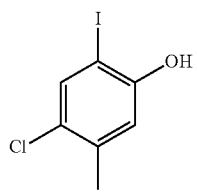

To a solution of 1-chloro-5-iodo-4-methoxy-2-methylbenzene (1.13 g) in DCM (20 mL) was added dropwise at 0° C. tribromoborane 1M in DCM (4.2 mL, CAS: 10294-33-4) over 15 minutes. The reaction mixture was stirred for 4 hours at rt. The reaction mixture was poured on H$_2$O (60 mL) and DCM (60 mL) and the layers were separated. The aqueous layer was extracted a second time with DCM (60 mL). The organic layers were washed with brine (60 mL), dried over MgSO₄, filtered and concentrated in vacuo to give the title compound as a light yellow solid (1.023 g, 95%). MS (ESI): m/z=266.907 [M−H]⁻.

Step 4: 4-Chloro-5-methyl-2-phenylphenol

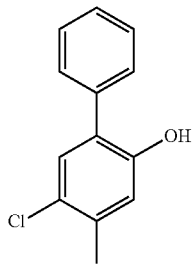

To a solution of 4-chloro-2-iodo-5-methylphenol (100 mg) in DME (2 mL) was added phenylboronic acid (45.4 mg, CAS: 98-80-6) and 2M aqueous Na₂CO₃ (1 mL). The reaction mixture was stirred for 15 minutes under argon atmosphere. Pd(II)acetate (4.18 mg, CAS: 3375-31-3) and triphenylphosphine (9.77 mg, CAS: 603-35-0) were added. The reaction mixture was stirred for 2 hours at 90° C. The reaction mixture was poured on 10% aqueous NaHCO₃ solution (30 mL) and EtOAc (30 mL) and the layers were separated. The aqueous layer was extracted a second time with EtOAc (30 mL). The organic layers were washed with brine (30 mL), dried over MgSO₄, filtered and concentrated under vacuum. The compound was purified by silica gel chromatography on a 20 g column using an MPLC (Flashmaster) system eluting with a gradient of n-heptane in EtOAc (100/0 to 70/40) to give the title compound as a light yellow oil (0.077 g, 95%). MS (EI): m/z=218 [M]⁺.

The following intermediates were made in analogy to intermediate B1, step 4, from 4-chloro-2-iodo-5-methylphenol (intermediate B1, step 3) and the corresponding aryl boronic acid or aryl borolane building block as indicated in the following table:

| Intermediate | Systematic Name | Building block/ intermediate | MS, m/z |
|---|---|---|---|
| B2 | 4-Chloro-2-(2-chlorophenyl)-5-methylphenol | 2-chlorophenylboronic acid CAS: 3900-89-8 | MS (EI): 252.0 [M]⁺ |
| B3 | 4-Chloro-2-(3-chlorophenyl)-5-methyphenol | 3-chlorophenylboronic acid CAS: 63503-60-6 | MS (ESI): 251.003 [M − H]⁻ |

-continued

| Intermediate | Systematic Name | Building block/ intermediate | MS, m/z |
|---|---|---|---|
| B4 | 4-Chloro-2-(4-chlorophenyl)-5-methylphenol | 4-chlorophenylboronic acid CAS: 1679-18-1 | MS (ESI): 251.003 [M − H]⁻ |
| B5 | 3-(5-Chloro-2-hydroxy-4-methylphenyl)benzonitrile | 3-cyanophenylboronic acid CAS: 150255-96-2 | MS (ESI): 242.048 [M − H]⁻ |
| B6 | 4-Chloro-5-methyl-2-(3-methylsulfonylphenyl)phenol | 3-(methylsulfonyl)phenylboronic acid CAS: 373384-18-0 | MS (ESI): 295.020 [M − H]⁻ |
| B7 | 4-Chloro-5-methyl-2-(2-methylsulfonylphenyl)phenol | 2-(methylsulfonyl)phenylboronic acid CAS: 330804-03-0 | MS (EI): 296.0 [M]⁺ |

-continued

| Intermediate | Systematic Name | Building block/ intermediate | MS, m/z |
|---|---|---|---|
| B8 | [3-(5-Chloro-2-hydroxy-4-methylphenyl)phenyl]-piperidin-1-ylmethanone | 3-(piperidine-1-carbonyl)phenylboronic acid CAS: 850568-34-2 | MS (ESI): 330.127 [M + H]$^+$ |
| B9 | 3-(5-Chloro-2-hydroxy-4-methylphenyl)-N-cyclohexylbenzamide | 3-(cyclohexylcarbamoyl)-phenylboronic acid CAS: 850567-25-8 | MS (ESI): 344.143 [M + H]$^+$ |
| B10 | [3-(5-Chloro-2-hydroxy-4-methylphenyl)phenyl]-morpholin-4-ylmethanone | 3-(morpholine-4-carbonyl)phenylboronic acid CAS: 723281-55-8 | MS (ESI): 332.104 [M + H]$^+$ |

-continued

| Intermediate | Systematic Name | Building block/ intermediate | MS, m/z |
|---|---|---|---|
| B11 | 3-(5-Chloro-2-hydroxy-4-methylphenyl)benzamide 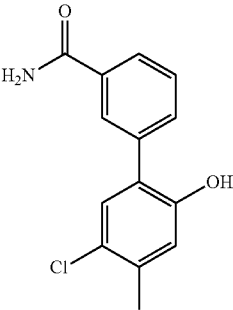 | 3-carbamoylphenylboronic acid CAS: 351422-73-6 | MS (ESI): 260.047 [M − H]− |
| B12 | 3-(5-Chloro-2-hydroxy-4-methylphenyl)-N,N-dimethylbenzamide 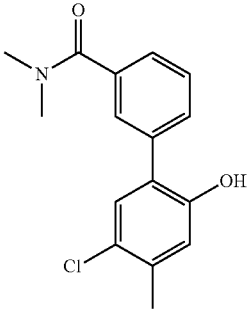 | 3-(dimethylcarbamoyl)-phenylboronic acid CAS: 373384-14-6 | MS (ESI): 290.095 [M + H]+ |
| B13 | 3-(5-Chloro-2-hydroxy-4-methylphenyl)-N-phenylbenzamide 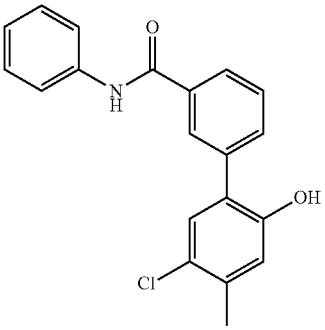 | 3-(phenylcarbamoyl)-phenylboronic acid CAS: 397843-71-9 | MS (ESI): 338.09 [M + H]+ |

| Intermediate | Systematic Name | Building block/ intermediate | MS, m/z |
|---|---|---|---|
| B14 | 3-Chloro-5-(5-chloro-2-hydroxy-4-methylphenyl)benzamide | 3-carbamoyl-5-chlorophenylboronic acid CAS: 957120-53-5 | MS (ESI): 294.01 [M − H]⁻ |
| B15 | 3-(5-Chloro-2-hydroxy-4-methylphenyl)-N-cyclopropyl-4-fluorobenzamide | 5-(cyclopropylcarbamoyl)-2-fluorophenylboronic acid CAS: 874289-54-0 | MS (ESI): 320.08 [M + H]⁺ |
| B17 | 3-(5-Chloro-2-hydroxy-4-methylphenyl)-N-(2-methoxyethyl)benzamide | N-(2-methoxyethyl)-3-(4,4,5,5-tetramethyl-1,3,2-dioxaborolan-2-yl)benzamide ( CAS: 1073353-64-6 | MS (ESI): 320.11 [M + H]⁺ |

-continued

| Intermediate | Systematic Name | Building block/ intermediate | MS, m/z |
|---|---|---|---|
| B18 | 4-Chloro-2-(2-chloropyridin-3-yl)-5-methylphenol | 2-chloropyridin-3-ylboronic acid CAS: 381248-04-0 | MS (ESI): 254.01 [M + H]$^+$ |
| B19 | 4-Chloro-2-(6-chloropyridin-2-yl)-5-methylphenol | 6-chloropyridine-2-boronic acid pinacol ester CAS: 652148-92-0 | MS (ESI): 224.998 [M + H]$^+$ |
| B20 | 5-(5-Chloro-2-hydroxy-4-methylphenyl)pyridine-3-carboxamide | 5-(4,4,5,5-tetramethyl-1,3,2-dioxaborolan-2-yl)nicotinamide CAS: 1169402-51-0 | MS (ESI): 263.06 [M + H]$^+$ |
| B21 | 4-Chloro-2-(6-methoxypyridin-2-yl)-5-methylphenol | 6-methoxypyridin-2-ylboronic acid CAS: 372963-51-4 | MS (ESI): 250.06 [M + H]$^+$ |

-continued

| Intermediate | Systematic Name | Building block/intermediate | MS, m/z |
|---|---|---|---|
| B36 | 3-(5-Chloro-2-hydroxy-4-methyl-phenyl)-N-(2-hydroxyethyl)benzamide | N-(4-hydroxyethyl)-3-(4,4,5,5-tetramethyl-1,3,2-dioxaborolan-2-yl)benzamide CAS: 943911-66-8 | MS (ESI): 306.1 [M + H]+ |
| B38 | 3-(5-Chloro-2-hydroxy-4-methyl-phenyl)-4-fluoro-N,N-dimethyl-benzamide | 5-(dimethylcarbamoyl)-2-fluorophenylboronic acid CAS: 874289-46-0 | MS (ESI): 308.1 [M + H]+. |
| B40 | [3-(5-Chloro-2-hydroxy-4-methyl-phenyl)-4-fluoro-phenyl]-morpholino-methanone | 2-fluoro-5-(morpholine-4-carobnyl)phenylboronic acid CAS: 1072951-41-7 | MS (ESI): 350.1 [M + H]+ |

-continued

| Intermediate | Systematic Name | Building block/ intermediate | MS, m/z |
|---|---|---|---|
| B42 | Methyl 3-(5-chloro-2-hydroxy-4-methyl-phenyl)benzoate | 3-(methoxycarbonyl)-phenylboronic acid CAS: 99769-19-4 | MS (ESI): 275.2 [M − H]⁻ |

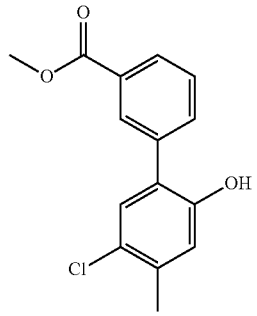

| | | | |
|---|---|---|---|
| B44 | Methyl 3-[[3-(5-chloro-2-hydroxy-4-methyl-phenyl)benzoyl]amino]propanoate | 3-(3-methoxy-3-oxopropylcarbamoyl)-phenylboronic acid CAS: 957034-72-9 | MS (ESI): 348.2 [M + H]⁺ |

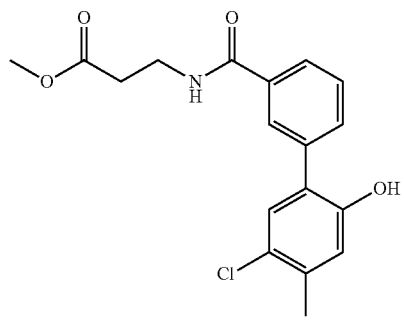

| | | | |
|---|---|---|---|
| B46 | Ethyl 2-[[3-(5-chloro-2-hydroxy-4-methyl-phenyl)benzoyl]amino]acetate | 3-(2-ethoxy-2-oxoethylcarbamoyl)phenylboronic acid CAS: 1072945-97-1 | MS (ESI): 348.1 [M + H]⁺ |

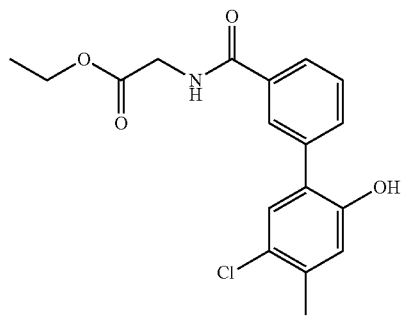

-continued

| Intermediate | Systematic Name | Building block/ intermediate | MS, m/z |
|---|---|---|---|
| B49 | Methyl 3-(5-chloro-2-hydroxy-4-methyl-phenyl)-4-methyl-benzoate 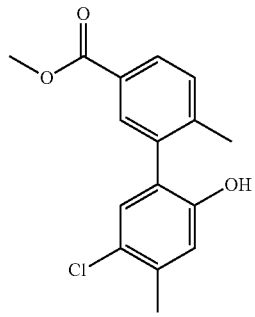 | 5-(methoxycarbonyl)-2-methylphenylboronic acid CAS: 876189-18-3 | MS (ESI): 289.2 [M − H]⁻ |
| B52 | 3-(5-Chloro-2-hydroxy-4-methyl-phenyl)-4-(trifluoromethoxy)benzamide 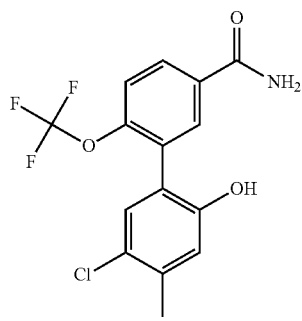 | 5-carbamoyl-2-(trifluoromethoxy)phenylboronic acid eMolecules #BB-4033 | MS (ESI): 346.1 [M + H]⁺ |
| B53 | 4-Chloro-2-(2-methoxy-3-pyridyl)-5-methyl-phenol 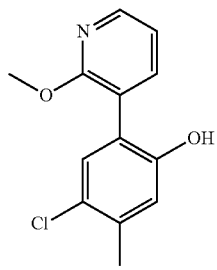 | 2-methoxypyridin-3-ylboronic acid CAS: 163105-90-6 | MS (ESI): 250.1 [M + H]⁺ |

Intermediate B16:

6-Hydroxy-biphenyl-3-carbonitrile

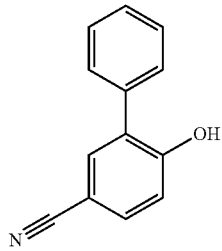 [SMILES: N#Cc1ccc(O)c(-c2ccccc2)c1]

Step 1: 4-Hydroxy-3-iodo-benzonitrile

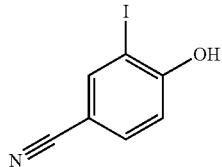

To a solution of 4-hydroxy-benzonitrile (5 g, CAS: 767-00-0) in NH₄OH (225 mL) was added a solution of KI (34.14 g, CAS: 7681-11-0) and I₂ (10.65 g, CAS: 7553-56-2) in H₂O (50 mL). The reaction mixture was stirred at rt for 16 hours. The reaction mixture was filtered and the filtrate was evaporated. The residue was dissolved in DCM (250 mL) and was washed with H₂O (2×150 mL), saturated aqueous NaS₂O₃ solution (100 mL) and brine (100 mL). The organic layer was dried over anhydrous Na₂SO₄, filtered and concentrated under reduced pressure to give the title compound (8.44 g, 82%) that was used in the next step without further purification. LC-MS: (ESI): m/z=244.0 [M–H]⁻.

Step 2: 6-Hydroxy-biphenyl-3-carbonitrile

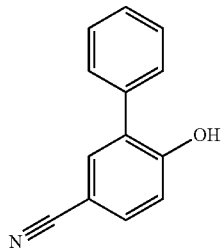 [SMILES: N#Cc1ccc(O)c(-c2ccccc2)c1]

The title compound was obtained in analogy to intermediate B1, step 4, from 4-hydroxy-3-iodo-benzonitrile and phenylboronic acid (CAS: 98-80-6) as a colorless solid (0.580 g, 73%). ¹H NMR (400 MHz, CDCl₃): 5.72 (1H, s), 7.03-7.07 (1H, d, J=4), 7.40-7.42 (2H, d, J=8), 7.44-7.56 (5H, m).

Intermediate B26:

4-Chloro-5-methyl-2-oxazol-5-yl-phenol

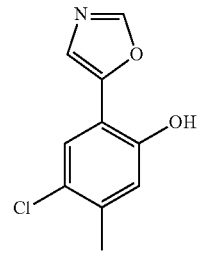

Step 1: 5-Chloro-2-methoxy-4-methyl-benzaldehyde

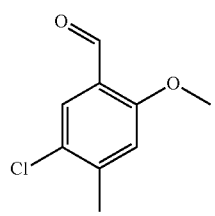

To a solution of 1-chloro-5-iodo-4-methoxy-2-methyl-benzene (1.0 g, intermediate B1, step 2) in anhydrous THF (25 mL) was added n-BuLi (1.7 mL, 2.5M solution in hexane) dropwise at −78° C. under nitrogen atmosphere and the reaction mixture was stirred at −78° C. for 2 hours. Then, DMF (0.329 mL) dissolved in anhydrous THF (2 mL) was added dropwise to the reaction mixture at −78° C. and the solution was stirred at −78° C. for 2 hours. The reaction mixture was quenched with saturated aqueous NH₄Cl solution and was extracted with EtOAc (2×50 mL). The combined organic layers were washed with brine (50 mL), dried over Na₂SO₄, filtered and evaporated under reduced pressure to give the title compound as yellow solid (0.685 g, 76%). Rf=0.6 (10% EtOAc/hexane).

Step 2: 5-(5-Chloro-2-methoxy-4-methyl-phenyl)-oxazole

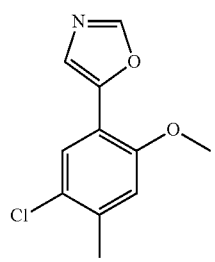

To a stirred solution of 5-chloro-2-methoxy-4-methyl-benzaldehyde (500 mg) in MeOH (20 mL) was added tosylmethyl isocyanide (582 mg, CAS: 36635-61-7), followed by K₂CO₃ (561 mg) and the resulting mixture was refluxed for 3 hours. Then, MeOH was evaporated and the residue was purified by flash chromatography over silica gel (5-10% EtOAc/hexane) to give the title compound as an off white solid (294 mg, 49%). MS (ESI): m/z=224.0 [M+H]⁺.

Step 3: 4-Chloro-5-methyl-2-oxazol-5-yl-phenol

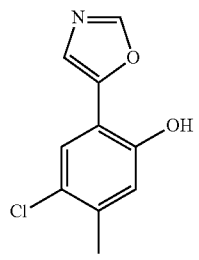

The title compound was obtained in analogy to intermediate B1, step 3, from 5-(5-chloro-2-methoxy-4-methyl-phenyl)-oxazole (292 mg) as a brown solid (0.266 g, 97%). MS (ESI): m/z=210.2 [M+H]⁺.

Intermediate B30:

4-Chloro-5-methyl-2-(2-methyl-2H-pyrazol-3-yl)-phenol

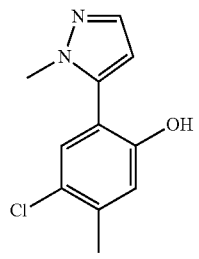

Step 1: 5-(5-Chloro-2-methoxy-4-methyl-phenyl)-1-methyl-1H-pyrazole

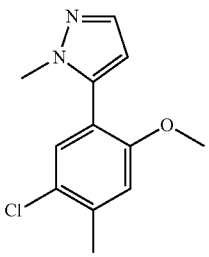 [SMILES: COc1cc(C)c(Cl)cc1-c1ccnn1C]

To a mixture of 1-chloro-5-iodo-4-methoxy-2-methyl-benzene (500 mg, intermediate B1, step 2), 1-methyl-5-(4,4,5,5-tetramethyl-[1,3,2]dioxaborolan-2-yl)-1H-pyrazole (442 mg, CAS: 847818-74-0) and K₂CO₃ (733 mg) in dioxane (12 ml) and water (4 ml) was added PdCl₂(PPh₃)₂—CH₂Cl₂ (25 mg) and the reaction mixture was heated to 110° C. for 16 h. The reaction mixture was diluted with ethyl acetate (50 ml), filtered through celite and the filtrate was evaporated. The resulting residue was purified by column chromatography over silica gel (0-20% EtOAc/hexane) to obtain 5-(5-chloro-2-methoxy-4-methyl-phenyl)-1-methyl-1H-pyrazole (365 mg, 87%) as brown sticky solid. MS (ESI): m/z=236.7 [M+H]⁺.

Step 2: 4-Chloro-5-methyl-2-(2-methyl-2H-pyrazol-3-yl)-phenol

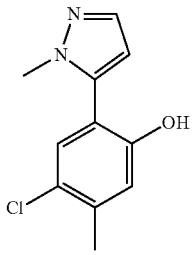

To a solution of 5-(5-chloro-2-methoxy-4-methyl-phenyl)-1-methyl-1H-pyrazole (355 mg) in DCM (20 ml) at 0° C. was added BBr₃ (1M solution in DCM, 3 mL) and the reaction mixture was stirred at 25° C. for 3 h. All volatiles were then removed in vacuo and the remaining residue was dissolved in DCM (50 ml) and washed with 10% aqueous NaHCO₃ solution and brine. The organic layer was dried over Na₂SO₄ and concentrated. The resulting crude material was purified by column chromatography over silica gel (0-30% EtOAc/hexane) to afford 4-chloro-5-methyl-2-(2-methyl-2H-pyrazol-3-yl)-phenol (138 mg, 41%) as yellow solid. MS (ESI): m/z=223 [M+H]⁺.

Intermediate B31:

4-Chloro-6-hydroxy-biphenyl-3-carbonitrile

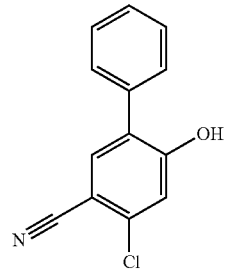 [SMILES: N#Cc1cc(-c2ccccc2)c(O)cc1Cl]

Method A:

Step 1: 5-Bromo-2-chloro-4-hydroxy-benzonitrile

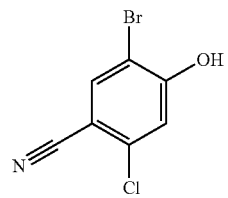 [SMILES: N#Cc1cc(Br)c(O)cc1Cl]

To a solution of 2-chloro-4-hydroxy-benzonitrile (4.0 g, CAS: 3336-16-1) in anhydrous acetonitrile (80 ml) was added TfOH (2.53 ml) drop wise at −30° C. and the reaction mixture was stirred at −30° C. for 10 min. Then NBS (6.49 g) was added and the mixture was stirred at −30° C. for 5 min. The reaction mixture was then allowed to warm to 25° C. and was stirred at 25° C. for 16 h. The reaction mixture was quenched with saturated aqueous sodium bisulfite solution and extracted with EtOAc. The combined organic layers were washed with brine, dried over Na$_2$SO$_4$ and filtered. The filtrate was evaporated under reduced pressure and the resulting residue was purified by column chromatography over silica gel (2-6% EtOAc/hexane) to afford 5-bromo-2-chloro-4-hydroxy-benzonitrile (1.2 g, 20%) as an off white solid. MS (ESI): m/z=231.6 [M+H]$^+$.

Step 2:
5-Bromo-2-chloro-4-methoxymethoxy-benzonitrile

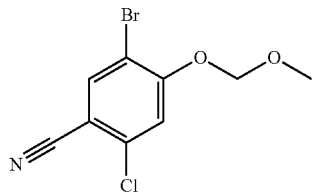

To a suspension of NaH (62 mg, 60% in mineral oil) in anhydrous THF (10 mL) at 0° C. was added a solution of 5-bromo-2-chloro-4-hydroxy-benzonitrile (300 mg) in anhydrous THF (5 mL) and the reaction mixture was stirred at 25° C. for 30 min. Then MOM-Cl (0.147 ml) was added dropwise and the reaction mixture was stirred at 25° C. for 3 h. The reaction mixture was quenched with water and was extracted with EtOAc. The combined organic layers were washed with brine, dried over Na$_2$SO$_4$ and evaporated under reduced pressure. The resulting crude material was purified by column chromatography over silica gel (0-3% EtOAc/hexane) to afford 5-bromo-2-chloro-4-methoxymethoxy-benzonitrile (315 mg, 88%) as an off white solid. $^1$H-NMR CDCl$_3$): 3.51 (s, 3H), 5.30 (s, 2H), 7.28 (s, 1H), 7.81 (s, 1H).

Step 3: 4-Chloro-6-hydroxy-biphenyl-3-carbonitrile

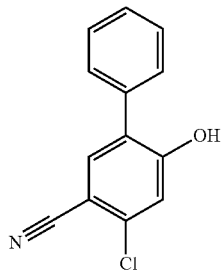 [SMILES: N#Cc1cc(-c2ccccc2)c(O)cc1Cl]

To a mixture of 5-bromo-2-chloro-4-methoxymethoxy-benzonitrile (100 mg) and phenyl boronic acid (132.3 mg, CAS: 98-80-6) in anhydrous DMF (50 mL) in a sealed tube was added K$_2$CO$_3$ (149.7 mg) at 25° C. and the reaction mixture was purged with argon for 10 min. Then Pd(dppf)Cl$_2$—CH$_2$Cl$_2$ complex (8.85 mg) was added and the mixture was again purged with argon for 10 min and then heated to 120° C. for 16 h. The reaction mixture was cooled to 25° C. and filtered. The filtrate was evaporated under reduced pressure and the resulting residue was purified by column chromatography over silica gel (5-7% EtOAc/hexane) to afford 4-chloro-6-hydroxy-biphenyl-3-carbonitrile (43 mg, 44%) as off white solid. $^1$H-NMR (δ, CDCl$_3$): 5.91 (s, 1H), 7.13 (s, 1H), 7.39 (dd, 2H), 7.44-7.56 (m, 4H).

Method B:

Step 1: 5-iodo-2-chloro-4-hydroxy-benzonitrile

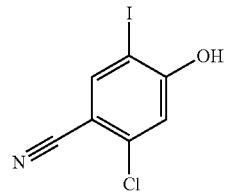 [SMILES: N#Cc1cc(I)c(O)cc1Cl]

To a solution of 2-chloro-4-hydroxybenzonitrile (1.18 g, CAS: 3336-16-1) in acetic acid (10 mL) and DCM (10 mL) was added concentrated sulfuric acid (100 μL) and then N-iodosuccinimide (1.66 g) in one portion at rt under an argon atmosphere. The mixture was stirred at rt for 16 hours. The reaction mixture was then poured into ice/water and was extracted two times with ethyl acetate. The organic layers were washed once with brine, dried over Na$_2$SO$_4$, filtered and evaporated. The crude material was adsorbed onto silica gel and was then purified by flash chromatography (ISCO, 100 g silica gel cartridge, gradient of 0% to 20% EtOAc in heptane). The fractions containing the desired product along with some di-iodinated side products were combined, evaporated and dried at high vacuum. The residue (1.42 g) was further purified by preparative HPLC (Column: Gemini NX 3u 50×4.6 mm; Eluent: 2% formic acid, 98% CH$_3$CN) to provide the title compound (770 mg) as an off white solid. MS (ESI−): m/z=278.0 [M−H]$^-$.

Step 2: 4-Chloro-6-hydroxy-biphenyl-3-carbonitrile

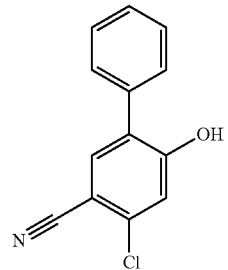 [SMILES: N#Cc1cc(-c2ccccc2)c(O)cc1Cl]

2-Chloro-4-hydroxy-5-iodobenzonitrile (350 mg), phenylboronic acid (160 mg) and sodium carbonate (398 mg) were combined with DMF (13.0 mL) and water (2.0 mL) at rt under an argon atmosphere. Then, [1,1'-bis(diphenylphosphino)ferrocene]di chloropalladium(II), complex with DCM (133 mg) was added to the orange suspension. The reaction mixture was three times evaporated and purged with argon and then heated to 80° C. for 3.5 hours. The mixture was cooled to room temperature, poured into ice/water and was then acidified with saturated NH$_4$Cl solution. The aqueous layer was extracted twice with ethyl acetate. The organic layers were washed with brine, dried over Na$_2$SO$_4$, filtered and evaporated. The crude material was purified by flash chromatography (ISCO, silica gel, 40 g cartridge, 100%

CH₂Cl₂ and then CH₂Cl₂/CH₃CN=96/4). The appropriate fractions were combined and evaporated to provide the title compound (150 mg) as an off white solid.

MS (EST): m/z=228.1 [M−H]⁻. NMR complies with the material described above from method A.

The following Intermediates were prepared in analogy to intermediate B31, either via method A from 5-bromo-2-chloro-4-hydroxy-benzonitrile (intermediate B31, step 1), or via method B from 5-iodo-2-chloro-4-hydroxy-benzonitrile, and the boronic acid precursors as indicated in the table below:

| Intermediate | Systematic Name | Building block/ intermediate | MS, m/z |
|---|---|---|---|
| B32 | 4-Chloro-4'-fluoro-6-hydroxy-biphenyl-3-carbonitrile 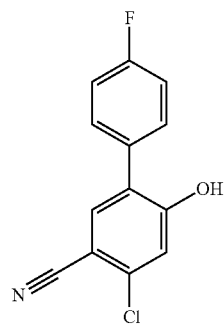 | 4-fluoro phenyl boronic acid CAS: 1765-93-1 Method A | MS (ESI): 245.6 [M + H]⁺ |
| B33 | 4'-Chloro-5'-cyano-2'-hydroxy-biphenyl-3-carboxylic acid methylamide 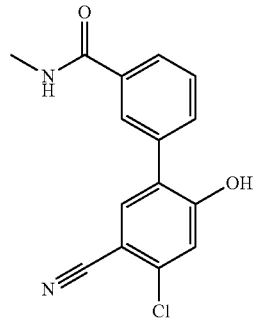 | 3-(N-methylamino-carbonyl) phenylboronic acid CAS: 832695-88-2 Method A | MS (ESI): 287.1 [M + H]⁺ |
| B84 | 2-chloro-5-(2-fluorophenyl)-4-hydroxybenzonitrile 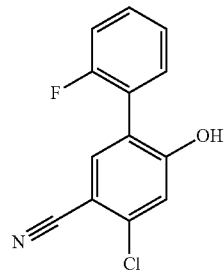 | 2-fluoro phenyl boronic acid CAS: 1993-03-9 Method B | MS (ESI): 248.1 [M + H]⁺ |
| B85 | 2-chloro-5-(3-fluorophenyl)-4-hydroxybenzonitrile 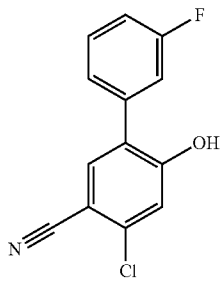 | 3-fluoro phenyl boronic acid CAS: 768-35-4 Method B | MS (ESI): 246.1 [M − H]⁻ |
| B89 | 2-chloro-5-(2-fluoro-5-propan-2-yloxyphenyl)-4-hydroxybenzonitrile 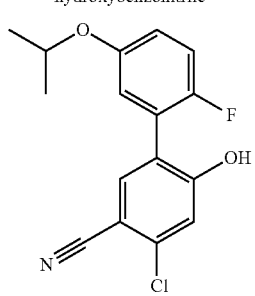 | (2-fluoro-5-propan-2-yloxyphenyl) boronic acid CAS: 849062-30-2 Method B | MS (ESI): 304.2 [M − H]⁻ |

Intermediate B35:

4-Chloro-6-hydroxy-3'-(5-methyl-[1,2,4]oxadiazol-3-yl)-biphenyl-3-carbonitrile

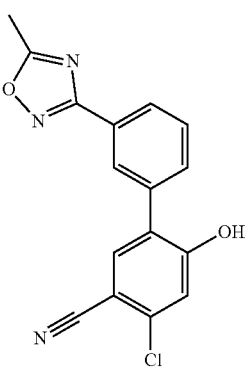

Step 1: 3-(4,4,5,5-Tetramethyl-[1,3,2]dioxaborolan-2-yl)-benzonitrile

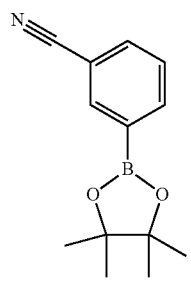 [SMILES: CC1(C)OB(c2cccc(C#N)c2)OC1(C)C]

To a solution of 3-cyanophenyl boronic acid (2.5 g, CAS: 150255-96-2) in anhydrous THF (150 ml) under an atmosphere of nitrogen were added pinacol (2.95 g) and Na$_2$SO$_4$ (10 g) at 25° C. The reaction mixture was stirred for 12 h at 25° C. under an atmosphere of nitrogen. Then, Na$_2$SO$_4$ was filtered off and all volatiles were evaporated. The residue was partitioned between ethyl acetate and water. The organic layer was then separated, dried over Na$_2$SO$_4$ and concentrated to afford the title compound (4.72 g) as off white solid which was directly used in the next reaction step without further characterization.

Step 2: N-Hydroxy-3-(4,4,5,5-tetramethyl-[1,3,2]dioxaborolan-2-yl)-benzamidine

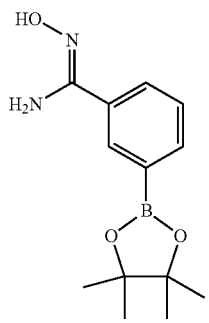 [SMILES: CC1(C)OB(c2cccc(/C(N)=N/O)c2)OC1(C)C]

To a solution of -(4,4,5,5-tetramethyl-[1,3,2]dioxaborolan-2-yl)-benzonitrile (4.65 g) in ethanol (150 ml) were added DIPEA (7.15 mL) and hydroxyl amine hydrochloride (3.53 g) at 25° C. The reaction mixture was then refluxed for 3 h. All volatiles were evaporated in vacuo and the residue was partitioned between ethyl acetate and water. The organic layer was separated, dried over Na$_2$SO$_4$ and concentrated to afford N-hydroxy-3-(4,4,5,5-tetramethyl-[1,3,2]dioxaborolan-2-yl)-benzamidine along with some impurities (5.7 g) as an off white, sticky solid. MS (ESI): m/z=262.8 [M+H]$^+$.

Step 3: 5-Methyl-3-[3-(4,4,5,5-tetramethyl-[1,3,2]dioxaborolan-2-yl)-phenyl]-[1,2,4]oxadiazole

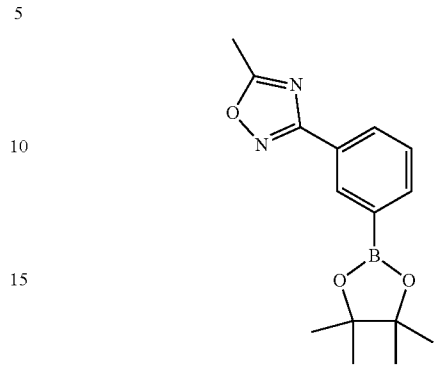

A solution of N-hydroxy-3-(4,4,5,5-tetramethyl-[1,3,2]dioxaborolan-2-yl)-benzamidine (5.7 g) in acetic anhydride (100 mL) was refluxed for 3 h. Acetic anhydride was evaporated and the residue was partitioned between water and ethyl acetate. The ethyl acetate layer was separated, washed with aqueous NaHCO$_3$ solution, water and brine and dried over Na$_2$SO$_4$ and concentrated. The crude product was purified by column chromatography over silica gel (0-5% EtOAc/hexane) to afford the title compound (3.5 g) as an off white solid. MS (ESI): m/z=287.0 [M+H]$^+$.

Step 4: 4-Chloro-6-hydroxy-3'-(5-methyl-[1,2,4]oxadiazol-3-yl)-biphenyl-3-carbonitrile

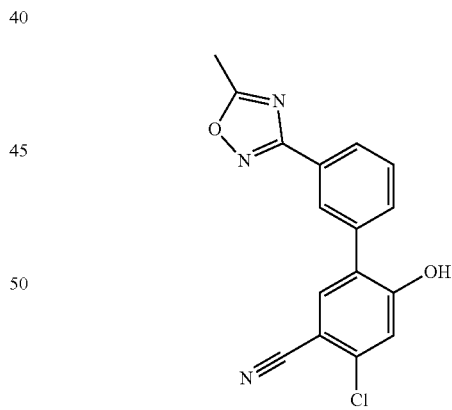

The title compound was prepared in analogy to Intermediate B31, step 3, from 5-bromo-2-chloro-4-methoxymethoxy-benzonitrile (Intermediate B32, step 2) (300 mg) and 5-methyl-3-[3-(4,4,5,5-tetramethyl-[1,3,2]dioxaborolan-2-yl)-phenyl]-[1,2,4]oxadiazole (932 mg) and was obtained as off white solid (190 mg, 56%). MS (ESI): m/z=310.2 [M–H]$^−$.

Intermediate B37:

4-Chloro-6-hydroxy-3'-(5-methyl-[1,3,4]oxadiazol-2-yl)-biphenyl-3-carbonitrile

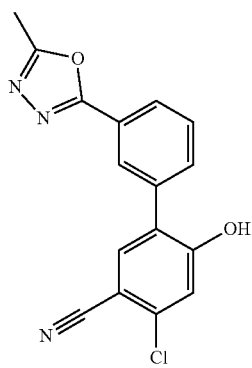 [SMILES: Cc1nnc(-c2cccc(-c3cc(C#N)c(Cl)cc3O)c2)o1]

Step 1: 4'-Chloro-5'-cyano-2'-hydroxy-biphenyl-3-carboxylic acid methyl ester

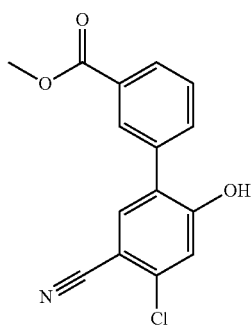 [SMILES: COC(=O)c1cccc(-c2cc(C#N)c(Cl)cc2O)c1]

The title compound was prepared in analogy to Intermediate B31, step 3, from 5-bromo-2-chloro-4-methoxymethoxy-benzonitrile (Intermediate B31, step 2) (1.0 g) and 3-methoxycabonyl phenyl boronic acid (973 mg, CAS: 99769-19-4) and was obtained as off white solid (430 mg, 41%). MS (ESI): m/z=286 [M–H]⁻.

Step 2: 4'-Chloro-5'-cyano-2'-methoxy-biphenyl-3-carboxylic acid methyl ester

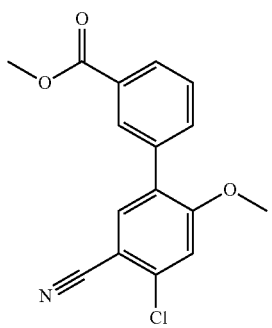

To a solution of 4'-chloro-5'-cyano-2'-hydroxy-biphenyl-3-carboxylic acid methyl ester (650 mg) in anhydrous DMF (30 mL) were added Cs$_2$CO$_3$ (1.10 g) and methyliodide (0.169 mL) at 25° C. The reaction mixture was stirred at 25° C. for 16 h and then filtered. The filtrate was evaporated under reduced pressure and the remaining residue was purified by column chromatography over silica gel (10-15% EtOAc/hexane) to afford the title compound (490 mg, 71%) as an off white solid that was used without further characterization.

Step 3: 4'-Chloro-5'-cyano-2'-methoxy-biphenyl-3-carboxylic acid

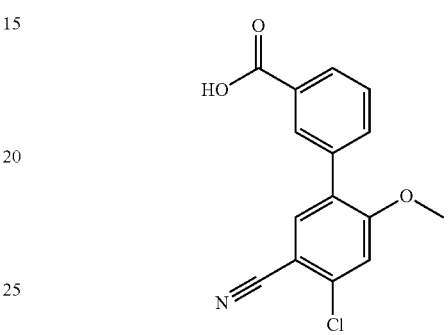

To a solution of 4'-chloro-5'-cyano-2'-methoxy-biphenyl-3-carboxylic acid methyl ester (490 mg) in mixture of THF and water (45 mL) was added LiOH—H$_2$O (136.6 mg) at 25° C. and the reaction mixture was stirred at rt for 12 h. The reaction mixture was then diluted with EtOAc (20 mL) and the layers were separated. The aqueous layer was acidified by addition of 6N HCl and was extracted with EtOAc. The combined extracts were washed with brine, dried over Na$_2$SO$_4$ and concentrated to obtain the title compound (410 mg, 88%) as an off white solid. MS (ESI): m/z=286.1 [M–H]⁻.

Step 4: 4'-Chloro-5'-cyano-2'-methoxy-biphenyl-3-carboxylic acid N'-acetyl-hydrazide

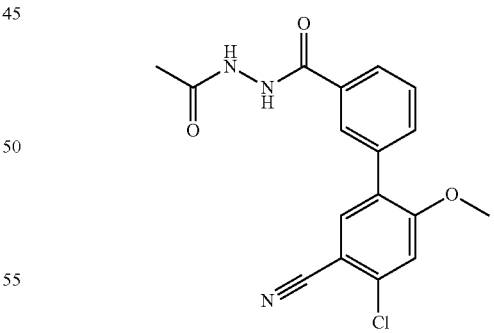

To a solution of 4'-chloro-5'-cyano-2'-methoxy-biphenyl-3-carboxylic acid (410 mg) in anhydrous DMF (30 mL) were added HBTU (812.1 mg) and DIPEA (0.76 mL) at 25° C. The reaction mixture was stirred for 10 min and then acetic acid hydrazide (211.42 mg) was added and stirring was continued for 16 h. The solvent was evaporated and to the remaining residue were added EtOAc and water. The organic layer was separated, dried over Na$_2$SO$_4$ and concentrated. The residue was purified by column chromatography over silica gel (2-3% MeOH/DCM) to afford the title compound (470 mg, 96%) as an off white solid. MS (ESI): m/z=344.2 [M+H]⁺.

Step 5: 4-Chloro-6-methoxy-3'-(5-methyl-[1,3,4] oxadiazol-2-yl)-biphenyl-3-carbonitrile

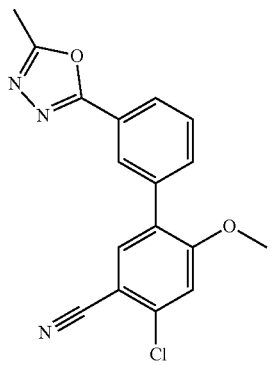 [SMILES: COc1cc(Cl)c(C#N)cc1-c1cccc(-c2nnc(C)o2)c1]

A solution of 4'-chloro-5'-cyano-2'-methoxy-biphenyl-3-carboxylic acid N'-acetyl-hydrazide (400 mg) in POCl₃ (10 mL) was heated to 110° C. for 6 h. The reaction mixture was then cooled to 25° C. and all volatiles were removed under reduced pressure. To the remaining residue was added sat. NaHCO₃ solution (15 mL) and the mixture was extracted with EtOAc. The combined extracts were dried over Na₂SO₄ and concentrated. The residue was purified by column chromatography over silica gel (10-15% EtOAc/hexane) to afford the title compound (130 mg, 34%) as an off white solid. MS (ESI): m/z=326.2 [M+H]⁺.

Step 6: 4-Chloro-6-hydroxy-3'-(5-methyl-[1,3,4] oxadiazol-2-yl)-biphenyl-3-carbonitrile

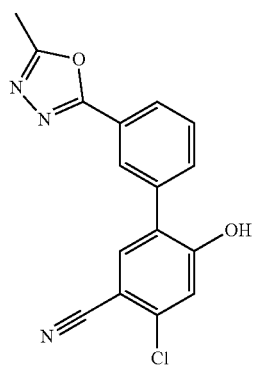 [SMILES: Cc1nnc(-c2cccc(-c3cc(C#N)c(Cl)cc3O)c2)o1]

To a solution of 4-chloro-6-methoxy-3'-(5-methyl-[1,3,4] oxadiazol-2-yl)-biphenyl-3-carbonitrile (110 mg) in anhydrous DCM (10 mL) was added BBr₃ (0.4 mL) at 0° C. The reaction mixture was stirred at 25° C. for 28 h. Again BBr₃ (0.5 mL) was added and reaction mixture was stirred for another 16 h. All volatiles were removed under reduced pressure and the residue was purified by column chromatography over silica gel (30-45% EtOAc/hexane) to afford the title compound (80 mg, 76%) as an off white solid. MS (ESI): m/z=310.2 [M−H]⁻.

Intermediate B39:

3-(4-Chloro-5-cyano-2-hydroxy-phenyl)-N,N-dimethyl-benzamide

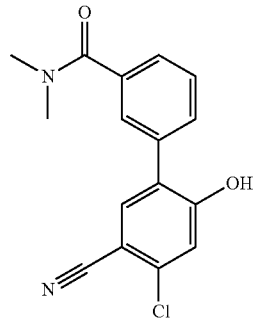 [SMILES: CN(C)C(=O)c1cccc(-c2cc(C#N)c(Cl)cc2O)c1]

Step 1: 3-[4-Chloro-5-cyano-2-(methoxymethoxy) phenyl]-N,N-dimethyl-benzamide

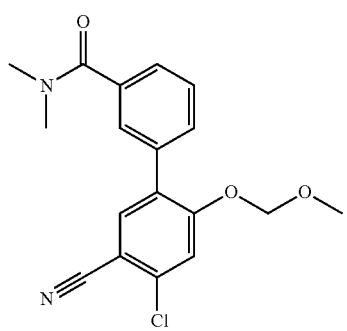

The title compound was prepared in analogy to Intermediate B31, step 3, from 5-bromo-2-chloro-4-methoxymethoxy-benzonitrile (Intermediate B31, step 2) (48.9 mg) and 3-(dimethylcarbamoyl)phenylboronic acid (40.9 mg, CAS: 373384-14-6) and was obtained as light yellow gum (43 mg, 71%). MS (ESI): m/z=698.3 [2M+H]⁺.

Step 2: 3-(4-Chloro-5-cyano-2-hydroxy-phenyl)-N, N-dimethyl-benzamide

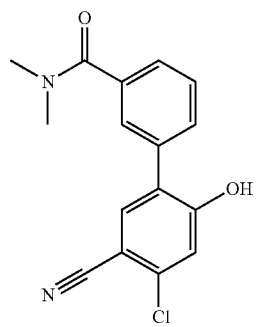 [SMILES: CN(C)C(=O)c1cccc(-c2cc(C#N)c(Cl)cc2O)c1]

To solution of 3-[4-chloro-5-cyano-2-(methoxymethoxy) phenyl]-N,N-dimethyl-benzamide (40.0 mg) in dioxane (1 mL) was added dropwise 4N HCl in dioxane (1500) at 0° C. The reaction mixture was then stirred at rt for 4 h. Additional 4N HCl in dioxane (100 μl) was added and the resulting suspension was stirred at rt overnight. The reaction mixture was concentrated to dryness and then co-evaporated from DCM three times. The resulting off white solid (34 mg, 97%) was used in the next reaction step without further purification. MS (ESI): m/z=301.1 [M+H]⁺.

Intermediate B41:

2-Chloro-4-hydroxy-5-[3-(morpholine-4-carbonyl)phenyl]benzonitrile

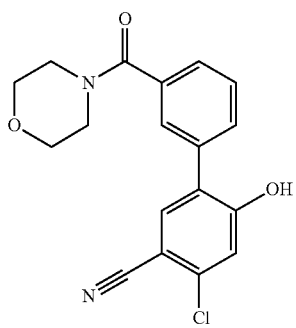 [SMILES: N#Cc1cc(-c2cccc(C(=O)N3CCOCC3)c2)c(O)cc1Cl]

Step 1: 2-Chloro-4-(methoxymethoxy)-5-[3-(morpholine-4-carbonyl)phenyl]benzonitrile

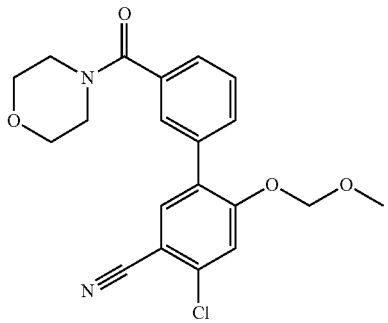 [SMILES: COCOc1cc(Cl)c(C#N)cc1-c1cccc(C(=O)N2CCOCC2)c1]

The title compound was prepared in analogy to Intermediate B31, step 3, from 5-bromo-2-chloro-4-methoxymethoxy-benzonitrile (Intermediate B31, step 2) (50.0 mg) and 3-(morpholine-4-carbonyl)phenylboronic acid (51.0 mg, CAS: 723281-55-8) and was obtained as white solid (53 mg, 76%). MS (ESI): m/z=387.2 [M+H]⁺.

Step 2: 2-Chloro-4-hydroxy-5-[3-(morpholine-4-carbonyl)phenyl]benzonitrile

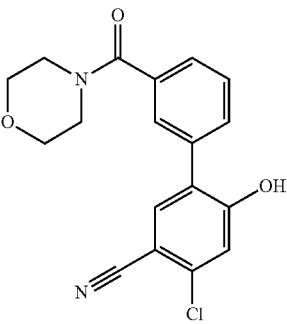

The title compound was prepared in analogy to Intermediate B39, step 2, from 2-chloro-4-(methoxymethoxy)-5l-[3-(morpholine-4-carbonyl)phenyl]benzonitrile (49.9 mg) and was obtained as off white solid (44 mg, 99%). MS (ESI): m/z=343.1 [M+H]⁺.

Intermediate B54:

2-Chloro-4-hydroxy-5-(2-methoxy-3-pyridyl)benzonitrile

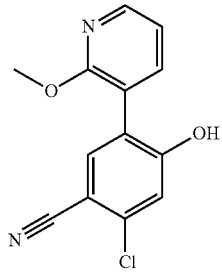 [SMILES: COc1ncccc1-c1cc(C#N)c(Cl)cc1O]

Step 1: 2-Chloro-4-(methoxymethoxy)-5-(2-methoxy-3-pyridyl)benzonitrile

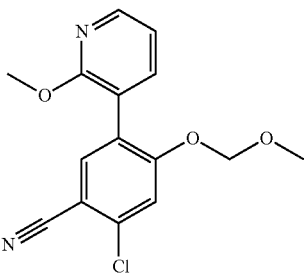 [SMILES: COCOc1cc(Cl)c(C#N)cc1-c1cccnc1OC]

The title compound was prepared in analogy to Intermediate B31, step 3, from 5-bromo-2-chloro-4-methoxymethoxy-benzonitrile (intermediate B31, step 2) (50.0 mg) and 2-methoxypyridin-3-ylboronic acid (33.2 mg, eMolecules # BB-4033) and was obtained as a white solid (43 mg, 78%). MS (ESI): m/z=305.1 [M+H]⁺.

Step 2: 2-Chloro-4-hydroxy-5-(2-methoxy-3-pyridyl)benzonitrile

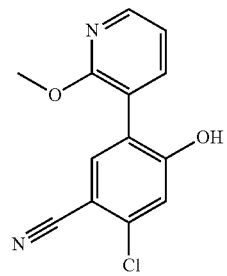 [SMILES: COc1ncccc1-c1cc(C#N)c(Cl)cc1O]

The title compound was prepared in analogy to Intermediate B39, step 2, from 2-chloro-4-(methoxymethoxy)-5-(2-methoxy-3-pyridyl)benzonitrile (41.1 mg) and was obtained as an off white solid (35.2 mg, 100%). MS (ESI): m/z=261.1 [M+H]$^+$.

Intermediate B58

4-Chloro-2-[2-fluoro-5-(2-methylpropoxy)phenyl]-5-methylphenol

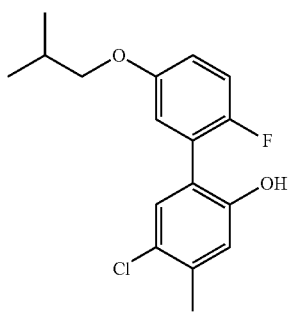 [SMILES: Cc1cc(O)c(-c2cc(OCC(C)C)ccc2F)cc1Cl]

4-Chloro-2-iodo-5-methylphenol (intermediate B1, step 3, (80 mg), (2-fluoro-5-isobutoxyphenyl)boronic acid (75.8 mg, CAS: 1217500-65-6) and sodium carbonate (94.7 mg) were combined with DMF (5.0 mL) and water (0.85 mL) at rt under an argon atmosphere. Then, [1,1'-bis(diphenylphosphino)ferrocene]dichloropalladium(II) complex with dichloromethane (31.6 mg, CAS: 95464-05-4) was added to the orange suspension. The reaction mixture was heated to 80° C. for 3 hours and was then cooled and kept at rt for 64 hours. The reaction mixture was poured into ice/water and was acidified with saturated NH$_4$Cl solution. The aqueous layer was extracted twice with ethyl acetate. The organic layers were washed once with brine, dried over Na$_2$SO$_4$, filtered and evaporated to dryness. The crude material was purified by flash chromatography (0% to 50% ethyl acetate in heptane) to give the title compound as a light yellow liquid (62 mg, 65%). MS (ESI): m/z=307.3 [M−H]$^+$.

The following intermediates were prepared in analogy to intermediate B58 from 4-chloro-2-iodo-5-methylphenol (Intermediate B1, step 3) and the corresponding building blocks indicated in the table below:

| Intermediate | Systematic Name | Building block/ intermediate | MS, m/z |
|---|---|---|---|
| B55 | 4-Chloro-2-(5-ethoxy-2-fluorophenyl)-5-methylphenol | 5-ethoxy-2-fluorophenyl-boronic acid CAS: 900174-60-9 | MS (ESI): 279.2 [M − H]$^-$ |
| B56 | 4-Chloro-2-(2-methoxyphenyl)-5-methylphenol | (2-methoxyphenyl) boronic acid CAS: 5720-06-9 | MS (ESI): 249.2 [M + H]$^+$ |
| B57 | 4-Chloro-2-(2-fluoro-5-propan-2-yloxyphenyl)-5-methylphenol | (2-fluoro-5-isopropoxy-phenyl) boronic acid CAS: 849062-30-2 | MS (ESI): 293.2 [M − H]$^-$ |
| B59 | 4-Chloro-2-[2-methoxy-5-(trifluoromethyl)phenyl]-5-methylphenol | (2-methoxy-5-(trifluoromethyl) phenyl) boronic acid CAS: 240139-82-6) | MS (ESI): 315.2 [M − H]$^-$ |

169

-continued

| Intermediate | Systematic Name | Building block/ intermediate | MS, m/z |
|---|---|---|---|
| B60 | 4-Chloro-2-(2-methoxy-5-propan-2-ylphenyl)-5-methylphenol | (5-isopropyl-2-methoxyphenyl) boronic acid CAS: 216393-63-4) | MS (ESI): 289.3 [M − H]⁻ |

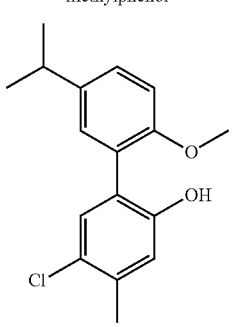

Intermediate B61

2-Chloro-5-[2-fluoro-5-(morpholine-4-carbonyl)phenyl]-4-hydroxybenzonitrile

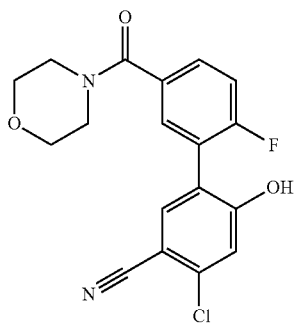 [SMILES: N#Cc1cc(-c2cc(C(=O)N3CCOCC3)ccc2F)c(O)cc1Cl]

Step 1: 2-Chloro-5-[2-fluoro-5-(morpholine-4-carbonyl)phenyl]-4-(methoxymethoxy)benzonitrile

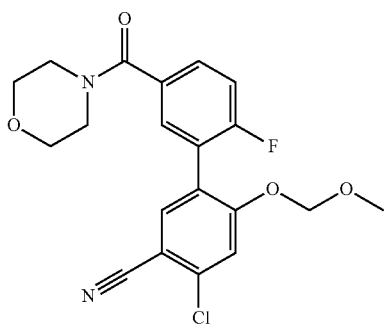 [SMILES: COCOc1cc(Cl)c(C#N)cc1-c1cc(C(=O)N2CCOCC2)ccc1F]

The title compound was prepared in analogy to Intermediate B58 from 5-bromo-2-chloro-4-methoxymethoxy-benzonitrile (intermediate B32, step 2) (100 mg) and (2-fluoro-5-(morpholine-4-carbonyl)phenyl)boronic acid (110 mg, CAS: 1072951-41-7) and was obtained as a light yellow foam (24 mg, 15%). MS (ESI): m/z=405.2 [M+H]⁺.

170

Step 2: 2-Chloro-5-[2-fluoro-5-(morpholine-4-carbonyl)phenyl]-4-hydroxybenzonitrile

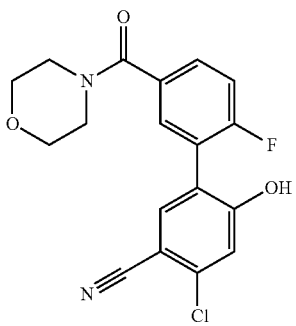

The title compound was prepared in analogy to Intermediate B39, step 2 from 2-chloro-5-[2-fluoro-5-(morpholine-4-carbonyl)phenyl]-4-(methoxymethoxy)benzonitrile (29 mg) and was obtained as an off-white solid (14 mg, 54%). MS (ESI): m/z=361.1 [M+H]⁺.

Intermediate B63

3-(5-Chloro-2-hydroxy-4-methylphenyl)-N-cyclopropyl-4-fluoro-N-methylbenzamide

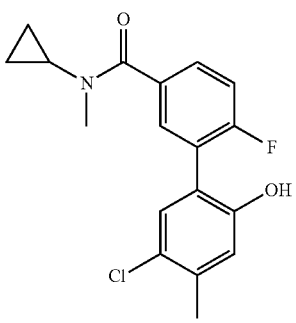 [SMILES: Cc1cc(O)c(-c2cc(C(=O)N(C)C3CC3)ccc2F)cc1Cl]

Step 1: 3-(5-Chloro-2-methoxy-4-methylphenyl)-N-cyclopropyl-4-fluorobenzamide

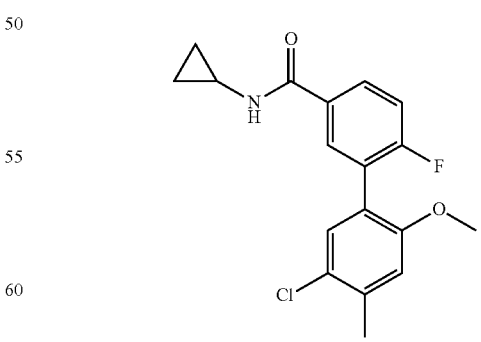

The title compound was prepared in analogy to Intermediate B58 from 1-chloro-5-iodo-4-methoxy-2-methylbenzene (intermediate B1, step 2) (265 mg) and (5-(cyclopropylcarbamoyl)-2-fluorophenyl)boronic acid (251 mg, CAS:

Step 2: 3-(5-Chloro-2-methoxy-4-methylphenyl)-N-cyclopropyl-4-fluoro-N-methylbenzamide

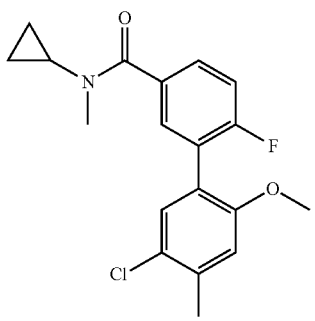 [SMILES: COc1cc(C)c(Cl)cc1-c1cc(C(=O)N(C)C2CC2)ccc1F]

Sodium hydride 60% dispersion in mineral oil (37.9 mg) was added to a solution of 3-(5-chloro-2-methoxy-4-methylphenyl)-N-cyclopropyl-4-fluorobenzamide (158 mg) in DMF (4.0 mL) at rt under an argon atmosphere. The mixture was stirred at rt for 45 minutes. Then, iodomethane (87.3 mg) was added dropwise over a period of 2 minutes and the mixture was stirred at rt for 3 hours. The reaction mixture was then poured into ice/water. The aqueous layer was extracted twice with ethyl acetate. The organic layers were washed once with brine, dried over Na$_2$SO$_4$, filtered and evaporated to dryness. The crude material was purified by flash chromatography (0% to 50% ethyl acetate in heptane) to give the title compound as a white foam (154 mg, 93%). MS (ESI): m/z=348.2 [M+H]$^+$.

Step 3: 3-(5-Chloro-2-hydroxy-4-methylphenyl)-N-cyclopropyl-4-fluoro-N-methylbenzamide

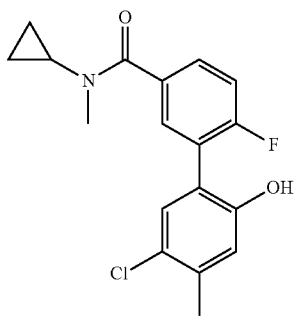 [SMILES: Cc1cc(O)c(-c2cc(C(=O)N(C)C3CC3)ccc2F)cc1Cl]

The title compound was prepared in analogy to Intermediate B1, step 3, from 3-(5-chloro-2-methoxy-4-methylphenyl)-N-cyclopropyl-4-fluoro-N-methylbenzamide (151 mg) and was obtained as an off-white foam (157 mg, 98%). MS (ESI): m/z=334.1 [M+H]$^+$.

Intermediate B62

[3-(5-Chloro-2-hydroxy-4-methylphenyl)-4-fluorophenyl]-pyrrolidin-1-ylmethanone

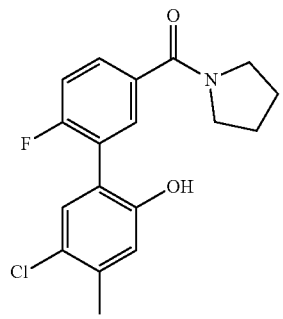 [SMILES: Cc1cc(O)c(-c2cc(C(=O)N3CCCC3)ccc2F)cc1Cl]

Step 1: Methyl 3-(5-chloro-2-methoxy-4-methylphenyl)-4-fluorobenzoate

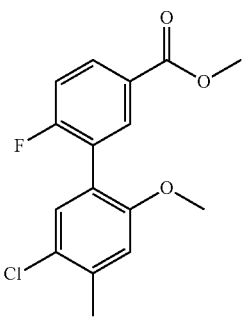 [SMILES: COC(=O)c1ccc(F)c(-c2cc(Cl)c(C)cc2OC)c1]

Methyl 3-bromo-4-fluorobenzoate (3.75 g) was dissolved in cyclopentylmethylether (70 mL) at room temperature under an argon atmosphere. Then, potassium acetate (6.32 g), 4,4,4',4',5,5,5',5'-octamethyl-2,2'-bi(1,3,2-dioxaborolane) (5.72 g) and [1,1'-bis(diphenylphosphino)ferrocene]dichloropalladium(II) complex with dichloromethane (526 mg CAS: 95464-05-4) were added to the mixture. The reaction mixture was heated to 95° C. for 4 hours and was then cooled down to rt for another hour. To the mixture was added sodium carbonate solution (15%, 26.2 mL), 1-chloro-5-iodo-4-methoxy-2-methylbenzene (intermediate B1, step 2) (6.06 g) and [1,1'-bis(diphenylphosphino)ferrocene]dichloropalladium(II) complex with DCM (526 mg, CAS: 95464-05-4). The mixture was heated again to 85° C. for 18 hours. Then, the reaction mixture was cooled to rt and poured into ice/water. The aqueous layer was extracted twice with cyclopentylmethylether. The organic layers were washed once with brine, dried over Na$_2$SO$_4$, filtered and evaporated to dryness. The crude material was purified by flash chromatography (0% to 50% ethyl acetate in heptane) to give the title compound as a light yellow solid (4.46 g, 67%). $^1$H NMR (400 MHz, CDCl$_3$): 2.43 (3H, s), 3.76 (3H, s), 3.91 (3H, s), 6.85 (1H, s), 7.14-7.18 (1H, t), 7.24 (1H, s), 8.0-8.07 (2H, m).

Step 2: 3-(5-Chloro-2-methoxy-4-methylphenyl)-4-fluorobenzoic acid

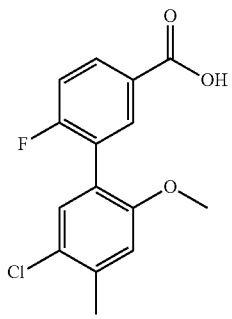 [SMILES: COc1cc(C)c(Cl)cc1-c1cc(C(=O)O)ccc1F]

LiOH 1M solution (2.51 mL) was added to a solution of methyl 3-(5-chloro-2-methoxy-4-methylphenyl)-4-fluorobenzoate (310 mg) in THF (6.0 mL) at room temperature. The mixture was stirred at rt for 18 hours. The reaction mixture was poured into ice/water and was acidified with HCl 1M solution to pH=1. The aqueous layer was extracted twice with ethyl acetate. The organic layers were washed once with brine, dried over $Na_2SO_4$, filtered and evaporated to dryness to give the title compound as a white solid (309 mg, 99%). MS (ESI): m/z=293.2 $[M-H]^-$.

Step 3: [3-(5-Chloro-2-methoxy-4-methylphenyl)-4-fluorophenyl]-pyrrolidin-1-ylmethanone

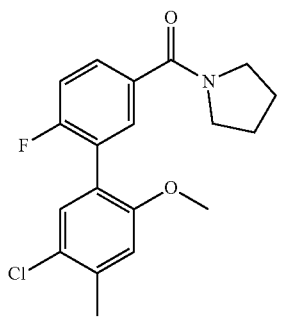 [SMILES: COc1cc(C)c(Cl)cc1-c1cc(C(=O)N2CCCC2)ccc1F]

3-(5-Chloro-2-methoxy-4-methylphenyl)-4-fluorobenzoic acid (100 mg), pyrrolidine (36.2 mg, CAS: 123-75-1) and 4-methylmorpholine (51.5 mg) were dissolved in DMF (4.0 mL) at rt under an argon atmosphere. 1-(3-Dimethylaminopropyl)-3-ethylcarbodiimide hydrochloride (97.6 mg) and 1-hydroxybenzotriazole hydrate (68.8 mg) were added to the light yellow solution. The mixture was stirred at rt for 2.5 hours. The reaction mixture was poured then into ice/water and was basified with 2M $Na_2CO_3$ solution. The aqueous layer was extracted twice with ethyl acetate. The organic layers were washed once with 1M HCl solution and once with brine, dried over $Na_2SO_4$, filtered and evaporated to dryness. The crude material was purified by flash chromatography (0% to 70% ethyl acetate in heptane) to give the title compound as a white solid (78 mg, 65%). MS (ESI): m/z=348.1 $[M+H]^+$.

Step 4: [3-(5-Chloro-2-hydroxy-4-methylphenyl)-4-fluorophenyl]-pyrrolidin-1-ylmethanone The title compound was prepared in analogy to Intermediate B1, step 3 from [3-(5-chloro-2-methoxy-4-methylphenyl)-4-fluorophenyl]-pyrrolidin-1-ylmethanone (74 mg) and was obtained as an off-white solid (83 mg, 99%). MS (ESI): m/z=334.2 $[M+H]^+$.

The following intermediates were obtained in analogy to Intermediate B62, by replacing pyrrolidine with the appropriate amine building block in Step 3 as indicated in the table below:

| Intermediate | Systematic Name | Building block/intermediate | MS, m/z |
| --- | --- | --- | --- |
| B64 | 3-(5-Chloro-2-hydroxy-4-methylphenyl)-4-fluoro-N-(2-hydroxyethyl)-N-methylbenzamide | 2-(methylamino)ethanol CAS: 109-83-1 | MS (ESI): 338.1 $[M + H]^+$ |

| Intermediate | Systematic Name | Building block/ intermediate | MS, m/z |
|---|---|---|---|
| B65 | 4-[3-(5-Chloro-2-hydroxy-4-methylphenyl)-4-fluorobenzoyl]-1-methylpiperazin-2-one 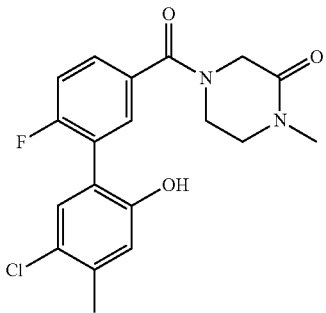 | 1-methylpiperazin-2-one CAS: 59702-07-7 | MS (ESI): 377.2 [M + H]+ |
| B66 | 4-[3-(5-Chloro-2-hydroxy-4-methylphenyl)-4-fluorobenzoyl]-1-methylpiperazin-2-one 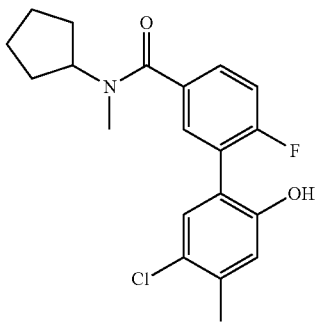 | N-methylcyclopentanamine CAS: 2439-56-7 | MS (ESI): 362.2 [M + H]+ |
| B68 | 3-(5-Chloro-2-hydroxy-4-methylphenyl)-4-fluoro-N-methyl-N-(thiophen-2-ylmethyl)benzamide 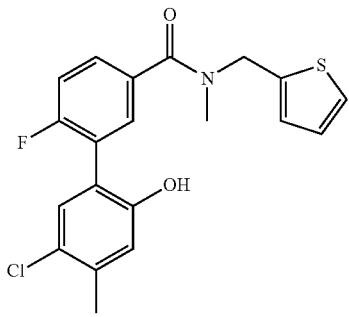 | N-methyl-1-(thiophen-2-yl)methanamine CAS: 58255-18-8 | MS (ESI): 390.1 [M + H]+ |

| Intermediate | Systematic Name | Building block/ intermediate | MS, m/z |
|---|---|---|---|
| B69 | [3-(5-Chloro-2-hydroxy-4-methylphenyl)-4-fluorophenyl]-piperidin-1-ylmethanone | piperidine CAS: 110-89-4 | MS (ESI): 348.2 [M + H]+. |
| B70 | 3-(5-Chloro-2-hydroxy-4-methylphenyl)-N-(cyclopropylmethyl)-4-fluoro-N-methylbenzamide | 1-cyclopropyl-N-methylmethanamine CAS: 18977-45-2 | MS (ESI): 348.1 [M + H]+ |
| B71 | 3-(5-Chloro-2-hydroxy-4-methylphenyl)-4-fluoro-N-methyl-N-(pyridin-2-ylmethyl)benzamide | N-methyl-1-(pyridin-2-yl)methanamine CAS: 21035-59-6 | MS (ESI): 385.1 [M + H]+ |

Intermediate B67

4-Chloro-2-[2-fluoro-5-(oxolan-3-ylmethoxy)phenyl]-5-methylphenol

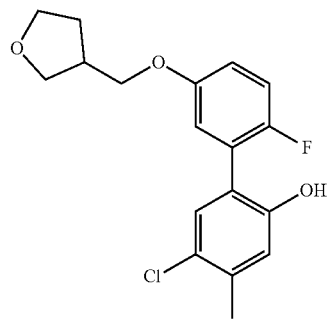 [SMILES: Cc1cc(O)c(-c2cc(OCC3CCOC3)ccc2F)cc1Cl]

Step 1: 3-[(3-Bromo-4-fluorophenoxy)methyl]oxolane

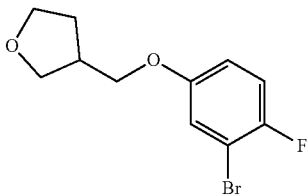 [SMILES: Fc1ccc(OCC2CCOC2)cc1Br]

Diisopropylazodicarboxylate (1.22 g) was added dropwise over a period of 5 minutes to a solution of 3-bromo-4-fluorophenol (1.05 g, CAS: 27407-11-0), (tetrahydrofuran-3-yl)methanol (674 mg, CAS: 15833-61-1) and triphenylphosphine (1.87 g) in THF (12 mL) at 0° C. under an argon atmosphere. The yellow solution was warmed up to rt and kept at this temperature for 4.5 hours. The reaction mixture was poured into ice/water and was basified with 2M NaOH solution to achieve pH=10. The aqueous layer was extracted twice with ethyl acetate. The organic layers were washed once with brine, dried over $Na_2SO_4$, filtered and evaporated to dryness. The crude material was purified by flash chromatography (0% to 60% ethyl acetate in heptane) to give the title compound as a light yellow liquid (1.26 g, 79%). MS (EI): m/z=274.0 [M]$^+$.

Step 2: 2-[2-Fluoro-5-(oxolan-3-ylmethoxy)phenyl]-4,4,5,5-tetramethyl-1,3,2-dioxaborolane

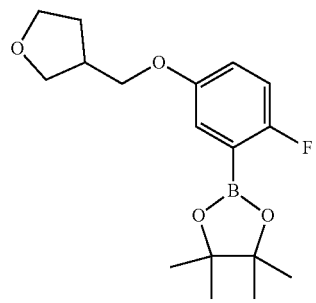 [SMILES: CC1(C)OB(c2cc(OCC3CCOC3)ccc2F)OC1(C)C]

A mixture of 4,4,4',4',5,5,5',5'-octamethyl-2,2'-bi(1,3,2-dioxaborolane) (129 mg), 3-[(3-bromo-4-fluorophenoxy)methyl]oxolane (100 mg), potassium acetate (107 mg) and [1,1'-bis(diphenylphosphino)ferrocene]dichloropalladium (II) complex with dichloromethane (14.8 mg, CAS: 95464-05-4) in 1,4-dioxane (4.0 mL) were purged three times with argon and was then heated to 85° C. for 20 hours under an argon atmosphere. The reaction mixture was cooled down to rt and poured then into ice/water. The aqueous layer was extracted twice with ethyl acetate. The organic layers were washed once with brine, dried over $Na_2SO_4$, filtered and evaporated to dryness. The crude material was purified by flash chromatography (0% to 20% ethyl acetate in heptane) to give the title compound as a colorless liquid (90 mg, 62%, purity approx. 80%). MS (EI): m/z=322.0 [M]$^+$.

Step 3: 4-Chloro-2-[2-fluoro-5-(oxolan-3-ylmethoxy)phenyl]-5-methylphenol

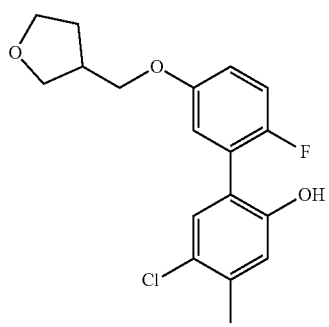 [SMILES: Cc1cc(O)c(-c2cc(OCC3CCOC3)ccc2F)cc1Cl]

The title compound was prepared in analogy to Intermediate B58 from 4-chloro-2-iodo-5-methylphenol (Intermediate B1, step 3) (58 mg) and 2-[2-fluoro-5-(oxolan-3-ylmethoxy)phenyl]-4,4,5,5-tetramethyl-1,3,2-dioxaborolane (83.5 mg) and was obtained as a light yellow oil (29 mg, 39%). MS (ESI): m/z=337.1 [M+H]$^+$.

The following intermediates were obtained in analogy to Intermediate B67, by replacing (tetrahydrofuran-3-yl)methanol in step 1 with the appropriate alcohol building block as indicated in the table below:

| Intermediate | Systematic Name | Building block/ intermediate | MS, m/z |
|---|---|---|---|
| B72 | 4-Chloro-2-[2-fluoro-5-(oxan-4-ylmethoxy)phenyl]-5-methylphenol | (tetrahydro-2H-pyran-4-yl)methanol CAS: 14774-37-9 | MS (ESI): 351.1 [M + H]$^+$ |
| B74 | 4-Chloro-2-[2-fluoro-5-(oxolan-2-ylmethoxy)phenyl]-5-methylphenol | (tetrahydrofuran-2-yl)methanol CAS: 97-99-4 | MS (ESI): 335.2 [M − H]$^−$ |

Intermediate B75

2-[3-(5-Chloro-2-hydroxy-4-methylphenyl)-4-fluorophenoxy]-N,N-dimethylacetamide

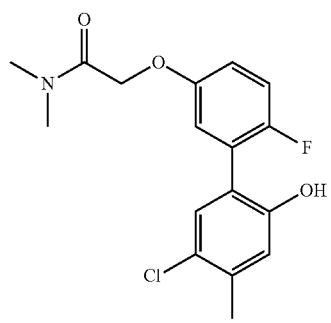 [SMILES: Cc1cc(O)c(-c2cc(OCC(=O)N(C)C)ccc2F)cc1Cl]

Step 1:
2-(3-Bromo-4-fluorophenoxy)-N,N-dimethylacetamide

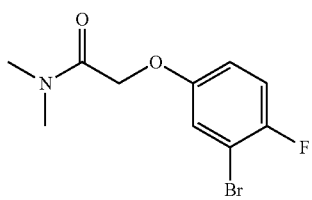

3-Bromo-4-fluorophenol (500 mg, CAS 27407-11-0), 2-chloro-N,N-dimethyl acetamide (573 mg) and potassium carbonate (832 mg) were combined with acetone (15 mL) at rt under an argon atmosphere. The mixture was heated to reflux for 18 hours and was then kept at rt for 1 hour. The reaction mixture was poured then into ice/water and the aqueous layer was extracted twice with ethyl acetate. The organic layers were washed once with brine, dried over Na$_2$SO$_4$, filtered and evaporated to dryness. The crude material was purified by flash chromatography (0% to 80% ethyl acetate in heptane) to give the title compound as a light yellow liquid (934 mg, 91%, purity approx. 70%). MS (ESI): m/z=278.1 [M+H]$^+$.

183

Step 2: 2-[4-Fluoro-3-(4,4,5,5-tetramethyl-1,3,2-dioxaborolan-2-yl)phenoxy]-N,N-dimethylacetamide

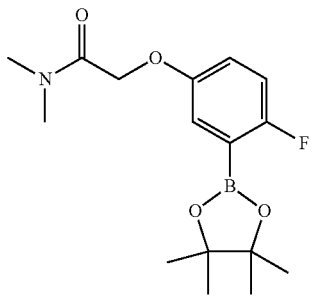 [SMILES: CN(C)C(=O)COc1ccc(F)c(B2OC(C)(C)C(C)(C)O2)c1]

The title compound was prepared in analogy to Intermediate B67, step 2 from 2-(3-bromo-4-fluorophenoxy)-N,N-dimethylacetamide (930 mg) and was obtained as a colorless oil (188 mg, 18%, purity 70%). MS (ESI): m/z=324.2 [M+H]⁻.

Step 3: 2-[3-(5-Chloro-2-hydroxy-4-methylphenyl)-4-fluorophenoxy]-N,N-dimethylacetamide

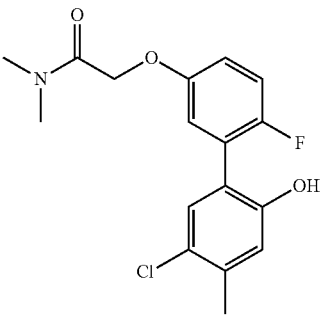 [SMILES: Cc1cc(O)c(-c2cc(OCC(=O)N(C)C)ccc2F)cc1Cl]

The title compound was prepared in analogy to Intermediate B58 from 4-chloro-2-iodo-5-methylphenol (intermediate B1, step 3) (108 mg) and 2-[4-fluoro-3-(4,4,5,5-tetramethyl-1,3,2-dioxaborolan-2-yl)phenoxy]-N,N-dimethylacetamide (186 mg, purity 70%) and was obtained as a light brown foam (63 mg, 46%). MS (ESI): m/z=338.1 [M+H]⁺.

Intermediate B73

3-(5-Chloro-2-hydroxy-4-methylphenyl)-4-fluoro-N-(2-methoxyethyl)-N-methylbenzamide

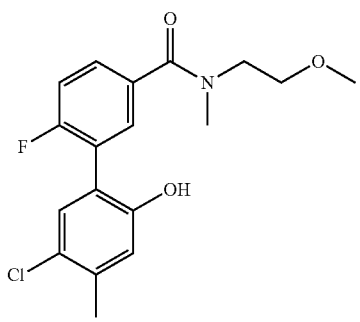 [SMILES: COCCN(C)C(=O)c1ccc(F)c(-c2cc(Cl)c(C)cc2O)c1]

184

Step 1: 3-(5-Chloro-2-hydroxy-4-methylphenyl)-4-fluorobenzoic acid

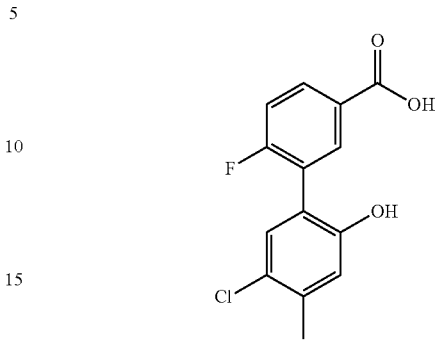

3-(5-Chloro-2-methoxy-4-methylphenyl)-4-fluorobenzoic acid (Intermediate B62, step 2) (145 mg) was combined with dichloromethane (5.0 mL) at 0° C. under an argon atmosphere. Then, boron tribromide 1M solution in dichloromethane (1.23 mL) was added dropwise over a period of 2 minutes. The resulting yellow solution was then kept at rt for 6 hours. The reaction mixture was poured then into ice/water and the aqueous layer was extracted twice with ethyl acetate. The organic layers were washed once with brine, dried over Na₂SO₄, filtered and evaporated to dryness to give the title compound as a light brown solid (146 mg, 100%). MS (ESI): m/z=559.2 [2M−H]⁻.

Step 2: 3-(5-Chloro-2-hydroxy-4-methylphenyl)-4-fluoro-N-(2-methoxyethyl)-N-methylbenzamide

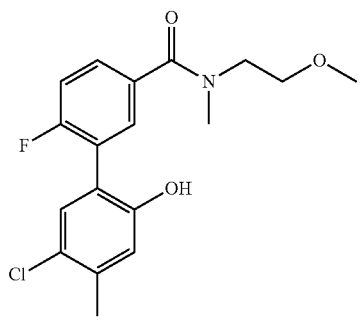 [SMILES: COCCN(C)C(=O)c1ccc(F)c(-c2cc(Cl)c(C)cc2O)c1]

The title compound was obtained in analogy to Intermediate B62, step 3 from 3-(5-chloro-2-hydroxy-4-methylphenyl)-4-fluorobenzoic acid (50 mg) using 2-methoxy-N-methylethanamine (24 mg, CAS: 38256-93-8) in place of pyrrolidine and was obtained as a white foam (40 mg, 63%). MS (ESI): m/z=352.1 [M+H]⁺.

Intermediate B76

1-[[3-(5-Chloro-2-hydroxy-4-methylphenyl)-4-fluorophenyl]methyl]-4-methylpiperazine-2,5-dione

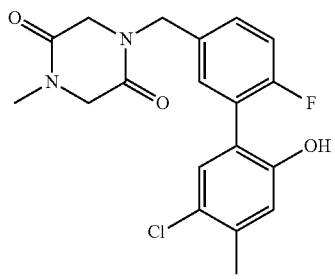

Step 1: 2-Bromo-4-(bromomethyl)-1-fluorobenzene

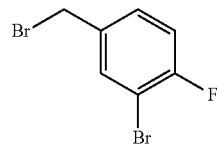

Tetrabromomethane (7.28 g) was added to a solution of 3-bromo-4-fluorophenyl)methanol (3.0 g, CAS: 77771-03-0) in THF (50 mL) at 0° C. under an argon atmosphere. Then, a solution of triphenylphosphine (5.76 g) in THF (30 mL) was added dropwise over a period of 40 minutes. The mixture was warmed up to rt and kept at this temperature for 65 hours. The reaction mixture was poured then into ice/water and was extracted two times with ethyl acetate. The organic layers were washed once with brine, dried over $Na_2SO_4$, filtered and evaporated to dryness. The crude material was purified by flash chromatography (0% to 10% ethyl acetate in heptane) to give the title compound as a light yellow liquid (5.10 g, 95%, purity 70%). MS (EI): m/z=267.9 [M]+.

Step 2: 1-[(3-Bromo-4-fluorophenyl)methyl]-4-methylpiperazine-2,5-dione

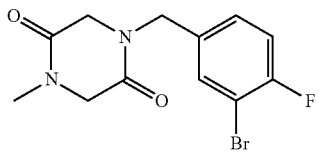 [SMILES: CN1CC(=O)N(Cc2ccc(F)c(Br)c2)CC1=O]

1-Methylpiperazine-2,5-dione (150 mg, CAS: 5625-52-5) was dissolved in DMF (5.0 mL) at rt under an argon atmosphere. The mixture was cooled down to 0° C. and sodium hydride 60% dispersion in mineral oil (103 mg) was added in one portion. The suspension was stirred at 0° C. for 10 minutes and then warmed up to rt for 45 minutes. Then, 2-bromo-4-(bromomethyl)-1-fluorobenzene (627 mg) was added dropwise over a period of 5 minutes. The mixture was stirred at rt for 16 hours. The reaction mixture was poured then into ice/water and the aqueous layer was extracted twice with ethyl acetate. The organic layers were washed once with brine, dried over $Na_2SO_4$, filtered and evaporated to dryness. The crude material was purified by flash chromatography (0% to 10% methanol in dichloromethane) to give the title compound as a light brown gum (121 mg, 32%). MS (ESI): m/z=315.0 [M+H]+.

Step 3: 1-[[4-Fluoro-3-(4,4,5,5-tetramethyl-1,3,2-dioxaborolan-2-yl)phenyl]methyl]-4-methylpiperazine-2,5-dione

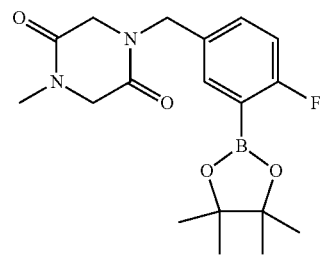 [SMILES: CN1CC(=O)N(Cc2ccc(F)c(B3OC(C)(C)C(C)(C)O3)c2)CC1=O]

The title compound was prepared in analogy to Intermediate B67, step 2, from 1-[(3-bromo-4-fluorophenyl)methyl]-4-methylpiperazine-2,5-dione (120 mg) and was obtained as a light brown gum (102 mg, 52%, purity 70%). MS (ESI): m/z=363.2 [M+H]+.

Step 4: 1-[[3-(5-Chloro-2-hydroxy-4-methylphenyl)-4-fluorophenyl]methyl]-4-methylpiperazine-2,5-dione

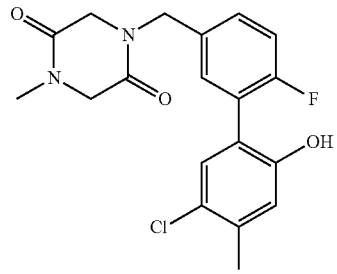 [SMILES: Cc1cc(O)c(-c2cc(CN3CC(=O)N(C)CC3=O)ccc2F)cc1Cl]

The title compound was prepared in analogy to Intermediate B58 from 4-chloro-2-iodo-5-methylphenol (intermediate B1, step 3) (52 mg) and 1-[[4-fluoro-3-(4,4,5,5-tetramethyl-1,3,2-dioxaborolan-2-yl)phenyl]methyl]-4-methylpiperazine-2,5-dione (100 mg, purity ~70%) and was obtained as a light brown foam (28 mg, 37%). MS (ESI): m/z=377.1 [M+H]+.

The following intermediates were obtained in analogy to intermediate B76, by replacing 1-methylpiperazine-2,5-dione in Step 2 with the appropriate amide building block as indicated in the table below:

| Intermediate | Systematic Name | Building block/ intermediate | MS, m/z |
|---|---|---|---|
| B81 | 1-[[3-(5-Chloro-2-hydroxy-4-methylphenyl)-4-fluorophenyl]methyl]pyrrolidin-2-one | pyrrolidin-2-one CAS: 616-45-5 | MS (ESI): 334.0 [M + H]$^+$ |
| B82 | 3-[[3-(5-Chloro-2-hydroxy-4-methylphenyl)-4-fluorophenyl]methyl]-1,3-oxazolidin-2-one | oxazolidin-2-one CAS: 497-25-6 | MS (ESI): 334.1 [M − H]$^-$ |

Intermediate B78

N-[[3-(5-Chloro-2-hydroxy-4-methylphenyl)-4-fluorophenyl]methyl]-2-methoxy-N-methylacetamide Step 1: N-[(3-Bromo-4-fluorophenyl)methyl]-2-methoxyacetamide

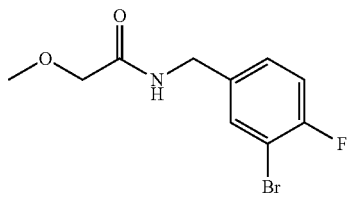

2-Methoxyacetic acid (165 mg, CAS: 625-45-6), (3-bromo-4-fluorophenyl)-methanamine hydrochloride (529 mg, CAS: 202865-68-7) and 4-methylmorpholine (741 mg) were dissolved in DMF (6.0 mL) at rt under an argon atmosphere. 1-(3-Dimethylaminopropyl)-3-ethylcarbodiimide hydrochloride (527 mg) and 1-hydroxybenzotriazole hydrate (371 mg) were added to the light yellow solution. The mixture was stirred at rt for 16 hours. The reaction mixture was poured then into ice/water and was basified with 2M Na$_2$CO$_3$ solution. The aqueous layer was extracted twice with ethyl acetate. The organic layers were washed once with brine, dried over Na$_2$SO$_4$, filtered and evaporated to dryness. The crude material was purified by flash chromatography (0% to 80% ethyl acetate in heptane) to give the title compound as a white solid (503 mg, 98%). MS (ESI): m/z=278.0 [M+H]$^+$.

Step 2: N-[(3-Bromo-4-fluorophenyl)methyl]-2-methoxy-N-methylacetamide

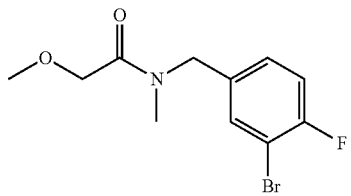 [SMILES: COCC(=O)N(C)Cc1ccc(F)c(Br)c1]

The title compound was prepared in analogy to Intermediate B63, step 2, from N-[(3-bromo-4-fluorophenyl)methyl]-2-methoxyacetamide (290 mg) and was obtained as a colorless liquid (198 mg, 62%). MS (ESI): m/z=290.0 [M+H]$^+$.

Step 3: N-[[4-Fluoro-3-(4,4,5,5-tetramethyl-1,3,2-dioxaborolan-2-yl)phenyl]methyl]-2-methoxy-N-methylacetamide

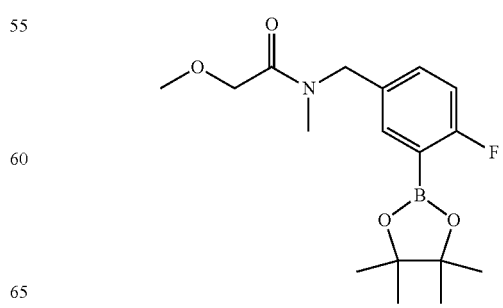

The title compound was prepared in analogy to Intermediate B67, step 2, from N-[(3-bromo-4-fluorophenyl)methyl]-2-methoxy-N-methylacetamide (199 mg) and was obtained as a light yellow liquid (262 mg, 57%, purity ~50%). MS (ESI): m/z=338.2 [M+H]$^+$.

Step 4: N-[[3-(5-Chloro-2-hydroxy-4-methylphenyl)-4-fluorophenyl]methyl]-2-methoxy-N-methylacetamide

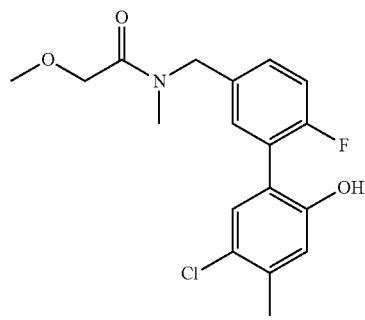 [SMILES: COCC(=O)N(C)Cc1ccc(F)c(-c2cc(Cl)c(C)cc2O)c1]

The title compound was prepared in analogy to Intermediate B58 from 4-chloro-2-iodo-5-methylphenol (intermediate B1, step 3) (102 mg) and N-[[4-fluoro-3-(4,4,5,5-tetramethyl-1,3,2-dioxaborolan-2-yl)phenyl]methyl]-2-methoxy-N-methylacetamide (256 mg, purity ~50%) and was obtained as a yellow gum (106 mg, 64%, purity ~80%). MS (ESI): m/z=352.1 [M+H]$^+$.

The following intermediates were obtained in analogy to intermediate B78, by replacing 2-methoxyacetic acid in Step 1 with the appropriate carboxylic acid building block as indicated in the table below:

| Intermediate | Systematic Name | Building block/intermediate | MS, m/z |
|---|---|---|---|
| B80 | N-[[3-(5-Chloro-2-hydroxy-4-methylphenyl)-4-fluorophenyl]methyl]-N-methylcyclopropanecarboxamide | cyclopropanecarboxylic acid CAS: 1759-53-1 | MS (ESI): 348.1 [M + H]$^+$ |

Intermediate B79

N-[[3-(5-Chloro-2-hydroxy-4-methylphenyl)-4-fluorophenyl]methyl]cyclopropane-carboxamide

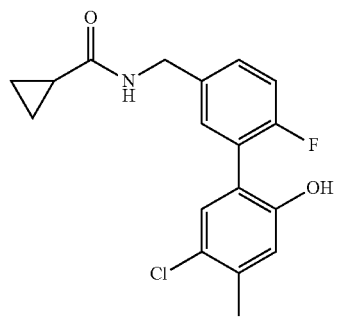 [SMILES: Cc1cc(O)c(-c2cc(CNC(=O)C3CC3)ccc2F)cc1Cl]

Step 1: N-[(3-Bromo-4-fluorophenyl)methyl]cyclopropanecarboxamide

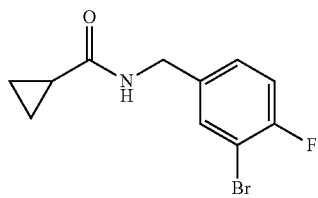 [SMILES: O=C(NCc1ccc(F)c(Br)c1)C1CC1]

The title compound was prepared in analogy to Intermediate B78, step 1, from cyclopropanecarboxylic acid (127 mg, CAS: 1759-53-1) and was obtained as a white powder (444 mg, 100%). MS (ESI): m/z=272.0 [M+H]$^+$.

Step 2: N-[[4-Fluoro-3-(4,4,5,5-tetramethyl-1,3,2-dioxaborolan-2-yl)phenyl]methyl]-cyclopropanecarboxamide

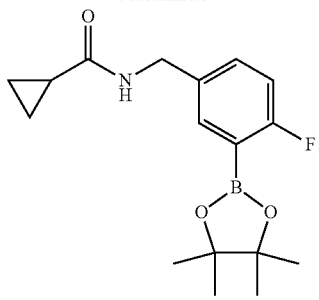 [SMILES: CC1(C)OB(c2cc(CNC(=O)C3CC3)ccc2F)OC1(C)C]

The title compound was prepared in analogy to Intermediate B67, step 2, from N-[(3-bromo-4-fluorophenyl)methyl]cyclopropanecarboxamide (217 mg) and was obtained as a light yellow oil (257 mg, 61%, purity ~60%). MS (ESI): m/z=320.2 [M+H]$^+$.

Step 3: N-[[3-(5-Chloro-2-hydroxy-4-methylphenyl)-4-fluorophenyl]methyl]cyclopropane-carboxamide

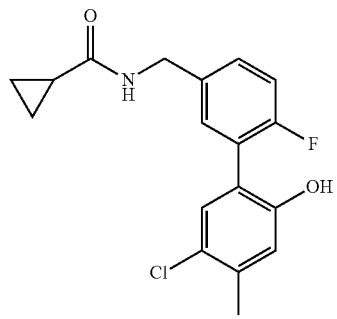

The title compound was prepared in analogy to intermediate B58 from 4-chloro-2-iodo-5-methylphenol (intermediate B1, step 3) (119 mg) and N-[[4-fluoro-3-(4,4,5,5-tetramethyl-1,3,2-dioxaborolan-2-yl)phenyl]methyl]-cyclopropanecarboxamide (236 mg, purity ~60%) and was obtained as a light yellow foam (63 mg, 42%). MS (ESI): m/z=334.1 [M+H]$^+$.

The following intermediates were obtained in analogy to intermediate B79, by replacing cyclopropanecarboxylic acid in step 1 with the appropriate carboxylic acid building block as indicated in the table below:

| Intermediate | Systematic Name | Building block/intermediate | MS, m/z |
| --- | --- | --- | --- |
| B83 | N-[[3-(5-Chloro-2-hydroxy-4-methylphenyl)-4-fluorophenyl]methyl]-2-methoxyacetamide | 2-methoxyacetic acid CAS: 625-45-6 | MS (ESI): 336.1 [M − H]$^-$ |

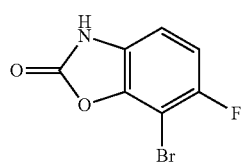

Intermediate B77

7-(5-Chloro-2-hydroxy-4-methylphenyl)-6-fluoro-3-methyl-1,3-benzoxazol-2-one

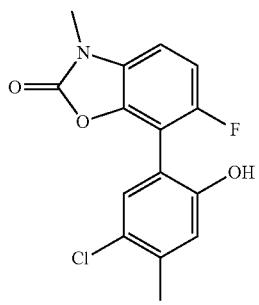 [SMILES: Cc1cc(O)c(-c2c(F)ccc3c2oc(=O)n3C)cc1Cl]

Step 1: 7-Bromo-6-fluoro-3H-1,3-benzoxazol-2-one

A solution of 1,1'-carbonyldiimidazole (378 mg) in tetrahydrofuran (6.0 mL) was added to a suspension of 6-amino-2-bromo-3-fluorophenol (400 mg, CAS: 1257535-00-4) in THF (5.0 mL) at rt under an argon atmosphere. The mixture was stirred at rt for 4 hours. The reaction mixture was poured then into ice/water and the aqueous layer was extracted twice with ethyl acetate. The organic layers were washed once with brine, dried over Na$_2$SO$_4$, filtered and evaporated to dryness. The crude material was purified by flash chromatography (0% to 100% ethyl acetate in heptane) to give the title compound as an orange solid (298 mg, 65%). MS (ESI): m/z=230.0 [M−H]$^-$.

Step 2: 7-Bromo-6-fluoro-3-methyl-1,3-benzoxazol-2-one

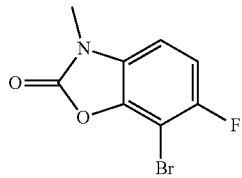

The title compound was prepared in analogy to Intermediate B63, step 2, from 7-bromo-6-fluoro-3H-1,3-benzoxazol-2-one (290 mg) and was obtained as a light brown foam (263 mg, 84%). MS (EI): m/z=245.0 [M]⁺.

Step 3: 2-(5-Chloro-2-methoxy-4-methylphenyl)-4,4,5,5-tetramethyl-1,3,2-dioxaborolane

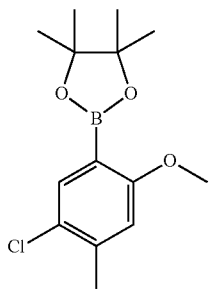 [SMILES: COc1cc(C)c(Cl)cc1B1OC(C)(C)C(C)(C)O1]

The title compound was prepared in analogy to Intermediate B67, step 2, from 1-chloro-5-iodo-4-methoxy-2-methylbenzene (Intermediate B1, step 2) (300 mg) and was obtained as an off-white solid (75 mg, 21%, purity ~80%). MS (ESI): m/z=311.1 [M+H]⁺.

Step 4: 7-(5-Chloro-2-methoxy-4-methylphenyl)-6-fluoro-3-methyl-1,3-benzoxazol-2-one

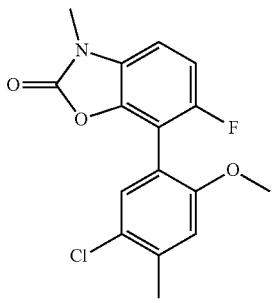 [SMILES: COc1cc(C)c(Cl)cc1-c1c(F)ccc2c1oc(=O)n2C]

The title compound was prepared in analogy to Intermediate B58 from 7-bromo-6-fluoro-3-methyl-1,3-benzoxazol-2-one (Intermediate B77, step 2) (38 mg) and 2-(5-chloro-2-methoxy-4-methylphenyl)-4,4,5,5-tetramethyl-1,3,2-dioxaborolane (71 mg, purity ~80%) and was obtained as an off-white solid (18 mg, 36%). MS (ESI): m/z=322.0 [M+H]⁺.

Step 5: 7-(5-Chloro-2-hydroxy-4-methylphenyl)-6-fluoro-3-methyl-1,3-benzoxazol-2-one

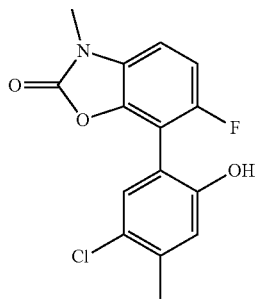 [SMILES: Cc1cc(O)c(-c2c(F)ccc3c2oc(=O)n3C)cc1Cl]

The title compound was prepared in analogy to Intermediate B1, step 3, from 7-(5-chloro-2-methoxy-4-methylphenyl)-6-fluoro-3-methyl-1,3-benzoxazol-2-one (18 mg) and was obtained as a light brown solid (15 mg, 79%, purity 90%). MS (ESI): m/z=306.1 [M−H]⁻.

Intermediate B86

3-(5-Chloro-2-hydroxy-4-methylphenyl)-4-(trifluoromethoxy)benzonitrile

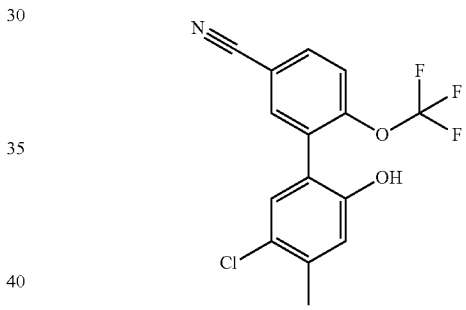

Cyclopentyl methyl ether (5 mL) was purged three times with argon and was then combined with 3-bromo-4-(trifluoromethoxy)benzonitrile (130 mg, CAS: 191602-89-8), potassium acetate (144 mg), 4,4,4',4',5,5,5',5'-octamethyl-2,2'-bi(1,3,2-dioxaborolane) (130 mg) and [1,1'-bis(diphenylphosphino)ferrocene]dichloropalladium(II) DCM complex (20 mg). The mixture was heated to 95° C. for 4 hours under an argon atmosphere. The reaction mixture was allowed to cool to rt and was then combined with argon-purged sodium carbonate solution (15% in water, 600 µL), 4-chloro-2-iodo-5-methylphenol (131 mg, obtained in Intermediate B1, step 3) and [1,1'-bis(diphenylphosphino)ferrocene]dichloropalladium(II) DCM complex (20 mg). The reaction mixture was again heated to 86° C. for 18 hours. The reaction mixture was cooled to rt and was poured then into ice/water. The aqueous layer was extracted twice with ethyl acetate and the organic layers were washed once with brine, dried over Na₂SO₄, filtered and evaporated. The residue was purified by flash chromatography (silica gel, 20 g cartridge, gradient of 0% to 20% ethyl acetate in heptane) to provide the title compound as a light yellow solid (48 mg). MS (ESI⁻): m/z=326.3 [M−H]⁻.

The following intermediates were made in analogy to Intermediate B86 by replacing 3-bromo-4-(trifluoromethoxy)benzonitrile with the corresponding aryl-bromide and, if appropriate, 4-chloro-2-iodo-5-methylphenol with the corresponding aryl-iodide as described in the following table:

| Intermediate | Systematic Name | Building blocks/ intermediates | MS, m/z |
|---|---|---|---|
| B88 | 2-chloro-5-(2-fluoro-3-methoxyphenyl)-4-hydroxybenzonitrile | 1-bromo-2-fluoro-3-methoxy-benzene (CAS: 95970-22-2) and 2-chloro-4-hydroxy-5-iodoben-zonitrile (Intermediate B31, Method B, step 1) | MS (ESI): 278.1 [M + H]$^+$ |
| B90 | 4-chloro-2-(2-fluoro-3-methoxyphenyl)-5-methylphenol | 1-bromo-2-fluoro-3-methoxy-benzene (CAS: 95970-22-2) and 4-chloro-2-iodo-5-methylphenol (Intermediate B1, step 3) | MS (ESI): 267.1 [M + H]$^+$ |
| B91 | 2-chloro-5-(2,3-difluorophenyl)-4-hydroxybenzonitrile | 1-bromo-2,3-difluoro-benzene (CAS: 38573-88-5) and 2-chloro-4-hydroxy-5-iodoben-zonitrile (Intermediate B31, Method B, step 1) | MS (ESI$^-$): 264.1 [M − H]$^-$ |
| B92 | 4-chloro-2-(5-cyclopropyloxy-2-fluorophenyl)-5-methylphenol | 2-bromo-4-cyclopro-pyloxy-1-fluoro-benzene (CAS: 1243469-64-8) and 4-chloro-2-iodo-5-methylphenol (Intermediate B1, step 3) | MS (ESI): 293.1 [M + H]$^+$ |
| B93 | 2-chloro-5-(5-chloro-2-fluorophenyl)-4-hydroxybenzonitrile | 2-bromo-4-chloro-1-fluoro-benzene (CAS: 1996-30-1) and 2-chloro-4-hydroxy-5-iodoben-zonitrile (Intermediate B31, Method B, step 1) | MS (ESI$^-$): 280.1 [M − H]$^-$ |
| B94 | 2-chloro-5-(2,5-difluorophenyl)-4-hydroxybenzonitrile | 2-bromo-1,4-difluoro-benzene (CAS: 399-94-0) and 2-chloro-4-hydroxy-5-iodoben-zonitrile (Intermediate B31, Method B, step 1) | MS (ESI$^-$): 264.1 [M − H]$^-$ |
| B95 | 2-chloro-5-(5-cyclopropyloxy-2-fluorophenyl)-4-hydroxybenzonitrile | 2-bromo-4-cyclopro-pyloxy-1-fluoro-benzene (CAS: 1243469-64-8) and 2-chloro-4-hydroxy-5-iodoben-zonitrile (Intermediate B31, Method B, step 1) | MS (ESI$^-$): 302.2 [M − H]$^-$ |
| B96 | 2-chloro-5-[2-fluoro-5-(trifluoromethyl)phenyl]-4-hydroxybenzonitrile | 2-bromo-1-fluoro-4-(trifluoro-methyl)benzene (CAS: 68322-84-9) and 2-chloro-4-hydroxy-5-iodoben-zonitrile (Intermediate B31, Method B, step 1) | MS (ESI$^-$): 314.2 [M − H]$^-$ |

Intermediate B87

2-Chloro-5-[2-fluoro-5-(oxolan-2-ylmethoxy)phenyl]-4-hydroxybenzonitrile

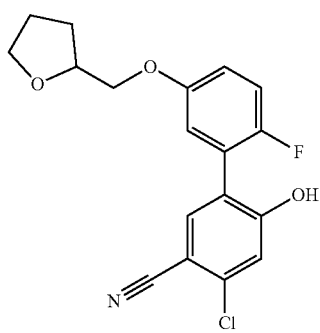 [SMILES: N#Cc1cc(-c2cc(OCC3CCCO3)ccc2F)c(O)cc1Cl]

This material was prepared in analogy to Intermediate B67, steps 1-3, by replacing in step 1 (tetrahydrofuran-3-yl)methanol with (tetrahydrofuran-2-yl)methanol (CAS: 97-99-4), and in step 3 4-chloro-2-iodo-5-methylphenol with 2-chloro-4-hydroxy-5-iodobenzonitrile (made in Intermediate B31, Method B, step 1). Light brown oil: MS (ESI): 348.1 [M+H]$^+$.

Intermediate B97

2-Chloro-5-[2-fluoro-5-(trifluoromethoxy)phenyl]-4-hydroxybenzonitrile

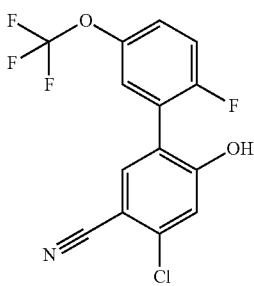 [SMILES: N#Cc1cc(-c2cc(OC(F)(F)F)ccc2F)c(O)cc1Cl]

This material was made in analogy to Intermediate B86 from 2-bromo-1-fluoro-4-(trifluoromethoxy)benzene (210 mg, CAS: 286932-57-8) and 2-chloro-4-hydroxy-5-iodobenzonitrile (204 mg, Intermediate B31, Method B, Step 1) to provide the title compound as a colorless solid (130 mg, 47%). MS (m/z): 330.1 [M−H]$^−$.

Intermediate B98

2-Chloro-5-[2-fluoro-5-(2,2,2-trifluoroethoxy)phenyl]-4-hydroxybenzonitrile

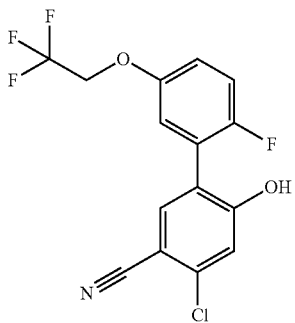 [SMILES: N#Cc1cc(-c2cc(OCC(F)(F)F)ccc2F)c(O)cc1Cl]

Step 1:
2-Bromo-1-fluoro-4-(2,2,2-trifluoroethoxy)benzene

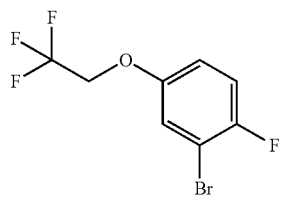 [SMILES: Fc1ccc(OCC(F)(F)F)cc1Br]

3-Bromo-4-fluorophenol (500 mg, CAS: 27407-11-0), 1,1,1-trifluoro-2-iodoethane (824 mg, CAS: 353-83-3) and potassium carbonate (1.09 g) were combined with DMF (10.0 mL) at room temperature under an argon atmosphere. The mixture was heated to 80° C. for 2 hours and then at 60° C. for another 16 hours. TLC showed a lot of starting material. More 1,1,1-trifluoro-2-iodoethane (824 mg) and potassium carbonate (724 mg) were added and the mixture was heated again at 80° C. for 64 hours. The reaction mixture was then cooled and poured into ice/water. The aqueous layer was basified with sat. Na$_2$CO$_3$ solution and was extracted twice with ethyl acetate. The organic layers were washed once with brine, dried over Na$_2$SO$_4$, filtered and evaporated. Residual DMF was removed by co-evaporation with toluene. The crude material was purified by flash chromatography (ISCO, silica gel, 25 g cartridge, 0% to 20% ethyl acetate in heptane) to give the title compound as a light yellow liquid (601 mg, 80%). MS (EI, m/z): 272.0 [M]$^+$.

Step 2: 2-Chloro-5-[2-fluoro-5-(2,2,2-trifluoroethoxy)phenyl]-4-hydroxybenzonitrile

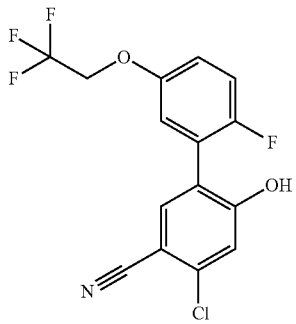 [SMILES: N#Cc1cc(-c2cc(OCC(F)(F)F)ccc2F)c(O)cc1Cl]

This material was made in analogy to Intermediate B86 from 2-bromo-1-fluoro-4-(2,2,2-trifluoroethoxy)benzene (220 mg) and 2-chloro-4-hydroxy-5-iodobenzonitrile (203 mg, Intermediate B31, Method B, Step 1) to provide the title compound as an off-white solid (8 mg, 3%). (MS (m/z): 346.1 [M+H]$^+$.

Intermediates C

Intermediate C3

4-Chloro-5-fluoro-2-isopropyl-phenol

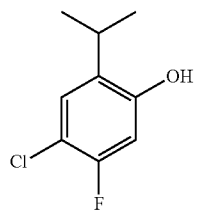

Step 1: 4-Chloro-5-fluoro-2-isopropenyl-phenol

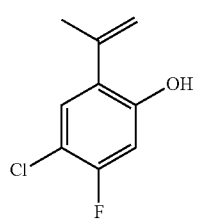

To a solution of 4-chloro-5-fluoro-2-iodo-phenol (500 mg, CAS: 1235407-15-4) in DMF (8 mL) were added isopropenylboronic acid pinacol ester (771 mg, CAS: 126726-62-3) and K$_2$CO$_3$ (761 mg) and the reaction mixture was purged with argon for 30 min. Then Pd(dppf)Cl$_2$ DCM complex (45 mg, CAS: 14221-01-3) was added and the reaction mixture was stirred at 90° C. for 16 hours. The solvent was evaporated, the residue was diluted with H$_2$O (40 mL) and extracted with EtOAc (3×25 mL). The combined organic layers were washed with brine (30 mL), dried over anhydrous Na$_2$SO$_4$, filtered and concentrated under reduced pressure. The crude material was purified by flash chromatography over silica gel (2-4% EtOAc/hexane) to give the title compound as a colorless liquid (263 mg, 76%). $^1$H-NMR (400 MHz, CDCl$_3$) 2.07 (3H, s), 5.15 (1H, s), 5.42 (1H, s), 5.73 (1H, bs), 6.73 (1H, d, J=8), 7.12 (1H, d, J=8).

Step 2: 4-Chloro-5-fluoro-2-isopropyl-phenol

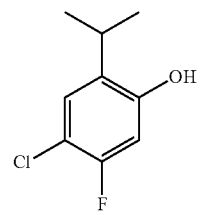

A solution of 4-chloro-5-fluoro-2-isopropenyl-phenol (524 mg) in MeOH (30 mL) was purged with argon for 15 min. Then, 10% palladium on carbon (130 mg, CAS: 7440-05-3) was added and the reaction mixture was purged with argon for another 5 min. The reaction mixture was stirred under hydrogen (balloon) for 16 hours at rt. The reaction mixture was filtered through a celite bed, the celite bed was washed with EtOAc (20 mL) and the filtrate was evaporated to give the title compound as a green liquid (513 mg, 97%). $^1$H-NMR (400 MHz, CDCl$_3$) 1.25 (6H, m), 3.07-3.14 (1H, m), 4.99 (1H, s), 6.58 (1H, d, J=12), 7.13 (1H, d, J=8).

Intermediate C4:

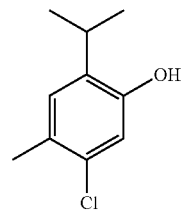

5-Chloro-2-isopropyl-4-methyl-phenol

Step 1: 1-Chloro-4-iodo-5-methoxy-2-methyl-benzene

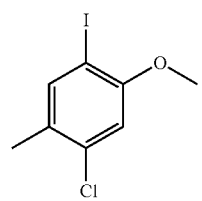

The title compound was obtained in analogy to Intermediate A14, step 5, from 4-chloro-2-methoxy-5-methyl-phenylamine (CAS: 62492-42-6) as a brown liquid. $^1$H-NMR (400 MHz, CDCl$_3$): 2.25 (3H, s), 3.83 (3H, s), 6.79 (1H, s), 7.60 (1H, s).

Step 2: 5-Chloro-2-iodo-4-methyl-phenol

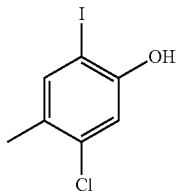

The title compound was obtained in analogy to Intermediate B1, step 3, from 1-chloro-4-iodo-5-methoxy-2-methyl-benzene as a yellow liquid. ¹H-NMR (400 MHz, CDCl₃): 2.25 (3H, s), 5.17 (1H, s), 6.99 (1H, s), 7.49 (1H, s).

Step 3: 5-Chloro-2-isopropenyl-4-methyl-phenol

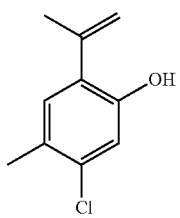

The title compound was obtained in analogy to Intermediate C3, step 1, from 5-chloro-2-iodo-4-methyl-phenol and isopropenylboronic acid pinacol ester (CAS: 126726-62-3) as a yellow liquid. ¹H-NMR (400 MHz, CDCl₃): 2.20 (3H, s), 2.26 (3H, s) 5.10 (1H, s), 5.38 (1H, s), 6.93 (1H, s), 6.94 (1H, s).

Step 4: 5-Chloro-2-isopropyl-4-methyl-phenol

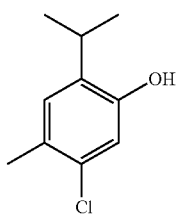

The title compound was obtained in analogy to Intermediate C3, step 2, from 5-chloro-2-isopropenyl-4-methyl-phenol by hydrogenation as a colorless liquid. ¹H-NMR (400 MHz, CDCl₃) 1.22 (6H, m), 2.27 (3H, s), 3.08-3.11 (1H, m), 4.63 (1H, s), 6.75 (1H, s), 6.93 (1H, s).

Intermediate C9:

2-(5-Chloro-2-hydroxy-4-methyl-phenyl)-2-methyl-propionitrile

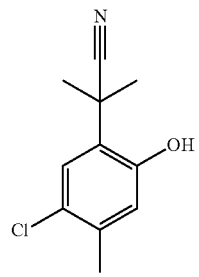

Step 1: 4-Chloro-2-fluoro-5-methyl-phenol

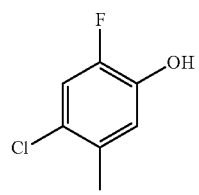

To a solution of 2-fluoro-5-methyl-phenol (5.0 g, CAS: 63762-79-8) in AcOH (50 mL) were added NCS (5.82 g, CAS: 128-09-6) and triflic acid (1.76 mL, CAS: 1493-13-6) and the reaction mixture was refluxed for 24 hours. The solvent was evaporated under reduced pressure and the compound was purified by flash chromatography over silica gel (40-50% EtOAc/hexane) to get the title compound as a colorless liquid (3.5 g, 55%). ¹H-NMR (400 MHz, CDCl₃): 2.26 (3H, s), 6.85 (1H, d, J=8), 7.07 (1H, d, J=8).

Step 2: 1-Benzyloxy-4-chloro-2-fluoro-5-methyl-benzene

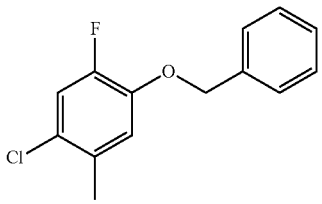 [SMILES: Cc1cc(OCc2ccccc2)c(F)cc1Cl]

To a stirred solution of 4-chloro-2-fluoro-5-methyl-phenol (3.25 g) in CH₃CN (50 mL) were added Cs₂CO₃ (13.19 g, CAS: 534-17-8) and benzyl bromide (2.66 mL, CAS: 100-39-0) and the reaction mixture was refluxed for 2 hours. The reaction mixture was filtered through a celite bed and the filtrate was evaporated. The compound was purified by column chromatography (10% EtOAc/hexane) to give the title compound as a white solid (3.94 g, 78%). ¹H-NMR (400 MHz, CDCl₃): 2.27 (3H, s), 5.09 (2H, s), 6.85 (1H, d, J=8), 7.09 (1H, d, J=12), 7.30-7.42 (5H, m).

Step 3: 2-(2-Benzyloxy-5-chloro-4-methyl-phenyl)-2-methyl-propionitrile

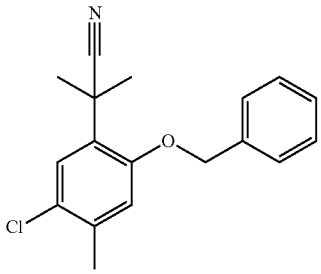 [SMILES: Cc1cc(OCc2ccccc2)c(C(C)(C)C#N)cc1Cl]

To a stirred solution of 1-benzyloxy-4-chloro-2-fluoro-5-methyl-benzene (1.0 g) in anhydrous toluene (10 mL) in a sealed tube were added isobutyronitrile (1.43 mL, CAS: 78-82-0) and KHMDS (6 mL, CAS: 40949-94-8, 1M solution in toluene) and the reaction mixture was stirred at 60° C. for 12 hours. The reaction mixture was poured into $H_2O$ (20 mL) and extracted with EtOAc (2×30 mL). The combined organic extract was dried over $Na_2SO_4$ and evaporated under reduced pressure. The compound was purified by flash chromatography over silica gel (3-20% EtOAc/hexane) to give the title compound as a brown solid (167 mg, 14%). $^1$H-NMR (400 MHz, $CDCl_3$): 1.74 (6H, s), 2.32 (3H, s), 5.15 (2H, s), 6.85 (1H, s), 7.28 (1H, s), 7.31-7.51 (5H, m).

Step 4: 2-(5-Chloro-2-hydroxy-4-methyl-phenyl)-2-methyl-propionitrile

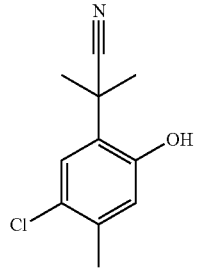

To a stirred solution of 2-(2-benzyloxy-5-chloro-4-methyl-phenyl)-2-methyl-propionitrile (420 mg) in dry DCM (20 mL) at −78° C. was added $BCl_3$ (2.8 mL, 1M solution in DCM, CAS: 10294-34-5) and the reaction mixture was stirred at 25° C. for 4 hours. The reaction mixture was quenched with saturated aqueous $Na_2CO_3$ solution and was extracted with DCM (2×20 mL). The combined organic layers were dried over $Na_2SO_4$, filtered and evaporated under reduced pressure. The residue was purified by flash chromatography over silica gel (0-10% EtOAc/hexane) to give the title product as a brown solid (50 mg, some impurities). $^1$H-NMR (400 MHz, $CDCl_3$): 1.76 (6H, s), 2.28 (3H, s), 6.57 (1H, s), 7.29 (1H, s).

Intermediate C1-A:

3-Chloro-6-[(4-chloro-2-isopropyl-5-methyl-phenoxy)methyl]pyridazine

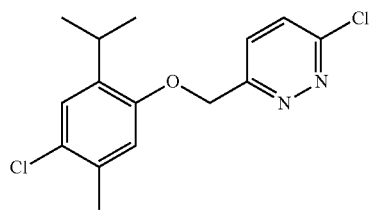 [SMILES: Cc1cc(OCc2ccc(Cl)nn2)c(C(C)C)cc1Cl]

To a solution of 3-chloro-6-chloromethyl-pyridazine (81 mg, CAS: 120276-59-7) in acetone (5 mL) was added 4-chloro-2-isopropyl-5-methyl-phenol (92 mg, CAS: 89-68-9) and $K_2CO_3$ (104 mg) and the reaction mixture was heated at reflux for 16 hours. The reaction mixture was poured into $H_2O$ (50 mL) and EtOAc (75 mL) and the layers were separated. The organic layer was washed with $H_2O$ (50 mL), dried over $Na_2SO_4$, filtered and concentrated in vacuo to give the title compound as a light yellow solid (0.072 g, 46%). MS (ESI): m/z=311.07 [M]$^+$.

Intermediate C2-A:

3-Chloro-6-(4-chloro-2-cyclopropyl-5-methyl-phenoxymethyl)-pyridazine

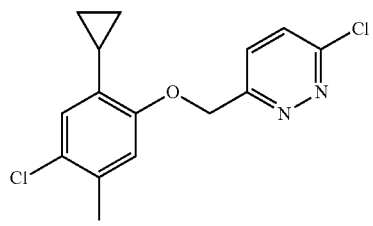 [SMILES: Cc1cc(OCc2ccc(Cl)nn2)c(C2CC2)cc1Cl]

To a solution of 3-chloro-6-chloromethyl-pyridazine (200 mg, CAS: 120276-59-7) in $CH_3CN$ (10 mL) were added 4-chloro-2-cyclopropyl-5-methyl-phenol (82 mg, Intermediate A19), $K_2CO_3$ (109 mg, CAS: 584-08-7) and tetrabutylammonium iodide (16 mg, CAS: 311-28-4) and the reaction mixture was heated to reflux for 16 hours. The solvent was evaporated under reduced pressure and the product was purified by flash chromatography over silica gel (30-40% EtOAc/hexane) to give the title compound as a yellow solid (48 mg, 35%). $^1$H-NMR (400 MHz, $CDCl_3$): 0.61-0.65 (2H, m), 0.90-0.95 (2H, m), 2.07-2.09 (1H, m), 2.28 (3H, s), 5.41 (2H, s), 6.73 (1H, s), 6.83 (1H, s), 7.56 (1H, d, J=8), 7.74 (1H, d, J=8).

The following intermediates were made in analogy to Intermediate C2-A from commercial 3-chloro-6-chloromethyl-pyridazine (CAS: 120276-59-7) and the proper phenol building block as indicated in the following table:

| Intermediate | Systematic Name | Building block/ intermediate | Analytical data |
| --- | --- | --- | --- |
| C3-A | 3-Chloro-6-(4-chloro-5-fluoro-2-isopropyl-phenoxymethyl)-pyridazine | 4-Chloro-5-fluoro-2-isopropyl-phenol Intermediate C3 | $^1$H-NMR (400 MHz, CDCl$_3$): 1.22 (6H, m), 3.26-3.29 (1H, m), 5.36 (2H, s), 6.73 (1H, d, J = 8), 7.20 (1H, d, J = 8), 7.58 (1H, d, J = 8), 7.65 (1H, d, J = 8). |
| C4-A | 3-Chloro-6-(5-chloro-2-isopropyl-4-methyl-phenoxymethyl)-pyridazine | 5-Chloro-2-isopropyl-4-methyl-phenol Intermediate C4 | $^1$H-NMR (400 MHz, CDCl$_3$): 1.22 (6H, m), 2.25 (3H, s), 3.08-3.13 (1H, m), 4.65 (2H, s), 4.62 (d, J = 16), 4.76 (d, J = 8), 6.93 (1H, s), 6.99 (1H, s) |
| C5-A | 3-Chloro-6-(4-chloro-2-cyclobutyl-5-methyl-phenoxymethyl)-pyridazine | 4-chloro-2-cyclobutyl-5-methyl-phenol Intermediate A31 | $^1$H-NMR (400 MHz, CDCl$_3$): 1.82-1.86 (1H, m), 1.98-2.16 (4H, m), 3.66-3.72 (5H, m), 5.35 (2H, s), 6.70 (1H, s), 7.17 (1H, s), 7.56 (1H, d, J = 8), 7.65 (1H, d, J = 8) |
| C6-A | 3-Chloro-6-(4-chloro-2-cyclohexyl-5-methyl-phenoxymethyl)-pyridazine | 4-chloro-2-cyclohexyl-5-methyl-phenol Intermediate A20 | $^1$H-NMR (400 MHz, CDCl$_3$): 1.24-1.42 (7H, m), 1.82-1.83 (3H, m), 2.88-2.92 (1H, m), 5.38 (2H, s), 6.72 (1H, s), 7.15 (1H, s), 7.57 (1H, d, J = 8), 7.67 (1H, d, J = 8). |
| C7-A | 3-Chloro-6-[4-chloro-5-methyl-2-(tetrahydro-pyran-4-yl)-phenoxymethyl]-pyridazine | 4-chloro-5-methyl-2-(tetrahydro-pyran-4-yl)-phenol Intermediate A21 | $^1$H-NMR (400 MHz, CDCl$_3$): 1.70-1.84 (4H, m), 2.30 (3H, s), 3.11-3.16 (1H, m), 3.48-3.54 (2H, m), 4.05-4.08 (2H, m), 5.40 (2H, s), 6.75 (1H, s), 7.57-7.62 (3H, m). |

| Intermediate | Systematic Name | Building block/ intermediate | Analytical data |
|---|---|---|---|
| C8-A | 3-(2-tert-Butyl-4-chloro-5-methyl-phenoxymethyl)-6-chloro-pyridazine 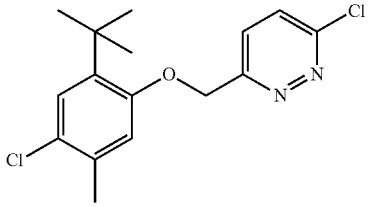 | 2-tert-butyl-4-chloro-5-methyl-phenol CAS: 30894-16-7 | $^1$H-NMR (400 MHz, CDCl$_3$): 1.37 (9H, s), 2.28 (3H, s), 5.43 (2H, s), 6.74 (1H, s), 7.24 (1H, s), 7.56 (1H, d, J = 8), 7.68 (1H, d, J = 8). |
| C9-A | 2-[5-Chloro-2-(6-chloro-pyridazin-3-ylmethoxy)-4-methyl-phenyl]-2-methyl-propionitrile 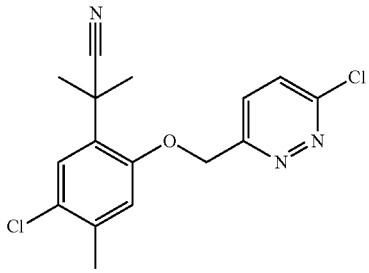 | 2-(5-chloro-2-hydroxy-4-methyl-phenyl)-2-methyl-propionitrile Intermediate C9 | MS (EI): m/z = 337.5 [M + H]$^+$ |

The following intermediates of type C were made in analogy to Intermediate C2-A from commercial 3-chloro-6-chloromethyl-pyridazine (CAS: 120276-59-7) and the proper phenol building block as indicated in the following table:

| Intermediate | Systematic Name | Building block/intermediate | Analytical data |
|---|---|---|---|
| C10-A | 3-chloro-6-[[4-chloro-2-(2-methoxypyridin-3-yl)-5-methylphenoxy]methyl]-pyridazine 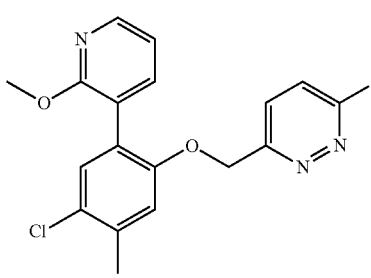 | 4-chloro-2-(2-methoxypyridin-3-yl)-5-methylphenol Intermediate B53 | MS (ESI, m/z): 376.1 [M + H]$^+$ |

| Intermediate | Systematic Name | Building block/intermediate | Analytical data |
|---|---|---|---|
| C12-A | 2-chloro-4-[(6-chloropyridazin-3-yl)methoxy]-5-phenylbenzonitrile | 2-chloro-4-hydroxy-5-phenylbenzonitrile Intermediate B31 | MS (ESI, m/z): 356.1 [M + H]$^+$ |
| C13-A | 4-tert-butyl-5-[(6-chloro-pyridazin-3-yl)methoxy]-2-methyl-benzonitrile | 4-tert-butyl-5-hydroxy-2-methylbenzonitrile Intermediate A17 | MS (ESI, m/z): 316.2 [M + H]$^+$ |
| C14-A | 2-chloro-4-[(6-chloropyridazin-3-yl)methoxy]-5-(5-cyclo-propyloxy-2-fluorophenyl)-benzonitrile | 2-chloro-5-(5-cyclopropyloxy-2-fluorophenyl)-4-hydroxybenzonitrile Intermediate B95 | MS (ESI, m/z): 430.1 [M + H]$^+$ |

Intermediates D

Intermediate D9:

2-tert-Butyl-5-methyl-4-methylsulfonyl-phenol

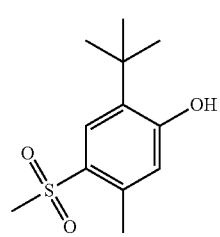 [SMILES: Cc1cc(O)c(C(C)(C)C)cc1S(C)(=O)=O]

Step 1: 4-Bromo-2-tert-butyl-5-methyl-phenol

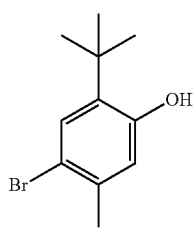

To a solution of 2-tert-butyl-5-methylphenol (1.0 g, CAS: 88-60-8) was added N-bromosuccinimide (1.19 g) and the reaction mixture was stirred for 15 h. The reaction mixture was then poured onto saturated NH$_4$Cl solution and was extracted with EtOAc. The combined organic layers were dried over Na$_2$SO$_4$ and were concentrated in vacuo. The residue was purified by chromatography (silica gel, 20 g, gradient of EtOAc in heptane) to give the title compound (1.4 g, 93%) as a yellow oil. MS (ESI): m/z=244.2 [M+H]⁺.

Step 2:
1-Benzyloxy-4-bromo-2-tert-butyl-5-methyl-benzene

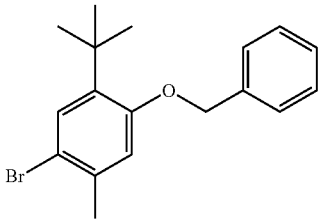 [SMILES: Cc1cc(OCc2ccccc2)c(C(C)(C)C)cc1Br]

To a solution of 4-bromo-2-tert-butyl-5-methyl-phenol (1.4 g, in DMF (15 mL) was slowly added NaH (302 mg, 55% in mineral oil) and the reaction mixture was stirred for 30 minutes at rt. Then, benzylchloride (765 mg, 696 µL) was added and the reaction mixture was stirred for 2 h. The reaction mixture was poured onto saturated NH₄Cl solution and was extracted with EtOAc. The combined organic layers were dried over Na₂SO₄ and were concentrated in vacuo to afford the title compound (1.9 g, 97%) as white powder which was used in the next reaction step without further characterization.

Step 3: 1-Benzyloxy-2-tert-butyl-5-methyl-4-methylsulfonyl-benzene

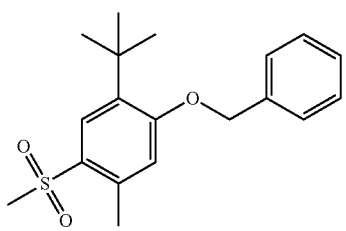 [SMILES: Cc1cc(OCc2ccccc2)c(C(C)(C)C)cc1S(C)(=O)=O]

To a mixture of 1-benzyloxy-4-bromo-2-tert-butyl-5-methyl-benzene (1.9 g), L-proline (525 mg) and copper(I) iodide (869 mg) in DMF (10 mL) were added sodium hydroxide (182 mg) and sodium methanesulfinate (1.16 g) and the reaction mixture was heated to 135° C. in a sealed tube for 15 h. The reaction mixture was poured onto saturated NH₄Cl solution and was extracted with EtOAc. The combined organic layers were dried over Na₂SO₄ and were concentrated in vacuo. The residue was purified by chromatography (silica gel, 20 g, 0% to 50% EtOAc in heptane) to obtain the title compound (1.33 g, 69%) as a white solid. MS (ESI): m/z=331.13 [M−H]⁻.

Step 4: 2-tert-Butyl-5-methyl-4-methyl sulfonyl-phenol

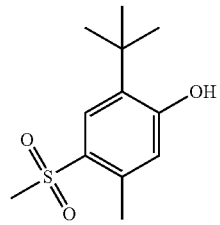 [SMILES: Cc1cc(O)c(C(C)(C)C)cc1S(C)(=O)=O]

To a solution of 1-benzyloxy-2-tert-butyl-5-methyl-4-methylsulfonyl-benzene (1.2 g) in a mixture of MeOH (100 mL) and EtOAc (100 mL) was added Pd(C) (10% on charcoal, 200 mg) under an atmosphere of argon. The reaction vessel was then evacuated and purged with hydrogen and the reaction mixture was stirred for 18 h. The reaction mixture was filtered over dicalite and the filtrate was concentrated in vacuo to give the title compound (865 mg, 99%) as a white solid. MS (ESI): m/z=241.09 [M−H]⁻.

Intermediate D26-B:

3-Bromomethyl-1-(4-methoxy-benzyl)-6-methylsulfanyl-1H-pyrazolo[3,4-d]pyrimidine

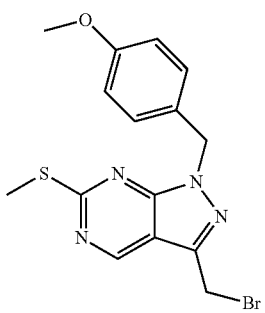 [SMILES: COc1ccc(Cn2nc(CBr)c3cnc(SC)nc32)cc1]

Step 1: 4-Hydrazino-2-methylsulfanyl-pyrimidine-5-carboxylic acid ethyl ester

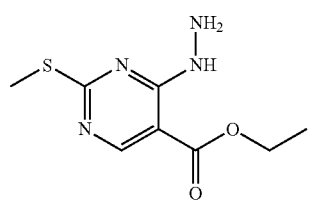

To a solution of hydrazine hydrate (6.28 mL) in ethanol (100 mL) was added drop wise a solution of 4-chloro-2-methylsulfanyl-pyrimidine-5-carboxylic acid ethyl ester (10 g, CAS: 5909-24-0) in ethanol (250 mL) at 0° C. and the reaction mixture was stirred at 25° C. for 1 h. All volatiles were removed under reduced pressure to afford the title compound (12.0 g) as an off white solid which was used in the next reaction step without additional purification. MS (ESI): m/z=229.5 [M+H]⁺.

Step 2: 6-Methylsulfanyl-1,2-dihydro-pyrazolo[3,4-d]pyrimidin-3-one

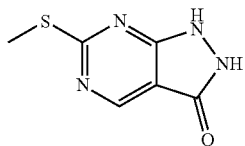

A solution of 4-hydrazino-2-methylsulfanyl-pyrimidine-5-carboxylic acid ethyl ester (12.0 g) in 10% aqueous KOH solution (300 mL) was refluxed for 15 min. The reaction mixture was then cooled to 0° C. and was acidified with 25% aq. AcOH. The resulting precipitate was filtered off, dried under reduced pressure and co-evaporated with toluene to afford the title compound (6.3 g, 66%) as off white solid. MS (ESI): m/z=183.2 [M+H]$^+$.

Step 3: 3-Bromo-6-methylsulfanyl-1H-pyrazolo[3,4-d]pyrimidine

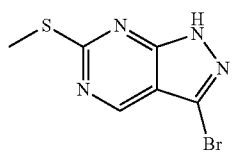

A mixture of 6-methylsulfanyl-1,2-dihydro-pyrazolo[3,4-d]pyrimidin-3-one (4.5 g) and POBr$_3$ (21.21 g) was heated in a sealed tube to 170° C. for 8 h. The reaction mixture was cooled to 25° C., diluted with water and basified with 25% aq. ammonia solution and was then extracted with EtOAc. The combined organic layers were washed with brine, dried over Na$_2$SO$_4$, filtered and evaporated under reduced pressure to afford the title compound (2.41 g, 40%) as a light brown solid. MS (ESI): m/z=245.1 [M+H]$^+$.

Step 4: 3-Bromo-1-(4-methoxy-benzyl)-6-methylsulfanyl-1H-pyrazolo[3,4-d]pyrimidine

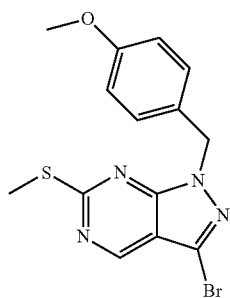 [SMILES: COc1ccc(Cn2nc(Br)c3cnc(SC)nc32)cc1]

To a solution of 3-bromo-6-methylsulfanyl-1H-pyrazolo[3,4-d]pyrimidine (3.6 g) in anhydrous DMF (100 mL) was added Cs$_2$CO$_3$ (7.16 g) at 25° C. and the reaction mixture was stirred at 25° C. for 15 min. Then, 1-(chloromethyl)-4-methoxy-benzene (2.39 mL) was added dropwise at 25° C. and the reaction mixture was stirred at 25° C. for 16 h. The reaction mixture was filtered and the filtrate was diluted with water and extracted with EtOAc. The combined organic extracts were dried over Na$_2$SO$_4$, filtered and evaporated under reduced pressure. The residue was purified by column chromatography over silica gel (3-6% EtOAc in hexane) to afford the title compound (4 g, 75%) as an off white solid. MS (ESI): m/z=367.1 [M+H]$^+$.

Step 5: 1-(4-Methoxy-benzyl)-6-methylsulfanyl-1H-pyrazolo[3,4-d]pyrimidine-3-carboxylic acid methyl ester

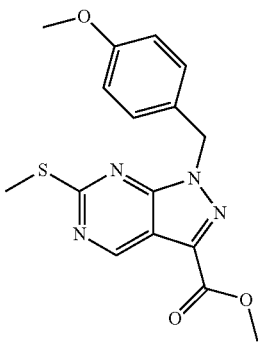

To a solution of 3-bromo-1-(4-methoxy-benzyl)-6-methylsulfanyl-1H-pyrazolo[3,4-d]pyrimidine (2.0 g) in a mixture of anhydrous DMF (30 mL) and MeOH (25 mL) were added Pd(OAc)$_2$ (98 mg), DPPP (135 mg) followed by Et$_3$N (2.34 mL) at 25° C. The reaction mixture was stirred under an atmosphere of carbon monoxide at 70 PSI and at 70° C. for 16 h. The reaction mixture was filtered through celite and the solvent was evaporated under reduced pressure. The residue was purified by column chromatography over silica gel (15-20% EtOAc in hexane) to afford the title compound (1.38 g, 73%) as off white solid. MS (ESI): m/z=345.3 [M+H]$^+$.

Step 6: [1-(4-Methoxy-benzyl)-6-methylsulfanyl-4,7-dihydro-1H-pyrazolo[3,4-d]pyrimidin-3-yl]-methanol

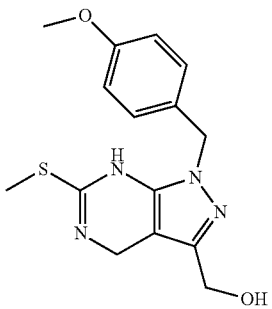 [SMILES: COc1ccc(Cn2nc(CO)c3c2NC(SC)=NC3)cc1]

A suspension of NaBH$_4$ (2.64 g) and CaCl$_2$ (3.87 g) in a mixture of THF (90 mL) and EtOH (90 mL) was cooled to 0° C. and a solution of -(4-methoxy-benzyl)-6-methylsulfanyl-1H-pyrazolo[3,4-d]pyrimidine-3-carboxylic acid methyl ester (3.0 g) in anhydrous THF (60 mL) was added drop wise. The reaction mixture was stirred at 0° C. for 2 h and was then quenched by slow addition of water at 0° C., followed by dilution with EtOAc. The organic layer was separated and the aqueous layer was extracted with EtOAc. The combined organic layers were washed with brine, dried over Na$_2$SO$_4$, filtered and evaporated to afford the title compound (2.67 g, 97%) as an off white solid. MS (ESI): m/z=319.2 [M+H]$^+$.

Step 7: [1-(4-Methoxy-benzyl)-6-methylsulfanyl-1H-pyrazolo[3,4-d]pyrimidin-3-yl]-methanol

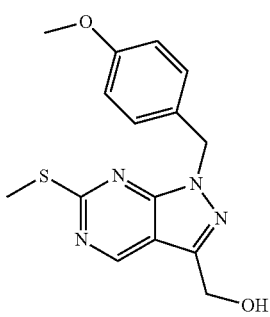 [SMILES: COc1ccc(Cn2nc(CO)c3cnc(SC)nc32)cc1]

A suspension of [1-(4-methoxy-benzyl)-6-methylsulfanyl-4,7-dihydro-1H-pyrazolo[3,4-d]pyrimidin-3-yl]-methanol (2.67 g) and chloranil (2.064 g) in anhydrous toluene (100 mL) was refluxed for 2 h. The reaction mixture was cooled to 25° C. and EtOAc and water were added. The organic layer was separated, washed with brine, dried over Na$_2$SO$_4$ and evaporated under reduced pressure. The resulting residue was purified by column chromatography over silica gel (50-70% EtOAc in hexane) to afford the title compound (2.2 g, 83%) as an off white solid. MS (ESI): m/z=317.0 [M+H]$^+$.

Step 8: 3-Bromomethyl-1-(4-methoxy-benzyl)-6-methylsulfanyl-1H-pyrazolo[3,4-d]pyrimidine

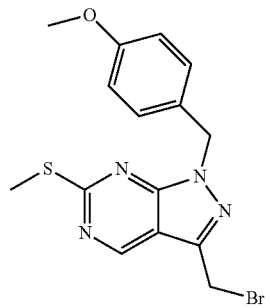 [SMILES: COc1ccc(Cn2nc(CBr)c3cnc(SC)nc32)cc1]

To a solution of [1-(4-methoxy-benzyl)-6-methylsulfanyl-1H-pyrazolo[3,4-d]pyrimidin-3-yl]-methanol (1.5 g) in anhydrous acetonitrile (100 mL) was added PBr$_3$ (0.586 mL) dropwise at 25° C. and the reaction mixture was stirred at 25° C. for 2 h. The mixture was diluted with EtOAc and washed with saturated aqueous NaHCO$_3$ solution and brine. The organic layer was dried over Na$_2$SO$_4$, filtered and evaporated under reduced pressure. The resulting residue was purified by column chromatography over silica gel (10-14% EtOAc in hexane) to afford the title compound (1.26 g, 70%) as an off white solid. MS (ESI): m/z=381.0 [M+H]$^+$.

Intermediate D3-A:

tert-Butyl 3-[(2-tert-butyl-4-chloro-5-methyl-phenoxy)methyl]pyrazolo[3,4-b]pyridine-1-carboxylate

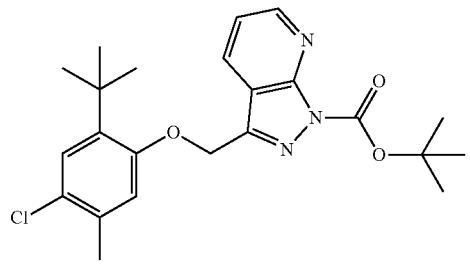 [SMILES: Cc1cc(OCc2nn(C(=O)OC(C)(C)C)c3ncccc23)c(C(C)(C)C)cc1Cl]

A suspension of 2-tert-butyl-4-chloro-5-methyl-phenol (61.0 mg, CAS: 30894-16-7), tert-butyl 3-(bromomethyl)pyrazolo[3,4-b]pyridine-1-carboxylate (95.8 mg, CAS: 174180-76-8, prepared according to WO200876223A1) and potassium carbonate (106 mg) in acetone (2.5 mL) was heated to 50° C. for 3 h. Acetone was removed in vacuo and the residue was diluted with saturated NH$_4$Cl solution. The mixture was extracted with EtOAc and the combined organic layers were washed with brine, dried over Na$_2$SO$_4$ and evaporated. The residue was purified by chromatography (20 g silica gel; heptane/EtOAc 90:10-75:25) to obtain the title compound as white solid (89 mg, 67%). MS (ESI): m/z=428.4 [M−H]$^−$.

The following intermediates were synthesized from suitable building blocks in analogy to Intermediate D3-A:

| Inter. | Systematic Name | Building blocks | MS, m/z |
| --- | --- | --- | --- |
| D4-A | tert-Butyl 3-[(2-tert-butyl-4-cyano-5-methyl-phenoxy)methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate A16 | 321.2 [M—CO$_2$tBu + H]$^+$ |

| Inter. | Systematic Name | Building blocks | MS, m/z |
| --- | --- | --- | --- |
| D5-A | tert-Butyl 3-[(4-chloro-2-isoxazol-5-yl-5-methyl-phenoxy)methyl]pyrazolo[3,4-b]pyridine-1-carboxylate | tert-butyl 3-(bromomethyl)pyrazolo[3,4-b]pyridine-1-carboxylate (CAS: 174180-76-8) and 4-chloro-2-(5-isoxazolyl)-5-methylphenol (CAS: 213690-32-5) | 441.3 [M + H]$^+$ |
| D6-A | tert-Butyl 3-[(2-tert-butyl-4-chloro-5-methyl-phenoxy)methyl]-6-fluoro-pyrazolo[3,4-b]pyridine-1-carboxylate | tert-butyl 3-(bromomethyl)-6-fluoro-pyrazolo[3,4-b]pyridine-1-carboxylate (CAS: 920036-30-2, prepared according to *J. Med. Chem.* 2008, 51, 6503-6511) and 2-tert-butyl-4-chloro-5-methyl-phenol (CAS: 30894-16-7) | 348.2 [M—CO$_2$tBu + H]$^+$ |
| D9-A | tert-Butyl 3-[(2-tert-butyl-5-methyl-4-methylsulfonyl-phenoxy)methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate D9 | 474.3 [M + H]$^+$ |
| D10-A | tert-Butyl 3-[(2-tert-butyl-5-methyl-4-methylsulfonyl-phenoxy)methyl]indazole-1-carboxylate | tert-butyl 3-(bromomethyl)-1H-indazole-1-carboxylate (CAS 174180-42-8) and Intermediate D9 | 373.2 [M—CO$_2$tBu + H]$^+$ |

| Inter. | Systematic Name | Building blocks | MS, m/z |
| --- | --- | --- | --- |
| D12-A | tert-Butyl 3-[(2-tert-butyl-4-chloro-5-fluoro-phenoxy)methyl]-6-fluoro-pyrazolo[3,4-b]pyridine-1-carboxylate | tert-butyl 3-(bromomethyl)-6-fluoro-pyrazolo[3,4-b]pyridine-1-carboxylate (CAS: 920036-30-2) and Intermediate A2 | 450.2 [M − H]− |
| D16-A | tert-Butyl 3-[[4-chloro-2-[3-(2-methoxyethylcarbamoyl)phenyl]-5-methyl-phenoxy]methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate B17 | 451.2 [M + H]+ |
| D18-A | tert-Butyl 3-[[4-chloro-2-[3-(dimethylcarbamoyl)phenyl]-5-methyl-phenoxy]methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate B12 | 421.2 [M + H]+ |
| D39-A | tert-Butyl 3-[[4-chloro-2-[2-fluoro-5-(4-methyl-3-oxo-piperazine-1-carbonyl)phenyl]-5-methyl-phenoxy]methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate B65 | 508.2 [M—CO2tBu + H]+ |

-continued

| Inter. | Systematic Name | Building blocks | MS, m/z |
|---|---|---|---|
| D40-A | tert-Butyl 3-[[4-chloro-2-[2-fluoro-5-[2-methoxyethyl(methyl)carbamoyl]-phenyl]-5-methyl-phenoxy]methyl]pyrazolo[3,4-b]pyridine-1-carboxylate | tert-butyl 3-(bromomethyl) pyrazolo[3,4-b]pyridine-1-carboxylate (CAS: 174180-76-8) and Intermediate B73 | 584.3 [M + H]+ |
| D41-A | tert-Butyl 3-[[4-chloro-2-[2-fluoro-5-(4-methyl-3-oxo-piperazine-1-carbonyl)phenyl]-5-methyl-phenoxy]methyl]indazole-1-carboxylate | tert-butyl 3-(bromomethyl)-1H-indazole-1-carboxylate (CAS 174180-42-8) and Intermediate B65 | 507.2 [M—CO2tBu + H]+ |
| D42-A | tert-Butyl 3-[[4-chloro-2-[2-fluoro-5-(pyrrolidine-1-carbonyl)phenyl]-5-methyl-phenoxy]methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate B62 | 565.2 [M + H]+ |
| D43-A | tert-Butyl 3-[[5-chloro-4-cyano-2-[2-fluoro-5-(pyrrolidine-1-carbonyl)phenyl]phenoxy]methyl]pyrazolo[3,4-b]pyridine-1-carboxylate | tert-butyl 3-(bromomethyl)pyrazolo[3,4-b]pyridine-1-carboxylate (CAS: 174180-76-8) and Intermediate D43 | 576.18 [M + H]+ |

| Inter. | Systematic Name | Building blocks | MS, m/z |
|---|---|---|---|
| D45-A | tert-Butyl 3-[(2-tert-butyl-4-methylsulfonyl-phenoxy)methyl]pyrazolo[3,4-b]pyridine-1-carboxylate 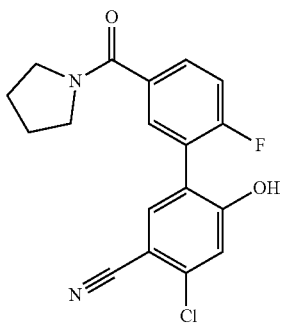 [SMILES: N#Cc1cc(-c2cc(C(=O)N3CCCC3)ccc2F)c(O)cc1Cl] | tert-butyl 3-(bromomethyl)pyrazolo[3,4-b]pyridine-1-carboxylate (CAS: 174180-76-8) and Intermediate A15 | 360.1 [M—CO$_2$tBu + H]$^+$ |

Intermediate D43:

2-Chloro-5-[2-fluoro-5-(pyrrolidine-1-carbonyl)phenyl]-4-hydroxy-benzonitrile

Step 1: 2-Chloro-5-[2-fluoro-5-(pyrrolidine-1-carbonyl)phenyl]-4-(methoxymethoxy)benzonitrile

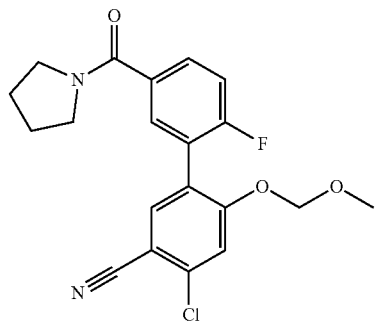 [SMILES: COCOc1cc(Cl)c(C#N)cc1-c1cc(C(=O)N2CCCC2)ccc1F]

The title compound was prepared in analogy to Intermediate B31, step 3, from 5-bromo-2-chloro-4-methoxymethoxy-benzonitrile (Intermediate B31, step 2) (80 mg) and (2-fluoro-5-(pyrrolidine-1-carbonyl)phenyl)boronic acid (82.3 mg, CAS: 874289-42-6) and was obtained as a white foam (60 mg, 52%). MS (ESI): m/z=389.2 [M+H]$^+$.

Step 2: 2-Chloro-5-[2-fluoro-5-(pyrrolidine-1-carbonyl)phenyl]-4-hydroxy-benzonitrile To a suspension of 4-chloro-2'-fluoro-6-(methoxymethoxy)-5'-(pyrrolidine-1-carbonyl)-[1,1'-biphenyl]-3-carbonitrile (50 mg) in dioxane (3 mL) was added 4M HCl in dioxane (257 µL) dropwise over a period of 2 minutes at rt. The resulting solution was stirred at rt for 2 h. Then again, 4M HCl in dioxane (129 µL) was added and stirring was continued for 5 h. The reaction mixture was evaporated to dryness and the residue was purified by recrystallization from DCM and heptane to afford the title compound (40 mg, 88%) as a white solid. MS (ESI): m/z=386.2 [M+CH$_3$CN+H]$^+$.

Intermediate D44-B:

3-(Chloromethyl)-1-tritylpyrazolo[3,4-c]pyridine

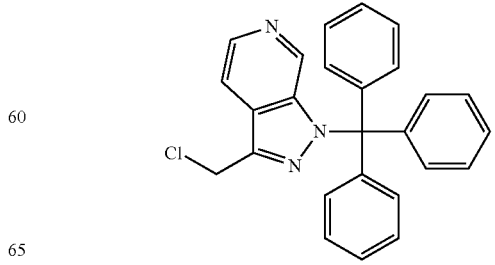

Step 1: Ethyl 1-tritylpyrazolo[3,4-c]pyridine-3-carboxylate

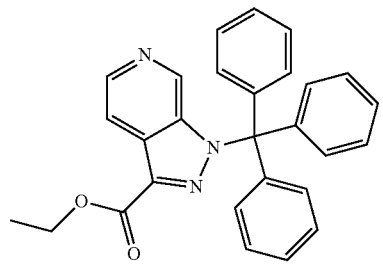 [SMILES: CCOC(=O)c1nn(C(c2ccccc2)(c2ccccc2)c2ccccc2)c2cnccc12]

In a 20 mL round-bottomed flask, ethyl 1H-pyrazolo[3,4-c]pyridine-3-carboxylate (CAS: 1053656-33-9, 500 mg) was combined with DMF (3 mL). Triethylamine (397 mg) was added to give a light brown solution. The mixture was cooled at 0° C. and then [chloro(diphenyl)methyl]-benzene (802 mg) was slowly added. The reaction mixture was stirred for 4 h. The reaction mixture was poured into 20 mL ethyl acetate and the organic solution was washed with H$_2$O (2×10 mL). The aqueous washings were re-extracted with ethyl acetate. The organic layers were combined, dried over Na$_2$SO$_4$ and concentrated in vacuo. Residual DMF was removed by addition of toluene followed by evaporation in vacuo. The crude material was purified by flash chromatography (silica gel, 20 g, gradient of 0% to 60% ethyl acetate in heptane) to give the title compound as a colorless foam (700 mg). MS (m/z): 434.18 [M+H]$^+$.

Step 2: (1-Tritylpyrazolo[3,4-c]pyridin-3-yl)methanol

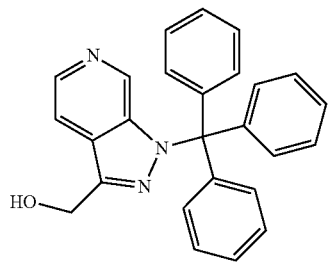 [SMILES: OCc1nn(C(c2ccccc2)(c2ccccc2)c2ccccc2)c2cnccc12]

In a 20 mL round-bottomed flask, ethyl 1-trityl-1H-pyrazolo[3,4-c]pyridine-3-carboxylate (700 mg) was combined with CH$_2$Cl$_2$ (3 mL) and was then cooled to −78° C. Diisobutylalumnium hydride solution (1 M in CH$_2$Cl$_2$, 3.2 mL) was added slowly and the mixture was allowed to stir at −78° C. for 2 h. The reaction mixture was poured into 20 mL ethyl acetate and Rochelle salt solution (10 mL) and was extracted with ethyl acetate (2×10 mL). The organic layers were combined, dried over Na$_2$SO$_4$ and concentrated in vacuo to give a white foam (500 mg), that was used without further purification. MS (m/z): 392.17 [M+H]$^+$.

Step 3: 3-(Chloromethyl)-1-tritylpyrazolo[3,4-c]pyridine

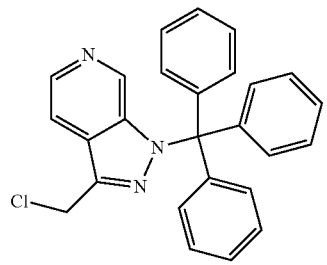 [SMILES: ClCc1nn(C(c2ccccc2)(c2ccccc2)c2ccccc2)c2cnccc12]

In a 20 mL round-bottomed flask, (1-trityl-1H-pyrazolo[3,4-c]pyridin-3-yl)methanol (55 mg) was combined with CH$_2$Cl$_2$ (3 mL) and the mixture was cooled to 0° C. Thionyl chloride (20.4 μL) was then added dropwise. The ice bath was removed and the reaction was allowed to stir at rt for 1 hr. The mixture was quenched with aq. sodium bicarbonate solution and the organic layer was separated, washed with brine and dried over Na$_2$SO$_4$. The solution was concentrated in vacuo to provide the title compound as a colorless foam (53 mg). MS (m/z): 410.14 [M+H]$^+$.

Intermediate D54-B 3-(Chloromethyl)-1-tritylpyrazolo[4,3-c]pyridine

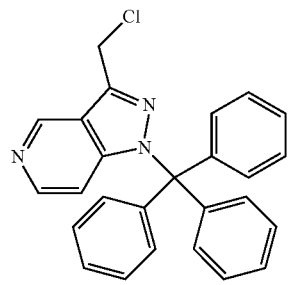

Step 1: Ethyl 1H-pyrazolo[4,3-c]pyridine-3-carboxylate

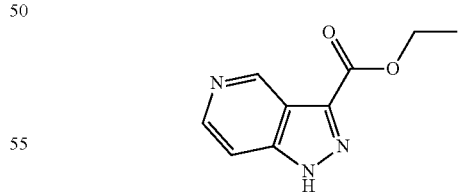

Under an argon atmosphere, thionyl chloride (241 mg, 147 μl) was added to a solution of 1H-pyrazolo[4,3-c]pyridine-3-carboxylic acid (300 mg, CAS: 932702-11-9) in ethanol (20 mL). The mixture was then heated to reflux and was allowed to stir for 2 hours. The mixture was cooled to room temperature and was quenched with sat. Na$_2$CO$_3$ solution. The aqueous layer was extracted twice with ethyl acetate (80 mL). The organic layers were washed once with brine, dried over Na$_2$SO$_4$, filtered, evaporated and dried at high vacuum to provide the title compound as a light yellow powder (228 mg, 62%). MS (m/z): 192.1 [M+H]+.

Steps 2-4: 3-(Chloromethyl)-1-tritylpyrazolo[4,3-c]pyridine

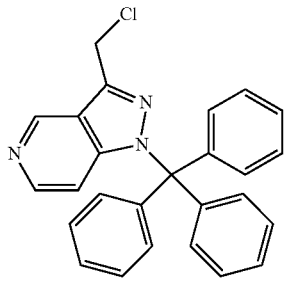 [SMILES: ClCc1nn(C(c2ccccc2)(c2ccccc2)c2ccccc2)c2ccncc12]

This material was obtained as a solid in exact analogy to Intermediate D44-B, Steps 1-3, from ethyl 1H-pyrazolo[4,3-c]pyridine-3-carboxylate (obtained above in Step 1) first by tritylation, then reduction to the hydroxymethyl derivative, and finally chlorination. MS (m/z): 410.2 [M+H]+.

Intermediates F

Intermediate F1:

tert-Butyl 3-(bromomethyl)pyrazole-1-carboxylate

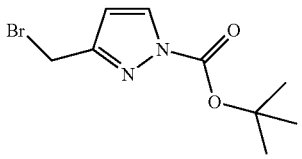

Step 1: tert-Butyl 3-methylpyrazole-1-carboxylate

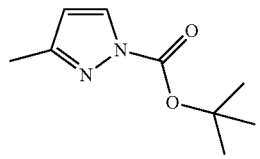

To a solution of 3-methyl-1H-pyrazole (500 mg) in acetonitrile (10 mL) were added di-tert-butyl dicarbonate (1.59 g, 1.7 mL) and DMAP (74.4 mg) at 0° C. The mixture was allowed to warm to rt and was stirred for 2 h. Then, EtOAc was added and the mixture was washed with 0.1 N HCl, saturated NaHCO$_3$ solution and brine, dried with Na$_2$SO$_4$ and evaporated. The crude product (containing ~15% of tert-butyl 5-methylpyrazole-1-carboxylate) was used in the next reaction step without further purification.

Step 2: tert-Butyl 3-(bromomethyl)pyrazole-1-carboxylate

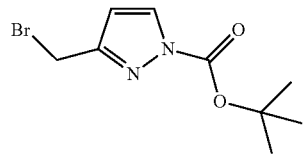

A mixture of tert-butyl 3-methylpyrazole-1-carboxylate (1.24 g), NBS (1.7 g) and benzoyl peroxide (308 mg) in CCl$_4$ (50 mL) was heated to reflux for 4 h. The mixture was then cooled to 0° C., filtered and evaporated. The residue was purified by column chromatography (100 g SiO$_2$, n-heptane/EtOAc 100/0 to 90/10) to provide the title compound (481 mg, 27%) as a colorless oil. MS (ESI): m/z=161.0 [M−CO$_2$tBu+H]+.

Intermediate F3:

Methyl 5-(hydroxymethyl)-2-tetrahydropyran-2-yl-pyrazole-3-carboxylate

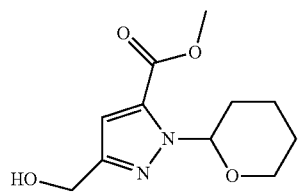 [SMILES: COC(=O)c1cc(CO)nn1C1CCCCO1]

Step 1: Dimethyl 1-tetrahydropyran-2-ylpyrazole-3,5-dicarboxylate

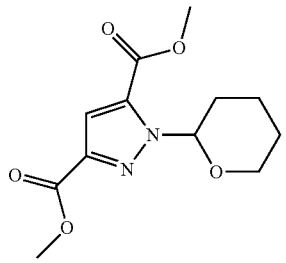 [SMILES: COC(=O)c1cc(C(=O)OC)n(C2CCCCO2)n1]

TFA (74.0 mg, 50 µL) was added to a suspension of dimethyl 1H-pyrazole-3,5-dicarboxylate (1.546 g, CAS: 4077-76-3) in toluene (15 mL) and the mixture was heated to 80° C. Then, 3,4-dihydro-2H-pyran (828 mg, 900 µL) was added and the reaction mixture was refluxed overnight. The mixture was cooled to rt and the solvent was evaporated. The residue was dissolved in water and was extracted with EtOAc. The combined organic layers were washed with brine, dried with Na$_2$SO$_4$, filtered and evaporated. The residue was purified by chromatography (50 g silica gel; heptane/EtOAc 100/0 to 50/50) to obtain the title compound (1.95 g, 87%) as a white solid. MS (ESI): m/z=185.1 [M−THP+H]+.

Step 2: Methyl 5-(hydroxymethyl)-2-tetrahydropyran-2-yl-pyrazole-3-carboxylate

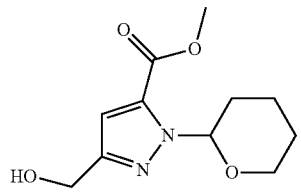 [SMILES: COC(=O)c1cc(CO)nn1C1CCCCO1]

To a solution of dimethyl 1-tetrahydropyran-2-ylpyrazole-3,5-dicarboxylate (1.95 g) in a mixture of THF (40 mL) and diethyl ether (80 mL) was added a 1M solution of DIBAL-H in toluene (16.0 mL) dropwise at −78° C. and the mixture was stirred for 3 h at −78° C. Then, more DIBAL-H 1 M in toluene (8 mL) was added and the mixture was stirred for another hour. The mixture was warmed to 0° C. and water (15 mL) was added dropwise. The white suspension was evaporated and the remaining white cake was suspended in MeOH (120 mL), flushed with $CO_2$ (g) for 10 minutes and then refluxed for 5.5 h. The mixture was filtered and the filtrate was concentrated. The remaining material was purified by chromatography (50 g silica gel, heptane/EtOAc 100/0 to 1/2) to obtain the title compound (810 mg, 47%) as a white solid. MS (ESI): m/z=157.0 [M−THP+H]$^+$.

Examples A: Triazolones with $R_4 \neq$ Aryl

Example A1

3-[(2-tert-Butyl-4-chloro-5-methylphenoxy)methyl]-4-methyl-1H-1,2,4-triazol-5-one

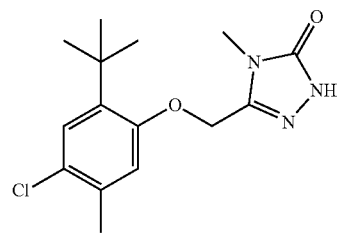 [SMILES: Cc1cc(OCc2n[nH]c(=O)n2C)c(C(C)(C)C)cc1Cl]

2-(tert-Butyl)-4-chloro-5-methylphenol (CAS: 30894-16-7, 250 mg), 3-(chloromethyl)-4-methyl-1H-1,2,4-triazol-5(4H)-one (CAS: 1338226-21-3; 279 mg), potassium carbonate (348 mg) and potassium iodide (20.9 mg) were combined in acetone (10.0 mL) at rt under an argon atmosphere. The mixture was then heated to reflux for 3 hours and was then kept at rt for another 16 hours. TLC showed no residual starting material at that time. The reaction mixture was then poured into ice/water and the aqueous layer was extracted twice with ethyl acetate. The organic layers were washed once with brine, dried over $Na_2SO_4$, filtered and evaporated. The crude material was purified by flash chromatography on silica gel with 0% to 70% ethyl acetate in heptane as an eluent to provide the title compound as a colorless solid (60 mg). MS (m/z): 310.2 [MH]$^+$.

The following examples were synthesized from the suitable building blocks/intermediates and known 3-(chloromethyl)-4-methyl-1H-1,2,4-triazol-5(4H)-one in analogy to Example A1:

| Ex. | Systematic Name | Building block/intermediate | MS, m/z |
|---|---|---|---|
| A2 | 3-[(2-tert-butyl-4-chloro-5-fluorophenoxy)methyl]-4-methyl-1H-1,2,4-triazol-5-one | Intermediate A1 | 314.2 [M + H]$^+$ |
| A3 | 3-[(3,3-dimethyl-6-propan-2-yl-1,2-dihydroinden-5-yl)oxymethyl]-4-methyl-1H-1,2,4-triazol-5-one | 6-Isopropyl-3,3-dimethyl-2,3-dihydro-1H-inden-5-ol CAS: 1588508-77-3 made according to WO2014048865 | 316.2 [M + H]$^+$ |

| Ex. | Systematic Name | | Building block/intermediate | MS, m/z |
|---|---|---|---|---|
| A4 | 3-[[2-tert-butyl-4-(3-methyl-1,2,4-oxadiazol-5-yl)phenoxy]methyl]-4-methyl-1H-1,2,4-triazol-5-one 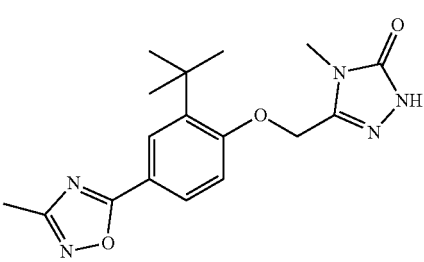 | | 2-tert-butyl-4-(3-methyl-1,2,4-oxadiazol-5-yl)phenol Intermediate A4 | 344.2 [M + H]⁺ |
| A5 | 3-[[2-tert-butyl-4-[1-(2-trimethylsilylethoxymethyl)imidazol-2-yl]phenoxy]methyl]-4-methyl-1H-1,2,4-triazol-5-one 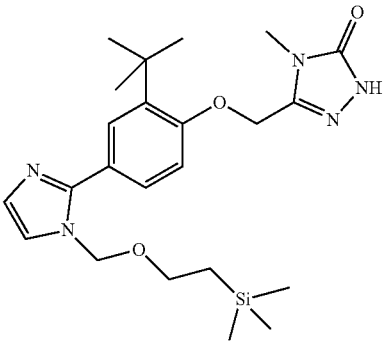 | | 2-tert-butyl-4-[1-(2-trimethylsilylethoxymethyl)-imidazol-2-yl]phenol Intermediate A5 | 457.9 [M + H]⁺ |
| A6 | 3-[[2-tert-butyl-4-(1-methylimidazol-2-yl)phenoxy]methyl]-4-methyl-1H-1,2,4-triazol-5-one 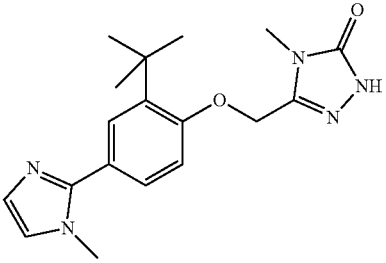 | | 2-tert-butyl-4-(1-methylimidazol-2-yl)phenol Intermediate A6 | 342.0 [M + H]⁺ |
| A7 | 3-[[2-tert-butyl-4-(1,3-oxazol-2-yl)phenoxy]methyl]-4-methyl-1H-1,2,4-triazol-5-one 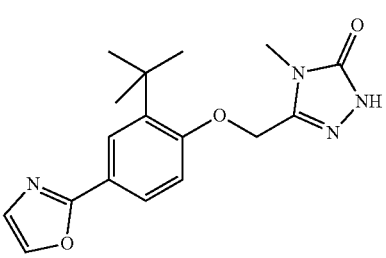 | | 2-tert-butyl-4-(1,3-oxazol-2-yl)phenol Intermediate A7 | 329.0 [M + H]⁺ |

-continued

| Ex. | Systematic Name | Building block/intermediate | MS, m/z |
|---|---|---|---|
| A8 | 3-[(2-tert-butyl-4-morpholin-4-ylphenoxy)methyl]-4-methyl-1H-1,2,4-triazol-5-one 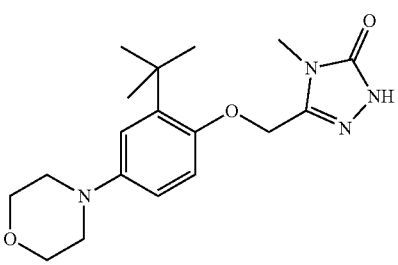 | 2-tert-butyl-4-morpholin-4-ylphenol<br>Intermediate A8 | 347.0<br>[M + H]+ |
| A9 | 3-[[2-tert-butyl-4-(3-methylimidazol-4-yl)phenoxy]methyl]-4-methyl-1H-1,2,4-triazol-5-one 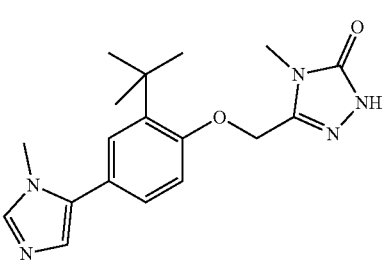 | 2-tert-butyl-4-(3-methylimidazol-4-yl)phenol<br>Intermediate A9 | 342.0<br>[M + H]+ |
| A10 | 3-[[2-tert-butyl-4-(5-methyl-1,3,4-oxadiazol-2-yl)phenoxy]methyl]-4-methyl-1H-1,2,4-triazol-5-one 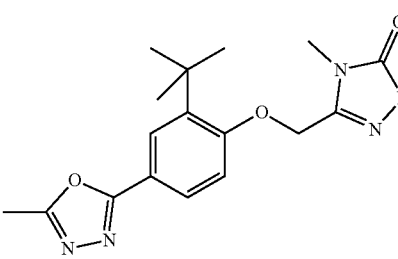 | 2-tert-butyl-4-(5-methyl-1,3,4-oxadiazol-2-yl)phenol<br>Intermediate A10 | 344.1<br>[M + H]+ |
| A11 | 4-[(4-methyl-5-oxo-1H-1,2,4-triazol-3-yl)methoxy]-3-propan-2-ylbenzonitrile 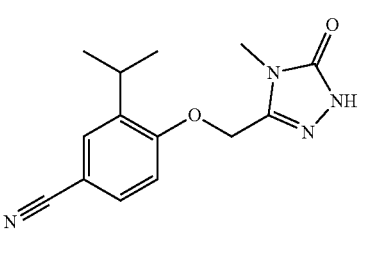 | 4-hydroxy-3-propan-2-ylbenzonitrile<br>CAS: 46057-54-9<br>Made from 2-isopropylphenol according to WO2005023762 | 271.12<br>[M − H]− |
| A12 | 2-methyl-4-[(4-methyl-5-oxo-1H-1,2,4-triazol-3-yl)methoxy]-5-propan-2-ylbenzonitrile 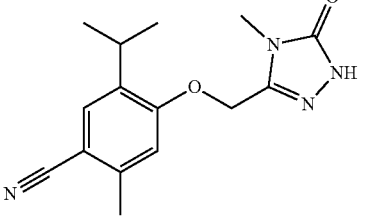 | 4-hydroxy-6-methyl-3-propan-2-ylbenzonitrile<br>CAS: 858026-56-9<br>Made from 2-isopropyl-5-methlyphenol according to WO2005023762 | 285.14<br>[M − H]− |

| Ex. | Systematic Name | Building block/intermediate | MS, m/z |
|---|---|---|---|
| A13 | 3-tert-butyl-4-[(4-methyl-5-oxo-1H-1,2,4-triazol-3-yl)methoxy]benzonitrile | 3-tert-butyl-4-hydroxybenzonitrile CAS: 4910-04-7 | 287.15 [M + H]⁺ |
| A14 | 3-[(4-chloro-2-cyclopropyl-5-methylsulfonylphenoxy)methyl]-4-methyl-1H-1,2,4-triazol-5-one | 4-chloro-2-cyclopropyl-5-methylsulfonylphenol Intermediate A14 | 358.06 [M + H]⁺ and 375.09 [M + NH₄]⁺ |
| A15 | 3-[(2-tert-butyl-4-methylsulfonylphenoxy)methyl]-4-methyl-1H-1,2,4-triazol-5-one | 2-tert-butyl-4-methylsulfonylphenol Intermediate A15 | 340.13 [M + H]⁺ |
| A16 | 5-tert-butyl-2-methyl-4-[(4-methyl-5-oxo-1H-1,2,4-triazol-3-yl)methoxy]benzonitrile | 5-tert-butyl-4-hydroxy-2-methylbenzonitrile Intermediate A16 | 301.17 [M + H]⁺ |

-continued

| Ex. | Systematic Name | Building block/intermediate | MS, m/z |
|---|---|---|---|
| A17 | 4-tert-butyl-2-methyl-5-[(4-methyl-5-oxo-1H-1,2,4-triazol-3-yl)methoxy]benzonitrile | 4-tert-butyl-5-hydroxy-2-methylbenzonitrile Intermediate A17 | 301.17 [M + H]+ |
| A18 | 3-[[2-tert-butyl-4-[3-(2-trimethylsilyl-ethoxymethyl)imidazol-4-yl]phenoxy]-methyl]-4-methyl-1H-1,2,4-triazol-5-one | 2-tert-Butyl-4-[3-(2-trimethylsilanyl-ethoxymethyl)-3H-imidazol-4-yl]-phenol Intermediate A18 | 458.10 [M + H]+ |
| A19 | 3-[(4-chloro-2-cyclopropyl-5-methylphenoxy)methyl]-4-methyl-1H-1,2,4-triazol-5-one | 4-chloro-2-cyclopropyl-5-methylphenol Intermediate A19 | 294.0 [M + H]+ |
| A20 | 3-[(4-chloro-2-cyclopropyl-5-methylphenoxy)methyl]-4-methyl-1H-1,2,4-triazol-5-one | 4-chloro-2-cyclohexyl-5-methylphenol Intermediate A20 | 336.0 [M + H]+ |

-continued

| Ex. | Systematic Name | Building block/intermediate | MS, m/z |
|---|---|---|---|
| A21 | 3-[[4-chloro-5-methyl-2-(oxan-4-yl)phenoxy]methyl]-4-methyl-1H-1,2,4-triazol-5-one | 4-chloro-5-methyl-2-(oxan-4-yl)phenol Intermediate A21 | 338.0 [M + H]+ |
| A22 | 2-chloro-4-cyclopropyl-5-[(4-methyl-5-oxo-1H-1,2,4-triazol-3-yl)methoxy]benzonitrile | 2-chloro-4-cyclopropyl-5-hydroxy-benzonitrile Intermediate A22 | 305.0 [M + H]+ |
| A23 | N-[2-chloro-4-cyclopropyl-5-[(4-methyl-5-oxo-1H-1,2,4-triazol-3-yl)methoxy]phenyl]methanesulfonamide | N-(2-chloro-4-cyclopropyl-5-hydroxyphenyl)methane-sulfonamide Intermediate A23 | 373.0 [M + H]+ |
| A24 | 4-tert-butyl-3-[(4-methyl-5-oxo-1H-1,2,4-triazol-3-yl)methoxy]benzonitrile | 4-tert-butyl-3-hydroxybenzonitrile Intermediate A24 | 287.0 [M + H]+ |

| Ex. | Systematic Name | Building block/intermediate | MS, m/z |
|---|---|---|---|
| A25 | 4-tert-butyl-3-[(4-methyl-5-oxo-1H-1,2,4-triazol-3-yl)methoxy]benzamide 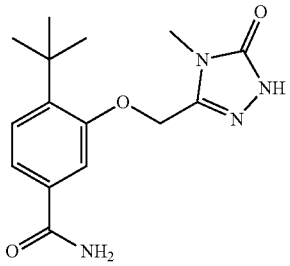 | 4-tert-butyl-3-hydroxybenzamide Intermediate A25 | 305.6 [M + H]$^+$ |

Example A26

5-tert-Butyl-2-methyl-4-[(5-oxo-4-propan-2-yl-1H-1,2,4-triazol-3-yl)methoxy]benzonitrile

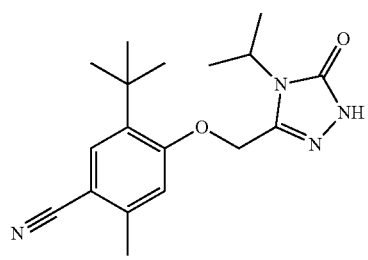 [SMILES: Cc1cc(OCc2n[nH]c(=O)n2C(C)C)c(C(C)(C)C)cc1C#N]

Step 1: 3-(Benzyloxymethyl)-4-isopropyl-1H-1,2,4-triazol-5(4H)-one

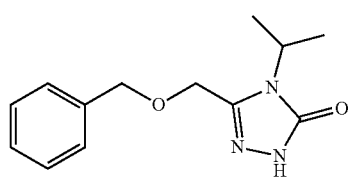 [SMILES: CC(C)n1c(COCc2ccccc2)n[nH]c1=O]

To a suspension of N-isopropylhydrazinecarboxamide hydrochloride (CAS: 35578-82-6, 1.0 g) in THF (12.5 mL) was added 2-(benzyloxy)acetyl chloride (1.2 g) and the mixture was cooled to 0° C. To the mixture was then added dropwise 5M aq. sodium hydroxide (2.67 mL) over 3 minutes and the reaction mixture was vigorously stirred at room temperature for 2.5 hours. THF was then removed by evaporation in vacuo. The remaining brown, viscous suspension was treated with 2M aq. sodium hydroxide (6.51 mL) and was heated to 95° C. (oil bath temperature) for 16 hours. After cooling, the turbid solution was adjusted to pH 4 using 25% aq. HCl. Ethyl acetate was added and the layers were separated. The aqueous layer was extracted twice with ethyl acetate. The organic layers were washed with brine, dried over MgSO$_4$, filtered, treated with silica gel and evaporated. The residue was purified by silica gel chromatography with a gradient of n-heptane in ethyl acetate (100/0 to 0/100) to provide the title compound (0.705 g). MS (m/z): 248.14 [M+H]$^+$.

Step 2: 3-(Hydroxymethyl)-4-propan-2-yl-1H-1,2,4-triazol-5-one

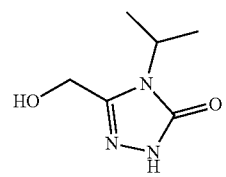

To a solution of 3-(benzyloxymethyl)-4-isopropyl-1H-1,2,4-triazol-5(4H)-one (0.70 g) in ethanol (12 mL) under argon was added palladium hydroxide on carbon (20%, 298 mg) and the reaction mixture was stirred under a hydrogen atmosphere at room temperature and 0.5 bar overpressure over 18 hours. The reaction mixture was then filtered and the solid was washed with ethanol (10 mL). The filtrate was evaporated to provide the title compound as a colorless solid (0.391 g). MS (m/z): 157.0 [M]$^+$.

Step 3: 3-(Chloromethyl)-4-propan-2-yl-1H-1,2,4-triazol-5-one

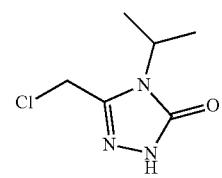

To a suspension of 3-(hydroxymethyl)-4-isopropyl-1H-1,2,4-triazol-5(4H)-one (0.30 g) in acetonitrile (6 mL) was added thionyl chloride (261 mg) and the suspension rapidly turned into a solution. The mixture was stirred at room temperature for 16 hours. The reaction mixture was evaporated and the residue was twice treated with toluene and evaporated again to remove the remaining thionyl chloride. The residue, an off-white solid, was triturated with n-heptane in an ultrasonic bath. The suspension was then filtered, washed with n-heptane and the solid was dried in vacuo to provide the title compound (0.37 g) as a colorless solid. MS (m/z): 175.0 [M]⁺.

Step 4: 5-tert-Butyl-2-methyl-4-[(5-oxo-4-propan-2-yl-1H-1,2,4-triazol-3-yl)methoxy]benzonitrile This material was obtained from in analogy to Example 1 from 3-(chloromethyl)-4-propan-2-yl-1H-1,2,4-triazol-5-one and 5-tert-butyl-4-hydroxy-2-methylbenzonitrile (Intermediate A16) to provide the title compound as a light brown solid. MS (m/z): 329.20 [M+H]⁺.

Example A27

4-Methyl-3-[(5-methyl-2-propan-2-ylphenoxy)methyl]-1H-1,2,4-triazol-5-one

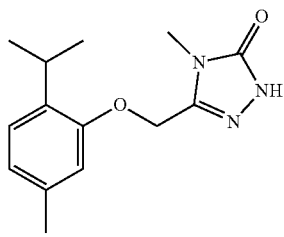 [SMILES: Cc1ccc(C(C)C)c(OCc2n[nH]c(=O)n2C)c1]

Step 1: 4-Methyl-3-[(5-methyl-2-propan-2-ylphenoxy)methyl]-5-methylsulfonyl-1,2,4-triazole

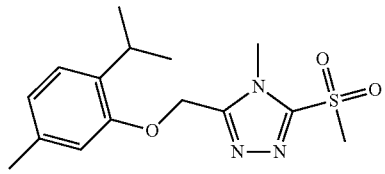 [SMILES: Cc1ccc(C(C)C)c(OCc2nnc(S(C)(=O)=O)n2C)c1]

To a solution of 2-isopropyl-5-methylphenol (300 mg, CAS: 89-83-8) in acetone (20 mL) was added K₂CO₃ (387 mg) and 3-(iodomethyl)-4-methyl-5-(methylsulfonyl)-4H-1,2,4-triazole (783 mg, CAS: 1068603-49-5, made according to WO2008119662). The reaction mixture was stirred over night at 60° C. and was then extracted with water (150 mL) and EtOAc (150 mL). The organic layer was washed with water (150 mL), dried over Na₂SO₄, filtered and evaporated. The crude material was purified by column chromatography (gradient of up to 50% EtOAc in DCM) to provide the title compound as a yellow gum (0.241 g). MS (m/z): 324.14 [M+H]⁺.

Step 2: 3-Methoxy-4-methyl-5-[(5-methyl-2-propan-2-ylphenoxy)methyl]-1,2,4-triazole

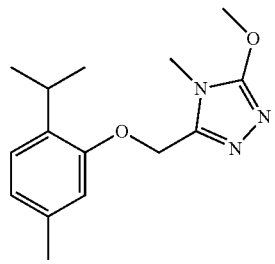 [SMILES: COc1nnc(COc2cc(C)ccc2C(C)C)n1C]

To a suspension of 4-methyl-3-[(5-methyl-2-propan-2-ylphenoxy)methyl]-5-methylsulfonyl-1,2,4-triazole (241 mg) in methanol (8 mL) was added sodium methoxide in methanol (0.6 mL, 5.4 M). The reaction mixture was heated at 85° C. under reflux. After 2 h, the reaction was stopped and cooled. The mixture was diluted with EtOAc (50 mL), washed with sat. aqueous NaHCO₃ (50 mL) and sat. NaCl solution (20 mL) and was then dried over Na₂SO₄ and concentrated in vacuo. The desired product was obtained as such as a light yellow solid and was used without further purification (0.2 g, containing some starting material). MS (m/z): 276.17 [M+H]⁺.

Step 3: 4-Methyl-3-[(5-methyl-2-propan-2-ylphenoxy)methyl]-1H-1,2,4-triazol-5-one

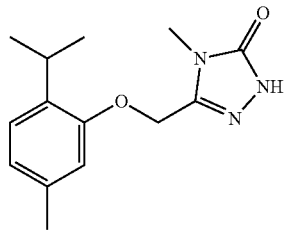 [SMILES: Cc1ccc(C(C)C)c(OCc2n[nH]c(=O)n2C)c1]

To a solution of 3-methoxy-4-methyl-5-[(5-methyl-2-propan-2-ylphenoxy)methyl]-1,2,4-triazole (113 mg) in AcOH (29 mL) was added HBr (19.5 mL of a 48% solution) at rt and the reaction mixture was stirred over night. The solution was concentrated (at 50-70° C. water bath temperature) and was then diluted with DCM (50 mL) and washed with 2M KHCO₃ solution (30 mL). The organic layer was dried with Na₂SO₄, filtered and concentrated to give the title compound as a light yellow solid (0.094 g). MS (m/z): 262.2 [M+H]⁺.

The following Examples were synthesized from the suitable building blocks/intermediates in analogy to Example A1, Steps 1-3:

| Ex. | Systematic Name | Building block/intermediate | MS, m/z |
|---|---|---|---|
| A28 | 3-[(4-chloro-5-methyl-2-propan-2-ylphenoxy)methyl]-4-methyl-1H-1,2,4-triazol-5-one | 4-chloro-5-methyl-2-propan-2-ylphenol CAS: 89-68-9 | 296.12 [M + H]+ |
| A29 | 3-[(4-chloro-2-propan-2-ylphenoxy)methyl]-4-methyl-1H-1,2,4-triazol-5-one | 4-chloro-2-propan-2-ylphenol CAS: 54461-05-1 | 282.10 [M + H]+ |
| A30 | 3-[(6-cyclopropyl-2-methyl-1,3-benzothiazol-5-yl)oxymethyl]-4-methyl-1H-1,2,4-triazol-5-one | 6-cyclopropyl-2-methylbenzo[d]thiazol-5-ol Intermediate A30 | 317.11 [M + H]+ |
| A31 | 3-[(4-chloro-2-cyclobutyl-5-methylphenoxy)methyl]-4-methyl-1H-1,2,4-triazol-5-one | 4-chloro-2-cyclobutyl-5-methylphenol Intermediate A31 | 308.2 [M + H]+ |

Example A32

3-[[2-tert-butyl-4-(1H-imidazol-2-yl)phenoxy]methyl]-4-methyl-1H-1,2,4-triazol-5-one

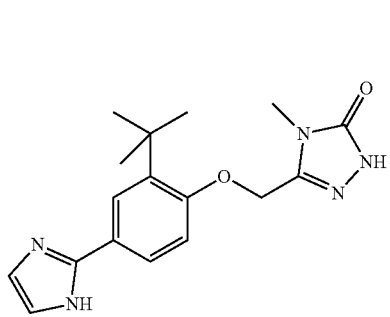 [SMILES: Cn1c(COc2ccc(-c3ncc[nH]3)cc2C(C)(C)C)n[nH]c1=O]

To a solution of 3-[[2-tert-butyl-4-[1-(2-trimethylsilylethoxymethyl)imidazol-2-yl]phenoxy]methyl]-4-methyl-1H-1,2,4-triazol-5-one (45 mg), obtained in Example A5, in anhydrous THF (10 mL) at 0° C. was added 2N aqueous HCl (3 mL) at 0° C. and the reaction mixture was stirred at 25° C. for 8 h. The solvent was evaporated under reduced pressure and the residue was diluted with water, basified using saturated aq. NaHCO₃ solution and extracted with DCM (2×30 mL). The combined organic layers were washed with brine, dried over Na₂SO₄ and evaporated under reduced pressure. The residue was purified column chromatography over silica gel (gradient of 3-5% MeOH in DCM) to afford the title compound (12 mg) as an off white solid. MS (m/z): 328.1 [M+H]⁺.

The following Example was synthesized from the suitable building blocks/intermediates in analogy to Example A32, with the exception that the solvent THF was replaced by DCM and that 2N HCl was replaced by trifluoroacetic acid.

Example A34

4-tert-Butyl-2-chloro-5-[(4-methyl-5-oxo-1H-1,2,4-triazol-3-yl)methoxy]benzonitrile

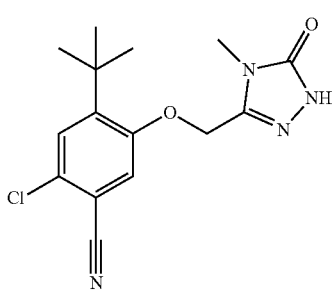 [SMILES: Cn1c(COc2cc(C#N)c(Cl)cc2C(C)(C)C)n[nH]c1=O]

This material was made in analogy to Example A1 from Intermediate A34 and commercial 3-(chlormethyl)-4-methyl-1H-1,2,4-triazol-5(4H)-one (CAS: 1338226-21-3) as a colorless solid. MS (m/z): 321.2 [M+H]⁺.

Example A35

5-tert-butyl-2-chloro-4-[(4-methyl-5-oxo-1H-1,2,4-triazol-3-yl)methoxy]benzonitrile

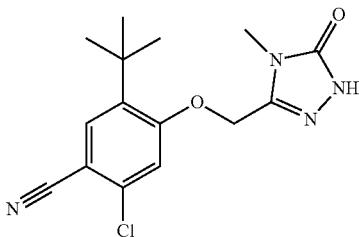 [SMILES: Cn1c(COc2cc(Cl)c(C#N)cc2C(C)(C)C)n[nH]c1=O]

| Ex. | Systematic Name | Building block/intermediate | MS, m/z |
|---|---|---|---|
| A33 | 3-[[2-tert-butyl-4-(1H-imidazol-5-yl)phenoxy]methyl]-4-methyl-1H-1,2,4-triazol-5-one | Example A18 | 328.20 [M + H]⁺ |

To 5-tert-butyl-2-chloro-4-hydroxy-benzonitrile (2.29 g, 10.9 mmol) in N-methyl-pyrrolidinone (55 mL) was added NaH (568 mg, 14.2 mmol). The mixture was stirred at room temperature for 30 min. 3-(Chloromethyl)-4-methyl-1H-1,2,4-triazol-5(4H)-one (1.93 g, 13.11 mmol) was dissolved in N-methyl-pyrrolidinone (20 mL) and added dropwise via addition funnel over 30 min. Upon complete addition, water (160 mL) was slowly added to the reaction. After stirring until cooled to room temperature, the reaction was filtered and solids dried to give 3.15 g of the title compound as a white solid (90% yield). MS (m/z): 321.5 [M+H]$^+$.

Example A36

5-tert-butyl-2-fluoro-4-[(4-methyl-5-oxo-1H-1,2,4-triazol-3-yl)methoxy]benzonitrile

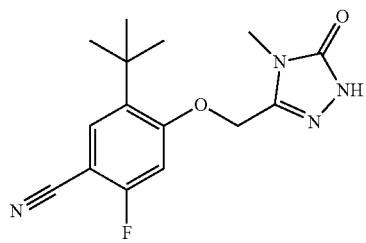

The title compound was prepared in analogy to example A35, from 5-tert-butyl-2-fluoro-4-hydroxy-benzonitrile (0.118 g) and 3-(chloromethyl)-4-methyl-1H-1,2,4-triazol-5(4H)-one (0.108 g) and was obtained (17 mg, 9%) as a white solid. MS (m/z): 305.5 [M+H]$^+$.

Examples B: Triazolones with $R_A$=Aryl and Heteroaryl

Example B1

3-[(4-Chloro-5-methyl-2-phenylphenoxy)methyl]-4-methyl-1H-1,2,4-triazol-5-one

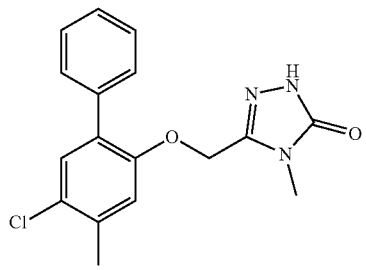 [SMILES: Cc1cc(OCc2n[nH]c(=O)n2C)c(-c2ccccc2)cc1Cl]

To a solution of 4-chloro-5-methyl-2-phenylphenol (62.2 mg, Intermediate B1) in acetone (2 mL) was added K$_2$CO$_3$ (42.6 mg) and 3-(chloromethyl)-4-methyl-1H-1,2,4-triazol-5(4H)-one (35 mg, CAS: 1338226-21-3). The reaction mixture was stirred for 2 hours at reflux. The reaction mixture was poured on 10% aqueous NH$_4$Cl solution (30 mL) and EtOAc (30 mL) and the layers were separated. The aqueous layer was extracted a second time with EtOAc (30 mL). The organic layers were washed with brine (30 mL), dried over MgSO$_4$, filtered and concentrated in vacuo. The residue was purified by silica gel chromatography on a 20 g column using an Flashmaster MPLC-system eluting with a gradient of DCM:MeOH (100/0 to 50/50) to give the title compound as an off-white solid (7 mg, 9%). MS (ESI): m/z=330.100 [M+H]$^+$.

The following Examples were synthesized from the suitable building blocks/intermediates and known 3-(chloromethyl)-4-methyl-1H-1,2,4-triazol-5(4H)-one in analogy to Example B1:

| Ex. | Systematic Name | Building block/intermediate | MS, m/z |
| --- | --- | --- | --- |
| B2 | 3-[[4-chloro-2-(2-chlorophenyl)-5-methyl-phenoxy]methyl]-4-methyl-1H-1,2,4-triazol-5-one 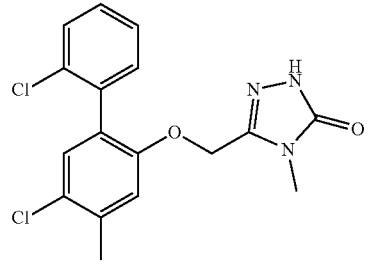 | 4-chloro-2-(2-chlorophenyl)-5-methylphenol Intermediate B2 | 364.06 [M + H]$^+$ |

| Ex. | Systematic Name | Building block/intermediate | MS, m/z |
|---|---|---|---|
| B3 | 3-[[4-chloro-2-(3-chlorophenyl)-5-methyl-phenoxy]methyl]-4-methyl-1H-1,2,4-triazol-5-one 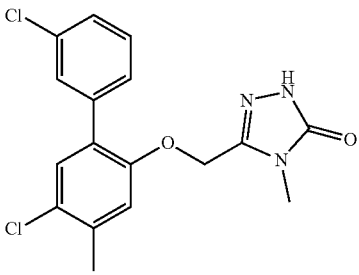 | 4-chloro-2-(3-chlorophenyl)-5-methylphenol<br>Intermediate B3 | 364.06 [M + H]⁺ |
| B4 | 3-[[4-chloro-2-(4-chlorophenyl)-5-methyl-phenoxy]methyl]-4-methyl-1H-1,2,4-triazol-5-one 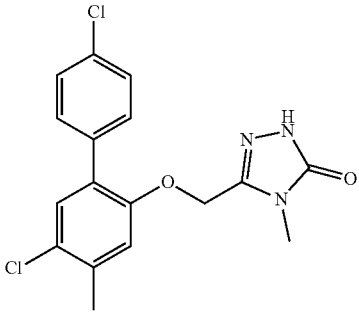 | 4-chloro-2-(4-chlorophenyl)-5-methylphenol<br>Intermediate B4 | 364.06 [M + H]⁺ |
| B5 | 3-[5-chloro-4-methyl-2-[(4-methyl-5-oxo-1H-1,2,4-triazol-3-yl)methoxy]phenyl]benzonitrile 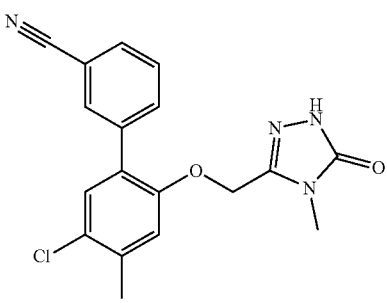 | 3-(5-chloro-2-hydroxy-4-methylphenyl)benzonitrile<br>Intermediate B5 | 355.10 [M + H]⁺ |
| B6 | 3-[[4-chloro-5-methyl-2-(3-methylsulfonylphenyl)phenoxy]methyl]-4-methyl-1H-1,2,4-triazol-5-one 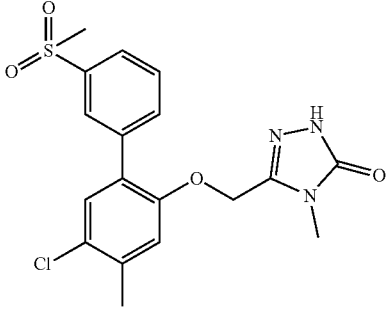 | 4-chloro-5-methyl-2-(3-methylsulfonylphenyl)phenol<br>Intermediate B6 | 408.08 [M + H]⁺ |

-continued

| Ex. | Systematic Name | Building block/intermediate | MS, m/z |
|---|---|---|---|
| B7 | 3-[[4-chloro-5-methyl-2-(2-methylsulfonylphenyl)phenoxy]methyl]-4-methyl-1H-1,2,4-triazol-5-one 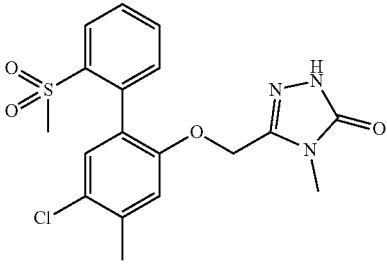 | 4-chloro-5-methyl-2-(2-methylsulfonylphenyl)phenol Intermediate B7 | 408.08 [M + H]+ |
| B8 | 3-[[4-chloro-5-methyl-2-[3-(piperidine-1-carbonyl)phenyl]phenoxy]methyl]-4-methyl-1H-1,2,4-triazol-5-one 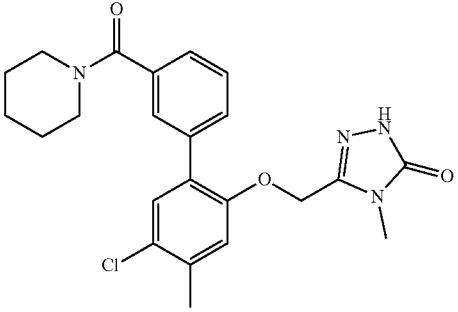 | [3-(5-chloro-2-hydroxy-4-methylphenyl)phenyl]-piperidin-1-ylmethanone Intermediate B8 | 441.17 [M + H]+ |
| B9 | 3-[5-chloro-4-methyl-2-[(4-methyl-5-oxo-1H-1,2,4-triazol-3-yl)methoxy]phenyl]-N-cyclohexylbenzamide 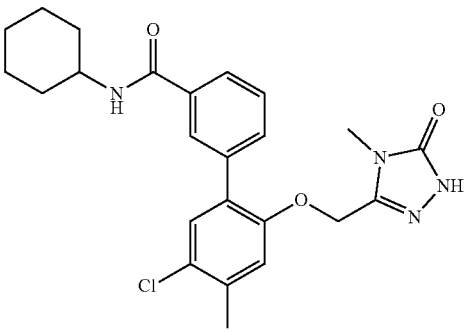 | 3-(5-chloro-2-hydroxy-4-methylphenyl)-N-cyclohexylbenzamide Intermediate B9 | 455.19 [M + H]+ |
| B10 | 3-[[4-chloro-5-methyl-2-[3-(morpholine-4-carbonyl)phenyl]phenoxy]methyl]-4-methyl-1H-1,2,4-triazol-5-one 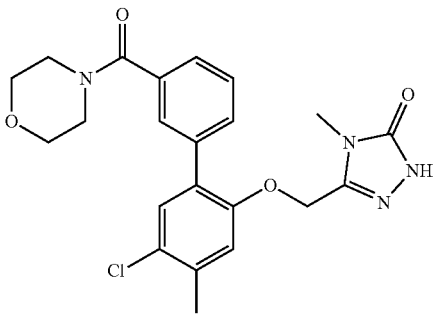 | [3-(5-chloro-2-hydroxy-4-methylphenyl)phenyl]-morpholin-4-ylmethanone Intermediate B10 | 443.15 [M + H]+ |

| Ex. | Systematic Name | Building block/intermediate | MS, m/z |
|---|---|---|---|
| B11 | 3-[5-chloro-4-methyl-2-[(4-methyl-5-oxo-1H-1,2,4-triazol-3-yl)methoxy]phenyl]benzamide | 3-(5-chloro-2-hydroxy-4-methylphenyl)benzamide Intermediate B11 | 373.11 [M − H]⁻ |
| B12 | 3-[5-chloro-4-methyl-2-[(4-methyl-5-oxo-1H-1,2,4-triazol-3-yl)methoxy]phenyl]-N,N-dimethylbenzamide | 3-(5-chloro-2-hydroxy-4-methylphenyl)-N,N-dimethylbenzamide Intermediate B12 | 401.14 [M + H]⁺ |
| B13 | 3-[5-chloro-4-methyl-2-[(4-methyl-5-oxo-1H-1,2,4-triazol-3-yl)methoxy]phenyl]-N-phenylbenzamide | 3-(5-chloro-2-hydroxy-4-methylphenyl)-N-phenylbenzamide Intermediate B13 | 449.14 [M + H]⁺ |
| B14 | 3-chloro-5-[5-chloro-4-methyl-2-[(4-methyl-5-oxo-1H-1,2,4-triazol-3-yl)methoxy]phenyl]benzamide | 3-chloro-5-(5-chloro-2-hydroxy-4-methylphenyl)benzamide Intermediate B14 | 407.07 [M + H]⁺ |

-continued

| Ex. | Systematic Name | Building block/intermediate | MS, m/z |
|---|---|---|---|
| B15 | 3-[5-chloro-4-methyl-2-[(4-methyl-5-oxo-1H-1,2,4-triazol-3-yl)methoxy]phenyl]-N-cyclopropyl-4-fluorobenzamide | 3-(5-chloro-2-hydroxy-4-methylphenyl)-N-cyclopropyl-4-fluorobenzamide Intermediate B15 | 431.13 [M + H]+ |
| B16 | 4-[(4-Methyl-5-oxo-1H-1,2,4-triazol-3-yl)methoxy]-3-phenylbenzonitrile | 6-hydroxy-biphenyl-3-carbonitrile Intermediate B16 | 307.2 [M + H]+ |
| B17 | 3-[5-chloro-4-methyl-2-[(4-methyl-5-oxo-1H-1,2,4-triazol-3-yl)methoxy]phenyl]-N-(2-methoxyethyl)benzamide | 3-(5-chloro-2-hydroxy-4-methylphenyl)-N-(2-methoxyethyl)benzamide Intermediate B17 | 431.15 [M + H]+ |
| B18 | 3-[[4-chloro-2-(2-chloropyridin-3-yl)-5-methylphenoxy]methyl]-4-methyl-1H-1,2,4-triazol-5-one | 4-chloro-2-(2-chloropyridin-3-yl)-5-methylphenol Intermediate B18 | 365.06 [M + H]+ |

| Ex. | Systematic Name | Building block/intermediate | MS, m/z |
|---|---|---|---|
| B19 | 3-[[4-chloro-2-(6-chloropyridin-2-yl)-5-methylphenoxy]methyl]-4-methyl-1H-1,2,4-triazol-5-one 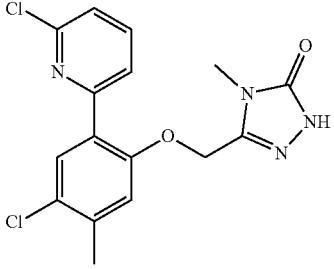 | 4-chloro-2-(6-chloropyridin-2-yl)-5-methylphenol Intermediate B19 | 365.10 [M + H]+ |
| B20 | 5-[5-chloro-4-methyl-2-[(4-methyl-5-oxo-1H-1,2,4-triazol-3-yl)methoxy]phenyl]pyridine-3-carboxamide 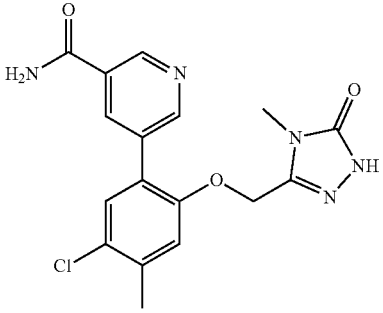 | 5-(5-chloro-2-hydroxy-4-methylphenyl)pyridine-3-carboxamide Intermediate B20 (Reaction carried out in DMF at 75° C. for 2.5 hours) | 374.01 [M + H]+ |
| B21 | 3-[[4-chloro-2-(6-methoxypyridin-2-yl)-5-methylphenoxy]methyl]-4-methyl-1H-1,2,4-triazol-5-one 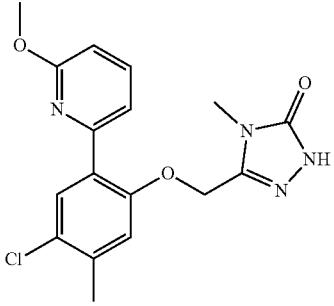 | 4-chloro-2-(6-methoxypyridin-2-yl)-5-methylphenol Intermediate B21 | 361.11 [M + H]+ |
| B25 | 3-[[4-chloro-5-methyl-2-(1,2-oxazol-5-yl)phenoxy]methyl]-4-methyl-1H-1,2,4-triazol-5-one 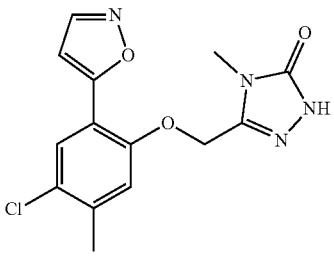 | 4-chloro-2-(5-isoxazolyl)-5-methylphenol CAS: 213690-32-5 | 321.08 [M + H]+ |

-continued

| Ex. | Systematic Name | Building block/intermediate | MS, m/z |
|---|---|---|---|
| B26 | 3-[[4-Chloro-5-methyl-2-(1,3-oxazol-5-yl)phenoxy]methyl]-4-methyl-1H-1,2,4-triazol-5-one 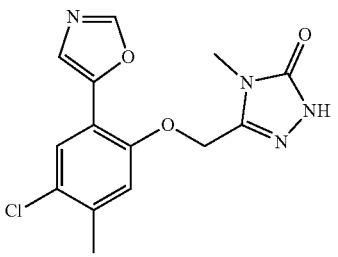 | 4-chloro-5-methyl-2-oxazol-5-yl-phenol Intermediate B26 | 321.0 [M + H]+ |
| B30 | 3-[[4-Chloro-5-methyl-2-(2-methylpyrazol-3-yl)phenoxy]methyl]-4-methyl-1H-1,2,4-triazol-5-one 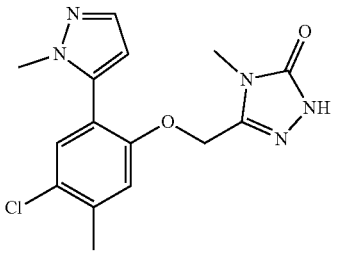 | 4-chloro-5-methyl-2-(2-methyl-2H-pyrazol-3-yl)-phenol Intermediate B30 | 333.8 [M + H]+ |
| B31 | 2-Chloro-4-[(4-methyl-5-oxo-1H-1,2,4-triazol-3-yl)methoxy]-5-phenylbenzonitrile 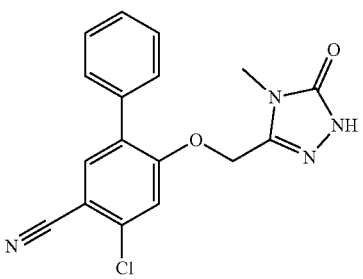 | 4-chloro-6-hydroxy-biphenyl-3-carbonitrile Intermediate B31 | 341.1 [M + H]+ |
| B32 | 2-Chloro-5-(4-fluorophenyl)-4-[(4-methyl-5-oxo-1H-1,2,4-triazol-3-yl)methoxy]benzonitrile 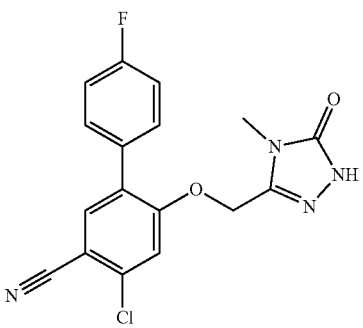 | 4-chloro-4'-fluoro-6-hydroxy-biphenyl-3-carbonitrile Intermediate B32 | 359.0 [M + H]+ |

-continued

| Ex. | Systematic Name | Building block/intermediate | MS, m/z |
| --- | --- | --- | --- |
| B33 | 3-[4-Chloro-5-cyano-2-[(4-methyl-5-oxo-1H-1,2,4-triazol-3-yl)methoxy]phenyl]-N-methylbenzamide | 4'-chloro-5'-cyano-2'-hydroxy-biphenyl-3-carboxylic acid methylamide Intermediate B33 | 398.3 [M + H]$^+$ |
| B35 | 2-Chloro-5-[3-(5-methyl-1,2,4-oxadiazol-3-yl)phenyl]-4-[(4-methyl-5-oxo-1H-1,2,4-triazol-3-yl)methoxy]benzonitrile | 4-chloro-6-hydroxy-3'-(5-methyl-[1,2,4]oxadiazol-3-yl)-biphenyl-3-carbonitrile Intermediate B35 | 423.1 [M + H]$^+$ |
| B36 | 3-[5-Chloro-4-methyl-2-[(4-methyl-5-oxo-1H-1,2,4-triazol-3-yl)methoxy]phenyl]-N-(2-hydroxyethyl)benzamide | 3-(5-chloro-2-hydroxy-4-methyl-phenyl)-N-(2-hydroxyethyl)benzamide Intermediate B36 | 417.2 [M + H]$^+$ |

-continued

| Ex. | Systematic Name | Building block/intermediate | MS, m/z |
|---|---|---|---|
| B37 | 2-Chloro-5-[3-(5-methyl-1,3,4-oxadiazol-2-yl)phenyl]-4-[(4-methyl-5-oxo-1H-1,2,4-triazol-3-yl)methoxy]benzonitrile | 4-chloro-6-hydroxy-3'-(5-methyl-[1,3,4]oxadiazol-2-yl)-biphenyl-3-carbonitrile Intermediate B37 | 423.1 [M + H]$^+$ |
| B38 | 3-[5-Chloro-4-methyl-2-[(4-methyl-5-oxo-1H-1,2,4-triazol-3-yl)methoxy]phenyl]-4-fluoro-N,N-dimethylbenzamide | 3-(5-chloro-2-hydroxy-4-methyl-phenyl)-4-fluoro-N,N-dimethyl-benzamide Intermediate B38 | 419.2 [M + H]$^+$ |
| B39 | 3-[4-Chloro-5-cyano-2-[(4-methyl-5-oxo-1H-1,2,4-triazol-3-yl)methoxy]phenyl]-N,N-dimethylbenzamide | 3-(4-chloro-5-cyano-2-hydroxy-phenyl)-N,N-dimethyl-benzamide Intermediate B39 | 412.1 [M + H]$^+$ |

-continued

| Ex. | Systematic Name | Building block/intermediate | MS, m/z |
|---|---|---|---|
| B40 | 3-[[4-Chloro-2-[2-fluoro-5-(morpholine-4-carbonyl)phenyl]-5-methylphenoxy]methyl]-4-methyl-1H-1,2,4-triazol-5-one | [3-(5-chloro-2-hydroxy-4-methyl-phenyl)-4-fluoro-phenyl]-morpholino-methanone Intermediate B40 | 461.2 [M + H]+ |
| B41 | 2-Chloro-4-[(4-methyl-5-oxo-1H-1,2,4-triazol-3-yl)methoxy]-5-[3-(morpholine-4-carbonyl)phenyl]benzonitrile | 2-chloro-4-hydroxy-5-[3-(morpholine-4-carbonyl)phenyl]benzonitrile Intermediate B41 | 454.2 [M + H]+ |
| B42 | Methyl 3-[5-chloro-4-methyl-2-[(4-methyl-5-oxo-1H-1,2,4-triazol-3-yl)methoxy]phenyl]benzoate | methyl 3-(5-chloro-2-hydroxy-4-methyl-phenyl)benzoate Intermediate B42 | 388.1 [M + H]+ |
| B44 | Methyl 3-[[3-[5-chloro-4-methyl-2-[(4-methyl-5-oxo-1H-1,2,4-triazol-3-yl)methoxy]phenyl]benzoyl]amino]propanoate | methyl 3-[[3-(5-chloro-2-hydroxy-4-methyl-phenyl)benzoyl]amino]propanoate Intermediate B44 | 459.2 [M + H]+ |

-continued

| Ex. | Systematic Name | Building block/intermediate | MS, m/z |
|---|---|---|---|
| B46 | Ethyl 2-[[3-[5-chloro-4-methyl-2-[(4-methyl-5-oxo-1H-1,2,4-triazol-3-yl)methoxy]phenyl]benzoyl]amino]acetate 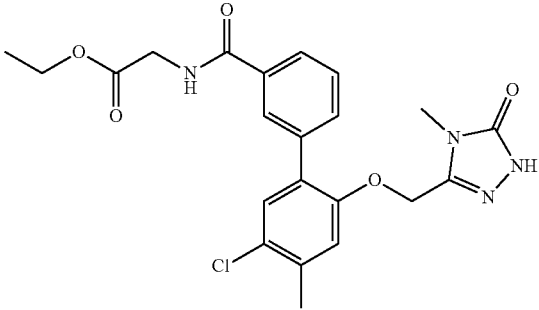 | ethyl 2-[[3-(5-chloro-2-hydroxy-4-methyl-phenyl)benzoyl]amino]acetate Intermediate B46 | 459.2 [M + H]⁺ |
| B49 | Methyl 3-[5-chloro-4-methyl-2-[(4-methyl-5-oxo-1H-1,2,4-triazol-3-yl)methoxy]phenyl]-4-methylbenzoate 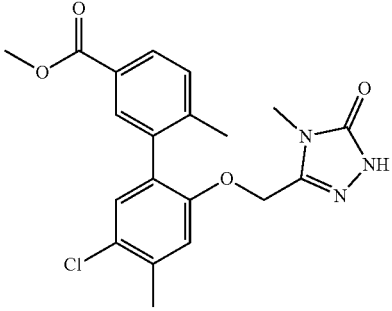 | methyl 3-(5-chloro-2-hydroxy-4-methyl-phenyl)-4-methyl-benzoate Intermediate B49 | 402.1 [M + H]⁺ |
| B52 | 3-[5-Chloro-4-methyl-2-[(4-methyl-5-oxo-1H-1,2,4-triazol-3-yl)methoxy]phenyl]-4-(trifluoromethoxy)benzamide 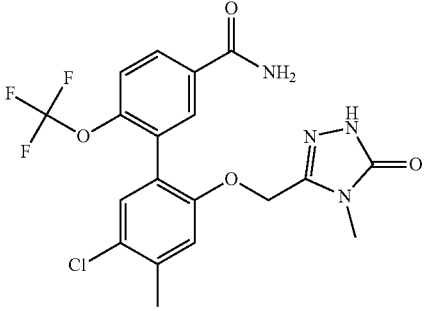 | 3-(5-chloro-2-hydroxy-4-methyl-phenyl)-4-(trifluoromethoxy)benzamide Intermediate B52 | 457.2 [M + H]⁺ |
| B53 | 3-[[4-Chloro-2-(2-methoxypyridin-3-yl)-5-methylphenoxy]methyl]-4-methyl-1H-1,2,4-triazol-5-one 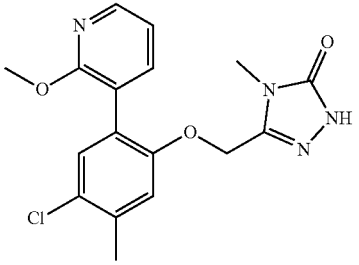 | 4-chloro-2-(2-methoxy-3-pyridyl)-5-methyl-phenol Intermediate B53 | 361.1 [M + H]⁺ |

-continued

| Ex. | Systematic Name | Building block/intermediate | MS, m/z |
|---|---|---|---|
| B54 | 2-Chloro-5-(2-methoxypyridin-3-yl)-4-[(4-methyl-5-oxo-1H-1,2,4-triazol-3-yl)methoxy]benzonitrile | 2-chloro-4-hydroxy-5-(2-methoxy-3-pyridyl)benzonitrile Intermediate B54 | 372.1 [M + H]⁺ |
| B55 | 3-[[4-Chloro-2-(5-ethoxy-2-fluorophenyl)-5-methylphenoxy]methyl]-4-methyl-1H-1,2,4-triazol-5-one | 4-chloro-2-(5-ethoxy-2-fluorophenyl)-5-methylphenol Intermediate B55 | 392.1 [M + H]⁺ |
| B56 | 3-[[4-chloro-2-(2-methoxyphenyl)-5-methylphenoxy]methyl]-4-methyl-1H-1,2,4-triazol-5-one | 4-chloro-2-(2-methoxyphenyl)-5-methylphenol Intermediate B56 | 306.1 [M + H]⁺ |
| B57 | 3-[[4-chloro-2-(2-fluoro-5-propan-2-yloxyphenyl)-5-methylphenoxy]methyl]-4-methyl-1H-1,2,4-triazol-5-one | 4-chloro-2-(2-fluoro-5-propan-2-yloxyphenyl)-5-methylphenol Intermediate B57 | 406.2 [M + H]⁺ |

The MS values in the table use [M + H]$^+$ notation.

-continued

| Ex. | Systematic Name | Building block/intermediate | MS, m/z |
|---|---|---|---|
| B58 | 3-[[4-Chloro-2-[2-fluoro-5-(2-methylpropoxy)phenyl]-5-methylphenoxy]methyl]-4-methyl-1H-1,2,4-triazol-5-one | 4-chloro-2-[2-fluoro-5-(2-methylpropoxy)phenyl]-5-methylphenol Intermediate B58 | 420.2 [M + H]+ |
| B59 | 3-[[4-chloro-2-[2-methoxy-5-(trifluoromethyl)phenyl]-5-methylphenoxy]methyl]-4-methyl-1H-1,2,4-triazol-5-one | 4-chloro-2-[2-methoxy-5-(trifluoromethyl)phenyl]-5-methylphenol Intermediate B59 | 428.2 [M + H]+ |
| B60 | 3-[[4-chloro-2-(2-methoxy-5-propan-2-ylphenyl)-5-methylphenoxy]methyl]-4-methyl-1H-1,2,4-triazol-5-one | 4-chloro-2-(2-methoxy-5-propan-2-ylphenyl)-5-methylphenol Intermediate B60 | 402.3 [M + H]+ |
| B61 | 2-Chloro-5-[2-fluoro-5-(morpholine-4-carbonyl)phenyl]-4-[(4-methyl-5-oxo-1H-1,2,4-triazol-3-yl)methoxy]benzonitrile | 2-chloro-5-[2-fluoro-5-(morpholine-4-carbonyl)phenyl]-4-hydroxybenzonitrile Intermediate B61 | 472.2 [M + H]+ |

| Ex. | Systematic Name | Building block/intermediate | MS, m/z |
| --- | --- | --- | --- |
| B62 | 3-[[4-Chloro-2-[2-fluoro-5-(pyrrolidine-1-carbonyl)phenyl]-5-methylphenoxy]methyl]-4-methyl-1H-1,2,4-triazol-5-one | [3-(5-chloro-2-hydroxy-4-methylphenyl)-4-fluorophenyl]-pyrrolidin-1-ylmethanone<br>Intermediate B62 | 445.2<br>[M + H]⁺ |
| B63 | 3-[5-Chloro-4-methyl-2-[(4-methyl-5-oxo-1H-1,2,4-triazol-3-yl)methoxy]phenyl]-N-cyclopropyl-4-fluoro-N-methylbenzamide | 3-(5-chloro-2-hydroxy-4-methylphenyl)-N-cyclopropyl-4-fluoro-N-methylbenzamide<br>Intermediate B63 | 445.3<br>[M + H]⁺ |
| B64 | 3-[5-Chloro-4-methyl-2-[(4-methyl-5-oxo-1H-1,2,4-triazol-3-yl)methoxy]phenyl]-4-fluoro-N-(2-hydroxyethyl)-N-methylbenzamide | 3-(5-chloro-2-hydroxy-4-methylphenyl)-4-fluoro-N-(2-hydroxyethyl)-N-methylbenzamide<br>Intermediate B64 | 449.2<br>[M + H]⁺ |

-continued

| Ex. | Systematic Name | Building block/intermediate | MS, m/z |
|---|---|---|---|
| B65 | 4-[3-[5-Chloro-4-methyl-2-[(4-methyl-5-oxo-1H-1,2,4-triazol-3-yl)methoxy]phenyl]-4-fluorobenzoyl]-1-methylpiperazin-2-one | 4-[3-(5-Chloro-2-hydroxy-4-methylphenyl)-4-fluorobenzoyl]-1-methylpiperazin-2-one Intermediate B65 | 488.3 [M + H]+ |
| B66 | 3-[5-Chloro-4-methyl-2-[(4-methyl-5-oxo-1H-1,2,4-triazol-3-yl)methoxy]phenyl]-N-cyclopentyl-4-fluoro-N-methylbenzamide | 3-(5-chloro-2-hydroxy-4-methylphenyl)-N-cyclopentyl-4-fluoro-N-methylbenzamide Intermediate B66 | 473.3 [M + H]+ |
| B67 | 3-[[4-Chloro-2-[2-fluoro-5-(oxolan-3-ylmethoxy)phenyl]-5-methylphenoxy]methyl]-4-methyl-1H-1,2,4-triazol-5-one | 4-Chloro-2-[2-fluoro-5-(oxolan-3-ylmethoxy)phenyl]-5-methylphenol Intermediate B67 | 448.3 [M + H]+ |
| B68 | 3-[5-Chloro-4-methyl-2-[(4-methyl-5-oxo-1H-1,2,4-triazol-3-yl)methoxy]phenyl]-4-fluoro-N-methyl-N-(thiophen-2-ylmethyl)benzamide | 3-(5-Chloro-2-hydroxy-4-methylphenyl)-4-fluoro-N-methyl-N-(thiophen-2-ylmethyl)benzamide Intermediate B68 | 501.3 [M + H]+ |

-continued

| Ex. | Systematic Name | Building block/intermediate | MS, m/z |
| --- | --- | --- | --- |
| B69 | 3-[[4-Chloro-2-[2-fluoro-5-(piperidine-1-carbonyl)phenyl]-5-methylphenoxy]methyl]-4-methyl-1H-1,2,4-triazol-5-one | [3-(5-chloro-2-hydroxy-4-methylphenyl)-4-fluorophenyl]-piperidin-1-ylmethanone Intermediate B69 | 459.3 [M + H]$^+$ |
| B70 | 3-[5-Chloro-4-methyl-2-[(4-methyl-5-oxo-1H-1,2,4-triazol-3-yl)methoxy]phenyl]-N-(cyclopropylmethyl)-4-fluoro-N-methylbenzamide | 3-(5-chloro-2-hydroxy-4-methylphenyl)-N-(cyclopropylmethyl)-4-fluoro-N-methylbenzamide Intermediate B70 | 459.3 [M + H]$^+$ |
| B71 | 3-[5-Chloro-4-methyl-2-[(4-methyl-5-oxo-1H-1,2,4-triazol-3-yl)methoxy]phenyl]-4-fluoro-N-methyl-N-(pyridin-2-ylmethyl)benzamide | 3-(5-chloro-2-hydroxy-4-methylphenyl)-4-fluoro-N-methyl-N-(pyridin-2-ylmethyl)benzamide Intermediate B71 | 496.2 [M + H]$^+$ |
| B72 | 3-[[4-Chloro-2-[2-fluoro-5-(oxan-4-ylmethoxy)phenyl]-5-methylphenoxy]methyl]-4-methyl-1H-1,2,4-triazol-5-one | 4-chloro-2-[2-fluoro-5-(oxan-4-ylmethoxy)phenyl]-5-methylphenol Intermediate B72 | 462.2 [M + H]$^+$ |

| Ex. | Systematic Name | Building block/intermediate | MS, m/z |
|---|---|---|---|
| B73 | 3-[5-Chloro-4-methyl-2-[(4-methyl-5-oxo-1H-1,2,4-triazol-3-yl)methoxy]phenyl]-4-fluoro-N-(2-methoxyethyl)-N-methylbenzamide | 3-(5-chloro-2-hydroxy-4-methylphenyl)-4-fluoro-N-(2-methoxyethyl)-N-methylbenzamide Intermediate B73 | 463.2 [M + H]$^+$ |
| B74 | 3-[[4-Chloro-2-[2-fluoro-5-(oxolan-2-ylmethoxy)phenyl]-5-methylphenoxy]methyl]-4-methyl-1H-1,2,4-triazol-5-one | 4-chloro-2-[2-fluoro-5-(oxolan-2-ylmethoxy)phenyl]-5-methylphenol Intermediate B74 | 448.2 [M + H]$^+$ |
| B75 | 2-[3-[5-Chloro-4-methyl-2-[(4-methyl-5-oxo-1H-1,2,4-triazol-3-yl)methoxy]phenyl]-4-fluorophenoxy]-N,N-dimethylacetamide | 2-[3-(5-chloro-2-hydroxy-4-methylphenyl)-4-fluorophenoxy]-N,N-dimethylacetamide Intermediate B75 | 449.2 [M + H]$^+$ |
| B76 | 1-[[3-[5-Chloro-4-methyl-2-[(4-methyl-5-oxo-1H-1,2,4-triazol-3-yl)methoxy]phenyl]-4-fluorophenoxy]methyl]-4-methylpiperazine-2,5-dione | 1-[[3-(5-chloro-2-hydroxy-4-methylphenyl)-4-fluorophenyl]methyl]-4-methylpiperazine-2,5-dione Intermediate B76 | 488.2 [M + H]$^+$ |

-continued

| Ex. | Systematic Name | Building block/intermediate | MS, m/z |
|---|---|---|---|
| B77 | 7-[5-Chloro-4-methyl-2-[(4-methyl-5-oxo-1H-1,2,4-triazol-3-yl)methoxy]phenyl]-6-fluoro-3-methyl-1,3-benzoxazol-2-one | 7-(5-chloro-2-hydroxy-4-methylphenyl)-6-fluoro-3-methyl-1,3-benzoxazol-2-one Intermediate B77 | 419.1 [M + H]$^+$ |
| B78 | N-[[3-[5-Chloro-4-methyl-2-[(4-methyl-5-oxo-1H-1,2,4-triazol-3-yl)methoxy]phenyl]-4-fluorophenyl]methyl]-2-methoxy-N-methylacetamide | N-[[3-(5-chloro-2-hydroxy-4-methylphenyl)-4-fluorophenyl]methyl]-2-methoxy-N-methylacetamide Intermediate B78 | 463.2 [M + H]$^+$ |
| B79 | N-[[3-[5-Chloro-4-methyl-2-[(4-methyl-5-oxo-1H-1,2,4-triazol-3-yl)methoxy]phenyl]-4-fluorophenyl]methyl]cyclopropane-carboxamide | N-[[3-(5-chloro-2-hydroxy-4-methylphenyl)-4-fluorophenyl]methyl]cyclopropane-carboxamide Intermediate B79 | 445.1 [M + H]$^+$ |
| B80 | N-[[3-[5-Chloro-4-methyl-2-[(4-methyl-5-oxo-1H-1,2,4-triazol-3-yl)methoxy]phenyl]-4-fluorophenyl]methyl]-N-methylcyclopropanecarboxamide | N-[[3-(5-chloro-2-hydroxy-4-methylphenyl)-4-fluorophenyl]methyl]-N-methylcyclopropane-carboxamide Intermediate B80 | 459.2 [M + H]$^+$ |

| Ex. | Systematic Name | Building block/intermediate | MS, m/z |
|---|---|---|---|
| B81 | 3-[[4-Chloro-2-[2-fluoro-5-[(2-oxopyrrolidin-1-yl)methyl]phenyl]-5-methylphenoxy]methyl]-4-methyl-1H-1,2,4-triazol-5-one | 1-[[3-(5-chloro-2-hydroxy-4-methylphenyl)-4-fluorophenyl]methyl]-pyrrolidin-2-one Intermediate B81 | 445.1 [M + H]⁺ |
| B82 | 3-[[3-[5-Chloro-4-methyl-2-[(4-methyl-5-oxo-1H-1,2,4-triazol-3-yl)methoxy]phenyl]-4-fluorophenyl]methyl]-1,3-oxazolidin-2-one | 3-[[3-(5-chloro-2-hydroxy-4-methylphenyl)-4-fluorophenyl]methyl]-1,3-oxazolidin-2-one Intermediated B82 | 447.1 [M + H]⁺ |
| B83 | N-[[3-[5-Chloro-4-methyl-2-[(4-methyl-5-oxo-1H-1,2,4-triazol-3-yl)methoxy]phenyl]-4-fluorophenyl]methyl]-2-methoxyacetamide | N-[[3-(5-chloro-2-hydroxy-4-methylphenyl)-4-fluorophenyl]methyl]-2-methoxyacetamide Intermediate B83 | 449.2 [M + H]⁺ |
| B84 | 2-chloro-5-(2-fluorophenyl)-4-[(4-methyl-5-oxo-1H-1,2,4-triazol-3-yl)methoxy]benzonitrile | 2-chloro-5-(2-fluorophenyl)-4-hydroxybenzonitrile Intermediate B84 | 359.1 [M + H]⁺ |

| Ex. | Systematic Name | Building block/intermediate | MS, m/z |
| --- | --- | --- | --- |
| B85 | 2-chloro-5-(3-fluorophenyl)-4-[(4-methyl-5-oxo-1H-1,2,4-triazol-3-yl)methoxy]benzonitrile | 2-chloro-5-(3-fluorophenyl)-4-hydroxybenzonitrile Intermediate B85 | 359.1 [M + H]⁺ |
| B86 | 3-[5-chloro-4-methyl-2-[(4-methyl-5-oxo-1H-1,2,4-triazol-3-yl)methoxy]phenyl]-4-(trifluoromethoxy)benzonitrile | 3-(5-chloro-2-hydroxy-4-methylphenyl)-4-(trifluoromethoxy)benzonitrile Intermediate B86 | 439.1 [M + H]⁺ |
| B87 | 2-chloro-5-[2-fluoro-5-(oxolan-2-ylmethoxy)phenyl]-4-[(4-methyl-5-oxo-1H-1,2,4-triazol-3-yl)methoxy]benzonitrile | 2-chloro-5-[2-fluoro-5-(oxolan-2-ylmethoxy)phenyl]-4-hydroxybenzonitrile Intermediate B87 | 459.2 [M + H]⁺ |
| B88 | 2-chloro-5-(2-fluoro-3-methoxyphenyl)-4-[(4-methyl-5-oxo-1H-1,2,4-triazol-3-yl)methoxy]benzonitrile | 2-chloro-5-(2-fluoro-3-methoxyphenyl)-4-hydroxybenzonitrile Intermediate B88 | 389.2 [M + H]⁺ |

| Ex. | Systematic Name | Building block/intermediate | MS, m/z |
|---|---|---|---|
| B89 | 2-chloro-5-(2-fluoro-5-propan-2-yloxyphenyl)-4-[(4-methyl-5-oxo-1H-1,2,4-triazol-3-yl)methoxy]benzonitrile | 2-chloro-5-(2-fluoro-5-propan-2-yloxyphenyl)-4-hydroxybenzonitrile Intermediate B89 | 417.3 [M + H]+ |
| B90 | 3-[[4-chloro-2-(2-fluoro-3-methoxyphenyl)-5-methylphenoxy]methyl]-4-methyl-1H-1,2,4-triazol-5-one | 4-chloro-2-(2-fluoro-3-methoxyphenyl)-5-methylphenol Intermediate B90 | 378.1 [M + H]+ |
| B91 | 2-chloro-5-(2,3-difluorophenyl)-4-[(4-methyl-5-oxo-1H-1,2,4-triazol-3-yl)methoxy]benzonitrile | 2-chloro-5-(2,3-difluorophenyl)-4-hydroxybenzonitrile Intermediate B91 | 377.1 [M + H]+ |
| B92 | 3-[[4-chloro-2-(5-cyclopropyloxy-2-fluorophenyl)-5-methylphenoxy]methyl]-4-methyl-1H-1,2,4-triazol-5-one | 4-chloro-2-(5-cyclopropyloxy-2-fluorophenyl)-5-methylphenol Intermediate B92 | 404.2 [M + H]+ |

| Ex. | Systematic Name | Building block/intermediate | MS, m/z |
|---|---|---|---|
| B93 | 2-chloro-5-(5-chloro-2-fluorophenyl)-4-[(4-methyl-5-oxo-1H-1,2,4-triazol-3-yl)methoxy]benzonitrile | 2-chloro-5-(5-chloro-2-fluorophenyl)-4-hydroxybenzonitrile Intermediate B93 | 393.1 [M + H]+ |
| B94 | 2-chloro-5-(2,5-difluorophenyl)-4-[(4-methyl-5-oxo-1H-1,2,4-triazol-3-yl)methoxy]benzonitrile | 2-chloro-5-(2,5-difluorophenyl)-4-hydroxybenzonitrile Intermediate B94 | 377.1 [M + H]+ |
| B95 | 2-chloro-5-(5-cyclopropyloxy-2-fluorophenyl)-4-[(4-methyl-5-oxo-1H-1,2,4-triazol-3-yl)methoxy]benzonitrile | 2-chloro-5-(5-cyclopropyloxy-2-fluorophenyl)-4-hydroxybenzonitrile Intermediate B95 | 415.2 [M + H]+ |

-continued

| Ex. | Systematic Name | Building block/intermediate | MS, m/z |
|---|---|---|---|
| B96 | 2-chloro-5-[2-fluoro-5-(trifluoromethyl)phenyl]-4-[(4-methyl-5-oxo-1H-1,2,4-triazol-3-yl)methoxy]benzonitrile 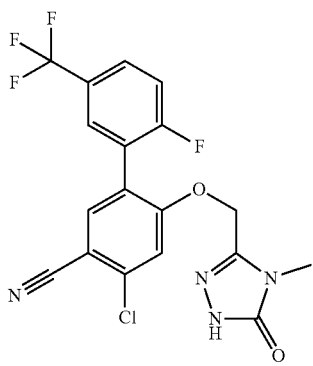 | 2-chloro-5-[2-fluoro-5-(trifluoromethyl)phenyl]-4-hydroxybenzonitrile Intermediate B96 | 427.2 [M + H]⁺ |

The following Examples of type B were synthesized from the suitable building blocks/intermediates and known 3-(chloromethyl)-4-methyl-1H-1,2,4-triazol-5(4H)-one in analogy to Example B1:

| Ex. | Systematic Name | Building block/intermediate | MS, m/z |
|---|---|---|---|
| B97 | 2-chloro-5-[2-fluoro-5-(trifluoromethoxy)phenyl]-4-[(4-methyl-5-oxo-1H-1,2,4-triazol-3-yl)methoxy]benzonitrile | 2-chloro-5-[2-fluoro-5-(trifluoromethoxy)phenyl]-4-hydroxybenzonitrile Intermediate B97 | 443.2 [M + H]⁺ |
| B98 | 2-chloro-5-[2-fluoro-5-(2,2,2-trifluoroethoxy)phenyl]-4-[(4-methyl-5-oxo-1H-1,2,4-triazol-3-yl)methoxy]benzonitrile 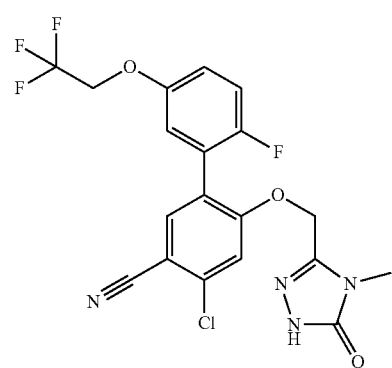 [SMILES: Cn1c(COc2cc(Cl)c(C#N)cc2-c2cc(OCC(F)(F)F)ccc2F)n[nH]c1=O] | 2-chloro-5-[2-fluoro-5-(2,2,2-trifluoroethoxy)phenyl]-4-hydroxybenzonitrile Intermediate B98 | 457.2 [M + H]⁺ |

Example B22

3-[(4-Chloro-5-methyl-2-pyrazin-2-ylphenoxy)methyl]-4-methyl-1H-1,2,4-triazol-5-one

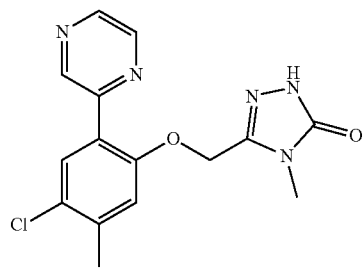 [SMILES: Cc1cc(OCc2n[nH]c(=O)n2C)c(-c2cnccn2)cc1Cl]

Step 1: 5-(4-Chloro-2-iodo-5-methyl-phenoxymethyl)-4-methyl-2,4-dihydro-[1,2,4]triazol-3-one

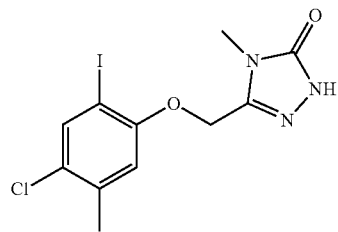 [SMILES: Cc1cc(OCc2n[nH]c(=O)n2C)c(I)cc1Cl]

The title compound was obtained in analogy to example B1 from 4-chloro-2-iodo-5-methyl-phenol (900 mg, Intermediate B1, step 3) and 3-(chloromethyl)-4-methyl-1H-1,2,4-triazol-5(4H)-one (35 mg, CAS: 1338226-21-3) as an off white solid (1.07 g, 84%). MS (ESI): m/z=380.1 [M+H]$^+$.

Step 2: 5-[(4-Chloro-2-iodo-5-methyl-phenoxy)methyl]-4-methyl-2-(2-trimethylsilylethoxymethyl)-1,2,4-triazol-3-one

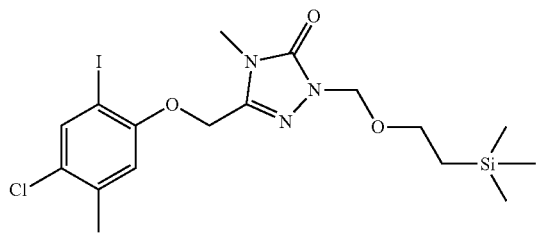 [SMILES: Cc1cc(OCc2nn(COCC[Si](C)(C)C)c(=O)n2C)c(I)cc1Cl]

To a slurry of NaH (192 mg, 60% in mineral oil, CAS: 7646-69-7) in anhydrous DMF (10 mL) was added a solution of 5-(4-chloro-2-iodo-5-methyl-phenoxymethyl)-4-methyl-2,4-dihydro-[1,2,4]triazol-3-one (1.21 g) in anhydrous DMF (20 mL) at rt and the resulting reaction mixture was stirred at rt for 30 min. Then, 2-(trimethylsilyl)ethoxymethyl chloride (0.85 mL, CAS: 76513-69-4) was added dropwise to the reaction mixture and the mixture was stirred at rt for 16 hours. The mixture was quenched with H$_2$O at 0° C. and the solvent was evaporated to dryness to get a residue which was dissolved in EtOAc (30 mL). The organic layer was washed with H$_2$O (30 mL) and brine (30 mL), dried over Na$_2$SO$_4$, filtered and evaporated under reduced pressure. The product was purified by flash chromatography (5-25% EtOAc/hexane) to give the title compound as brown liquid (0.735 g, 45%). MS (ESI): m/z=509.8 [M+H]$^+$.

Step 3: 5-[(4-Chloro-5-methyl-2-pyrazin-2-yl-phenoxy)methyl]-4-methyl-2-(2-trimethylsilylethoxymethyl)-1,2,4-triazol-3-one

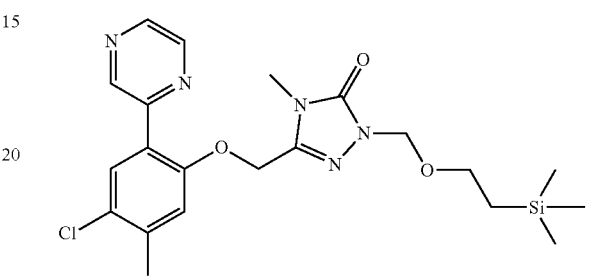

A mixture of 5-[(4-chloro-2-iodo-5-methyl-phenoxy)methyl]-4-methyl-2-(2-trimethylsilylethoxymethyl)-1,2,4-triazol-3-one (312 mg), 2-(tributylstannyl)pyrazine (339 mg, CAS: 205371-27-3) in anhydrous DMF (6 mL) was purged with argon for 30 min. Then Pd(PPh$_3$)$_4$ (14 mg, CAS: 14221-01-3) was added and the reaction mixture was heated at 120° C. for 16 hours under an argon atmosphere. The reaction mixture was filtered through celite bed. The filtrate was evaporated to get a residue which was dissolved in EtOAc (40 mL). The organic layer was washed with H$_2$O (40 mL) and brine (40 mL), dried over Na$_2$SO$_4$, filtered and evaporated under reduced pressure. The crude product was purified by flash chromatography over silica gel (15-35% EtOAc/hexane) to give the title compound as light yellow oil (0.187 g, 66%). MS (ESI): m/z=461.9 [M+H]$^+$.

Step 4: 3-[(4-Chloro-5-methyl-2-pyrazin-2-ylphenoxy)methyl]-4-methyl-1H-1,2,4-triazol-5-one

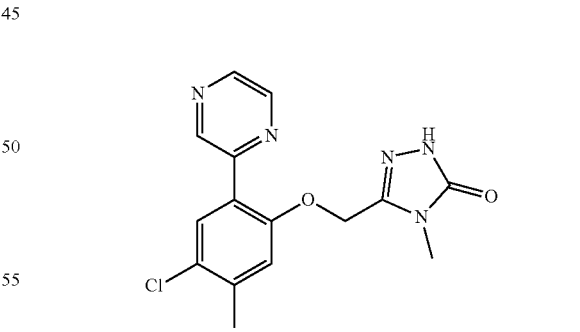

To a solution of 5-[(4-chloro-5-methyl-2-pyrazin-2-yl-phenoxy)methyl]-4-methyl-2-(2-trimethylsilylethoxymethyl)-1,2,4-triazol-3-one (210 mg) in DCM (5 mL) was added TFA (2 mL, CAS: 76-05-1) and the mixture was stirred at 25° C. for 3 hours. The solvent was evaporated to get a residue which was dissolved in EtOAc (30 mL) and washed with saturated aqueous NaHCO$_3$ solution (25 mL), H$_2$O (25 mL) and brine (25 mL). The organic layer was dried over Na$_2$SO$_4$, filtered and evaporated under reduced pressure. The resulting crude product was purified by prep HPLC (NH₄OAc/CH₃CN) to give the title compound as a white solid (0.052 g, 35%). LC-MS: (ESI): m/z=332.1 [M+H]⁺.

Example B23

3-[(4-Chloro-5-methyl-2-pyrimidin-2-yl-phenoxy)methyl]-4-methyl-1H-1,2,4-triazol-5-one

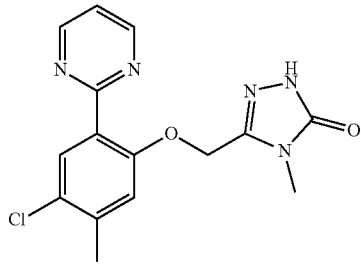 [SMILES: Cc1cc(OCc2n[nH]c(=O)n2C)c(-c2ncccn2)cc1Cl]

To a solution of 5-(4-chloro-2-iodo-5-methyl-phenoxymethyl)-4-methyl-2,4-dihydro-[1,2,4]triazol-3-one (150 mg, example B22, step 1) in dioxane (5 mL) were added 2-tributylstannanyl-pyrimidine (364 mg, CAS: 153435-63-3) and Pd(PPh₃)₄ (13 mg, CAS: 14221-01-3) and the reaction mixture was heated at 100° C. for 16 hours. The solvent was evaporated and the resulting crude product was purified by prep HPLC (NH₄OAc/CH₃CN) to give the title compound as a white solid (0.020 g, 15%). MS (ESI): m/z=332.3 [M+H]⁺.

Example B24

3-[[4-Chloro-5-methyl-2-[2-methyl-5-(trifluoromethyl)pyrazol-3-yl]phenoxy]methyl]-4-methyl-1H-1,2,4-triazol-5-one

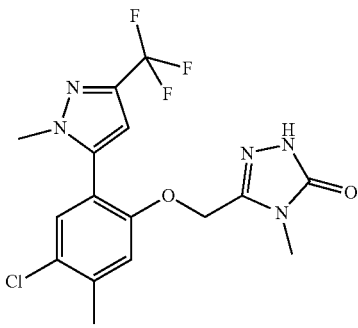 [SMILES: Cc1cc(OCc2n[nH]c(=O)n2C)c(-c2cc(C(F)(F)F)nn2C)cc1Cl]

Step 1: 3-(4-Chloro-2-iodo-5-methyl-phenoxymethyl)-5-methanesulfonyl-4-methyl-4H-[1,2,4]triazole

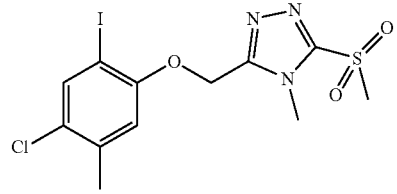 [SMILES: Cc1cc(OCc2nnc(S(C)(=O)=O)n2C)c(I)cc1Cl]

The title compound was obtained in analogy to example B1 from 4-chloro-2-iodo-5-methyl-phenol (0.1 g, Intermediate B1, step 3) and 3-(iodomethyl)-4-methyl-5-(methylsulfonyl)-4H-1,2,4-triazole (118 mg, prepared as described in US2008249151) as a colorless solid (0.145 g; 88%). MS (ESI): m/z=441.95 [M+H]⁺.

Step 2: 3-[[4-Chloro-5-methyl-2-[2-methyl-5-(trifluoromethyl)pyrazol-3-yl]phenoxy]methyl]-4-methyl-5-methylsulfonyl-1,2,4-triazole

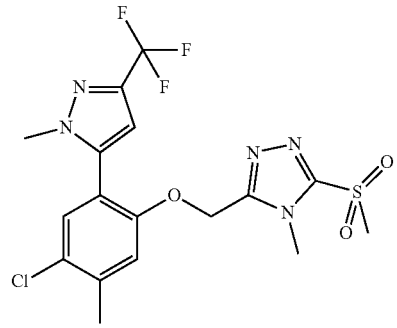 [SMILES: Cc1cc(OCc2nnc(S(C)(=O)=O)n2C)c(-c2cc(C(F)(F)F)nn2C)cc1Cl]

The title compound was obtained in analogy to Intermediate B1, step 4, from 3-(4-chloro-2-iodo-5-methyl-phenoxymethyl)-5-methanesulfonyl-4-methyl-4H-[1,2,4]triazole (0.066 g) and 1-methyl-5-(4,4,5,5-tetramethyl-1,3,2-dioxaborolan-2-yl)-3-(trifluoromethyl)-1H-pyrazole (0.049 g, CAS: 1025719-23-6) as a light brown gum (0.038 g; 55%). MS (ESI): m/z=464.08 [M+H]⁺.

Step 3: 3-[[4-Chloro-5-methyl-2-[2-methyl-5-(trifluoromethyl)pyrazol-3-yl]phenoxy]methyl]-5-methoxy-4-methyl-1,2,4-triazole

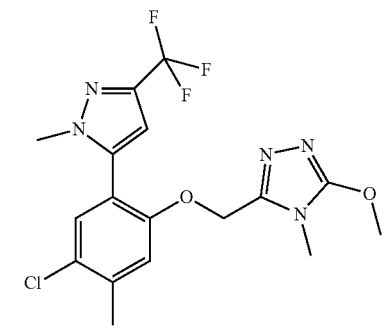

To a solution of 3-[[4-chloro-5-methyl-2-[2-methyl-5-(trifluoromethyl)pyrazol-3-yl]phenoxy]methyl]-4-methyl-5-methylsulfonyl-1,2,4-triazole (0.084 g) in MeOH (1 mL) was added 5.4M sodium methoxide solution in MeOH (134 µL, CAS: 124-41-4) and the solution was heated at reflux for 15 minutes. The reaction mixture was poured on sat. aq. NH₄Cl solution and
EtOAc and the layers were separated. The aqueous layer was extracted twice with EtOAc. The organic layers were dried over MgSO₄, filtered, treated with silica gel and evaporated. The compound was purified by silica gel chromatography on a 5 g column using an MPLC system eluting with a gradient of DCM:MeOH (100/0 to 90/10) to give the title compound as a colorless solid (0.054 g; 72%). MS (ESI): m/z=416.11 [M+H]⁺.

Step 4: 3-[[4-Chloro-5-methyl-2-[2-methyl-5-(trifluoromethyl)pyrazol-3-yl]phenoxy]methyl]-4-methyl-1H-1,2,4-triazol-5-one

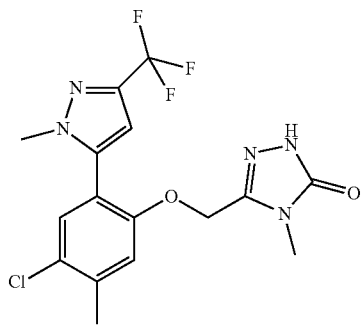 [SMILES: Cc1cc(OCc2n[nH]c(=O)n2C)c(-c2cc(C(F)(F)F)nn2C)cc1Cl]

To a solution of 3-[[4-chloro-5-methyl-2-[2-methyl-5-(trifluoromethyl)pyrazol-3-yl]phenoxy]methyl]-5-methoxy-4-methyl-1,2,4-triazole (0.05 g) in AcOH (826 µL) was added HBr 48% in H₂O (261 µL) and the clear, colorless solution was stirred at reflux for 15 minutes. Then, the reaction mixture was evaporated. The residue was taken up in aq. sat. NaHCO₃ solution and EtOAc and the layers were separated. The aqueous layer was extracted twice with EtOAc. The organic layers were washed with brine, dried over MgSO₄, filtered and evaporated.
The residue was purified by silica gel chromatography on a 5 g column using an MPLC (ISCO) system eluting with a gradient of n-heptane:EtOAc (100/0 to 0/100) to give the title compound as a colorless gum (0.036 g; 75%). MS (ESI): m/z=402.10 [M+H]⁺.

Example B27

3-[[4-Chloro-5-methyl-2-(3-methylimidazol-4-yl)phenoxy]methyl]-4-methyl-1H-1,2,4-triazol-5-one

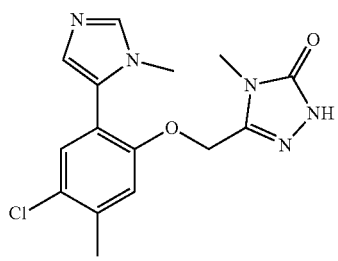 [SMILES: Cc1cc(OCc2n[nH]c(=O)n2C)c(-c2cncn2C)cc1Cl]

Step 1: 5-[4-Chloro-5-methyl-2-(3-methyl-3H-imidazol-4-yl)-phenoxymethyl]-4-methyl-2-(2-trimethylsilanyl-ethoxymethyl)-2,4-dihydro-[1,2,4]triazol-3-one

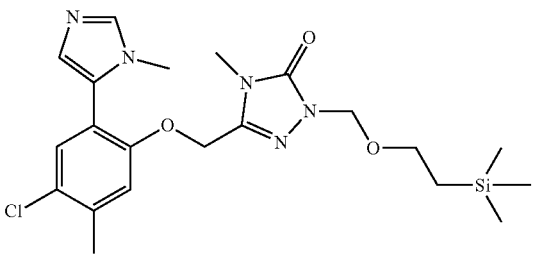 [SMILES: Cc1cc(OCc2nn(COCC[Si](C)(C)C)c(=O)n2C)c(-c2cncn2C)cc1Cl]

A mixture of 5-(4-chloro-2-iodo-5-methyl-phenoxymethyl)-4-methyl-2-(2-trimethylsilanyl-ethoxymethyl)-2,4-dihydro-[1,2,4]triazol-3-one (220 mg, example 22, step 2), 1-methyl-1H-imidazole-5-boronic acid pinacol ester (180 mg, CAS: 942070-72-6), potassium phosphate tribasic (183 mg, CAS: 7778-53-2), tricyclohexyl phosphine (2 mg, CAS: 2622-14-2) in dioxane (4 mL) and H₂O (20 mL) was purged with argon for 20 min. Then tris(dibenzylideneacetone) dipalladium(0) (4 mg, CAS: 52409-22-0) was added and the mixture was heated at 120° C. in microwave oven for 1 hour. The mixture was filtered through a celite bed. The filtrate was evaporated to get a residue which was dissolved in EtOAc (30 mL) and washed with H₂O (40 mL) and brine (40 mL). The organic layer was dried over Na₂SO₄, filtered and evaporated under reduced pressure. The resulting crude material was purified by flash chromatography over silica gel (1-5% MeOH/DCM) to give the title compound as a brown liquid (180 mg, 90%). MS (ESI): m/z=464.4 [M+H]⁺.

Step 2: 3-[[4-Chloro-5-methyl-2-(3-methylimidazol-4-yl)phenoxy]methyl]-4-methyl-1H-1,2,4-triazol-5-one

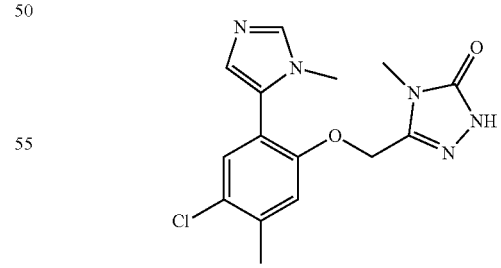

The title compound was obtained in analogy to Intermediate B22, step 4, from 5-[4-chloro-5-methyl-2-(3-methyl-3H-imidazol-4-yl)-phenoxymethyl]-4-methyl-2-(2-trimethylsilanyl-ethoxymethyl)-2,4-dihydro-[1,2,4]triazol-3-one (0.160 g) as an off white solid (28 mg, 24%). MS (ESI): m/z=334.0 [M+H]⁺.

Example B28

3-[[4-Chloro-2-(1H-imidazol-5-yl)-5-methylphenoxy]methyl]-4-methyl-1H-1,2,4-triazol-5-one

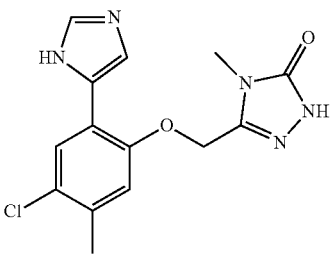 [SMILES: Cc1cc(OCc2n[nH]c(=O)n2C)c(-c2cnc[nH]2)cc1Cl]

Step 1: 5-Iodo-1-trityl-1H-imidazole

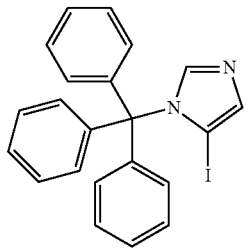 [SMILES: Ic1cncn1C(c1ccccc1)(c1ccccc1)c1ccccc1]

To a solution of 4-iodo-1H-imidazole (2.05 g, CAS: 71759-89-2) and trityl chloride (4.4 g, CAS: 76-83-5) in DMF (35 mL) was added triethylamine (3.04 mL, CAS: 121-44-8) at 0° C. The reaction mixture was slowly warmed to rt and was stirred for 48 hours. The reaction mixture was then poured into H$_2$O (150 mL). The solid was filtered, washed with H$_2$O (60 mL) and dried under reduced pressure. The resulting crude material was purified by flash chromatography using silica gel (EtOAc) to give the title compound as a white solid (4.3 g, 93%). Rf=0.50 (10% EtOAc/hexane).

Step 2: 5-Tributylstannanyl-1-trityl-1H-imidazole

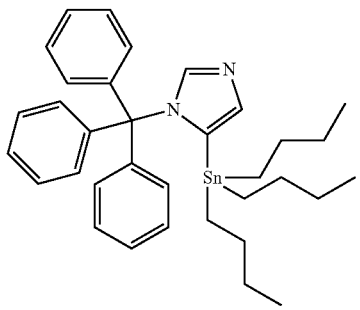 [SMILES: CCC[CH2][Sn]([CH2]CCC)([CH2]CCC)[c]1cncn1C(c1ccccc1)(c1ccccc1)c1ccccc1]

To a solution of 5-iodo-1-trityl-1H-imidazole (2.02 g) in DCM (50 mL) was added ethyl magnesium bromide (1.8 mL, 3M in diethyl ether, CAS: 925-90-6). The reaction was stirred under argon atmosphere at rt for 1 hour. Tributyltin chloride (1.5 mL, CAS: 1461-22-9) was added to the reaction mixture and the resulting mixture was stirred at rt overnight. The reaction mixture was diluted with DCM (100 mL) and successively washed with saturated aqueous NH$_4$Cl (100 mL), H$_2$O (100 mL) and brine (100 mL). The organic phase was dried over Na$_2$SO$_4$, filtered and evaporated to give the title compound as a white solid (2.7 g, 97%) which was used in the next step without further purification. Rf=0.60 (10% EtOAc/hexane).

Step 3: 5-[4-Chloro-5-methyl-2-(3-trityl-3H-imidazol-4-yl)-phenoxymethyl]-4-methyl-2,4-dihydro-[1,2,4]triazol-3-one

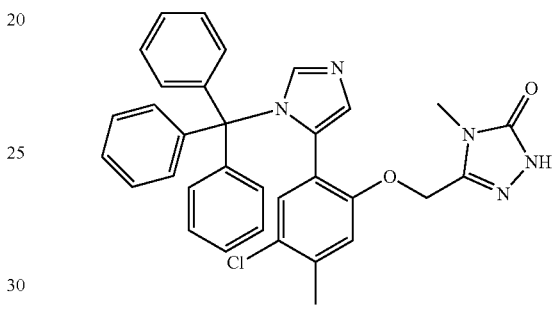

The title compound was obtained in analogy to example 23, from 5-(4-chloro-2-iodo-5-methyl-phenoxymethyl)-4-methyl-2,4-dihydro-[1,2,4]triazol-3-one (example 22, step 1) and 5-tributylstannanyl-1-trityl-1H-imidazole as a yellow solid. MS (EI): m/z=562.3 [M+H]$^+$.

Step 4: 3-[[4-Chloro-2-(1H-imidazol-5-yl)-5-methylphenoxy]methyl]-4-methyl-1H-1,2,4-triazol-5-one

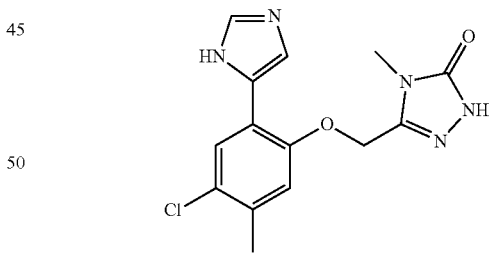

To a solution of 5-[4-chloro-5-methyl-2-(3-trityl-3H-imidazol-4-yl)-phenoxymethyl]-4-methyl-2,4-dihydro-[1,2,4]triazol-3-one (80 mg) in DCM (5 mL) was added HCl (0.5 mL, 4N in dioxane, CAS: 7647-01-0) at 25° C. and the resulting mixture was stirred for 4 hours. The reaction mixture was evaporated and the resulting material was purified by flash chromatography using silica gel (10% MeOH/DCM) to give the title compound as a white solid (12 mg, 26%). MS (ESI): m/z=320.2 [M+H]$^+$.

Example B29

3-[[4-Chloro-5-methyl-2-(1,3-oxazol-2-yl)phenoxy]methyl]-4-methyl-1H-1,2,4-triazol-5-one

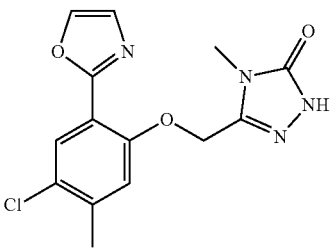 [SMILES: Cc1cc(OCc2n[nH]c(=O)n2C)c(-c2ncco2)cc1Cl]

The title compound was prepared in analogy to example B23 from 5-(4-chloro-2-iodo-5-methyl-phenoxymethyl)-4-methyl-2,4-dihydro-[1,2,4]triazol-3-one (150 mg, example B22, step 1) and 2-tributylstannanyloxazole (207 mg, CAS: 145214-05-7). The compound was obtained as white solid (9 mg, 7%). MS (ESI): m/z=320.9 [M+H]$^+$.

Example B34

2-Chloro-4-[(4-methyl-5-oxo-1H-1,2,4-triazol-3-yl)methoxy]-5-[3-(1H-pyrazol-3-yl)phenyl]benzonitrile

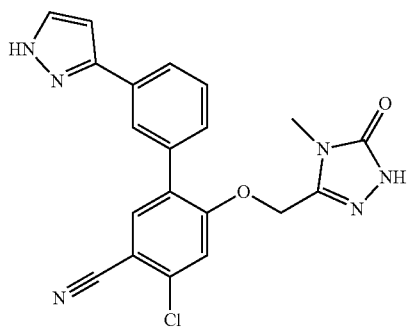 [SMILES: Cn1c(COc2cc(Cl)c(C#N)cc2-c2cccc(-c3cc[nH]n3)c2)n[nH]c1=O]

Step 1: 3'-Acetyl-4-chloro-6-hydroxy-biphenyl-3-carbonitrile and 3'-acetyl-4-chloro-6-methoxymethoxy-biphenyl-3-carbonitrile

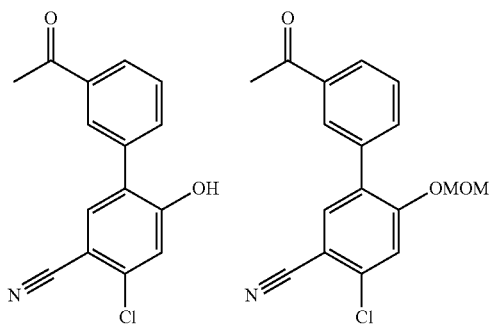

The title compound was prepared in analogy to Intermediate B31, step 3, from 5-bromo-2-chloro-4-methoxymethoxy-benzonitrile (Intermediate B31, step 2) (1.0 g) and 3-acetyl-phenyl boronic acid (886 mg, CAS: 204841-19-0). Note that in this case the MOM-protected phenol was used as a starting material.

These conditions provided the MOM protected phenol 3'-acetyl-4-chloro-6-methoxymethoxy-biphenyl-3-carbonitrile (270 mg, 24%, $^1$H-NMR (400 MHz, DMSO-D$_6$): 2.63 (s, 3H), 3.36 (s, 3H), 5.37 (s, 2H), 7.55 (s, 1H), 7.62 (t, 1H, J=7.6), 7.80 (d, 1H, J=7.6), 7.98 (d, 1H, J=7.6), 8.03 (s, 1H), 8.10 (s, 1H)), as well as the free phenol 3'-acetyl-4-chloro-6-hydroxy-biphenyl-3-carbonitrile (190 mg, 19%): $^1$H-NMR (400 MHz, DMSO-D$_6$): 2.63 (s, 3H), 7.19 (s, 1H), 7.53-7.63 (m, ~1H), 7.83 (d, 1H, J=8); 7.95 (d, 1H, J=7.8), 7.97 (s, 1H), 8.11 (s, 1H), 11.48 (s, 1H).

Note that depending on the reaction conditions, the MOM group may be partially lost in this reaction to give the free phenol 3'-acetyl-4-chloro-6-hydroxy-biphenyl-3-carbonitrile. This material can be subjected to step 2 below to re-introduce the MOM group. The MOM protected material from step 1 can be used directly in step 3.

Step 2: 3'-Acetyl-4-chloro-6-methoxymethoxy-biphenyl-3-carbonitrile

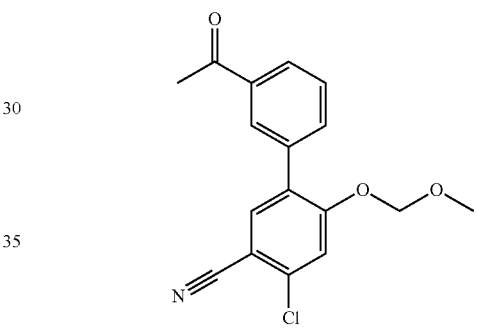

The title compound was prepared in analogy to Intermediate B31, step 2, from 3'-acetyl-4-chloro-6-hydroxy-biphenyl-3-carbonitrile (250 mg) by reaction with NaH (44 mg, 60% in mineral oil) and MOM-Cl (0.14 mL) and was obtained as an off white solid (183 mg, 63%). $^1$H-NMR (400 MHz, DMSO-D$_6$): 2.63 (s, 3H), 3.36 (s, 3H), 5.37 (s, 2H), 7.55 (s, 1H), 7.62 (t, 1H, J=7.6), 7.80 (d, 1H, J=7.6), 7.98 (d, 1H, J=7.6), 8.04 (s, 1H), 8.10 (s, 1H).

Step 3: 4-Chloro-3'-((E)-3-dimethylamino-acryloyl)-6-methoxymethoxy-biphenyl-3-carbonitrile

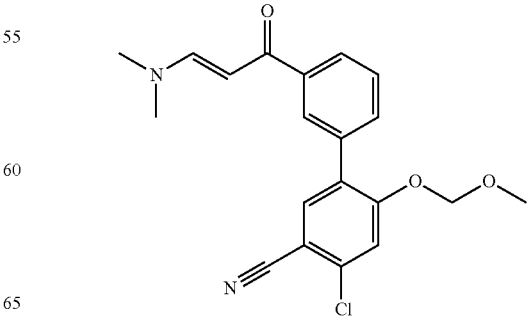

A solution of 3'-acetyl-4-chloro-6-methoxymethoxy-biphenyl-3-carbonitrile (180 mg) in DMF-DMA (2.5 mL) was heated to 80° C. for 16 h. The reaction mixture was cooled to 25° C. and all volatiles were evaporated under reduced pressure. The remaining residue was purified by column chromatography over silica gel (80-100% EtOAc/hexane) to afford the title compound (140 mg, 66%) as an off white solid. MS (ESI): m/z=370.9 [M+H]⁺.

Step 4: 3'-(1-tert-Butyl-1H-pyrazol-3-yl)-4-chloro-6-methoxymethoxy-biphenyl-3-carbonitrile

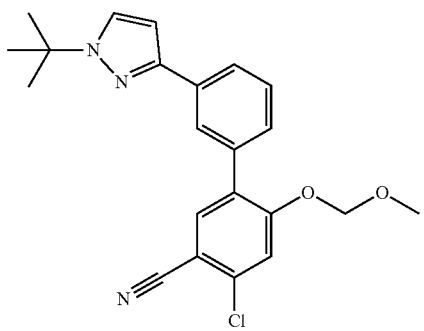 [SMILES: COCOc1cc(Cl)c(C#N)cc1-c1cccc(-c2ccn(C(C)(C)C)n2)c1]

To a solution of 4-chloro-3'-((E)-3-dimethylamino-acryloyl)-6-methoxymethoxy-biphenyl-3-carbonitrile (140 mg) in EtOH (20 mL) was added tert-butyl-hydrazine (70.37 mg, CAS: 7400-27-3) at 0° C. The reaction mixture was heated to reflux for 12 h. The mixture was then cooled to 25° C. and all volatiles were removed under reduced pressure. The residue was purified by column chromatography over silica gel (10-15% EtOAc/hexane) to obtain the title compound (110 mg, 73%) as an off white solid. MS (ESI): m/z=396.0 [M+H]⁺.

Step 5: 3'-(1-tert-Butyl-1H-pyrazol-3-yl)-4-chloro-6-hydroxy-biphenyl-3-carbonitrile

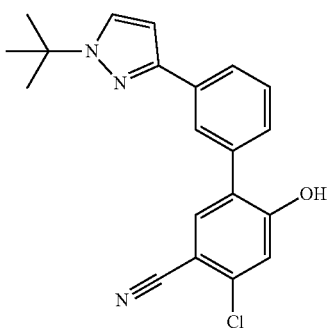 [SMILES: CC(C)(C)n1ccc(-c2cccc(-c3cc(C#N)c(Cl)cc3O)c2)n1]

To a solution of 3'-(1-tert-butyl-1H-pyrazol-3-yl)-4-chloro-6-methoxymethoxy-biphenyl-3-carbonitrile (110 mg) in anhydrous DCM (10 mL) was added HCl in dioxane (1 mL) at 0° C. and the reaction mixture was stirred at 25° C. for 32 h. The mixture was diluted with DCM (30 mL) and was washed with sat. NaHCO₃ solution and brine, dried over Na₂SO₄ and concentrated. The residue was purified by column chromatography over silica gel (1-2% MeOH/DCM) to afford the title compound (45 mg, 46%) as an off white solid. MS (ESI): m/z=352.2 [M+H]⁺.

Step 6: 3'-(1-tert-Butyl-1H-pyrazol-3-yl)-4-chloro-6-(4-methyl-5-oxo-4,5-dihydro-1H-[1,2,4]triazol-3-ylmethoxy)-biphenyl-3-carbonitrile

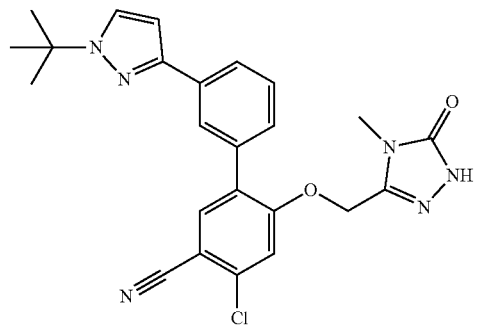 [SMILES: Cn1c(COc2cc(Cl)c(C#N)cc2-c2cccc(-c3ccn(C(C)(C)C)n3)c2)n[nH]c1=O]

The title compound was obtained in analogy to example B1 from 3'-(1-tert-butyl-1H-pyrazol-3-yl)-4-chloro-6-hydroxy-biphenyl-3-carbonitrile (80 mg) and 3-(chloromethyl)-4-methyl-1H-1,2,4-triazol-5(4H)-one (34 mg) as an off white solid (45 mg, 43%). MS (ESI): m/z=463.0 [M+H]⁺.

Step 7: 2-Chloro-4-[(4-methyl-5-oxo-1H-1,2,4-triazol-3-yl)methoxy]-5-[3-(1H-pyrazol-3-yl)phenyl]benzonitrile

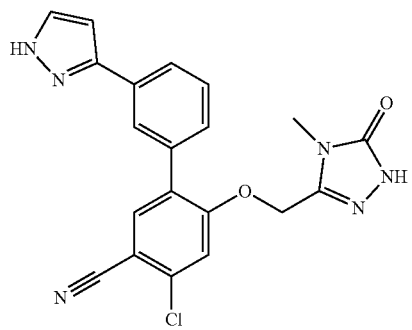 [SMILES: Cn1c(COc2cc(Cl)c(C#N)cc2-c2cccc(-c3cc[nH]n3)c2)n[nH]c1=O]

A solution of 3'-(1-tert-butyl-1H-pyrazol-3-yl)-4-chloro-6-(4-methyl-5-oxo-4,5-dihydro-1H-[1,2,4]triazol-3-yl-methoxy)-biphenyl-3-carbonitrile (45 mg) in formic acid (4 mL) was heated to 85° C. for 6 h. Then, all volatiles were removed and the residue was diluted with DCM (20 mL) and washed with water and brine, dried over Na₂SO₄ and concentrated. The resulting material was purified by column chromatography over silica gel (2-3% MeOH/DCM) to afford the title compound (15 mg, 37%) as an off white solid. MS (ESI): m/z=407.2 [M+H]⁺.

Example B43

3-[5-Chloro-4-methyl-2-[(4-methyl-5-oxo-1H-1,2,4-triazol-3-yl)methoxy]phenyl]benzoic acid

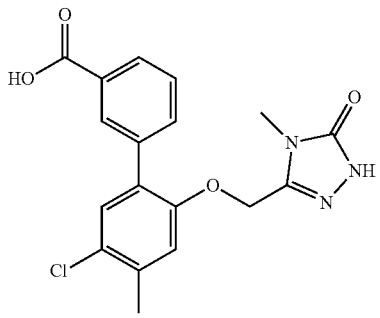 [SMILES: Cc1cc(OCc2n[nH]c(=O)n2C)c(-c2cccc(C(=O)O)c2)cc1Cl]

Methyl 3-[5-chloro-4-methyl-2-[(4-methyl-5-oxo-1H-1,2,4-triazol-3-yl)methoxy]phenyl]benzoate (36.0 mg, example B42) was suspended in THF (1.5 mL) at rt. MeOH was added dropwise until everything was dissolved. Then, a solution of lithiumhydroxide monohydrate (11.7 mg) in water (280 μL) was added dropwise. A small amount of white solid precipitated. Again, MeOH was added dropwise until everything was in solution. The colorless solution was then stirred at rt overnight. The volatiles were removed and the remaining residue was dissolved in water. The pH was adjusted to 2 by addition of 1N HCl. The precipitate was filtered off, washed with a small amount of water and dried to obtain the title compound as white solid (31 mg, 89%). MS (ESI): m/z=374.1 [M+H]$^+$.

The following examples were synthesized in analogy to Example B43:

| Ex. | Systematic Name | Starting Material | MS, m/z |
|---|---|---|---|
| B47 | 3-[[3-[5-Chloro-4-methyl-2-[(4-methyl-5-oxo-1H-1,2,4-triazol-3-yl)methoxy]phenyl]benzoyl]amino]-propanoic acid | Methyl 3-[[3-[5-chloro-4-methyl-2-[(4-methyl-5-oxo-1H-1,2,4-triazol-3-yl)methoxy]phenyl]benzoyl]-amino]propanoate Example B44 | 445.2 [M + H]$^+$ |
| B48 | 2-[[3-[5-Chloro-4-methyl-2-[(4-methyl-5-oxo-1H-1,2,4-triazol-3-yl)methoxy]phenyl]benzoyl]amino]acetic acid | Ethyl 2-[[3-[5-chloro-4-methyl-2-[(4-methyl-5-oxo-1H-1,2,4-triazol-3-yl)methoxy]phenyl]benzoyl]-amino]acetate Example B46 | 431.1 [M + H]$^+$ |

| Ex. | Systematic Name | Starting Material | MS, m/z |
|---|---|---|---|
| B50 | 3-[5-Chloro-4-methyl-2-[(4-methyl-5-oxo-1H-1,2,4-triazol-3-yl)methoxy]phenyl]-4-methylbenzoic acid | Methyl 3-[5-chloro-4-methyl-2-[(4-methyl-5-oxo-1H-1,2,4-triazol-3-yl)methoxy]phenyl]-4-methylbenzoate Example B49 | 388.2 [M + H]⁺ |

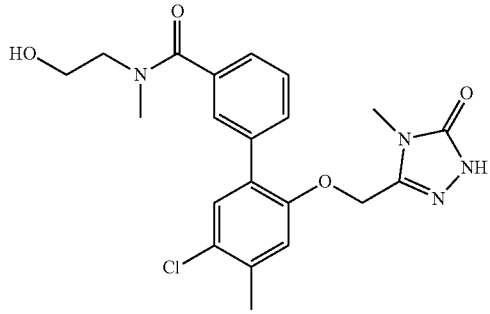 [SMILES: Cc1cc(OCc2n[nH]c(=O)n2C)c(-c2cccc(C(=O)N(C)CCO)c2)cc1Cl]

Example B45
3-[5-Chloro-4-methyl-2-[(4-methyl-5-oxo-1H-1,2,4-triazol-3-yl)methoxy]phenyl]-N-(2-hydroxyethyl)-N-methylbenzamide

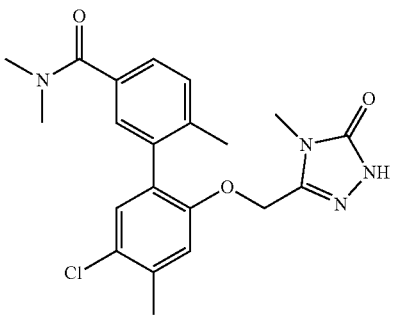 [SMILES: Cc1cc(OCc2n[nH]c(=O)n2C)c(-c2cc(C(=O)N(C)C)ccc2C)cc1Cl]

3-[5-Chloro-4-methyl-2-[(4-methyl-5-oxo-1H-1,2,4-triazol-3-yl)methoxy]phenyl]benzoic acid (23.0 mg, example B43) was dissolved in N,N-dimethylformamide (0.5 mL). Then, HATU (35.1 mg) and Hunig's base (19.9 mg, 26.9 µL) were added at rt, followed by a solution of 2-(methylamino)ethanol (6.47 mg) in N,N-dimethylformamide (0.5 mL). The light yellow solution was stirred at rt for 2 h. The reaction mixture was diluted with sat. NH₄Cl solution and was extracted with EtOAc. The combined organic extracts were washed with water and brine, dried over Na₂SO₄ and evaporated. The residue was purified by HPLC (Gemini NX column, acetonitrile/water (containing 0.05% formic acid) 85:15) to obtain the title compound as a white solid (10 mg, 38%). MS (ESI): m/z=431.2 [M+H]⁺.

Example B51
3-[5-Chloro-4-methyl-2-[(4-methyl-5-oxo-1H-1,2,4-triazol-3-yl)methoxy]phenyl]-N,N,4-trimethylbenzamide The title compound was obtained in analogy to example B47 from 3-[5-chloro-4-methyl-2-[(4-methyl-5-oxo-1H-1,2,4-triazol-3-yl)methoxy]phenyl]-4-methylbenzoic acid (23 mg, Example B50) and dimethylamine hydrochloride (6.77 mg) as a white solid (14 mg, 57%). MS (ESI): m/z=415.2 [M+H]⁺.

Examples C: Compounds with Pyridazinone Head Groups

Example C1

3-[(4-Chloro-5-methyl-2-propan-2-ylphenoxy)methyl]-1H-pyridazin-6-one

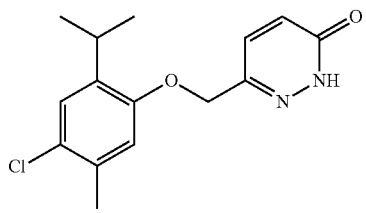 [SMILES: Cc1cc(OCc2ccc(=O)[nH]n2)c(C(C)C)cc1Cl]

To a solution of 3-chloro-6-[(4-chloro-2-isopropyl-5-methyl-phenoxy)methyl]pyridazine (60 mg, Intermediate C1-A) in EtOH (3 mL) was added aqueous 3M NaOH (0.642 mL) and the reaction mixture was heated at reflux for 16 hours. The reaction mixture was poured into H₂O and EtOAc and the layers were separated. The organic layer was dried over Na₂SO₄, filtered and concentrated in vacuo. The material was purified by flash chromatography over silica gel (0-3% MeOH/DCM) to give to give the title compound as an off-white solid (0.005 g, 9%). MS (ESI): m/z=293.11 [M]⁺.

Example C2

3-[(4-Chloro-2-cyclopropyl-5-methylphenoxy)methyl]-1H-pyridazin-6-one

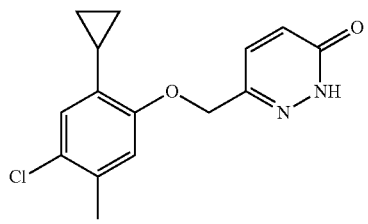 [SMILES: Cc1cc(OCc2ccc(=O)[nH]n2)c(C2CC2)cc1Cl]

A solution of 3-chloro-6-(4-chloro-2-cyclopropyl-5-methyl-phenoxymethyl)-pyridazine (45 mg, Intermediate C2-A) was refluxed in glacial acetic acid (5 mL) at 120° C. for 16 hours. Then, the solvent was removed under reduced pressure. The residue was dissolved in DCM and the organic part was washed with saturated solution of NaHCO₃ and brine, dried over anhydrous Na₂SO₄, filtered and concentrated under reduced pressure. The product was purified by prep. HPLC (NH₄OAc/CH₃CN) to give the title product as a white solid (30 mg, 71%). MS: (ESI): m/z=291.4 [M+H]⁺.

The following examples were synthesized from the suitable building blocks/intermediates in analogy to example C2:

| Ex. | Systematic Name | Building block/intermediate | MS, m/z |
|---|---|---|---|
| C3 | 3-[(4-chloro-5-fluoro-2-propan-2-ylphenoxy)methyl]-1H-pyridazin-6-one | 3-chloro-6-(4-chloro-5-fluoro-2-isopropyl-phenoxymethyl)-pyridazine Intermediate C3-A | 297.2 [M + H]⁺ |
| C4 | 3-[(5-chloro-4-methyl-2-propan-2-ylphenoxy)methyl]-1H-pyridazin-6-one | 3-chloro-6-(5-chloro-2-isopropyl-4-methyl-phenoxymethyl)-pyridazine Intermediate C4-A | 293.2 [M + H]⁺ |
| C5 | 3-[(4-chloro-2-cyclobutyl-5-methylphenoxy)methyl]-1H-pyridazin-6-one | 3-chloro-6-(4-chloro-2-cyclobutyl-5-methyl-phenoxymethyl)-pyridazine Intermediate C5-A | 305.2 [M + H]⁺ |

-continued

| Ex. | Systematic Name | Building block/ intermediate | MS, m/z |
|---|---|---|---|
| C6 | 3-[(4-chloro-2-cyclohexyl-5-methylphenoxy)methyl]-1H-pyridazin-6-one | 3-chloro-6-(4-chloro-2-cyclohexyl-5-methyl-phenoxymethyl)-pyridazine Intermediate C6-A | 333.3 [M + H]⁺ |
| C7 | 3-[[4-chloro-5-methyl-2-(oxan-4-yl)phenoxy]methyl]-1H-pyridazin-6-one | 3-chloro-6-[4-chloro-5-methyl-2-(tetrahydro-pyran-4-yl)-phenoxymethyl]-pyridazine Intermediate C7-A | 335.1 [M + H]⁺ |
| C8 | 3-[(2-tert-butyl-4-chloro-5-methylphenoxy)methyl]-1H-pyridazin-6-one | 3-(2-tert-butyl-4-chloro-5-methyl-phenoxymethyl)-6-chloro-pyridazine Intermediate C8-A | 307.3 [M + H]⁺ |
| C9 | 2-[5-chloro-4-methyl-2-[(6-oxo-1H-pyridazin-3-yl)methoxy]phenyl]-2-methylpropanenitrile | 2-[5-chloro-2-(6-chloro-pyridazin-3-ylmethoxy)-4-methyl-phenyl]-2-methyl-propionitrile Intermediate C9-A | 318.0 [M + H]⁺ |

Note: MS values reported as $[M + H]^+$.

The following examples of type C were synthesized from the suitable building blocks/intermediates in analogy to Example C2:

| Ex. | Systematic Name | Building block/intermediate | MS, m/z |
|---|---|---|---|
| C10 | 3-[[4-chloro-2-(2-methoxypyridin-3-yl)-5-methylphenoxy]methyl]-1H-pyridazin-6-one | 3-chloro-6-[[4-chloro-2-(2-methoxypyridin-3-yl)-5-methylphenoxy]methyl] pyridazine<br>Intermediate C10-A | 358.2 [M + H]$^+$ |
| C11 | 3-[[4-chloro-2-(2-hydroxypyridin-3-yl)-5-methylphenoxy]methyl]-1H-pyridazin-6-one<br><br>(material was obtained as the main product from the reaction providing example C10) | 3-chloro-6-[[4-chloro-2-(2-methoxypyridin-3-yl)-5-methylphenoxy]methyl]-pyridazine<br>Intermediate C10-A | 344.1 [M + H]$^+$ |
| C12 | 2-chloro-4-[(6-oxo-1H-pyridazin-3-yl)methoxy]-5-phenylbenzonitrile | 2-chloro-4-[(6-chloropyridazin-3-yl)methoxy]-5-phenylbenzonitrile<br>Intermediate C12-A | 338.1 [M + H]$^+$ |
| C13 | 4-tert-butyl-2-methyl-5-[(6-oxo-1H-pyridazin-3-yl)methoxy]benzonitrile | 4-tert-butyl-5-[(6-chloropyridazin-3-yl)methoxy]-2-methylbenzonitrile<br>Intermediate C13-A | 298.2 [M + H]$^+$ |

-continued

| Ex. | Systematic Name | Building block/intermediate | MS, m/z |
| --- | --- | --- | --- |
| C14 | 2-chloro-5-(5-cyclopropyloxy-2-fluorophenyl)-4-[(6-oxo-1H-pyridazin-3-yl)methoxy]benzonitrile | 2-chloro-4-[(6-chloro-pyridazin-3-yl)methoxy]-5-(5-cyclopropyloxy-2-fluorophenyl)benzonitrile Intermediate C14-A | 412.1 [M + H]+ |

Examples D: Compounds with Head Groups Related to Indazole, Aza-Indazole and Similar Example D2

3-[(4-Chloro-5-methyl-2-propan-2-ylphenoxy)methyl]-1H-indazole

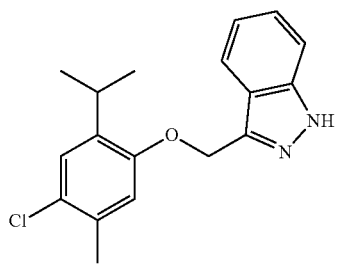 [SMILES: Cc1cc(OCc2n[nH]c3ccccc23)c(C(C)C)cc1Cl]

To a solution of 4-chloro-2-isopropyl-5-methylphenol (0.15 g, CAS: 89-68-9) in DMF (1.5 mL) was added sodium hydride (42.5 mg, 55-60% in mineral oil) and the mixture was stirred at rt for 15 minutes. A suspension of tert-butyl 3-(bromomethyl)-1H-indazole-1-carboxylate (253 mg CAS: 174180-42-8) in DMF (2.5 mL) was then added dropwise. After stirring at rt for 2.5 hours, the reaction mixture was poured on a mixture of saturated aqueous NH$_4$Cl solution and ethyl acetate and the layers were separated. The aqueous layer was extracted twice with ethyl acetate. The combined organic layers were washed twice with water and once with brine, dried over MgSO$_4$, filtered, and evaporated. The residue was purified by silica gel chromatography using an MPLC system (eluting with a gradient of n-heptane:ethyl acetate from 100/0 to 60/40). The resulting light brown oil (0.157 g) was dissolved in dichloromethane (1.5 mL). The solution was cooled to 0° C. and trifluoroacetic acid (1.85 g, 1.25 mL) was added. After stirring at rt for 1.25 hours, the reaction mixture was poured into a mixture of saturated aqueous NaHCO$_3$ solution and dichloromethane and the layers were separated. The aqueous layer was extracted twice with dichloromethane. The combined organic layers were washed once with brine, dried over MgSO$_4$, filtered and evaporated. The residue was purified by silica gel chromatography using an MPLC system (eluting with a gradient of n-heptane:ethyl acetate from 100/0 to 60/40) to afford the title compound as colorless oil (48 mg; 19%). MS (ESI): m/z=315.13 [M+H]+.

Example D3

3-[(2-tert-Butyl-4-chloro-5-methylphenoxy)methyl]-1H-pyrazolo[3,4-b]pyridine

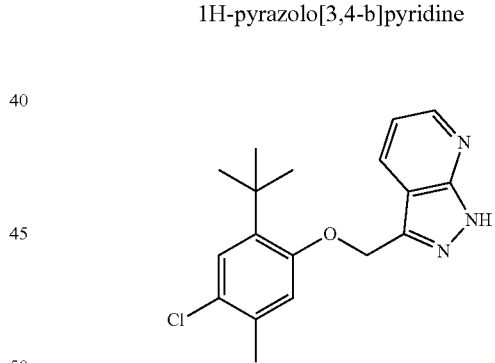

To a solution of Intermediate D3-A (85.1 mg) in dioxane (3 mL) was added 4N HCl in dioxane (495 µl) and the solution was stirred at rt. A white solid precipitated and the suspension was stirred at rt overnight. Then additional 4N HCl in dioxane (495µl) was added and after 4 h at rt again additional 4N HCl in dioxane (495 µl) was added and the mixture was stirred at rt for another 2 days. The white suspension was poured onto saturated NaHCO$_3$ solution and the resulting mixture was extracted with DCM. The combined organic layers were dried over Na$_2$SO$_4$ and evaporated. The residue was purified by chromatography (10 g silica gel; heptane/EtOAc 90/10-70/30) to afford the title compound (54 mg, 83%) as a white solid. MS (ESI): m/z=330.2 [M+H]+.

The following examples were synthesized in analogy to example D3.

| Ex. | Systematic Name | Intermediate | MS, m/z |
|---|---|---|---|
| D4 | 5-tert-Butyl-2-methyl-4-(1H-pyrazolo[3,4-b]pyridin-3-ylmethoxy)benzonitrile | Intermediate D4-A | 321.2 [M + H]+ |

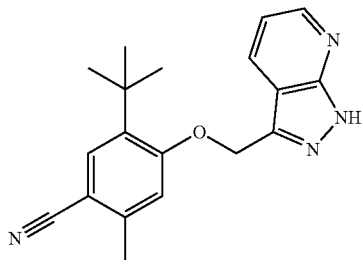

| Ex. | Systematic Name | Intermediate | MS, m/z |
|---|---|---|---|
| D5 | 5-[5-Chloro-4-methyl-2-(1H-pyrazolo[3,4-b]pyridin-3-ylmethoxy)phenyl]-1,2-oxazole | Intermediate D5-A | 341.2 [M + H]+ |

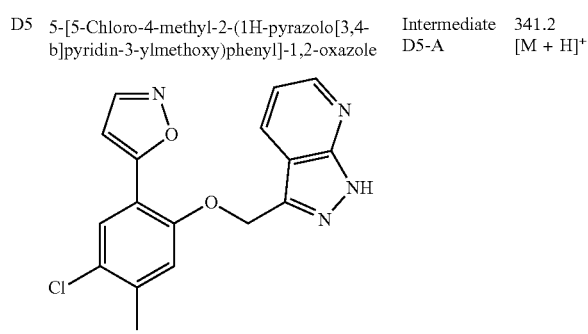

Example D6

3-[(2-tert-Butyl-4-chloro-5-methylphenoxy)methyl]-6-fluoro-1H-pyrazolo[3,4-b]pyridine

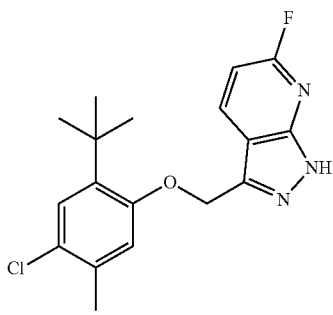 [SMILES: Cc1cc(OCc2n[nH]c3nc(F)ccc23)c(C(C)(C)C)cc1Cl]

A solution of Intermediate D6-A (55.1 mg) in a mixture of DCM (1 mL) and trifluoroacetic acid (0.4 mL) was stirred at rt for 1 h. Then, the solution was diluted with DCM and it was slowly added to saturated $Na_2CO_3$ solution. The mixture was extracted with DCM and the combined organic layers were washed with brine, dried over $Na_2SO_4$, filtered, and evaporated. The remaining residue was purified by chromatography (5 g silica gel; DCM/MeOH 98:2) to obtain the title compound (40 mg, 94%) as a white solid. MS (ESI): m/z=348.1 [M+H]+.

The following examples were synthesized in analogy to example D6.

| Ex. | Systematic Name | Intermediate | MS, m/z |
|---|---|---|---|
| D9 | 3-[(2-tert-butyl-5-methyl-4-methylsulfonyl-phenoxy)methyl]-1H-pyrazolo[3,4-b]pyridine | Intermediate D9-A | 374.2 [M + H]+ |

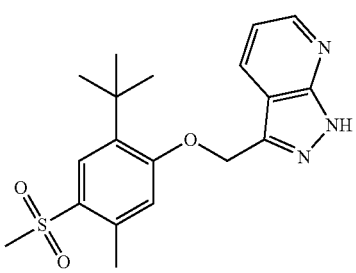

| Ex. | Systematic Name | Intermediate | MS, m/z |
|---|---|---|---|
| D10 | 3-[(2-tert-Butyl-5-methyl-4-methylsulfonyl-phenoxy)methyl]-1H-indazole | Intermediate D10-A | 373.2 [M + H]+ |

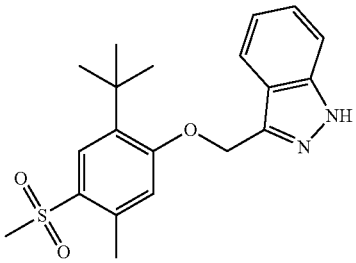

-continued

| Ex. | Systematic Name | Intermediate | MS, m/z |
|---|---|---|---|
| D12 | 3-[(2-tert-Butyl-4-chloro-5-fluorophenoxy)methyl]-6-fluoro-1H-pyrazolo[3,4-b]pyridine 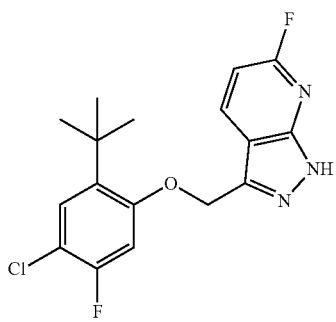 | Intermediate D12-A | 352.1 [M + H]⁺ |
| D16 | 3-[5-Chloro-4-methyl-2-(1H-pyrazolo[3,4-b]pyridin-3-ylmethoxy)phenyl]-N-(2-methoxyethyl)benzamide 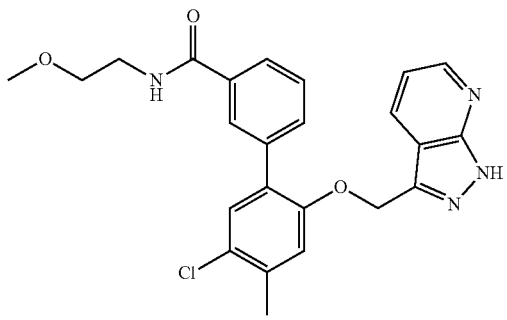 | Intermediate D16-A | 451.2 [M + H]⁺ |
| D18 | 3-[5-Chloro-4-methyl-2-(1H-pyrazolo[3,4-b]pyridin-3-ylmethoxy)phenyl]-N,N-dimethylbenzamide 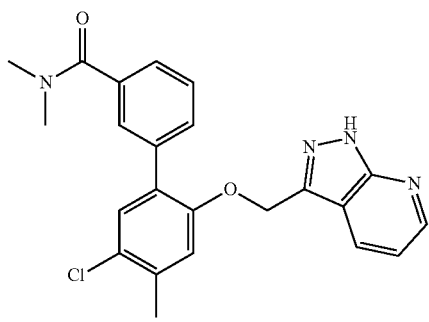 | Intermediate D18-A | 421.2 [M + H]⁺ |
| D39 | 4-[3-[5-Chloro-4-methyl-2-(1H-pyrazolo[3,4-b]pyridin-3-ylmethoxy)phenyl]-4-fluorobenzoyl]-1-methylpiperazin-2-one 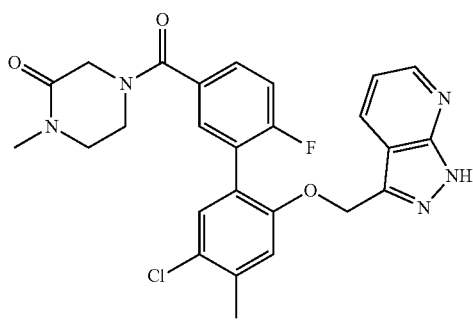 | Intermediate D39-A | 508.2 [M + H]⁺ |

-continued

| Ex. | Systematic Name | Intermediate | MS, m/z |
|---|---|---|---|
| D40 | 3-[5-Chloro-4-methyl-2-(1H-pyrazolo[3,4-b]pyridin-3-ylmethoxy)phenyl]-4-fluoro-N-(2-methoxyethyl)-N-methylbenzamide | Intermediate D40-A | 483.16 [M + H]+ |

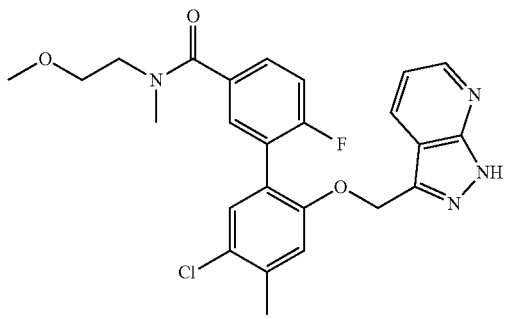

| | | | |
|---|---|---|---|
| D41 | 4-[3-[5-Chloro-2-(1H-indazol-3-ylmethoxy)-4-methylphenyl]-4-fluorobenzoyl]-1-methylpiperazin-2-one | Intermediate D41-A | 507.2 [M + H]+ |

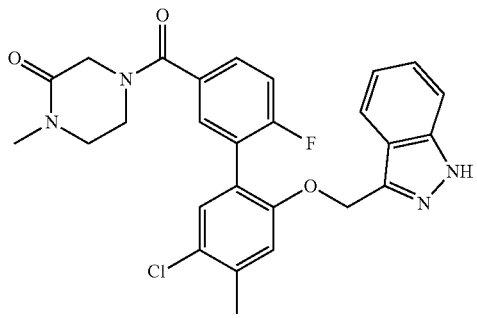

| | | | |
|---|---|---|---|
| D42 | [3-[5-Chloro-4-methyl-2-(1H-pyrazolo[3,4-b]pyridin-3-ylmethoxy)phenyl]-4-fluorophenyl]-pyrrolidin-1-ylmethanone | Intermediate D42-A | 465.14 [M + H]+ |

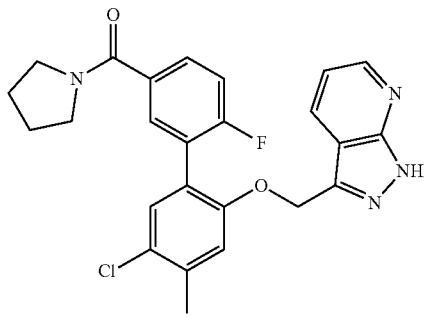

| | | | |
|---|---|---|---|
| D43 | 2-Chloro-5-[2-fluoro-5-(pyrrolidine-1-carbonyl)phenyl]-4-(1H-pyrazolo[3,4-b]pyridin-3-ylmethoxy)benzonitrile | Intermediate D43-A | 476.12 [M + H]+ |

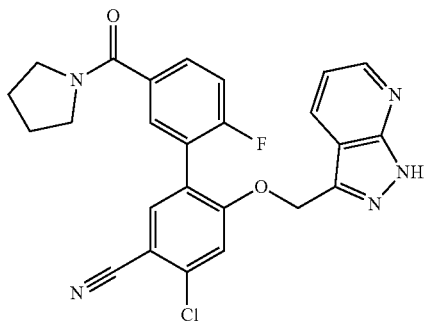

| Ex. | Systematic Name | Intermediate | MS, m/z |
|---|---|---|---|
| D45 | 3-[(2-tert-Butyl-4-methylsulfonylphenoxy)methyl]-1H-pyrazolo[3,4-b]pyridine 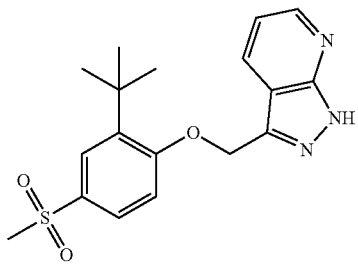 | Intermediate D45-A | 360.1 [M + H]+ |

Example D7

2-[[3-[(2-tert-Butyl-4-chloro-5-methylphenoxy)methyl]-1H-pyrazolo[3,4-b]pyridin-6-yl]amino]ethanol

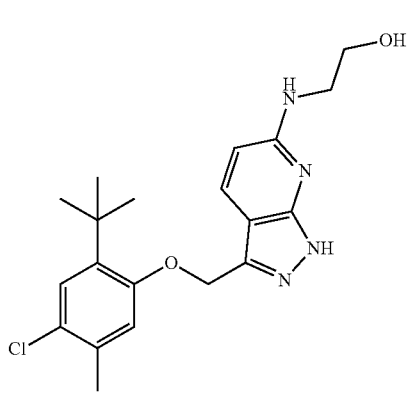 [SMILES: Cc1cc(OCc2n[nH]c3nc(NCCO)ccc23)c(C(C)(C)C)cc1Cl]

A solution of Intermediate D6-A (99.9 mg) and ethanolamine (136 mg, 135 µL) in N-methyl-2-pyrrolidinone (1.8 mL) was heated to 95° C. overnight. The solution was cooled to rt, diluted with half saturated brine and the mixture was extracted with EtOAc. The combined organic layers were washed with water and brine, dried over Na$_2$SO$_4$ and evaporated. The crude material was purified by chromatography (20 g silica gel; DCM/MeOH 100/0-95/5) to obtain a white solid which was further purified by prep. HPLC to afford the title compound (38 mg, 44%) as a white solid. MS (ESI): m/z=389.2 [M+H]+.

Example D8

2-[[3-[(2-tert-Butyl-4-chloro-5-methylphenoxy)methyl]-1H-pyrazolo[3,4-b]pyridin-6-yl]-methyl-amino]ethanol

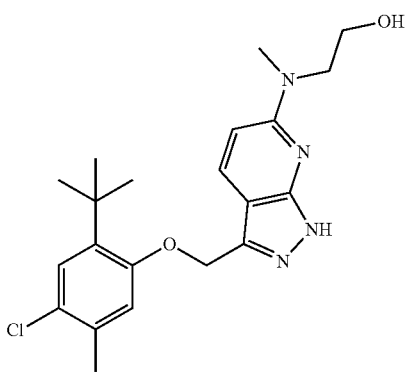 [SMILES: Cc1cc(OCc2n[nH]c3nc(N(C)CCO)ccc23)c(C(C)(C)C)cc1Cl]

A solution of Intermediate D6-A (99.9 mg) and 2-(methylamino)ethanol (167 mg, 178 µl) in N-methyl-2-pyrrolidinone (1.8 mL) was heated to 50° C. for 5 h. The solution was cooled to rt, diluted with half saturated brine and extracted with EtOAc. The combined organic layers were washed with water and brine, dried over Na$_2$SO$_4$ and evaporated. The residue was dissolved in DCM (2 mL) and trifluoroacetic acid (0.4 mL) was added. The solution was stirred at rt for 30 min and was then poured onto saturated Na$_2$CO$_3$ solution and the mixture was extracted with DCM. The combined organic layers were washed with brine, dried over Na$_2$SO$_4$ and evaporated. The residue was purified by column chromatography (5 g silica gel; DCM/MeOH 98/2-95/5) to afford the title compound (41 mg, 46%) as a white solid. MS (ESI): m/z=403.2 [M+H]+.

The following examples were synthesized in analogy to example D8.

| Ex. | Systematic Name | Intermediate/Amine | MS, m/z |
|---|---|---|---|
| D11 | 2-[[3-[(2-tert-Butyl-4-chloro-5-fluorophenoxy)methyl]-1H-pyrazolo[3,4-b]pyridin-6-yl]amino]ethanol | Intermediate D12-A and 2-aminoethanol | 393.2 [M + H]+ |
| D14 | 2-[[3-[(2-tert-Butyl-4-chloro-5-fluorophenoxy)methyl]-1H-pyrazolo[3,4-b]pyridin-6-yl]-methylamino]ethanol | Intermediate D12-A and 2-(methylamino)ethanol | 407.2 [M + H]+ |

Example D13

2-[[3-[(2-tert-Butyl-4-chloro-5-methylphenoxy)methyl]-1H-pyrazolo[3,4-b]pyridin-6-yl]oxy]ethanol

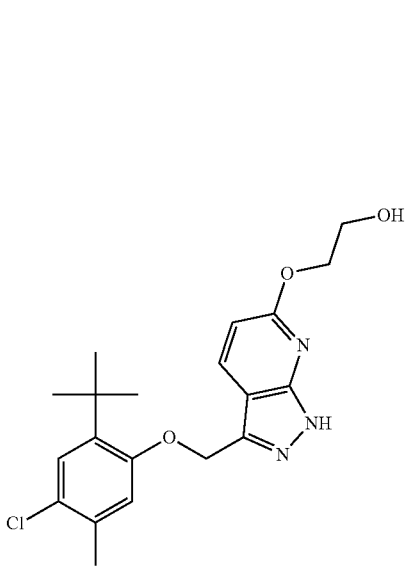

Step 1: 3-[(2-tert-Butyl-4-chloro-5-methyl-phenoxy)methyl]-6-fluoro-1-trityl-pyrazolo[3,4-b]pyridine

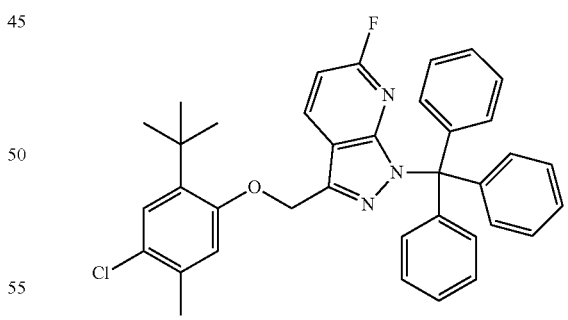

Sodium hydride (23.2 mg, 55% in mineral oil) was suspended in DMF (1 mL) and a solution of 3-[(2-tert-butyl-4-chloro-5-methylphenoxy)methyl]-6-fluoro-1H-pyrazolo[3,4-b]pyridine (148 mg, example D6) in DMF (1 mL) was added dropwise at 0° C. The resulting brown suspension was stirred at 0° C. for 10 min and then at rt for 20 min. A solution of trityl chloride (=[chloro(diphenyl)methyl]benzene) (125 mg) in DMF (1 mL) was then added at 0° C. and the reaction mixture was stirred at rt overnight. Water was added carefully and the mixture was extracted with EtOAc.

The combined organic layers were washed with water and brine, dried over $Na_2SO_4$ and evaporated. The residue was purified by chromatography (20 g silica gel; heptane/EtOAc 98/2-90/10) to obtain the title compound (186 mg, 74%) as a white solid. $^1$H-NMR (300 MHz, $CDCl_3$): 1.29 (s, 9H), 2.25 (s, 3H), 5.34 (s, 2H), 6.64 (dd, 1H), 6.92 (s, 1H), 7.19 (s, 1H), 7.20-7.35 (m, ~15H), 8.10 (dd, 1H).

Step 2: 3-[(2-tert-Butyl-4-chloro-5-methyl-phenoxy)methyl]-6-(2-tetrahydropyran-2-yloxyethoxy)-1-trityl-pyrazolo[3,4-b]pyridine

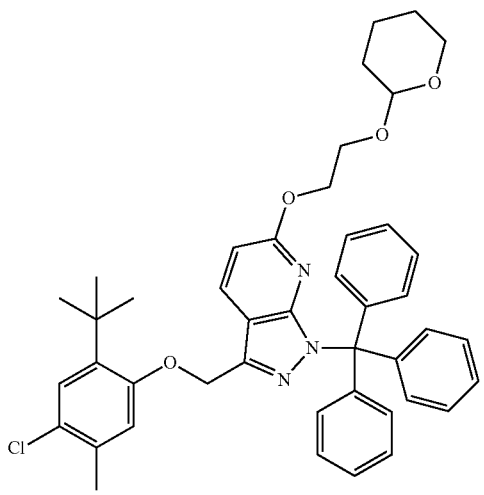 [SMILES: Cc1cc(OCc2nn(C(c3ccccc3)(c3ccccc3)c3ccccc3)c3nc(OCCOC4CCCCO4)ccc23)c(C(C)(C)C)cc1Cl]

Sodium hydride (7.68 mg, 55% in mineral oil) was suspended in DMA (1 mL). Then, a solution of 2-(tetrahydro-2H-pyran-2-yloxy)ethanol (25.7 mg, 23.9 CAS: 2162-31-4) in DMA (1.5 mL) was added dropwise at 0° C. and the resulting suspension was stirred at rt for 30 min. Then, a white turbid solution of 3-[(2-tert-butyl-4-chloro-5-methyl-phenoxy)methyl]-6-fluoro-1-trityl-pyrazolo[3,4-b]pyridine (83.2 mg) in DMA (1.5 ml) was added dropwise and the reaction mixture was stirred at rt for 3 h. The mixture was carefully diluted with water and was extracted with EtOAc. The combined organic layers were washed with water and brine, dried over $Na_2SO_4$ and evaporated. The residue was purified by flash chromatography (10 g silica gel; heptane/EtOAc 98/2-95/5) to obtain the title compound (91 mg, 90%) as a colorless oil. $^1$H-NMR (300 MHz, $CDCl_3$): 1.29 (s, ~9H); 1.45-1.88 (m, ~6H), 2.24 (s, 3H), 3.35-3.51 (m, 2H), 3.60-3.70 (m, 1H), 3.75-3.88 (m, 2H), 4.50 (m, 1H), 5.30 (s, 2H), 6.50 (d, 1H, J=8.4), 6.94 (s, 1H), 7.18 (s, 1H), 7.20-7.30 (m, ~15H), 7.86 (d, 1H, J=8.7).

Step 3: 2-[[3-[(2-tert-Butyl-4-chloro-5-methylphenoxy)methyl]-1H-pyrazolo[3,4-b]pyridin-6-yl]oxy]ethanol

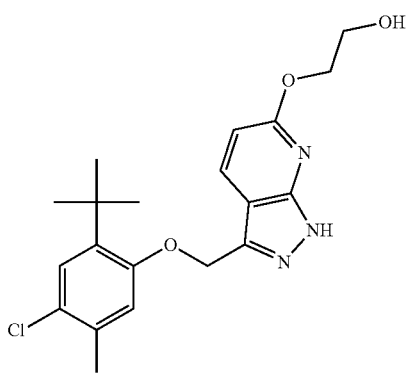 [SMILES: Cc1cc(OCc2n[nH]c3nc(OCCO)ccc23)c(C(C)(C)C)cc1Cl]

To a solution of 3-[(2-tert-butyl-4-chloro-5-methyl-phenoxy)methyl]-6-(2-tetrahydropyran-2-yloxyethoxy)-1-trityl-pyrazolo[3,4-b]pyridine (83.8 mg) in DCM (1.5 mL) was added trifluoroacetic acid (0.4 mL) dropwise and the mixture was stirred at rt for 30 min. The reaction mixture was diluted with DCM and was carefully added to saturated $Na_2CO_3$ solution. The resulting mixture was extracted with DCM and the combined extracts were washed with saturated $Na_2CO_3$ solution and brine, dried over $Na_2SO_4$, and evaporated. The residue was purified by chromatography (10 g silica gel; heptane/EtOAc 90/10-50/50) to obtain the title compound (36 mg, 79%) as white solid. MS (ESI): m/z=390.2 $[M+H]^+$.

Example D15

3-[[3-[(2-tert-Butyl-4-chloro-5-methylphenoxy)methyl]-1H-pyrazolo[3,4-b]pyridin-6-yl]oxy]propane-1,2-diol

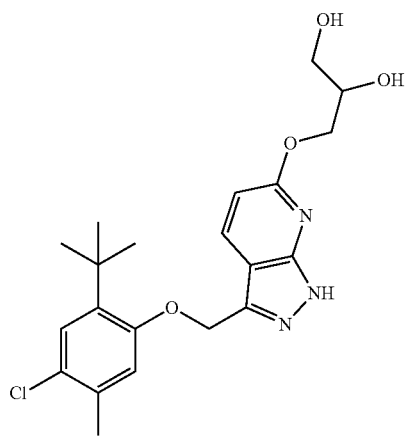 [SMILES: Cc1cc(OCc2n[nH]c3nc(OCC(O)CO)ccc23)c(C(C)(C)C)cc1Cl]

The title compound was prepared from 3-[(2-tert-butyl-4-chloro-5-methylphenoxy)methyl]-6-fluoro-1H-pyrazolo[3,4-b]pyridine (example D6) in analogy to example D13 using (2,2-dimethyl-1,3-dioxolan-4-yl)methanol instead of 2-(tetrahydro-2H-pyran-2-yloxy)ethanol in step 2 and was obtained as a white solid. MS (ESI): m/z=420.2 $[M+H]^+$.

Example D17

[3-[5-Chloro-4-methyl-2-(1H-pyrazolo[3,4-b]pyridin-3-ylmethoxy)phenyl]phenyl]-morpholin-4-yl-methanone

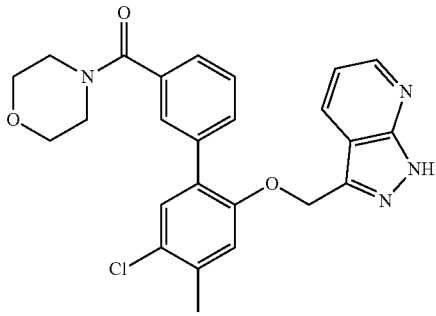 [SMILES: Cc1cc(OCc2n[nH]c3ncccc23)c(-c2cccc(C(=O)N3CCOCC3)c2)cc1Cl]

A suspension of Intermediate B10 (40.1 mg), tert-butyl 3-(bromomethyl)pyrazolo[3,4-b]pyridine-1-carboxylate (37.8 mg, CAS: 174180-76-8) and potassium carbonate (41.7 mg) in acetone (1.5 mL) was heated to 50° C. for 5.5 h. The reaction mixture was cooled to rt, diluted with water and extracted with EtOAc. The combined organic layers were washed with brine, dried over $Na_2SO_4$ and evaporated. The residue was dissolved in DCM (2 mL) and trifluoroacetic acid (0.2 mL) was added and the solution was stirred at rt for 2 h. The reaction mixture was quenched carefully by addition of saturated $Na_2CO_3$ solution and was extracted with DCM. The combined organic layers were washed with brine, dried over $Na_2SO_4$ and evaporated.

The residue was purified by chromatography (10 g silica gel; heptane/EtOAc 70/30-0/100) to obtain the title compound (40 mg, 71%) as white solid. MS (ESI): m/z=463.2 $[M+H]^+$.

The following examples were synthesized in analogy to Example D17.

| Ex. | Systematic Name | Building blocks | MS, m/z |
|---|---|---|---|
| D1 | 3-[(2-tert-Butyl-4-methylsulfonylphenoxy)methyl]-1H-indazole | tert-butyl 3-(bromomethyl)-1H-indazole-1-carboxylate (CAS 174180-42-8) and Intermediate A15 | 359.14 $[M + H]^+$ |
| D19 | 3-[5-Chloro-4-methyl-2-(1H-pyrazolo[3,4-b]pyridin-3-ylmethoxy)phenyl]-N-(2-hydroxyethyl)benzamide | tert-butyl 3-(bromomethyl)pyrazolo[3,4-b]pyridine-1-carboxylate (CAS: 174180-76-8) and Intermediate B36 | 437.2 $[M + H]^+$ |
| D20 | 3-[[4-Chloro-2-(2-methoxypyridin-3-yl)-5-methylphenoxy]methyl]-1H-pyrazolo[3,4-b]pyridine | tert-butyl 3-(bromomethyl)pyrazolo[3,4-b]pyridine-1-carboxylate (CAS: 174180-76-8) and Intermediate B53 | 381.1 $[M + H]^+$ |

-continued

| Ex. | Systematic Name | Building blocks | MS, m/z |
|---|---|---|---|
| D21 | 3-[5-Chloro-4-methyl-2-(1H-pyrazolo[3,4-b]pyridin-3-ylmethoxy)phenyl]-4-fluoro-N,N-dimethylbenzamide | tert-butyl 3-(bromomethyl)pyrazolo[3,4-b]pyridine-1-carboxylate (CAS: 174180-76-8) and Intermediate B38 | 439.2 [M + H]$^+$ |
| D22 | [3-[5-Chloro-4-methyl-2-(1H-pyrazolo[3,4-b]pyridin-3-ylmethoxy)phenyl]-4-fluorophenyl]-morpholin-4-ylmethanone | tert-butyl 3-(bromomethyl)pyrazolo[3,4-b]pyridine-1-carboxylate (CAS: 174180-76-8) and Intermediate B40 | 481.2 [M + H]$^+$ |
| D23 | 3-[(2-tert-Butyl-4-chloro-5-methylphenoxy)methyl]-1H-pyrazolo[4,3-b]pyridine | tert-butyl 3-(bromomethyl)pyrazolo[4,3-b]pyridine-1-carboxylate (CAS: 194278-49-4, prepared according to *J. Med. Chem.* 1997, 40, 2709) and 2-tert-butyl-4-chloro-5-methyl-phenol (CAS: 30894-16-7) | 330.2 [M + H]$^+$ |
| D24 | 3-[5-Chloro-4-methyl-2-(1H-pyrazolo[4,3-b]pyridin-3-ylmethoxy)phenyl]-N,N-dimethylbenzamide | tert-butyl 3-(bromomethyl)pyrazolo[4,3-b]pyridine-1-carboxylate (CAS: 194278-49-4) and Intermediate B12 | 421.2 [M + H]$^+$ |

-continued

| Ex. | Systematic Name | Building blocks | MS, m/z |
|---|---|---|---|
| D25 | 3-[(2-tert-Butyl-4-chloro-5-fluorophenoxy)methyl]-1H-pyrazolo[4,3-b]pyridine | tert-butyl 3-(bromomethyl)pyrazolo[4,3-b]pyridine-1-carboxylate (CAS: 194278-49-4) and Intermediate A2 | 334.2 [M + H]$^+$ |
| D28 | 3-[5-Chloro-4-methyl-2-(1H-pyrazolo[4,3-b]pyridin-3-ylmethoxy)phenyl]-4-fluoro-N,N-dimethylbenzamide | tert-butyl 3-(bromomethyl)pyrazolo[4,3-b]pyridine-1-carboxylate (CAS: 194278-49-4) and Intermediate B38 | 439.2 [M + H]$^+$ |
| D48 | 4-tert-butyl-2-methyl-5-(1H-pyrazolo[3,4-b]pyridin-3-ylmethoxy)benzonitrile | tert-butyl 3-(bromomethyl)pyrazolo[3,4-b]pyridine-1-carboxylate (CAS: 174180-76-8) and Intermediate A17 | 321.2 [M + H]$^+$ |

Example D26

2-[[3-[(2-tert-Butyl-4-chloro-5-methylphenoxy)methyl]-1H-pyrazolo[3,4-d]pyrimidin-6-yl]-methylamino]ethanol

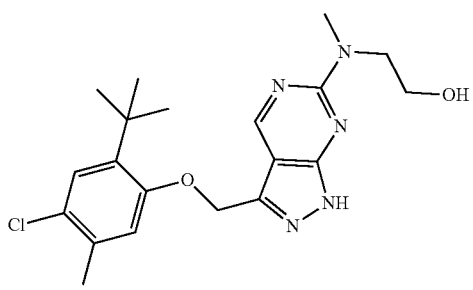 [SMILES: Cc1cc(OCc2n[nH]c3nc(N(C)CCO)ncc23)c(C(C)(C)C)cc1Cl]

Step 1: 3-(2-tert-Butyl-4-chloro-5-methyl-phenoxymethyl)-1-(4-methoxy-benzyl)-6-methylsulfanyl-1H-pyrazolo[3,4-]pyrimidine

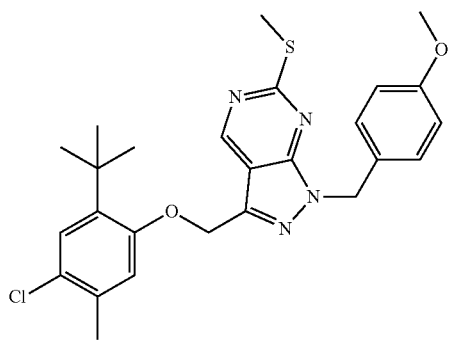 [SMILES: COc1ccc(Cn2nc(COc3cc(C)c(Cl)cc3C(C)(C)C)c3cnc(SC)nc32)cc1]

To a solution of 2-tert-butyl-4-chloro-5-methyl-phenol (851 mg, CAS: 30894-16-7) in anhydrous DMF (50 mL) were added Cs$_2$CO$_3$ (1.61 g) and TBAI (122 mg) at 25° C. and the reaction mixture was stirred at 25° C. for 15 min. Then, a solution of 3-bromomethyl-1-(4-methoxy-benzyl)-6-methylsulfanyl-1H-pyrazolo[3,4-d]pyrimidine (1.26 g, Intermediate D26-B) in anhydrous DMF (10 mL) was added at 25° C. and the reaction mixture was stirred for 16 h at 25° C. The mixture was filtered and the filtrate was diluted with EtOAc and washed with water and brine. The organic layer was dried over Na$_2$SO$_4$, filtered and evaporated under reduced pressure. The residue was purified by column chromatography over silica gel (5-10% EtOAc in hexane) to afford the title compound (1.41 g, 86%) as an off white solid. MS (ESI): m/z=497.1 [M+H]$^+$.

Step 2: 3-(2-tert-Butyl-4-chloro-5-methyl-phenoxymethyl)-6-methylsulfanyl-1H-pyrazolo[3,4-d]pyrimidine

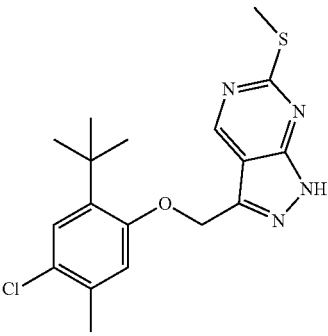 [SMILES: CSc1ncc2c(COc3cc(C)c(Cl)cc3C(C)(C)C)n[nH]c2n1]

A solution of 3-(2-tert-butyl-4-chloro-5-methyl-phenoxymethyl)-1-(4-methoxy-benzyl)-6-methylsulfanyl-1H-pyrazolo[3,4-]pyrimidine (1.4 g) in 30% HBr in AcOH (30 mL) was heated to 80° C. for 2 h. The reaction mixture was cooled to 25° C., diluted with EtOAc and washed with saturated NaHCO$_3$ solution and brine. The organic layer was dried over Na$_2$SO$_4$, filtered and evaporated under reduced pressure. The residue was purified by column chromatography over silica gel (15-50% EtOAc in hexane) to afford the title compound (750 mg, 71%) as an off white solid. MS (ESI): m/z=377.2 [M+H]$^+$.

Step 3: 3-(2-tert-Butyl-4-chloro-5-methyl-phenoxymethyl)-6-methanesulfonyl-1H-pyrazolo[3,4-d]pyrimidine

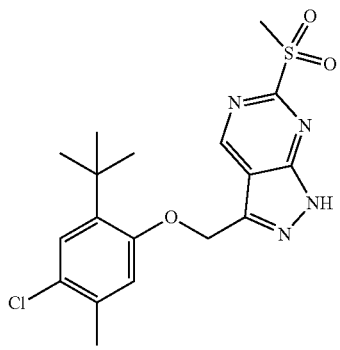 [SMILES: Cc1cc(OCc2n[nH]c3nc(S(C)(=O)=O)ncc23)c(C(C)(C)C)cc1Cl]

To a solution of 3-(2-tert-butyl-4-chloro-5-methyl-phenoxymethyl)-6-methylsulfanyl-1H-pyrazolo[3,4-d]pyrimidine (750 mg) in anhydrous THF (100 mL) was added m-CPBA (1.03 g) at 25° C. and the reaction mixture was stirred at 25° C. for 16 h. The mixture was diluted with EtOAc and washed with saturated aqueous sodium thiosulphate solution and brine. The organic layer was dried over Na$_2$SO$_4$, filtered and evaporated under reduced pressure. The resulting residue was purified by column chromatography over silica gel (30-50% EtOAc in hexane) to afford the title compound (580 mg, 71%) as an off white solid. MS (ESI): m/z=409.3 [M+H]$^+$.

Step 4: 2-{[3-(2-tert-Butyl-4-chloro-5-methyl-phenoxymethyl)-1H-pyrazolo[3,4-d]pyrimidin-6-yl]-methyl-amino}-ethanol

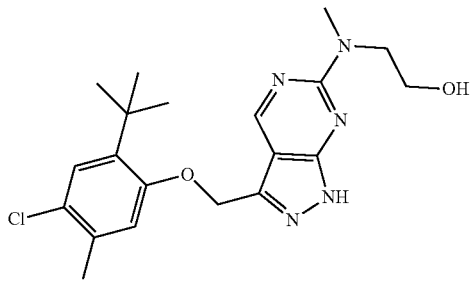 [SMILES: Cc1cc(OCc2n[nH]c3nc(N(C)CCO)ncc23)c(C(C)(C)C)cc1Cl]

To a solution of 3-(2-tert-butyl-4-chloro-5-methyl-phenoxymethyl)-6-methanesulfonyl-1H-pyrazolo[3,4-d]pyrimidine (45 mg) in dioxane (10 mL) at 25° C. were added 2-methylamino-ethanol (24.82 mg) followed by Et$_3$N (0.03 mL) and the reaction mixture was heated to reflux for 3 h. The mixture was cooled to 25° C. and all volatiles were removed under reduced pressure. The residue was purified by column chromatography over silica gel (60-70% EtOAc in hexane) to afford the title compound (12 mg, 27%) as an off white solid. MS (ESI): m/z=404.4 [M+H]$^+$.

The following examples were synthesized in analogy to example D26 from 3-(2-tert-butyl-4-chloro-5-methyl-phenoxymethyl)-6-methanesulfonyl-1H-pyrazolo[3,4-d]pyrimidine (example D26, step 3) under similar reaction conditions as described in example D26, step 4, with a suitable amine reagent:

| Ex. | Systematic Name | Amine reagent | MS, m/z |
| --- | --- | --- | --- |
| D27 | 3-[[3-[(2-tert-Butyl-4-chloro-5-methylphenoxy)methyl]-1H-pyrazolo[3,4-d]pyrimidin-6-yl]-methylamino]propane-1,2-diol | 3-methylamino-propane-1,2-diol | 434.2 [M + H]$^+$ |
| D29 | 1-[3-[(2-tert-Butyl-4-chloro-5-methylphenoxy)methyl]-1H-pyrazolo[3,4-d]pyrimidin-6-yl]azetidin-3-ol | 3-(hydroxy)azetidine hydrochloride | 402.3 [M + H]$^+$ |
| D30 | 2-[[3-[(2-tert-Butyl-4-chloro-5-methylphenoxy)methyl]-1H-pyrazolo[3,4-d]pyrimidin-6-yl]amino]ethanol | 2-amino-ethanol | 390.4 [M + H]$^+$ |

Example D31

2-[[3-[(2-tert-Butyl-4-chloro-5-methylphenoxy)methyl]-1H-pyrazolo[3,4-d]pyrimidin-6-yl]oxy]ethanol

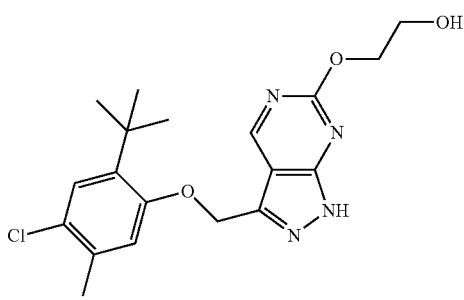 [SMILES: Cc1cc(OCc2n[nH]c3nc(OCCO)ncc23)c(C(C)(C)C)cc1Cl]

A mixture of 3-(2-tert-butyl-4-chloro-5-methyl-phenoxymethyl)-6-methanesulfonyl-1H-pyrazolo[3,4-d]pyrimidine (150 mg, example D26, step 3), ethane-1,2-diol (1 mL) and Et₃N (0.103 mL) was heated to 100° C. for 6 h. The reaction mixture was cooled to 25° C., diluted with EtOAc and washed with water and brine. The organic layer was dried over Na₂SO₄, filtered and evaporated under reduced pressure. The residue was purified by prep. HPLC to afford the title compound (29 mg, 20%) as off white solid. MS (ESI): m/z=391.2 [M+H]⁺.

Example D32

5-tert-Butyl-4-[[6-(3-hydroxyazetidin-1-yl)-1H-pyrazolo[3,4-d]pyrimidin-3-yl]methoxy]-2-methylbenzonitrile

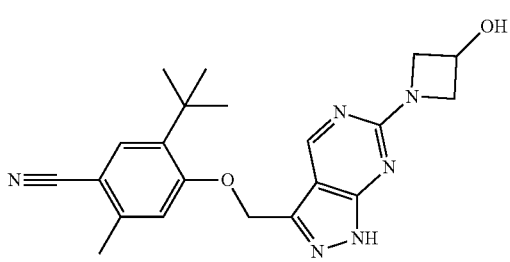 [SMILES: Cc1cc(OCc2n[nH]c3nc(N4CC(O)C4)ncc23)c(C(C)(C)C)cc1C#N]

Step 1: 5-tert-Butyl-4-[1-(4-methoxy-benzyl)-6-methylsulfanyl-1H-pyrazolo[3,4-d]pyrimidin-3-ylmethoxy]-2-methyl-benzonitrile

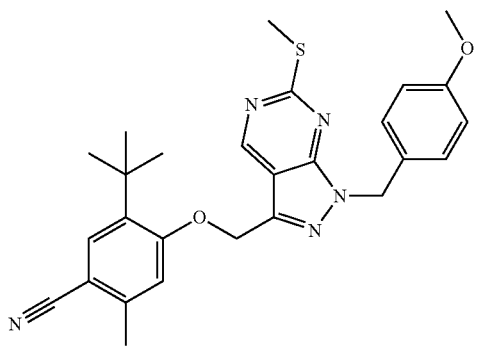 [SMILES: COc1ccc(Cn2nc(COc3cc(C)c(C#N)cc3C(C)(C)C)c3cnc(SC)nc32)cc1]

The title compound was prepared in analogy to example D26, step 1 from 3-bromomethyl-1-(4-methoxy-benzyl)-6-methylsulfanyl-1H-pyrazolo[3,4-d]pyrimidine (400 mg, Intermediate D26-B) and 5-tert-butyl-4-hydroxy-2-methyl-benzonitrile (259.31 mg, Intermediate A16) and was obtained as off white solid (450 mg, 87%). MS (ESI): m/z=488.5 [M+H]⁺.

Step 2: 5-tert-Butyl-2-methyl-4-(6-methylsulfanyl-1H-pyrazolo[3,4-d]pyrimidin-3-ylmethoxy)-benzonitrile

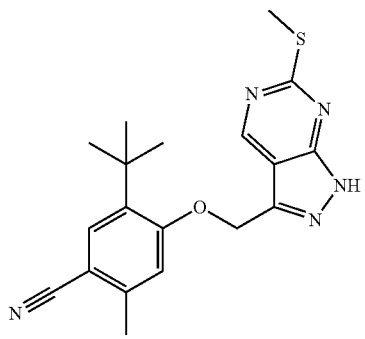 [SMILES: CSc1ncc2c(COc3cc(C)c(C#N)cc3C(C)(C)C)n[nH]c2n1]

The title compound was prepared in analogy to example D26, step 2 from 5-tert-butyl-4-[1-(4-methoxy-benzyl)-6-methylsulfanyl-1H-pyrazolo[3,4-d]pyrimidin-3-ylmethoxy]-2-methyl-benzonitrile (450 mg) and was obtained as an off white solid (225 mg, 66%). MS (ESI): m/z=368.2 [M+H]⁺.

Step 3: 5-tert-Butyl-4-(6-methanesulfonyl-1H-pyrazolo[3,4-d]pyrimidin-3-ylmethoxy)-2-methyl-benzonitrile

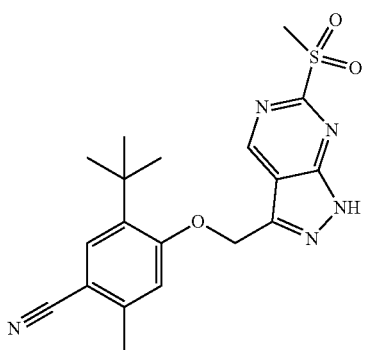 [SMILES: Cc1cc(OCc2n[nH]c3nc(S(C)(=O)=O)ncc23)c(C(C)(C)C)cc1C#N]

The title compound was prepared in analogy to example D26, step 3, from 5-tert-butyl-2-methyl-4-(6-methylsulfanyl-1H-pyrazolo[3,4-d]pyrimidin-3-ylmethoxy)-benzonitrile (700 mg) and was obtained as an off white solid (580 mg, 76%). MS (ESI): m/z=400.2 [M+H]⁺.

343

Step 4: 5-tert-Butyl-4-[[6-(3-hydroxyazetidin-1-yl)-1H-pyrazolo[3,4-d]pyrimidin-3-yl]methoxy]-2-methylbenzonitrile

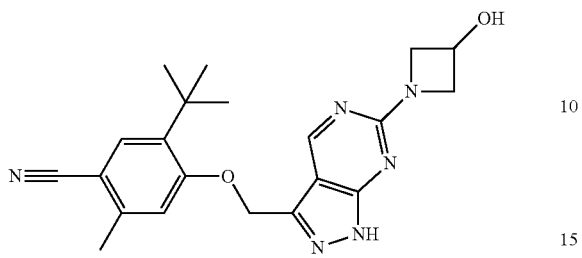

The title compound was prepared in analogy to example D26, step 4, from 5-tert-butyl-4-(6-methanesulfonyl-1H-pyrazolo[3,4-d]pyrimidin-3-ylmethoxy)-2-methyl-benzonitrile (100 mg) and 3-(hydroxy)azetidine hydrochloride (82.0 mg) and was obtained as an off white solid (35 mg, 36%). MS (ESI): m/z=393.3 [M+H]$^+$.

The following examples were synthesized in analogy to example D32 from from 5-tert-butyl-4-(6-methanesulfonyl-1H-pyrazolo[3,4-d]pyrimidin-3-ylmethoxy)-2-methyl-benzonitrile (example D32, step 3) under similar reaction conditions as described in example D26, step 4, with a suitable amine reagent:

344

Example D34

3-[[3-[(2-tert-Butyl-4-chloro-5-methylphenoxy)methyl]-1H-pyrazolo[3,4-(1]pyrimidin-6-yl]oxy]propane-1,2-diol

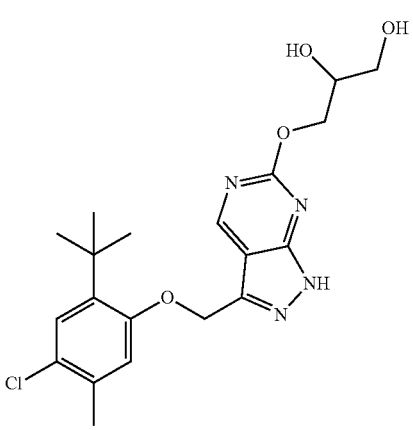 [SMILES: Cc1cc(OCc2n[nH]c3nc(OCC(O)CO)ncc23)c(C(C)(C)C)cc1Cl]

| Ex. | Systematic Name | Amine reagent | MS, m/z |
|---|---|---|---|
| D33 | 5-tert-Butyl-4-[[6-[2-hydroxyethyl(methyl)amino]-1H-pyrazolo[3,4-d]pyrimidin-3-yl]methoxy]-2-methylbenzonitrile | 2-methylamino-ethanol | 425.2 [M + H]$^+$ |
| | 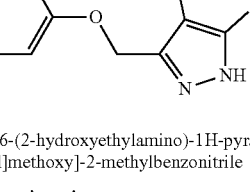 | | |
| D35 | 5-tert-Butyl-4-[[6-(2-hydroxyethylamino)-1H-pyrazolo[3,4-d]pyrimidin-3-yl]methoxy]-2-methylbenzonitrile | 2-amino-ethanol | 381.2 [M + H]$^+$ |
| | 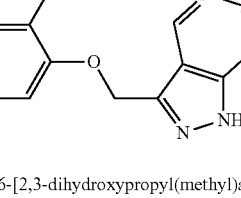 | | |
| D36 | 5-tert-Butyl-4-[[6-[2,3-dihydroxypropyl(methyl)amino]-1H-pyrazolo[3,4-d]pyrimidin-3-yl]methoxy]-2-methylbenzonitrile | 3-methylamino-propane-1,2-diol | 395.4 [M + H]$^+$ |
| | 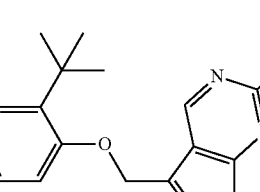 | | |

Step 1: 3-(2-tert-Butyl-4-chloro-5-methyl-phenoxymethyl)-6-(2,2-dimethyl-[1,3]dioxolan-4-ylmethoxy)-1H-pyrazolo[3,4-d]pyrimidine

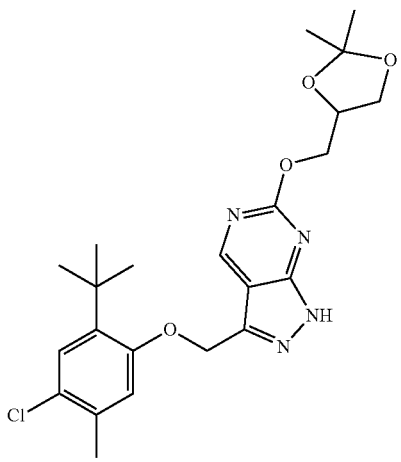 [SMILES: Cc1cc(OCc2n[nH]c3nc(OCC4COC(C)(C)O4)ncc23)c(C(C)(C)C)cc1Cl]

A mixture of 3-(2-tert-butyl-4-chloro-5-methyl-phenoxymethyl)-6-methanesulfonyl-1H-pyrazolo[3,4-d]pyrimidine (150 mg, example D26, step 3), (2,2-dimethyl-[1,3]dioxolan-4-yl)-methanol (1 mL) and Et$_3$N (0.103 mL) was heated to 100° C. for 3 h. The reaction mixture was cooled to 25° C. and all volatiles were evaporated under reduced pressure. The residue was diluted with EtOAc and the organic phase was washed water and brine. The organic layer was dried over Na$_2$SO$_4$ and evaporated under reduced pressure to afford the title compound that was used in the next reaction step without further purification. MS (ESI): m/z=461.1 [M+H]$^+$.

Step 2: 3-[3-(2-tert-Butyl-4-chloro-5-methyl-phenoxymethyl)-1H-pyrazolo[3,4-d]pyrimidin-6-yloxy]-propane-1,2-diol

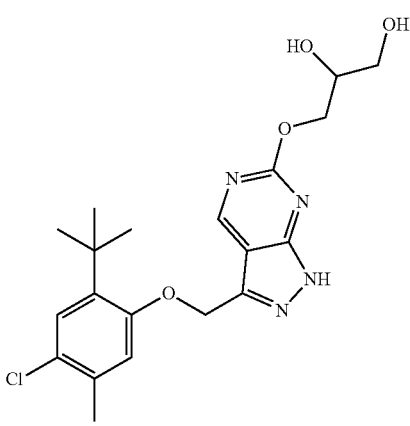 [SMILES: Cc1cc(OCc2n[nH]c3nc(OCC(O)CO)ncc23)c(C(C)(C)C)cc1Cl]

A solution of 3-(2-tert-butyl-4-chloro-5-methyl-phenoxymethyl)-6-(2,2-dimethyl-[1,3]dioxolan-4-ylmethoxy)-1H-pyrazolo[3,4-d]pyrimidine (135 mg) in 2N aqueous HCl (15 mL) was stirred at 25° C. for 16 h. The reaction mixture was diluted with DCM and the organic layer was separated, washed with saturated aqueous NaHCO$_3$ solution and brine, dried over Na$_2$SO$_4$ and evaporated under reduced pressure. The residue was purified by HPLC to afford the title compound (36 mg, 29%) as an off white solid. MS (ESI): m/z=421.2 [M+H]$^+$.

Example D37

5-tert-Butyl-4-[[6-(2,3-dihydroxypropoxy)-1H-pyrazolo[3,4-d]pyrimidin-3-yl]methoxy]-2-methylbenzonitrile

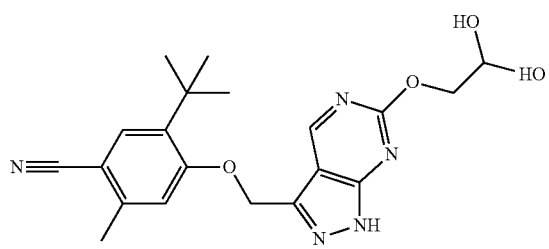 [SMILES: Cc1cc(OCc2n[nH]c3nc(OCC(O)O)ncc23)c(C(C)(C)C)cc1C#N]

The title compound was prepared in analogy to example D34, steps 1 and 2, from 5-tert-butyl-4-(6-methanesulfonyl-1H-pyrazolo[3,4-d]pyrimidin-3-ylmethoxy)-2-methyl-benzonitrile (150 mg, example D32, step 3) and was obtained as an off white solid (26 mg, 18%). MS (ESI): m/z=412.2 [M+H]$^+$.

Example D38

5-tert-Butyl-4-[[6-(2-hydroxyethoxy)-1H-pyrazolo[3,4-d]pyrimidin-3-yl]methoxy]-2-methylbenzonitrile

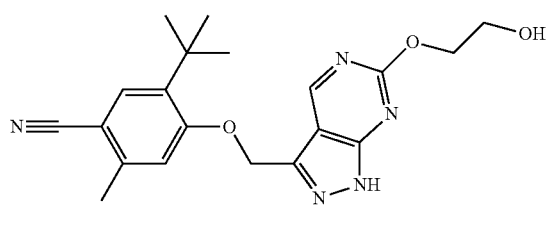 [SMILES: Cc1cc(OCc2n[nH]c3nc(OCCO)ncc23)c(C(C)(C)C)cc1C#N]

The title compound was prepared in analogy to example D31 from 5-tert-butyl-4-(6-methanesulfonyl-1H-pyrazolo[3,4-d]pyrimidin-3-ylmethoxy)-2-methyl-benzonitrile (105 mg, example D32, step 3) and was obtained as an off white solid (16 mg, 16%). MS (ESI): m/z=382.2 [M+H]$^+$.

Example D44

4-[3-[5-Chloro-4-methyl-2-(1H-pyrazolo[3,4-c]pyridin-3-ylmethoxy)phenyl]-4-fluorobenzoyl]-1-methylpiperazin-2-one

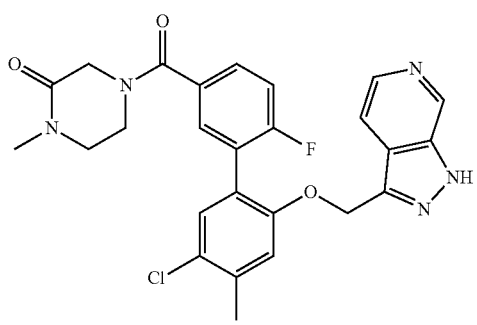 [SMILES: Cc1cc(OCc2n[nH]c3cnccc23)c(-c2cc(C(=O)N3CCN(C)C(=O)C3)ccc2F)cc1Cl]

Step 1: 4-[3-[5-Chloro-4-methyl-2-[(1-tritylpyrazolo[3,4-c]pyridin-3-yl)methoxy]phenyl]-4-fluorobenzoyl]-1-methylpiperazin-2-one

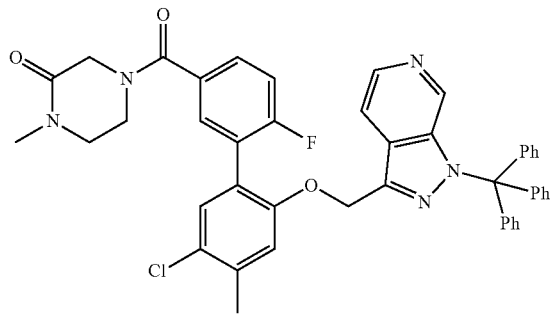 [SMILES: Cc1cc(OCc2nn(C(c3ccccc3)(c3ccccc3)c3ccccc3)c3cnccc23)c(-c2cc(C(=O)N3CCN(C)C(=O)C3)ccc2F)cc1Cl]

In a 20 mL round-bottomed flask, 4-(5'-chloro-6-fluoro-2'-hydroxy-4'-methyl-[1,1'-biphenyl]-3-carbonyl)-1-methylpiperazin-2-one (Intermediate B65, 50 mg), 3-(chloromethyl)-1-trityl-1H-pyrazolo[3,4-c]pyridine (Intermediate D44-B, 54.4 mg) and potassium carbonate (40.3 mg) were combined with acetone (6 mL) to give a white suspension. The mixture was then heated to 50° C. and was stirred for 4 h, but no reaction could be observed. Therefore, acetone was removed in vacuo and acetonitrile (6 mL) and cesium carbonate (95 mg) were added. The mixture was then heated again at 80° C. for 4 hours. The solvent was removed in vacuo and to the light brown residue was added saturated aqueous NH$_4$Cl solution. The mixture was extracted 3 times with ethyl acetate and the combined organic layers were dried over Na$_2$SO$_4$ and concentrated in vacuo to give a light brown foam. The crude material was purified by flash chromatography (silica gel, 20 g, gradient of 0% to 100% ethyl acetate in heptane, followed by 0% to 10% MeOH in DCM) to afford the title compound as a colorless foam (53 mg). MS (m/z): 750.26 [M+H]$^+$.

Step 2: 4-[3l-[5-Chloro-4-methyl-2-(1H-pyrazolo[3,4-c]pyridin-3-ylmethoxy)phenyl]-4-fluorobenzoyl]-1-methylpiperazin-2-one

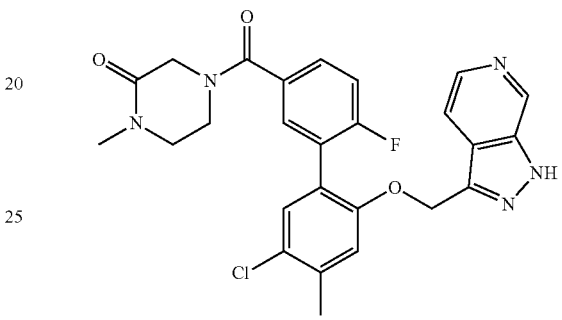

In a 10 mL round-bottomed flask, 4-(5'-chloro-6-fluoro-4'-methyl-2'-((1-trityl-1H-pyrazolo[3,4-c]pyridin-3-yl)methoxy)-[1,1'-biphenyl]-3-carbonyl)-1-methylpiperazin-2-one (50 mg) was dissolved in CH$_2$Cl$_2$ (2.9 mL) to give a colorless solution. TFA (444 µL) was added at rt and the reaction mixture was stirred for 30 min. TLC analysis confirmed the consumption of the starting material and formation of a single product. The reaction was then quenched by careful addition of sat. Na$_2$CO$_3$ solution. The mixture was extracted with DCM (2×25 mL) and the combined organic extracts were washed with brine, dried over Na$_2$SO$_4$, and evaporated to provide the title compound as a colorless foam (27.0 mg). MS (m/z): 508.15 [M+H]$^+$.

The following examples were synthesized from the suitable building blocks/intermediates in analogy to example D44, Steps 1-2:

| Ex. | Systematic Name | Building block/intermediates | MS, m/z |
|---|---|---|---|
| D46 | 3-[5-chloro-4-methyl-2-(1H-pyrazolo[3,4-c]pyridin-3-ylmethoxy)phenyl]-4-fluoro-N-(2-methoxyethyl)-N-methylbenzamide | Intermediate D44-B and Intermediate B64 | 483.3 [M + H]$^+$ |

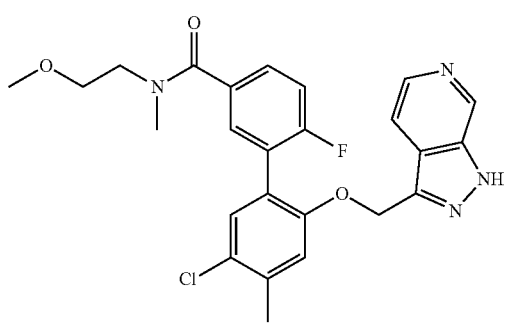

-continued

| Ex. | Systematic Name | Building block/intermediates | MS, m/z |
|---|---|---|---|
| D47 | 3-[[4-chloro-2-(2-methoxypyridin-3-yl)-5-methylphenoxy]methyl]-1H-pyrazolo[3,4-c]pyridine | Intermediate D44-B and Intermediate B53 | 381.2 [M + H]$^+$ |
| D49 | 4-tert-butyl-2-methyl-5-(1H-pyrazolo[3,4-c]pyridin-3-ylmethoxy)benzonitrile | Intermediate D44-B and Intermediate A17 | 321.2 [M + H]$^+$ |

The following additional examples of type D were synthesized from the suitable building blocks/intermediates in analogy to Example D44, Steps 1-2:

| Ex. | Systematic Name | Building block/intermediates | MS, m/z |
|---|---|---|---|
| D50 | 4-tert-butyl-2-chloro-5-(1H-pyrazolo[3,4-c]pyridin-3-ylmethoxy)benzonitrile | Intermediate D44-B and Intermediate A34 | 341.2 [M + H]$^+$ |

-continued

| Ex. | Systematic Name | Building block/ intermediates | MS, m/z |
|---|---|---|---|
| D51 | 2-chloro-5-(5-cyclopropyloxy-2-fluorophenyl)-4-(1H-pyrazolo[3,4-c]pyridin-3-ylmethoxy)benzonitrile | Intermediate D44-B and Intermediate B95 | 435.2 [M + H]+ |
| D54 | 2-chloro-5-[2-fluoro-5-(trifluoromethoxy)phenyl]-4-(1H-pyrazolo[4,3-c]pyridin-3-ylmethoxy)benzonitrile | Intermediate D54-B and Intermediate B97 | 463.1 [M + H]+ |

The following additional examples of type D were synthesized from the suitable building blocks/intermediates in analogy to Example D17:

| D52 | 4-tert-butyl-2-chloro-5-(1H-pyrazolo[3,4-b]pyridin-3-ylmethoxy)benzonitrile | tert-butyl 3-(bromomethyl)-pyrazolo[3,4-b]pyridine-1-carboxylate (CAS: 174180-76-8) and Intermediate A34 | 341.2 [M + H]+ |

| | | | |
|---|---|---|---|
| D53 | 2-chloro-5-(5-cyclopropyloxy-2-fluorophenyl)-4-(1H-pyrazolo[3,4-b]pyridin-3-ylmethoxy)benzonitrile 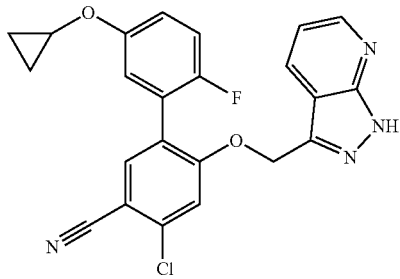 | tert-butyl 3-(bromomethyl)-pyrazolo[3,4-b]pyridine-1-carboxylate (CAS: 174180-76-8) and Intermediate B95 | 435.1 [M + H]+ |
| D55 | 2-chloro-5-[2-fluoro-5-(trifluoromethoxy)phenyl]-4-(1H-pyrazolo[3,4-b]pyridin-3-ylmethoxy)benzonitrile 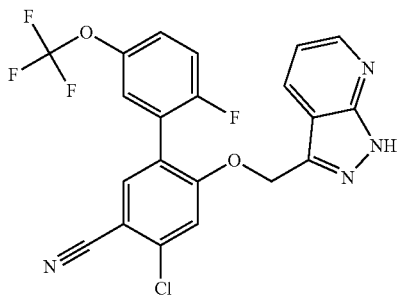 | tert-butyl 3-(bromomethyl)-pyrazolo[3,4-b]pyridine-1-carboxylate (CAS: 174180-76-8) and Intermediate B97 | 463.1 [M + H]+ |

Examples E: Examples Related to Tetrandro-Pyrazolopyridine Head Groups

Example E1 tert-Butyl 3-((2-tert-butyl-4-chloro-5-methylphenoxy)methyl)-6,7-dihydro-1H-pyrazolo[4,3-c]pyridine-5(4H)-carboxylate

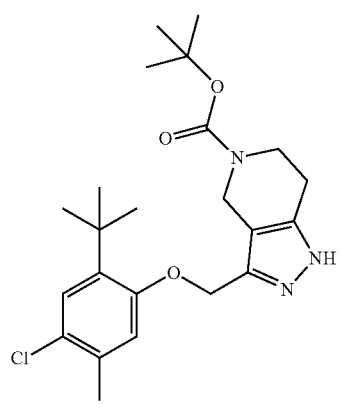 [SMILES: Cc1cc(OCc2n[nH]c3c2CN(C(=O)OC(C)(C)C)CC3)c(C(C)(C)C)cc1Cl]

Step 1: 5-tert-Butyl 3-ethyl 6,7-dihydro-1H-pyrazolo[4,3-c]pyridine-3,5(4H)-dicarboxylate

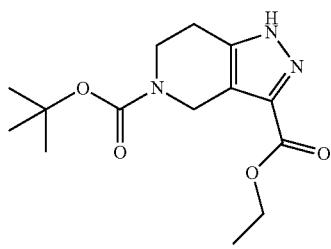 [SMILES: CCOC(=O)c1n[nH]c2c1CN(C(=O)OC(C)(C)C)CC2]

Di-tert-butyl-dicarbonate (1.04 g) was added to a suspension of ethyl 4,5,6,7-tetrahydro-1H-pyrazolo[4,3-c]pyridine-3-carboxylate (930 mg, CAS: 926926-62-7) in diethyl ether (45 mL) at 0° C. Following addition of the reagents, the reaction mixture was stirred at rt overnight. Water was added and the mixture was extracted with EtOAc. The combined organic layers were washed with water and brine, dried over $Na_2SO_4$ and evaporated. The residue was purified by column chromatography (50 g silica gel; heptane/EtOAc 70/30-45/55) to obtain the title compound as a white foam (1.079 g, 77%). MS (ESI): m/z=294.2 [M−H]−.

Step 2: tert-Butyl 3-(hydroxymethyl)-1,4,6,7-tetrahydropyrazolo[4,3-c]pyridine-5-carboxylate

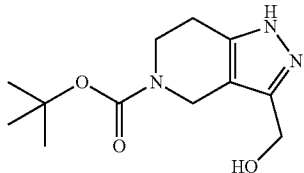 [SMILES: CC(C)(C)OC(=O)N1CCc2[nH]nc(CO)c2C1]

A solution of 5-tert-butyl 3-ethyl 6,7-dihydro-1H-pyrazolo[4,3-c]pyridine-3,5(4H)-dicarboxylate (60.0 mg) in THF (0.5 mL) was added dropwise at 0° C. to a white suspension of calcium chloride (90.1 mg) and sodium borohydride (61.4 mg) in a mixture of EtOH (1 mL) and THF (0.5 mL). The resulting white suspension was stirred at 0° C. overnight. Then, 0.1N HCl was added carefully and the mixture was extracted with EtOAc. The combined organic layers were washed with brine, dried over Na$_2$SO$_4$ and evaporated. The residue was purified by column chromatography (5 g silica gel; DCM/MeOH 98/2-95/5) to afford the title compound as a white solid (47 mg, 92%). MS (ESI): m/z=254.2 [M+H]$^+$.

Step 3: tert-Butyl 3-(chloromethyl)-1,4,6,7-tetrahydropyrazolo[4,3-c]pyridine-5-carboxylate

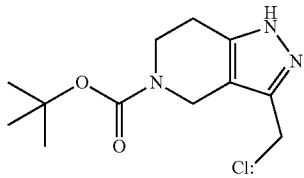

tert-Butyl 3-(hydroxymethyl)-1,4,6,7-tetrahydropyrazolo[4,3-c]pyridine-5-carboxylate (94.0 mg) was suspended in a mixture of DCM (1 mL), acetonitrile (1 mL) and THF (1 mL). Triphenyl-phosphine (102 mg) and carbon tetrachloride (285 mg, 179 µL) were added to the white suspension and the mixture was stirred at rt. After a while the reaction mixture turned into a colorless solution, which was stirred at rt for 2 d. Additional carbon tetrachloride (285 mg, 179 µL) was added and the solution was stirred for 1 more day at rt. Then, the mixture was concentrated to dryness and the residue was purified by column chromatography (20 g silica gel; DCM/MeOH 98/2-90/10) to obtain the title compound as white solid (37 mg, 35%). MS (ESI): m/z=272.2 [M+H]$^+$.

Step 4: tert-Butyl 3-((2-tert-butyl-4-chloro-5-methylphenoxy)methyl)-6,7-dihydro-1H-pyrazolo[4,3-c]pyridine-5(4H)-carboxylate

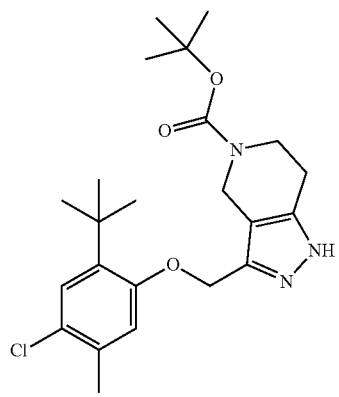 [SMILES: Cc1cc(OCc2n[nH]c3c2CN(C(=O)OC(C)(C)C)CC3)c(C(C)(C)C)cc1Cl]

A mixture of tert-butyl 3-(chloromethyl)-1,4,6,7-tetrahydropyrazolo[4,3-c]pyridine-5-carboxylate (45.1 mg), 2-tert-butyl-4-chloro-5-methyl-phenol (82.5 mg, CAS: 30894-16-7) and potassium carbonate (57.4 mg) in acetonitrile (2 mL) was heated to reflux for 5 h. The reaction mixture was cooled to rt and was then concentrated. The residue was partitioned between EtOAc and water. The aqueous layer was extracted with EtOAc and the combined organic layers were washed with brine, dried over Na$_2$SO$_4$ and evaporated. The remaining oil was purified by column chromatography (10 g silica gel; heptane/EtOAc 70/30-10/90) to afford the title compound as a white solid (19 mg, 26%). MS (ESI): m/z=434.3 [M+H]$^+$.

Example E2

1-(3-((2-tert-Butyl-4-chloro-5-methylphenoxy)methyl)-6,7-dihydro-1H-pyrazolo[4,3-c]pyridin-5(4H)-yl)ethanone

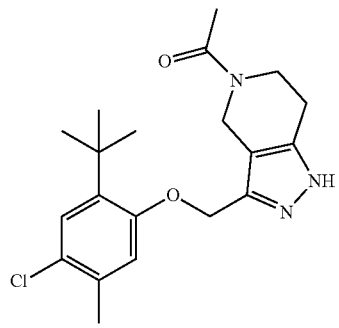 [SMILES: CC(=O)N1CCc2[nH]nc(COc3cc(C)c(Cl)cc3C(C)(C)C)c2C1]

Step 1: 5-tert-Butyl 3-ethyl 1-trityl-6,7-dihydro-4H-pyrazolo[4,3-c]pyridine-3,5-dicarboxylate and 5-tert-Butyl 3-ethyl 2-trityl-6,7-dihydro-4H-pyrazolo[4,3-c]pyridine-3,5-dicarboxylate

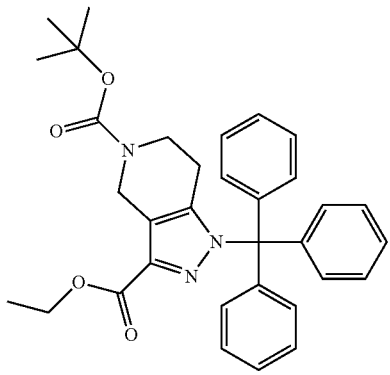

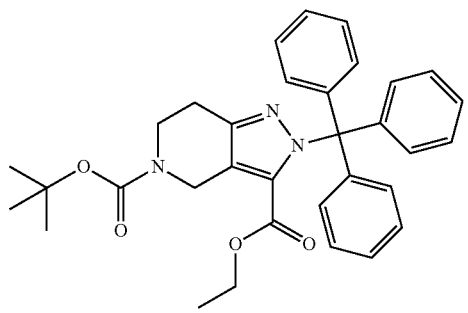

A solution of 5-tert-butyl 3-ethyl 6,7-dihydro-1H-pyrazolo[4,3-c]pyridine-3,5(4H)-dicarboxylate (1.17 g, example E1, step 1) in DMF (7 mL) was added dropwise to a suspension of sodium hydride (216 mg, 55% in mineral oil) in DMF (7 mL) at 0° C. The reaction mixture was stirred at 0° C. for 15 min and then at rt for 30 min. The mixture was then again cooled to 0° C. and a solution of [chloro(diphenyl)methyl]benzene (1.16 g) in DMF (7 mL) was added. The resulting suspension was stirred at rt for 2 d. Water was added carefully and the mixture was extracted with EtOAc. The combined extracts were washed with water (3 times) and brine, dried over $Na_2SO_4$ and evaporated. The residue was purified by column chromatography (120 g silica gel; heptane/EtOAc 95/5-25/75) to obtain 5-tert-butyl 3-ethyl 1-trityl-6,7-dihydro-4H-pyrazolo[4,3-c]pyridine-3,5-dicarboxylate (off white solid, 790 mg, 37%, MS (ESI): m/z=560.4 [M+Na]$^+$) as well as 5-tert-butyl 3-ethyl 2-trityl-6,7-dihydro-4H-pyrazolo[4,3-c]pyridine-3,5-dicarboxylate (white solid, 450 mg, 21%). MS (ESI): m/z=560.4 [M+Na]$^+$).

Step 2: tert-Butyl 3-(hydroxymethyl)-1-trityl-6,7-dihydro-4H-pyrazolo[4,3-c]pyridine-5-carboxylate

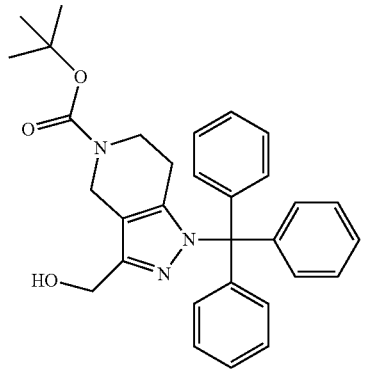 [SMILES: CC(C)(C)OC(=O)N1CCc2c(c(CO)nn2C(c2ccccc2)(c2ccccc2)c2ccccc2)C1]

To a solution of 5-tert-butyl 3-ethyl 1-trityl-6,7-dihydro-4H-pyrazolo[4,3-c]pyridine-3,5-dicarboxylate (200 mg) in THF (3 mL) was added dropwise diisobutylaluminum hydride (818 µM in toluene) at 0° C. After the addition, the colorless solution was stirred at rt overnight. 0.5 mL MeOH were added with vigorous stirring and the resulting solution was poured into a mixture of 20 mL 10 wt % Rochelle-salt solution and 20 mL EtOAc. This mixture was stirred at rt for 1 h and the layers were then separated. The aqueous layer was extracted with EtOAc and the combined organic layers were washed with brine, dried over $Na_2SO_4$ and evaporated. The residue was purified by column chromatography (20 g silica gel; heptane/EtOAc 80/20-50/50) to obtain the title compound as a white solid (156 mg, 85%). MS (ESI): m/z=518.4 [M+Na]$^+$).

Step 3: tert-Butyl 3-[(2-tert-butyl-4-chloro-5-methyl-phenoxy)methyl]-1-trityl-6,7-dihydro-4H-pyrazolo[4,3-c]pyridine-5-carboxylate

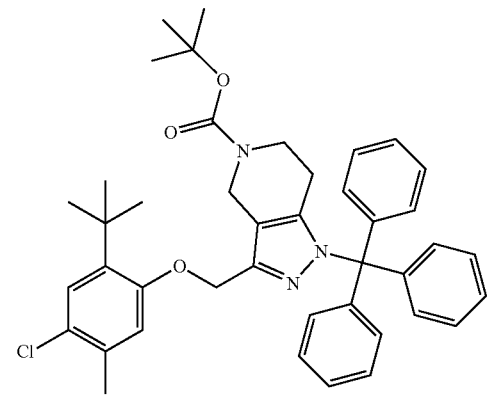 [SMILES: Cc1cc(OCc2nn(C(c3ccccc3)(c3ccccc3)c3ccccc3)c3c2CN(C(=O)OC(C)(C)C)CC3)c(C(C)(C)C)cc1Cl]

To a solution of tert-butyl 3-(hydroxymethyl)-1-trityl-6,7-dihydro-4H-pyrazolo[4,3-c]pyridine-5-carboxylate (100 mg) in 2-methyltetrahydrofuran (1 mL) was added triethylamine (22.5 mg, 30.9 µL) at 0° C. To this mixture was added dropwise methanesulfonyl chloride (24.3 mg, 16.5 µL) and the resulting mixture was stirred at 0° C. for 1 h. A white solid precipitated which was filtered off and washed with 2-methyltetrahydrofuran. The filtrate was concentrated and the remaining colorless oil was dissolved in DMA (0.5 mL) and the resulting solution was added dropwise to a suspension of 2-tert-butyl-4-chloro-5-methyl-phenol (40.1 mg, CAS: 30894-16-7), potassium iodide (56.9 mg) and cesium fluoride (153 mg) in DMA (1 mL). The reaction mixture was stirred at rt overnight. Water was added and the mixture was extracted with EtOAc. The combined organic layers were washed with water (3 times) and brine, dried over Na₂SO₄ and evaporated. The residue was purified by column chromatography (20 g silica gel; heptane/EtOAc 98/2-50/50) to obtain the title compound as an off white solid (49 mg, 36%). MS (ESI): m/z=674.5 [M−H]⁻.

Step 4: 3-[(2-tert-Butyl-4-chloro-5-methyl-phenoxy)methyl]-4,5,6,7-tetrahydro-1H-pyrazolo[4,3-c]pyridine

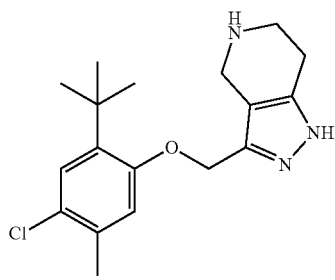 [SMILES: Cc1cc(OCc2n[nH]c3c2CNCC3)c(C(C)(C)C)cc1Cl]

Trifluoroacetic acid (0.2 mL) was added to a solution of tert-butyl 3-[(2-tert-butyl-4-chloro-5-methyl-phenoxy)methyl]-1-trityl-6,7-dihydro-4H-pyrazolo[4,3-c]pyridine-5-carboxylate (47.0 mg) in DCM (1 mL) at rt. After 30 min, saturated Na₂CO₃ solution was added carefully and the mixture was extracted with DCM. The combined extracts were washed with a small amount of brine, dried over Na₂SO₄ and evaporated. The residue was purified by column chromatography (5 g silica gel; DCM/MeOH 95/5-85/15) to obtain the title compound as a white solid (18 mg, 78%). MS (ESI): m/z=334.2 [M+H]⁺.

Step 5: 1-(3-((2-tert-Butyl-4-chloro-5-methylphenoxy)methyl)-6,7-dihydro-1H-pyrazolo[4,3-c]pyridin-5(4H)-yl)ethanone

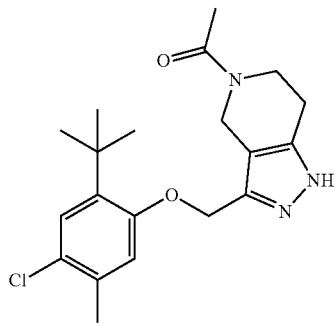 [SMILES: CC(=O)N1CCc2[nH]nc(COc3cc(C)c(Cl)cc3C(C)(C)C)c2C1]

A mixture of 3-[(2-tert-butyl-4-chloro-5-methyl-phenoxy)methyl]-4,5,6,7-tetrahydro-1H-pyrazolo[4,3-c]pyridine (15.0 mg), triethylamine (9.09 mg, 12.5 μL) and acetyl chloride (3.52 mg, 3.19 μL) in THF (0.5 mL) was stirred at rt overnight. Then. water was added and the mixture was extracted with EtOAc and then with DCM. The combined extracts were washed with brine, dried over Na₂SO₄ and evaporated. The residue was purified by column chromatography (5 g silica gel; DCM/MeOH 19/1) to obtain the title compound as a white solid (13 mg, 77%). MS (ESI): m/z=376.2 [M+H]⁺.

Example E3

1-(3-((2-tert-Butyl-4-chloro-5-methylphenoxy)methyl)-6,7-dihydro-1H-pyrazolo[4,3-c]pyridin-5(4H)-yl)-2-methoxyethanone

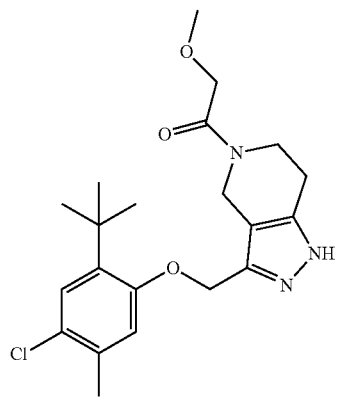 [SMILES: COCC(=O)N1CCc2[nH]nc(COc3cc(C)c(Cl)cc3C(C)(C)C)c2C1]

The title compound was prepared in analogy to example E2, step 5, from 3-[(2-tert-butyl-4-chloro-5-methyl-phenoxy)methyl]-4,5,6,7-tetrahydro-1H-pyrazolo[4,3-c]pyridine (15.0 mg) and 2-methoxyacetyl chloride (5.11 mg, 4.27 μL) and was obtained as a white solid (13 mg, 71%). MS (ESI): m/z=406.3 [M+H]⁺.

Example E4

3-((2-tert-Butyl-4-chloro-5-methylphenoxy)methyl)-4,5,6,7-tetrahydro-1H-pyrazolo[3,4-c]pyridine

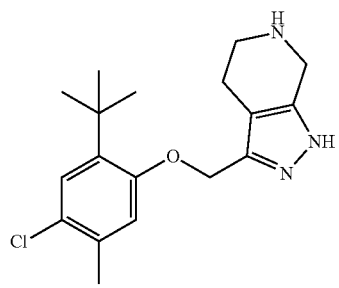 [SMILES: Cc1cc(OCc2n[nH]c3c2CCNC3)c(C(C)(C)C)cc1Cl]

Step 1: tert-Butyl 4-(1-diazo-2-ethoxy-2-oxo-ethyl)-4-hydroxy-piperidine-1-carboxylate

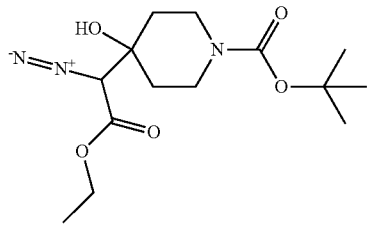

A lithium diisopropylamide solution was prepared by dropwise addition of nBuLi (19.1 mL, 1.6 M in hexane) to a solution of diisopropylamine (3.12 g, 4.4 mL) in dry THF (77 mL) at −78° C. This lithium diisopropylamide solution was then added dropwise over 1 hour to a solution of tert-butyl 4-oxopiperidine-1-carboxylate (3.854 g) and ethyl diazoacetate (2.31 g, 2.1 mL) in dry THF (115 mL) at −78° C. The mixture was stirred for 2 hours at −78° C. Then, AcOH (5.81 g, 5.54 mL) was added at −78° C. and the mixture was then kept at rt overnight. The solvent was removed under reduced pressure to approx. 1/10 of its volume and diethyl ether (400 mL) was added. The mixture was washed with saturated NaHCO₃ solution and was then dried over Na₂SO₄, filtered and evaporated. The remaining orange-brown viscous oil (6.46 g) was used without further analysis in the next reaction step.

Step 2: tert-Butyl 4-(1-diazo-2-ethoxy-2-oxo-ethyl)-3,6-dihydro-2H-pyridine-1-carboxylate

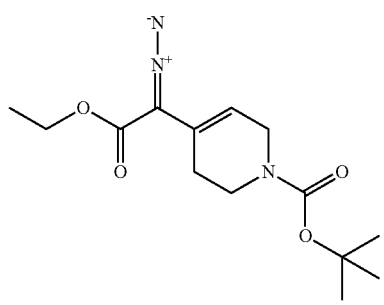

Pyridine (30.5 g, 31.2 mL) was added to a solution of tert-butyl 4-(1-diazo-2-ethoxy-2-oxo-ethyl)-4-hydroxy-cyclohexanecarboxylate (6.05 g) in MTBE (120 mL). The mixture was cooled to −10° C. and phosphorus oxychloride (5.92 g, 3.6 mL) was added dropwise over 8 minutes under vigorous stirring. The mixture was slowly warmed to rt and was stirred overnight. The mixture was cooled again to −10° C. and more phosphorus oxychloride (592 mg, 360 µL) was added dropwise. The reaction mixture was slowly warmed to rt and stirred for 3 h before 0.1M NaOH (193 mL) was added slowly. The mixture was extracted with EtOAc and the combined extracts were washed with brine, dried over Na₂SO₄, filtered and evaporated. The residue (6.2 g) was used in the next reaction step without further purification. MS (ESI): m/z=294.2 [M−H]⁻.

Step 3: 6-tert-Butyl 3-ethyl 1,4,5,7-tetrahydropyrazolo[3,4-c]pyridine-3,6-dicarboxylate

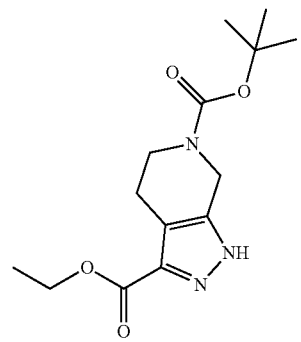 [SMILES: CCOC(=O)c1n[nH]c2c1CCN(C(=O)OC(C)(C)C)C2]

In a two-neck flask equipped with a dropping funnel and a distillation column, toluene (80 mL) was heated to reflux. A solution of tert-butyl 4-(1-diazo-2-ethoxy-2-oxo-ethyl)-3,6-dihydro-2H-pyridine-1-carboxylate (5.7 g) in a mixture of EtOAc (20 mL) and pyridine (8 mL) was added via the dropping funnel at the same rate as the rate of distillation. More toluene (7 mL) was added. The dark brown mixture was stirred for an hour and was then allowed to cool to rt. EtOAc (250 mL) was added and the mixture was washed with water (3 times) and brine, dried over Na₂SO₄, filtered and evaporated. The crude material was purified by column chromatography (50 g silica gel; heptane/EtOAc 9/1 to 1/1) to obtain the title compound as light brown solid (3.12 g, 55%). MS (ESI): m/z=294.2 [M−H]⁻.

Step 4: 6-tert-Butyl 3-ethyl 1-trityl-5,7-dihydro-4H-pyrazolo[3,4-c]pyridine-3,6-dicarboxylate, and 6-tert-Butyl 3-ethyl 2-trityl-5,7-dihydro-4H-pyrazolo[3,4-c]pyridine-3,6-dicarboxylate

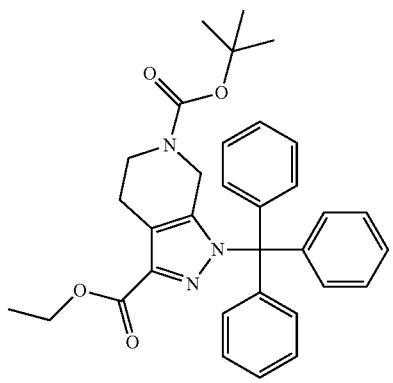

-continued

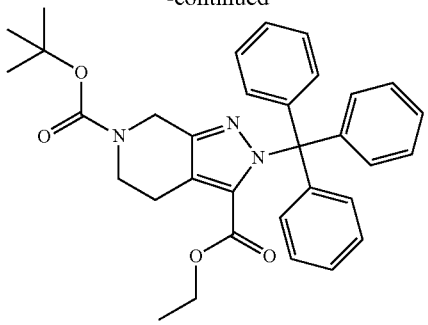

In analogy to example E2, step 1, 6-tert-butyl 3-ethyl 1,4,5,7-tetrahydropyrazolo[3,4-c]pyridine-3,6-dicarboxylate (980 mg) was converted into 6-tert-butyl 3-ethyl 1-trityl-5,7-dihydro-4H-pyrazolo[3,4-c]pyridine-3,6-dicarboxylate (white solid, 762 mg, 43%, MS (ESI): m/z=1097.8 [2M+Na]⁻) and 6-tert-butyl 3-ethyl 2-trityl-5,7-dihydro-4H-pyrazolo[3,4-c]pyridine-3,6-dicarboxylate (white solid, 510 mg, 29%). MS (ESI): m/z=560.4 [M+Na]⁺).

Step 5: tert-Butyl 3-(hydroxymethyl)-1-trityl-5,7-dihydro-4H-pyrazolo[3,4-c]pyridine-6-carboxylate

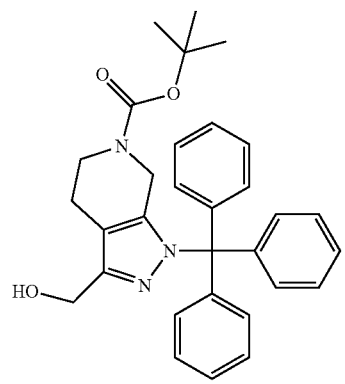 [SMILES: CC(C)(C)OC(=O)N1CCc2c(CO)nn(C(c3ccccc3)(c3ccccc3)c3ccccc3)c2C1]

From 6-tert-butyl 3-ethyl 1-trityl-5,7-dihydro-4H-pyrazolo[3,4-c]pyridine-3,6-dicarboxylate (715 mg) the title compound was obtained in analogy to example E2, step 2, as a white solid (581 mg, 88%). MS (ESI): m/z=496.3 [M+H]⁺.

Step 6: tert-Butyl 3-[(2-tert-butyl-4-chloro-5-methyl-phenoxy)methyl]-1-trityl-5,7-dihydro-4H-pyrazolo[3,4-c]pyridine-6-carboxylate

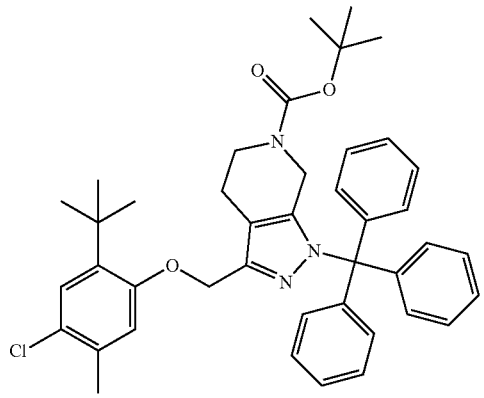 [SMILES: Cc1cc(OCc2nn(C(c3ccccc3)(c3ccccc3)c3ccccc3)c3c2CCN(C(=O)OC(C)(C)C)C3)c(C(C)(C)C)cc1Cl]

From tert-butyl 3-(hydroxymethyl)-1-trityl-5,7-dihydro-4H-pyrazolo[3,4-c]pyridine-6-carboxylate (100 mg) the title compound was obtained in analogy to example E2, step 3, as a light yellow foam (58 mg, 43%). MS (ESI): m/z=698.5 [M+Na]⁺.

Step 7: 3-((2-tert-Butyl-4-chloro-5-methylphenoxy)methyl)-4,5,6,7-tetrahydro-1H-pyrazolo[3,4-c]pyridine

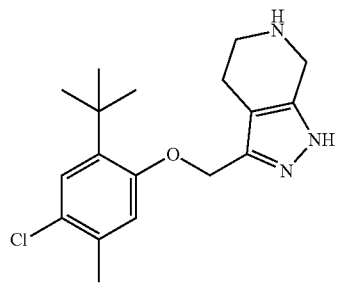 [SMILES: Cc1cc(OCc2n[nH]c3c2CCNC3)c(C(C)(C)C)cc1Cl]

From tert-butyl 3-[(2-tert-butyl-4-chloro-5-methyl-phenoxy)methyl]-1-trityl-5,7-dihydro-4H-pyrazolo[3,4-c]pyridine-6-carboxylate (75.7 mg) the title compound was obtained in analogy to example E2, step 4, as a light yellow solid (29 mg, 78%). MS (ESI): m/z=334.2 [M+H]⁺.

Example E5

1-(3-((2-tert-Butyl-4-chloro-5-methylphenoxy)methyl)-4,5-dihydro-1H-pyrazolo[3,4-c]pyridin-6(7H)-yl)ethanone

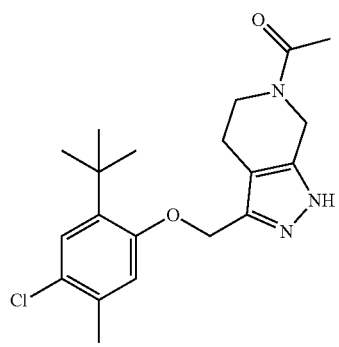 [SMILES: CC(=O)N1CCc2c(COc3cc(C)c(Cl)cc3C(C)(C)C)n[nH]c2C1]

The title compound was prepared in analogy to example E2, step 5, from 3-((2-tert-butyl-4-chloro-5-methylphenoxy)methyl)-4,5,6,7-tetrahydro-1H-pyrazolo[3,4-c]pyridine (25.0 mg example 4) and acetyl chloride (5.88 mg, 5.33 µL) and was obtained as a white solid (19 mg, 67%). MS (ESI): m/z=376.2 [M+H]⁺.

Example E6

1-(3-((2-tert-Butyl-4-chloro-5-methylphenoxy)methyl)-4,5-dihydro-1H-pyrazolo[3,4-c]pyridin-6(7H)-yl)-2-methoxyethanone

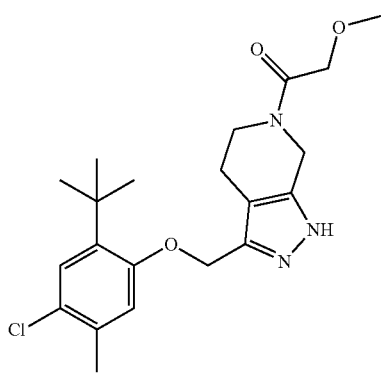 [SMILES: COCC(=O)N1CCc2c(COc3cc(C)c(Cl)cc3C(C)(C)C)n[nH]c2C1]

The title compound was prepared in analogy to example E2, step 5, from 3-((2-tert-butyl-4-chloro-5-methylphenoxy)methyl)-4,5,6,7-tetrahydro-1H-pyrazolo[3,4-c]pyridine (22.0 mg, example 4) and 2-methoxyacetyl chloride (7.51 mg, 6.27 µL) and was obtained as a white solid (17 mg, 64%). MS (ESI): m/z=406.2 [M+H]$^+$.

Example E7

3-((4-Chloro-2-(2-methoxypyridin-3-yl)-5-methylphenoxy)methyl)-4,5,6,7-tetrahydro-1H-pyrazolo[3,4-c]pyridine

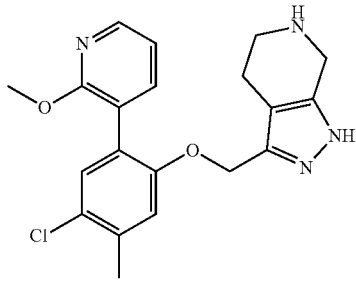 [SMILES: COc1ncccc1-c1cc(Cl)c(C)cc1OCc1n[nH]c2c1CCNC2]

Triethylamine (26.9 mg, 37.1 µL) was added to a solution of tert-butyl 3-(hydroxymethyl)-1-trityl-5,7-dihydro-4H-pyrazolo[3,4-c]pyridine-6-carboxylate (120 mg, obtained in example E4, step 5) in 2-methyltetrahydrofuran (1.5 mL) at 0° C. To the mixture was added dropwise methanesulfonyl chloride (29.1 mg, 19.7 µL) and the resulting mixture was stirred at 0° C. for 1 h. The suspension was then filtered, the filtercake was washed with 2-methyltetrahydrofuran and the filtrate was concentrated. The residue was dissolved in DMA (1.5 mL) and this solution was added dropwise to a suspension of 4-chloro-2-(2-methoxy-3-pyridyl)-5-methyl-phenol (60.4 mg, Intermediate B53), potassium iodide (68.2 mg) and cesium fluoride (184 mg) in DMA (1.5 mL) and the reaction mixture was stirred at rt overnight. Then, water was added and the mixture was extracted with EtOAc. The combined organic layers were washed with water (3 times) and brine, dried over Na$_2$SO$_4$ and evaporated. The residue was purified by column chromatography (20 g silica gel; heptane/EtOAc 90/10-50/50) to obtain a yellow foam (81 mg) that was dissolved in a mixture of DCM (2 mL) and trifluoroacetic acid (0.2 mL). This mixture was stirred at rt for 1 h. Then, saturated Na$_2$CO$_3$ solution was added carefully and the mixture was extracted with DCM. The combined organic layers were washed with a very small amount of brine, dried over Na$_2$SO$_4$ and evaporated. The remaining residue was purified by column chromatography (5 g silica gel; DCM/MeOH 95/5+DCM/MeOH/NH$_4$OH 8/1.9/0.1) to obtain the title compound as a white foam (21 mg, 23%). MS (ESI): m/z=385.2 [M+H]$^+$.

Example E8

1-(3-((4-Chloro-2-(2-methoxypyridin-3-yl)-5-methylphenoxy)methyl)-4,5-dihydro-1H-pyrazolo[3,4-c]pyridin-6(7H)-yl)ethanone

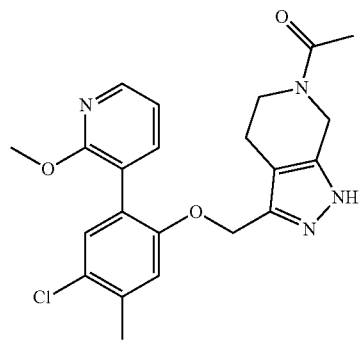 [SMILES: COc1ncccc1-c1cc(Cl)c(C)cc1OCc1n[nH]c2c1CCN(C(C)=O)C2]

The title compound was prepared in analogy to example E2, step 5, from 3-((4-chloro-2-(2-methoxypyridin-3-yl)-5-methylphenoxy)methyl)-4,5,6,7-tetrahydro-1H-pyrazolo[3,4-c]pyridine (25.0 mg, example E7) and acetyl chloride (5.88 mg, 5.33 µL) and was obtained as a white solid (8 mg, 42%). MS (ESI): m/z=427.2 [M+H]$^+$.

Examples F: Examples Related to Pyrazole Head Groups

Example F1

3-((2-tert-Butyl-4-chloro-5-methylphenoxy)methyl)-1H-pyrazole

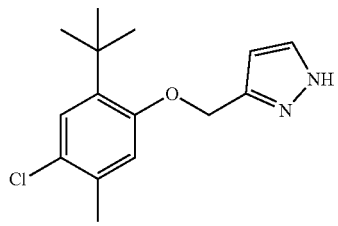 [SMILES: Cc1cc(OCc2cc[nH]n2)c(C(C)(C)C)cc1Cl]

Step 1: tert-Butyl 3-[(2-tert-butyl-4-chloro-5-methyl-phenoxy)methyl]pyrazole-1-carboxylate

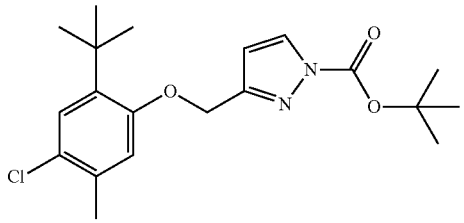 [SMILES: Cc1cc(OCc2ccn(C(=O)OC(C)(C)C)n2)c(C(C)(C)C)cc1Cl]

A mixture of tert-butyl 3-(bromomethyl)pyrazole-1-carboxylate (65.8 mg, Intermediate F1), 2-tert-butyl-4-chloro-5-methyl-phenol (50 mg, CAS: 30894-16-7) and potassium carbonate (87.1 mg) in acetone (5 mL) was heated to 50° C. After 6 h and after 7.5 h, more 2-tert-butyl-4-chloro-5-methylphenol (10 mg and 22 mg, respectively) was added and heating was continued for 4 h. Sat. NH$_4$Cl solution was added and the mixture was extracted with EtOAc. The combined extracts were washed with brine, dried with Na$_2$SO$_4$ and evaporated. The residue was purified by column chromatography (20 g SiO$_2$, n-heptane/EtOAc 100/0 to 65/35) to obtain the title compound (71 mg, 74%) as colorless oil. MS (ESI): m/z=279.2 [M–CO$_2$tBu+H]$^+$.

Step 2: 3-((2-tert-Butyl-4-chloro-5-methylphenoxy)methyl)-1H-pyrazole

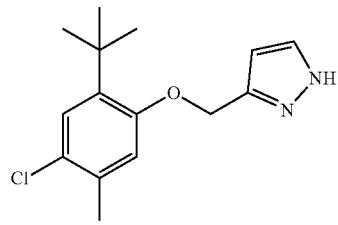 [SMILES: Cc1cc(OCc2cc[nH]n2)c(C(C)(C)C)cc1Cl]

A solution of tert-butyl 3-[(2-tert-butyl-4-chloro-5-methyl-phenoxy)methyl]pyrazole-1-carboxylate (65 mg) in a mixture of DCM (1 mL) and TFA (1 mL) was stirred at rt for 4 h. Then, saturated NaHCO$_3$ solution was added and the mixture was extracted with EtOAc. The combined extracts were washed with brine, dried with Na$_2$SO$_4$ and evaporated to provide the title compound (47 mg, 98%) as a colorless viscous oil. MS (ESI): m/z=279.2 [M+H]$^+$.

Example F2

4-((1H-Pyrazol-3-yl)methoxy)-5-tert-butyl-2-methylbenzonitrile

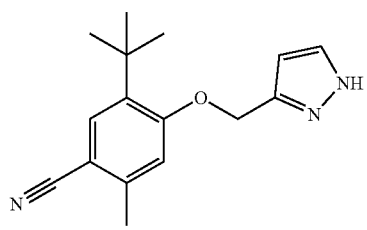 [SMILES: Cc1cc(OCc2cc[nH]n2)c(C(C)(C)C)cc1C#N]

The title compound was prepared in analogy to example F1, steps 1 and 2, from tert-butyl 3-(bromomethyl)pyrazole-1-carboxylate (Intermediate F1) and 5-tert-butyl-4-hydroxy-2-methyl-benzonitrile (Intermediate A16) and was obtained as white foam. MS (ESI): m/z=270.2 [M+H]$^+$.

Example F3

Methyl 3-((2-(tert-butyl)-4-chloro-5-methylphenoxy)methyl)-1H-pyrazole-5-carboxylate

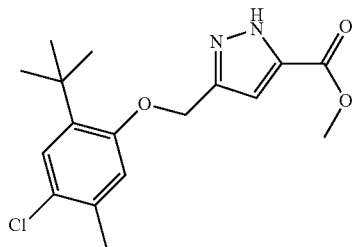 [SMILES: COC(=O)c1cc(COc2cc(C)c(Cl)cc2C(C)(C)C)n[nH]1]

Step 1: Methyl 5-[(2-tert-butyl-4-chloro-5-methylphenoxy)methyl]-2-tetrahydropyran-2-yl-pyrazole-3-carboxylate

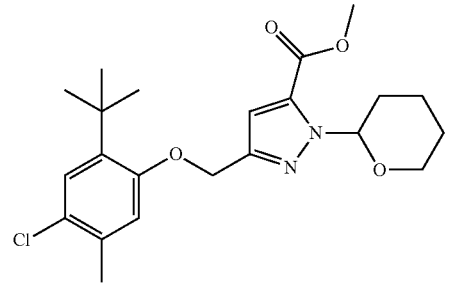 [SMILES: COC(=O)c1cc(COc2cc(C)c(Cl)cc2C(C)(C)C)nn1C1CCCCO1]

Triethylamine (29 mg, 40 µL) was added to a solution of methyl 5-(hydroxymethyl)-2-tetrahydropyran-2-yl-pyrazole-3-carboxylate (63 mg, Intermediate F3) in 2-methyl-tetrahydrofuran (1.5 mL) at 0° C. Then, methanesulfonyl chloride (30.9 mg, 21 µL) was added dropwise and the reaction mixture was stirred at 0° C. for 2 h. The white precipitate was filtered off and was washed with 2-methyl-tetrahydrofuran. The filtrate was concentrated and the residue was suspended in DMA (2.4 mL) and added to a suspension of 2-tert-butyl-4-chloro-5-methyl-phenol (52 mg, CAS: 30894-16-7), potassium iodide (76 mg) and cesium fluoride (197 mg) in DMA (1.5 mL). The reaction mixture was stirred overnight at rt. Then, water was added and the mixture was extracted with EtOAc. The combined extracts were washed with water and brine, dried with Na$_2$SO$_4$, filtered and evaporated. The residue was purified by chromatography (20 g silica gel; heptane/EtOAc 100/0 to 1/2) to provide the title compound (22 mg, 20%) as a waxy solid. MS (ESI): m/z=337.2 [M–THP+H]$^+$.

Step 2: Methyl 3-((2-(tert-butyl)-4-chloro-5-methyl-phenoxy)methyl)-1H-pyrazole-5-carboxylate

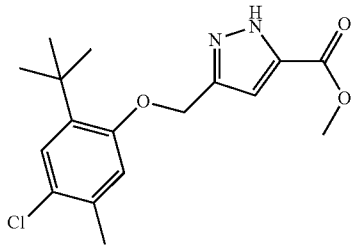

Methyl 5-[(2-tert-butyl-4-chloro-5-methyl-phenoxy)methyl]-2-tetrahydropyran-2-yl-pyrazole-3-carboxylate (22 mg) was suspended in MeOH (1 mL) and HCl (4 M in 1,4-dioxane, 70 µL) was added. The colorless solution was stirred at rt for 2 h before saturated NaHCO$_3$ solution (5 mL) was added. The mixture was evaporated to half of its volume and was then extracted with
EtOAc. The combined organic layers washed with brine (10 mL), dried over Na$_2$SO$_4$, filtered and evaporated. The residue was purified by chromatography (10 g silica gel; heptane/EtOAc 100/0 to 70/30) to afford the title compound (16 mg, 91%) as a white powder. MS (ESI): m/z=337.2 [M+H]$^+$.

Example F4

(3-((2-(tert-Butyl)-4-chloro-5-methylphenoxy)methyl)-1H-pyrazol-5-yl)(pyrrolidin-1-yl)methanone

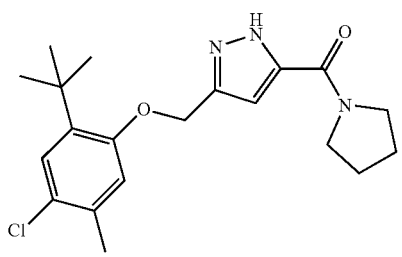 [SMILES: Cc1cc(OCc2cc(C(=O)N3CCCC3)[nH]n2)c(C(C)(C)C)cc1Cl]

Step 1: [5-[(2-tert-Butyl-4-chloro-5-methyl-phenoxy)methyl]-2-tetrahydropyran-2-yl-pyrazol-3-yl]-pyrrolidin-1-yl-methanone

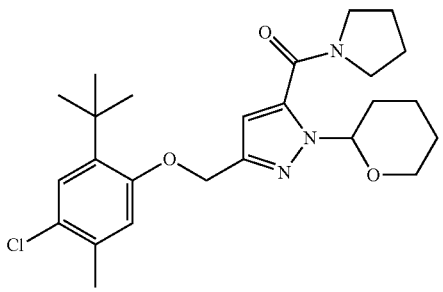 [SMILES: Cc1cc(OCc2cc(C(=O)N3CCCC3)n(C3CCCCO3)n2)c(C(C)(C)C)cc1Cl]

To a solution of pyrrolidine (12.9 mg, 15 µL) in DCM (0.3 mL) was added a 2M solution of trimethylaluminum in hexane (90 µL) dropwise at rt and the mixture was stirred for 15 minutes. Then, a solution of methyl 5-[(2-tert-butyl-4-chloro-5-methyl-phenoxy)methyl]-2-tetrahydropyran-2-yl-pyrazole-3-carboxylate (50 mg, example F3, step 1) in DCM (0.6 mL) was added slowly. The reaction mixture was heated to reflux overnight. The mixture was carefully diluted with 1 M HCl, extracted with DCM, and the combined organic layers were dried over Na$_2$SO$_4$, filtered and evaporated. The residue was purified by chromatography (20 g silica gel; heptane/EtOAc 100/0 to 1/1) to obtain the title compound (36 mg, 66%) as a colorless oil. MS (ESI): m/z=376.3 [M-THP+H]$^+$.

Step 2: (3-((2-(tert-Butyl)-4-chloro-5-methylphenoxy)methyl)-1H-pyrazol-5-yl)(pyrrolidin-1-yl)methanone

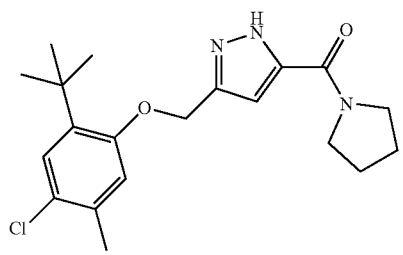 [SMILES: Cc1cc(OCc2cc(C(=O)N3CCCC3)[nH]n2)c(C(C)(C)C)cc1Cl]

The title compound was prepared in analogy to example F3, step 2, from [5-[(2-tert-butyl-4-chloro-5-methyl-phenoxy)methyl]-2-tetrahydropyran-2-yl-pyrazol-3-yl]-pyrrolidin-1-yl-methanone (36 mg) and was obtained as a white solid (21 mg, 71%). MS (ESI): m/z=376.3 [M+H]$^+$.

Example F5

3-((2-(tert-Butyl)-4-chloro-5-methylphenoxy)methyl)-N,N-dimethyl-1H-pyrazole-5-carboxamide

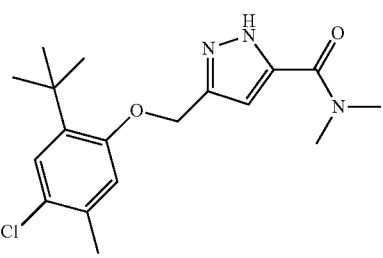 [SMILES: Cc1cc(OCc2cc(C(=O)N(C)C)[nH]n2)c(C(C)(C)C)cc1Cl]

The title compound was prepared in analogy to example F4, steps 1 and 2, from methyl 5-[(2-tert-butyl-4-chloro-5-methyl-phenoxy)methyl]-2-tetrahydropyran-2-yl-pyrazole-3-carboxylate (example F3, step 1) and dimethylamine hydrochloride and was obtained as a white solid. MS (ESI): m/z=350.3 [M+H]$^+$.

Example F6

4-[(2-tert-Butyl-4-chloro-5-methylphenoxy)methyl]-2H-triazole

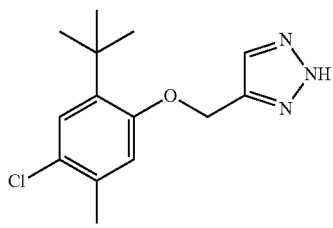 [SMILES: Cc1cc(OCc2cn[nH]n2)c(C(C)(C)C)cc1Cl]

Step 1: 1-tert-Butyl-5-chloro-4-methyl-2-prop-2-ynoxybenzene

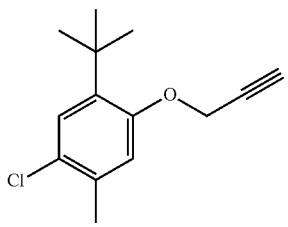 [SMILES: C#CCOc1cc(C)c(Cl)cc1C(C)(C)C]

In a 25 mL round-bottomed flask, 2-(tert-butyl)-4-chloro-5-methylphenol (CAS: 30894-16-7, 200 mg), 3-bromoprop-1-yne (80% in toluene) (225 mg, 163 µL) and potassium carbonate (209 mg) were combined with CH₃CN (4 mL) to give a white suspension. The reaction mixture was stirred for 15 h and was then concentrated in vacuo. The reaction mixture was poured into ethyl acetate (25 mL) and the organic layer was washed with H₂O (1×10 mL). The organic layer was dried over Na₂SO₄ and concentrated in vacuo to provide the title compound (180 mg, 74%). MS (m/z): 236.1 [M]⁺.

Step 2: 4-[(2-tert-Butyl-4-chloro-5-methylphenoxy)methyl]-2H-triazole

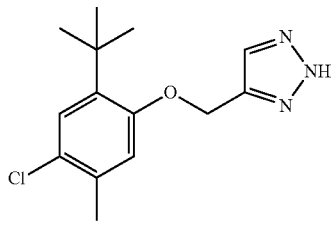 [SMILES: Cc1cc(OCc2cn[nH]n2)c(C(C)(C)C)cc1Cl]

In a 25 mL round-bottomed flask, 1-(tert-butyl)-5-chloro-4-methyl-2-(prop-2-yn-1-yloxy)benzene (180 mg) was combined with DMF (4 mL) and water (4 mL) to give a white suspension. Copper(II)sulfate pentahydrate (38 mg) and L-ascorbic acid sodium salt (304 mg) were added. The system was evacuated twice and flushed with nitrogen. Trimethylsilyl azide (746 mg) was added and the reaction mixture was heated to 90° C. for 2 h with stirring. The mixture was diluted with H₂O (50 mL) and ethyl acetate (100 mL) and the layers were separated. The aqueous phase was extracted with more ethyl acetate (2×50 mL). The organic layers were dried over Na₂SO₄ and concentrated in vacuo to give a crude oil. The crude material was purified by flash chromatography (20 g silica gel cartridge, 0% to 10% MeOH in CH₂Cl₂) to afford the title compound as a colorless foam (80 mg, 37%). MS (m/z): 280.2 [M+H]⁺.

Example F7

3-[(2-tert-Butyl-4-chloro-5-methylphenoxy)methyl]-5-phenyl-1H-pyrazole

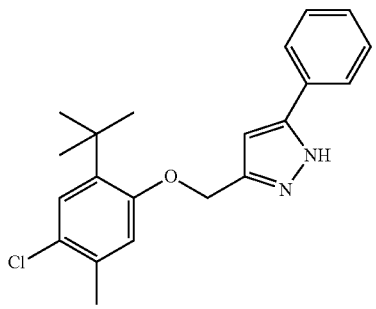 [SMILES: Cc1cc(OCc2cc(-c3ccccc3)[nH]n2)c(C(C)(C)C)cc1Cl]

Step 1: 3-(Chloromethyl)-5-phenyl-1H-pyrazole

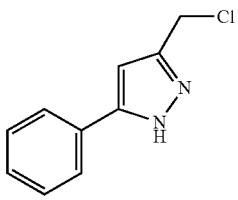 [SMILES: ClCc1cc(-c2ccccc2)[nH]n1]

This known intermediate (CAS: 755700-32-4) was made from (5-phenyl-1H-pyrazol-3-yl)methanol which is commercially available (CAS: 179057-19-3), as follows: In a 25 mL round-bottomed flask, (5-phenyl-1H-pyrazol-3-yl)methanol (50 mg) was combined with CH₂Cl₂ (3 mL) and the mixture was cooled to 0° C. under an argon atmosphere. Then, thionyl chloride (68.3 mg, 41.6 µL) was added dropwise over a period of 2 minutes and after 30 minutes the ice bath was removed. The reaction mixture was allowed to stir at RT for another 2 hours. The mixture was poured into ice and NaHCO₃ solution. The aqueous layer was then extracted twice with ethyl acetate and the organic layers where washed with brine, dried over Na₂SO₄ and concentrated in vacuo to give a crude light yellow solid (55 mg, 95%) that was used without further purification. MS (m/z): 193.0 [M+H]⁺.

Step 2: 3-[(2-tert-Butyl-4-chloro-5-methylphenoxy)methyl]-5-phenyl-1H-pyrazole

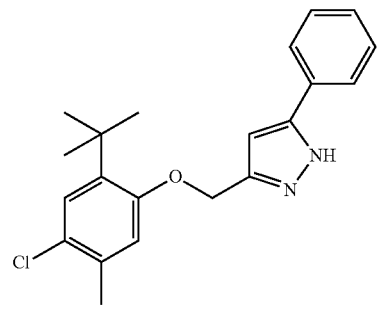 [SMILES: Cc1cc(OCc2cc(-c3ccccc3)[nH]n2)c(C(C)(C)C)cc1Cl]

2-(tert-Butyl)-4-chloro-5-methylphenol (CAS: 30894-16-7, 62.4 mg), potassium carbonate (233 mg) and 3-(chloromethyl)-5-phenyl-1H-pyrazole (55 mg) were combined with acetonitrile (4 mL) at RT under an argon atmosphere. The reaction mixture was then heated to 50° C. for 16 hours, whereas TLC confirmed formation of some product. The reaction mixture was poured into ice/water and the aqueous layer was basified with 2M NaOH solution and was extracted twice with ethyl acetate. The organic layers were washed once with brine, dried over $Na_2SO_4$, filtered and evaporated. The crude material was purified by flash chromatography (25 g silica gel cartridge, 0% to 40% ethyl acetate in heptane) to provide—besides some other unidentified materials—the title compound as a colorless solid (16 mg, 16%). MS (m/z): 355.2 $[M+H]^+$.

The following examples of type F were synthesized from the suitable phenol building blocks/intermediates in analogy to Example F7, step 2:

| Ex. | Systematic Name | Building block/intermediate | MS, m/z |
|---|---|---|---|
| F8 | 5-tert-Butyl-2-methyl-4-[(5-phenyl-1H-pyrazol-3-yl)methoxy]benzonitrile | 5-tert-Butyl-4-hydroxy-2-methylbenzonitrile Intermediate A16 | 346.2 $[M + H]^+$ |

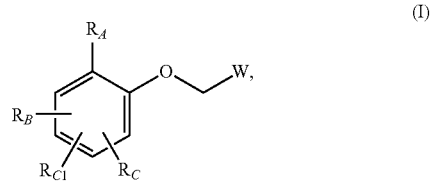

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |

|  | Per tablet |
|---|---|
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I):

$$\text{(I)}$$

with substituents $R_A$, $R_B$, $R_{C1}$, $R_C$, W wherein
R_A is $C_1$-$C_6$-alkyl;
R_B is cyano;
R_C and R_{C1} are independently selected from the group consisting of H, halogen, and $C_1$-$C_6$-alkyl;
W is ring system A:

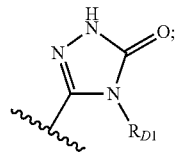

and R_{D1} is $C_1$-$C_6$-alkyl;
or a pharmaceutically acceptable salt thereof.

2. The compound according to claim 1, or a pharmaceutically acceptable salt thereof, wherein R_A is isopropyl or tert-butyl.

3. The compound according to claim 1, or a pharmaceutically acceptable salt thereof, wherein R_C is H or halogen.

4. The compound according to claim 1, or a pharmaceutically acceptable salt thereof, wherein R_{C1} is halogen.

5. The compound according to claim 1, or a pharmaceutically acceptable salt thereof, wherein R_A is isopropyl.

6. The compound according to claim 1, or a pharmaceutically acceptable salt thereof, wherein R_A is tert-butyl.

7. The compound according to claim 1, or a pharmaceutically acceptable salt thereof, wherein R_C is H.

8. The compound according to claim 1, or a pharmaceutically acceptable salt thereof, wherein R_C is $C_1$-$C_6$-alkyl.

9. The compound according to claim 1, or a pharmaceutically acceptable salt thereof, wherein R_{C1} is H.

10. The compound according to claim 1, or a pharmaceutically acceptable salt thereof, wherein R_{D1} is methyl.

11. The compound according to claim 1, wherein the compound is of formula I(b),

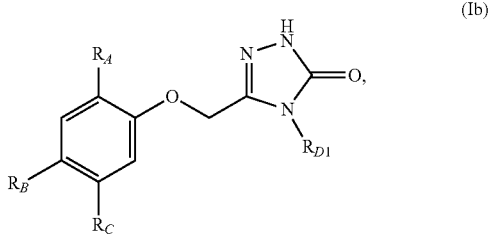

wherein R_A, R_B, R_C, and R_{D1} are as defined for formula (I), or a pharmaceutically acceptable salt thereof.

12. The compound according to claim 1, wherein the compound is:
 4-[(4-methyl-5-oxo-1H-1,2,4-triazol-3-yl)methoxy]-3-propan-2-ylbenzonitrile;
 2-methyl-4-[(4-methyl-5-oxo-1H-1,2,4-triazol-3-yl)methoxy]-5-propan-2-ylbenzonitrile;
 3-tert-butyl-4-[(4-methyl-5-oxo-1H-1,2,4-triazol-3-yl)methoxy]benzonitrile;
 5-tert-butyl-2-methyl-4-[(4-methyl-5-oxo 1H-1,2,4-triazol-3-yl)methoxy]benzonitrile;
 4-tert-butyl-2-methyl-5-[(4-methyl-5-oxo-1H-1,2,4-triazol-3-yl)methoxy]benzonitrile; or
 4-tert-butyl-3-[(4-methyl-5-oxo-1H-1,2,4-triazol-3-yl)methoxy]benzonitrile;
 or a pharmaceutically acceptable salt thereof.

13. The compound according to claim 1, wherein the compound is:
 4-tert-butyl-2-chloro-5-((4-methyl-5-oxo-1H-1,2,4-triazol-3-yl)methoxy)benzonitrile;
 5-tert-butyl-2-chloro-4-[(4-methyl-5-oxo-1H-1,2,4-triazol-3-yl)methoxy]benzonitrile; or
 5-tert-butyl-2-fluoro-4-[(4-methyl-5-oxo-1H-1,2,4-triazol-3-yl)methoxy]benzonitrile,
 or a pharmaceutically acceptable salt thereof.

14. A pharmaceutical composition comprising a compound according to claim 1, or a pharmaceutically acceptable salt thereof, and a therapeutically inert carrier.

15. A compound according to claim 1 of formula (I), or a pharmaceutically acceptable salt thereof, when manufactured by the process comprising the reaction of a compound of formula (II) in the presence of a compound of formula (III),

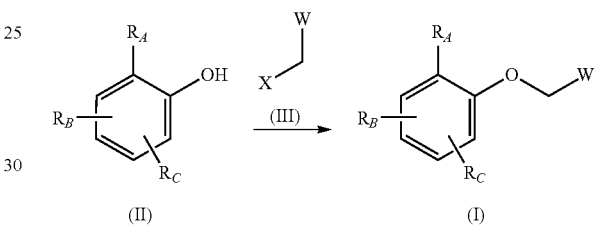

wherein X is halogen, mesylate, or tosylate;
and R_A, R_B, R_C, and W are as defined in formula (I).

16. A pharmaceutical composition comprising a compound according to claim 12, or a pharmaceutically acceptable salt thereof, and a therapeutically inert carrier.

17. A pharmaceutical composition comprising a compound according to claim 13, or a pharmaceutically acceptable salt thereof, and a therapeutically inert carrier.

18. The compound according to claim 13, wherein the compound is 4-tert-butyl-2-chloro-5-((4-methyl-5-oxo-1H-1,2,4-triazol-3-yl)methoxy)benzonitrile, or a pharmaceutically acceptable salt thereof.

19. A pharmaceutical composition comprising a compound according to claim 18, or a pharmaceutically acceptable salt thereof, and a therapeutically inert carrier.

20. The compound according to claim 13, wherein the compound is 5-tert-butyl-2-chloro-4-[(4-methyl-5-oxo-1H-1,2,4-triazol-3-yl)methoxy]benzonitrile, or a pharmaceutically acceptable salt thereof.

21. A pharmaceutical composition comprising a compound according to claim 20, or a pharmaceutically acceptable salt thereof, and a therapeutically inert carrier.

22. The compound according to claim 13, wherein the compound is 5-tert-butyl-2-fluoro-4-[(4-methyl-5-oxo-1H-1,2,4-triazol-3-yl)methoxy]benzonitrile, or a pharmaceutically acceptable salt thereof.

23. A pharmaceutical composition comprising a compound according to claim 22, or a pharmaceutically acceptable salt thereof, and a therapeutically inert carrier.

* * * * *